US008470571B2

(12) United States Patent
Damude et al.

(10) Patent No.: US 8,470,571 B2

(45) Date of Patent: Jun. 25, 2013

(54) DELTA-8 DESATURASE AND ITS USE IN MAKING POLYUNSATURATED FATTY ACIDS

(75) Inventors: Howard Glenn Damude, Hockessin, DE (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 99 days.

(21) Appl. No.: 13/238,766

(22) Filed: Sep. 21, 2011

(65) Prior Publication Data

US 2012/0015420 A1 Jan. 19, 2012

Related U.S. Application Data

(62) Division of application No. 12/298,563, filed as application No. PCT/US2007/010257 on Apr. 26, 2007, now Pat. No. 8,058,517.

(60) Provisional application No. 60/795,810, filed on Apr. 28, 2006, provisional application No. 60/837,789, filed on Aug. 15, 2006.

(51) Int. Cl.

| | |
|---|---|
| *C12P 7/64* | (2006.01) |
| *C12N 9/00* | (2006.01) |
| *C12N 9/02* | (2006.01) |
| *C12N 1/20* | (2006.01) |
| *C12N 15/00* | (2006.01) |
| *C07H 21/04* | (2006.01) |

(52) U.S. Cl.

USPC ........ 435/189; 435/134; 435/183; 435/252.3; 435/320.1; 536/23.2

(58) Field of Classification Search

None

See application file for complete search history.

(56) References Cited

U.S. PATENT DOCUMENTS

| | | | |
|---|---|---|---|
| 5,968,809 | A | 10/1999 | Knutzon |
| 5,972,664 | A | 10/1999 | Knutzon et al. |
| 6,051,754 | A | 4/2000 | Knutzon |
| 6,075,183 | A | 6/2000 | Knutzon et al. |
| 6,136,574 | A | 10/2000 | Knutzon et al. |
| 6,410,288 | B1 | 6/2002 | Knutzon et al. |
| 6,459,018 | B1 | 10/2002 | Knutzon et al. |
| 6,825,017 | B1 | 11/2004 | Browse et al. |
| 7,144,155 | B2 | 12/2006 | Underwood et al. |
| 7,145,961 | B2 | 12/2006 | Carbonari |
| 7,402,735 | B2 | 7/2008 | Browse et al. |
| 7,550,286 | B2 | 6/2009 | Damude et al. |
| 7,588,931 | B2 | 9/2009 | Damude et al. |
| 7,659,120 | B2 | 2/2010 | Yadav et al. |
| 7,807,849 | B2 | 10/2010 | Singh et al. |
| 7,932,077 | B2 | 4/2011 | Damude et al. |
| 2005/0132441 | A1 | 6/2005 | Damude et al. |

FOREIGN PATENT DOCUMENTS

| | | |
|---|---|---|
| WO | WO 98/46763 | 10/1998 |
| WO | WO 98/46764 | 10/1998 |
| WO | WO 98/55625 | 12/1998 |
| WO | WO 00/12720 | 3/2000 |
| WO | WO 00/34439 A1 | 6/2000 |
| WO | WO 00/40705 | 7/2000 |
| WO | WO 02/26946 | 4/2002 |
| WO | WO 2004071176 | 6/2004 |
| WO | WO 2004/057001 | 7/2004 |
| WO | WO 2004071467 | 8/2004 |
| WO | WO 2004/101753 | 11/2004 |
| WO | WO 2004/101757 | 11/2004 |
| WO | WO 2005/103253 | 11/2005 |
| WO | WO 2006/012325 | 2/2006 |
| WO | WO 2006/012326 | 2/2006 |

OTHER PUBLICATIONS

U.S. Appl. No. 11/166,003, filed Jun. 25, 2004, Howard Glenn Damude.

U.S. Appl. No. 60/583,041, filed Jun. 25, 2004, Howard Glenn Damude.

U.S. Appl. No. 60/739,989, filed Nov. 23, 2005, Howard Glenn Damude et al.

Spychalla et al., Identification of an Animal W-3 Fatty Acid Desaturase by Heterologous Expression in Arabidopis, Proc. Natl. Acad. Sci., 1997, vol. 94:1142-1147.

Wallis et al., The 8-Desaturase of Euglena Gracilis: An Alternate Pathway for Synthesis of 20-Carbon Polyunsaturated Fatty Acids, Arch. Biochem. and Biophys., 1999, vol. 365:307-316.

Qi et al., Production of Very Long Chain Polyunsaturated Omega-3 and Omega-6 Fatty Acids in Plants, Nat. Biotech., 2004, vol. 22:739-745.

Sayanova et al., The Alternative Pathway C20 B-Desaturase From the Non-Photosynthetic Organism *Acanthamoeba castellanii* is an Atypical Cytochrome B-5 Fusion Desaturase, FEBS Lett., 2006, vol. 580:1946-1952.

National Center for Biotechnology Information General Identifier No. 83027409, Dec. 7, 2005, Y.B. Zhang et al., Identification and Charaterization of a Novel 6-Fatty Acid Desaturase Gene From *Rhizopus stolonifer*, ABB96724.

National Center for Biotechnology Information General Identifier No. 83027408, Dec. 7, 2005, Y.B. Zhang et al., Identification and Charaterization of a Novel 6-Fatty Acid Desaturase Gene From *Rhizopus stolonifer*, DQ291156.

National Center for Biotechnology Information General Identifier No. 60499699, Nov. 1, 2005, H. Lu et al., Identification and Charaterization of a Novel 6-Fatty Acid Desaturase Gene From *Rhizopus nigricans*, AAX22052.

National Center for Biotechnology Information General Identifier No. 60499698, Nov. 1, 2005, H. Lu et al., Identification and Charaterization of a Novel 6-Fatty Acid Desaturase Gene From *Rhizopus nigricans*, AY795076.

National Center for Biotechnology Information General Identifier No. 34221934, Jul. 28, 2004, E. Sakuradani et al., Gene Cloning and Functional Analysis of a Second Delta 6-Fatty Acid Desaturase From an Arachidonic Acid-Producing *Mortierella* Fungus, BAC82361.

(Continued)

*Primary Examiner* — Christian Fronda

(57) ABSTRACT

Isolated nucleic acid fragments and recombinant constructs comprising such fragments encoding a delta-8 desaturase along with a method of making long-chain polyunsaturated fatty acids (PUFAs) using this delta-8 desaturase in plants and oleaginous yeast are disclosed.

5 Claims, 16 Drawing Sheets

OTHER PUBLICATIONS

Sakuradani et al., Gene Cloning and Functional Analysis of a Second 6-Fatty Acid Desaturase From an Arachidonic Acid-Producing *Mortierella* Fungus, Biosci. Biotechnol. Biochem., 2003, vol. 67:704-711.

National Center for Biotechnology Information General Identifier No. 17226123, Mar. 9, 2006, B. Qi et al., Identification of a CDNA Encoding a Novel C18-Delta (9) Polyunsaturated Fatty Acid-Specific Elongating Activity From the Docosahexaenoic Acid (DHA)-Producing Microalga, *Isochrysis galbana*, AAL37626.

National Center for Biotechnology Information General Identifier No. 17226122, Mar. 9, 2006, Qi et al., Identification of a CDNA Encoding a Novel C18-Delta (9) Polyunsaturated Fatty Acid-Specific Elongating Activity From the Docosahenaenoic Acid (DHA)-Producing Microalga, *Isochrysis galbana*, AF390174.

Tonon et al., Identification of a Very Long Chain Polyunsaturated Fatty Acid DELTA4-desaturase from the Microalga *Pavlova lutheri*. vol. 553(3), pp. 440-444, Oct. 23, 2003.

Restriciton Requirment, dated Sep. 16, 2010.

Non-Final Office Action, dated Dec. 14, 2010.

Notice of Allowance and Fee Due, dated Jan. 5, 2011.

pY118
8253 bp
amp
f1 ori
ARS 18
Ura3
SalI (5997)
GPD
NotI (6971)
PvDes Correct
NotI (1)
XPR2
ColE1

FIG. 8A

| Event | Fatty acid composition (wt.%) | | | | | | | | | | C20 % delta-8 | EDA % delta-8 | ERA % delta-8 | Ratio (EDA/ERA) |
|---|---|---|---|---|---|---|---|---|---|---|---|---|---|---|
| | 16:0 | 18:0 | 18:1 | LA | GLA | ALA | EDA | DGLA | ERA | ETA | desat | desat | desat | % desat |
| 1890-3-5-1 | 18.4 | 2.0 | 6.3 | 22.9 | 2.1 | 10.5 | 3.2 | 24.9 | 4.7 | 5.2 | 79.3 | 88.7 | 52.6 | 1.7 |
| -2 | 18.8 | 2.0 | 5.9 | 19.8 | 4.8 | 8.0 | 4.1 | 26.3 | 4.9 | 5.4 | 77.8 | 86.4 | 52.1 | 1.7 |
| -3 | 18.8 | 2.1 | 9.4 | 23.1 | 2.8 | 11.2 | 4.6 | 19.2 | 4.8 | 4.1 | 71.1 | 80.5 | 45.8 | 1.8 |
| -4 | 15.7 | 1.8 | 10.9 | 28.8 | 2.8 | 10.8 | 4.6 | 18.4 | 3.1 | 3.1 | 73.6 | 80.0 | 49.8 | 1.6 |
| -5 | 17.0 | 1.6 | 7.9 | 30.4 | 3.0 | 10.9 | 2.4 | 21.3 | 2.5 | 3.0 | 83.1 | 89.9 | 54.0 | 1.7 |
| -6 | 17.5 | 1.6 | 6.4 | 24.3 | 4.4 | 9.9 | 2.9 | 24.5 | 4.0 | 4.5 | 80.8 | 89.4 | 53.3 | 1.7 |
| -7 | 17.2 | 1.5 | 5.5 | 27.2 | 3.3 | 12.3 | 2.6 | 22.0 | 3.7 | 4.5 | 80.9 | 89.4 | 55.3 | 1.6 |
| -8 | 15.3 | 1.6 | 8.5 | 30.4 | 0.3 | 13.1 | 17.8 | 2.9 | 9.3 | 0.7 | 11.9 | 14.1 | 7.4 | 1.9 |
| -9 | 20.8 | 3.0 | 6.9 | 19.0 | 4.2 | 5.4 | 5.3 | 25.1 | 5.5 | 4.8 | 73.3 | 82.4 | 46.3 | 1.8 |
| -10 | 16.2 | 1.3 | 9.4 | 29.4 | 2.8 | 11.2 | 2.6 | 21.1 | 2.6 | 3.3 | 82.4 | 89.0 | 55.9 | 1.6 |
| -11 | 18.3 | 1.7 | 4.8 | 25.6 | 4.2 | 9.8 | 3.8 | 23.9 | 3.9 | 4.0 | 78.4 | 86.4 | 50.1 | 1.7 |
| -12 | 15.6 | 1.6 | 4.8 | 31.9 | 1.7 | 16.1 | 2.2 | 18.3 | 3.7 | 4.0 | 79.2 | 89.3 | 52.3 | 1.7 |
| Ave | 17.5 | 1.8 | 7.2 | 26.1 | 3.0 | 10.8 | 4.7 | 20.7 | 4.4 | 3.9 | 72.7 | 80.5 | 47.9 | 1.7 |
| 1890-4-2-1 | 16.6 | 1.8 | 13.7 | 30.0 | 1.1 | 9.8 | 5.0 | 17.5 | 3.1 | 1.5 | 70.2 | 77.8 | 33.5 | 2.3 |
| -2 | 18.3 | 1.5 | 10.9 | 31.5 | 1.0 | 16.1 | 3.9 | 13.3 | 2.5 | 0.9 | 68.8 | 77.2 | 27.2 | 2.8 |
| -3 | 16.5 | 1.6 | 7.6 | 28.9 | 1.5 | 16.6 | 4.5 | 13.4 | 7.0 | 2.5 | 58.2 | 75.0 | 26.7 | 2.8 |
| -4 | 13.6 | 1.5 | 9.2 | 31.7 | 0.6 | 20.7 | 8.9 | 6.5 | 6.6 | 0.7 | 31.7 | 42.1 | 10.1 | 4.2 |
| -5 | 15.7 | 2.1 | 10.8 | 31.5 | 1.3 | 19.7 | 3.4 | 10.3 | 3.3 | 1.9 | 64.4 | 75.3 | 35.7 | 2.1 |
| Ave | 16.1 | 1.7 | 10.4 | 30.7 | 1.1 | 16.6 | 5.1 | 12.2 | 4.5 | 1.5 | 58.7 | 69.5 | 26.6 | 2.9 |
| 1890-5-1-1 | 13.6 | 1.8 | 19.7 | 24.3 | 0.5 | 13.8 | 8.1 | 9.5 | 7.7 | 0.9 | 39.7 | 53.8 | 11.0 | 4.9 |
| -2 | 15.7 | 1.7 | 7.2 | 30.5 | 1.1 | 13.0 | 5.7 | 16.8 | 6.2 | 2.2 | 61.6 | 74.7 | 26.5 | 2.8 |
| -3 | 17.0 | 1.3 | 7.7 | 33.9 | 0.4 | 25.8 | 3.3 | 6.2 | 3.5 | 1.0 | 51.5 | 65.4 | 22.0 | 3.0 |
| -4 | 19.5 | 2.1 | 9.0 | 28.0 | 2.7 | 9.4 | 6.9 | 15.8 | 4.5 | 2.2 | 61.3 | 69.7 | 32.5 | 2.1 |
| -5 | 15.3 | 1.2 | 7.5 | 34.4 | 1.0 | 22.4 | 3.9 | 9.9 | 3.5 | 0.9 | 59.5 | 71.8 | 20.9 | 3.4 |
| Ave | 16.2 | 1.6 | 10.2 | 30.2 | 1.1 | 16.9 | 5.6 | 11.6 | 5.1 | 1.4 | 54.7 | 67.1 | 22.6 | 3.3 |

Fatty acid compositions listed in Table 8 are expressed as weight percent (wt. %). 16:0=palmitic acid, 18:0=stearic acid, 18:1=oleic acid, LA=linoleic acid, GLA=gamma-linoleic acid, ALA=alpha-linolenic acid, EDA=eicosadienoic acid, DGLA= dihomo-gamma-Linolenic, ERA=eicosatrienoic acid, ETA=eicosatetraenoic acid.

FIG. 8B

| Event | Fatty acid composition (wt. %) | | | | | | | | | | C20 % delta-8 | EDA % delta-8 | ERA % delta-8 | Ratio (EDA/ERA) |
|---|---|---|---|---|---|---|---|---|---|---|---|---|---|---|
| | 16:0 | 18:0 | 18:1 | LA | GLA | ALA | EDA | DGLA | ERA | ETA | desat | desat | desat | % desat |
| 1890-5-2-1 | 15.2 | 1.3 | 11.3 | 31.1 | 2.2 | 13.8 | 5.1 | 14.5 | 4.0 | 1.5 | 63.9 | 74.1 | 27.3 | 2.7 |
| -2 | 15.5 | 1.1 | 10.9 | 37.1 | 1.2 | 13.1 | 3.7 | 13.1 | 3.2 | 1.2 | 67.5 | 77.9 | 28.2 | 2.8 |
| -3 | 16.3 | 1.7 | 12.1 | 27.1 | 1.1 | 9.8 | 7.5 | 16.9 | 5.7 | 1.7 | 58.4 | 69.1 | 22.9 | 3.0 |
| -4 | 14.6 | 1.4 | 11.5 | 36.7 | 1.2 | 12.9 | 2.9 | 14.2 | 2.8 | 1.8 | 73.8 | 83.1 | 39.7 | 2.1 |
| -5 | 14.9 | 1.4 | 18.3 | 27.8 | 1.3 | 7.8 | 11.7 | 9.8 | 6.4 | 0.6 | 36.5 | 45.7 | 8.0 | 5.7 |
| Ave | 15.3 | 1.4 | 12.8 | 32.0 | 1.4 | 11.5 | 6.2 | 13.7 | 4.4 | 1.4 | 60.0 | 70.0 | 25.2 | 3.3 |
| 1890-5-4-1 | 15.6 | 1.1 | 9.7 | 35.9 | 1.3 | 14.8 | 3.9 | 12.6 | 4.1 | 1.0 | 63.1 | 76.5 | 20.4 | 3.7 |
| -2 | 14.4 | 1.5 | 12.1 | 28.1 | 1.6 | 12.1 | 7.0 | 15.6 | 5.9 | 1.8 | 57.4 | 68.9 | 23.5 | 2.9 |
| -3 | 14.2 | 1.0 | 11.6 | 32.9 | 1.1 | 10.8 | 7.5 | 15.0 | 4.7 | 1.2 | 57.0 | 66.7 | 20.2 | 3.3 |
| -4 | 15.0 | 1.1 | 13.3 | 37.2 | 1.0 | 17.7 | 2.8 | 9.1 | 2.2 | 0.7 | 66.5 | 76.7 | 25.4 | 3.0 |
| -5 | 16.2 | 1.2 | 8.6 | 31.4 | 2.3 | 9.8 | 6.7 | 19.3 | 3.5 | 0.9 | 66.5 | 74.2 | 21.3 | 3.5 |
| -6 | 14.6 | 1.7 | 10.5 | 28.0 | 1.4 | 14.1 | 7.8 | 15.1 | 5.7 | 1.2 | 54.9 | 66.1 | 17.7 | 3.7 |
| -7 | 14.2 | 1.7 | 14.5 | 31.6 | 1.0 | 11.4 | 7.3 | 13.5 | 3.9 | 0.9 | 56.3 | 65.0 | 19.2 | 3.4 |
| -8 | 14.7 | 1.2 | 10.8 | 34.9 | 1.0 | 15.4 | 4.1 | 13.6 | 3.2 | 1.2 | 67.0 | 76.9 | 26.7 | 2.9 |
| -9 | 15.8 | 1.1 | 8.0 | 25.5 | 1.7 | 8.6 | 9.2 | 22.6 | 5.7 | 1.7 | 62.0 | 71.0 | 22.9 | 3.1 |
| -10 | 16.5 | 1.4 | 9.3 | 32.9 | 1.9 | 10.7 | 6.2 | 16.3 | 3.5 | 1.2 | 64.4 | 72.4 | 26.4 | 2.7 |
| -11 | 14.4 | 1.0 | 9.1 | 35.2 | 1.9 | 14.7 | 5.5 | 14.3 | 3.0 | 0.8 | 64.1 | 72.2 | 22.0 | 3.3 |
| -12 | 15.0 | 1.5 | 16.1 | 24.7 | 1.2 | 8.4 | 8.5 | 17.0 | 6.3 | 1.3 | 55.3 | 66.8 | 17.1 | 3.9 |
| Ave | 15.0 | 1.3 | 11.1 | 31.5 | 1.4 | 12.4 | 6.4 | 15.3 | 4.3 | 1.2 | 61.2 | 71.1 | 21.9 | 3.3 |
| 1890-6-2-1 | 13.8 | 1.1 | 8.4 | 28.6 | 3.0 | 10.4 | 7.5 | 17.9 | 7.0 | 2.2 | 58.2 | 70.4 | 24.1 | 2.9 |
| -2 | 13.3 | 1.3 | 15.7 | 31.0 | 0.9 | 13.2 | 6.8 | 12.2 | 4.8 | 0.9 | 52.8 | 64.1 | 15.1 | 4.2 |
| -3 | 18.2 | 1.8 | 6.5 | 31.0 | 3.1 | 13.7 | 5.5 | 14.5 | 4.2 | 1.4 | 61.9 | 72.4 | 24.9 | 2.9 |
| -4 | 16.9 | 1.6 | 8.6 | 34.0 | 1.0 | 15.8 | 3.8 | 13.1 | 3.5 | 1.5 | 66.5 | 77.4 | 30.2 | 2.6 |
| -5 | 15.1 | 1.7 | 10.7 | 30.1 | 1.9 | 8.9 | 7.8 | 16.0 | 6.4 | 1.4 | 55.0 | 67.2 | 18.0 | 3.7 |
| Ave | 15.5 | 1.5 | 10.0 | 31.0 | 2.0 | 12.4 | 6.3 | 14.7 | 5.2 | 1.5 | 58.9 | 70.3 | 22.5 | 3.3 |

Fatty acid compositions listed in Table 8 are expressed as weight percent (wt. %). 16:0=palmitic acid, 18:0=stearic acid, 18:1=oleic acid, LA=linoleic acid, GLA=gamma-linoleic acid, ALA=alpha-linolenic acid, EDA=eicosadienoic acid, DGLA= dihomo-gamma-Linolenic, ERA=eicosatrienoic acid, ETA=eicosatetraenoic acid.

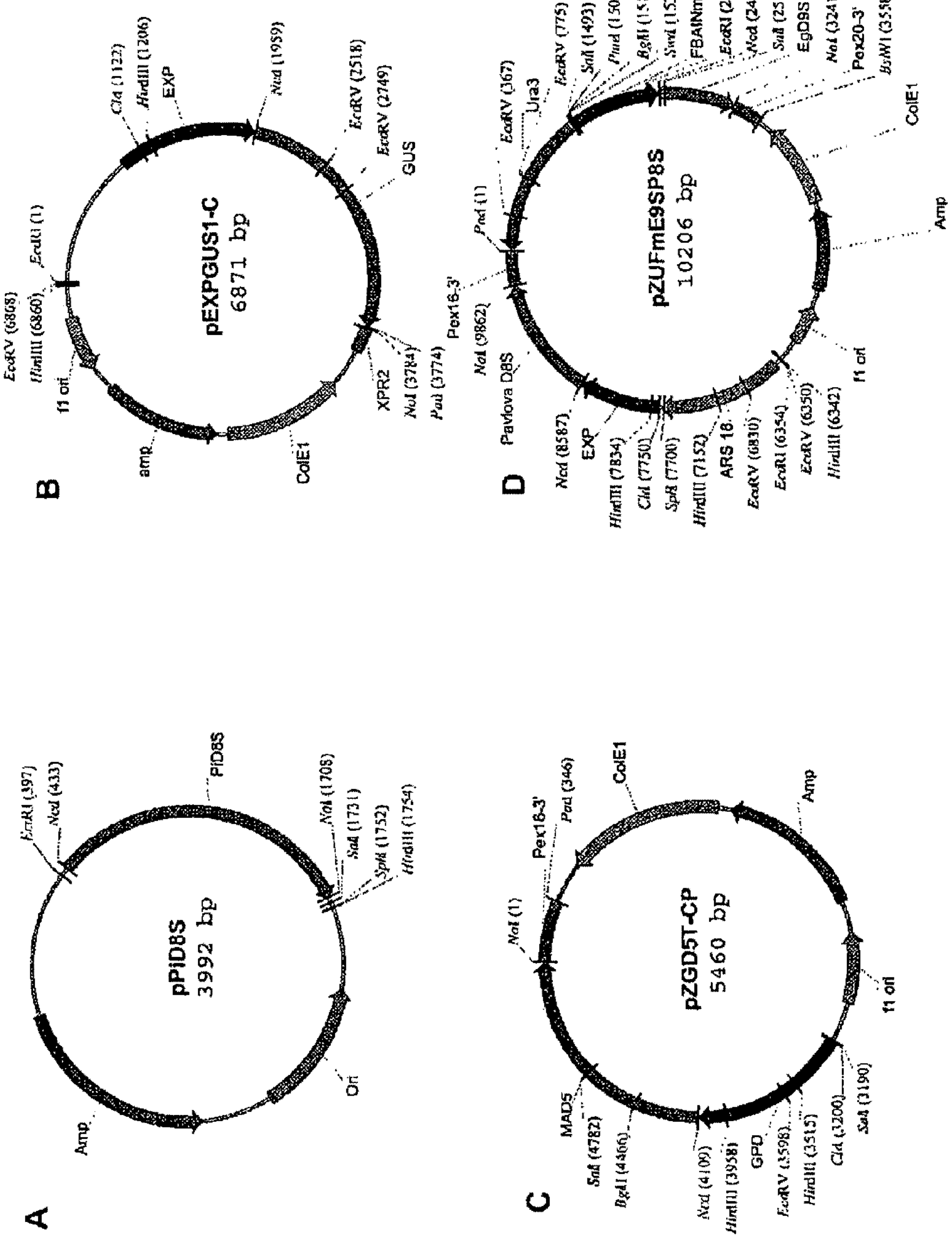
FIG. 11
A
pPlD8S
3992 bp
EcoRI (397)
NcoI (433)
PlD8S
NotI (1708)
SalI (1731)
SphI (1752)
HindIII (1754)
Ori
Amp
B
pEXPGUS1-C
6871 bp
ClaI (1122)
HindIII (1206)
EXP
NcoI (1959)
EcoRV (2518)
EcoRV (2749)
GUS
XPR2
NotI (3784)
PacI (3774)
ColE1
amp
f1 ori
HindIII (6860)
EcoRV (6868)
EcoRI (1)
C
pZGD5T-CP
5460 bp
NotI (1)
Pex16-3'
PacI (346)
ColE1
Amp
f1 ori
SalI (3190)
ClaI (3200)
HindIII (3515)
EcoRV (3598)
GPD
HindIII (3958)
NcoI (4109)
BglII (4366)
SalI (4782)
MAD5
D
pZUFmE9SP8S
10206 bp
PacI (1)
EcoRV (367)
Ura3
EcoRV (775)
SalI (1493)
PmeI (1502)
BglII (1516)
SwaI (1538)
FBAINm
EcoRI (2339)
NcoI (2461)
SalI (2514)
EgD8S
NotI (3241)
Pex20-3'
BsiWI (3558)
ColE1
Amp
f1 ori
HindIII (6342)
EcoRV (6350)
EcoRI (6354)
EcoRV (6830)
ARS 18
HindIII (7152)
SphI (7700)
ClaI (7750)
HindIII (7834)
EXP
NcoI (8587)
Pavlova D8S
NotI (9862)
Pex16-3'

FIG. 13A

```
         10        20        30        40
1    MGKGGDGGAQAVSGTDASL----AEVSSVDSKSVHVVLYG  SEQ ID NO16 (Pavlova lutheri).pro
1    MGRGGDSSGQAHPAAELAVPSDRAEVSNADSKALHIVLYG  SEQ ID NO76 (Pavlova salina).pro
1    MK----S-KRQALP----------------------LTID  SEQ ID NO77 (Euglena gracilis).pro
1    MS----TLDRQSIFTIKELESISQRIHDGDEEAMKFIIID  SEQ ID NO17 (Rhizopus stolonifer).pro
1    MS----TLDRQSIFTIKELESISQRIHDGDEEAMKFIIID  SEQ ID NO2 (Rhizopus stolonifer).pro

         50        60        70        80
37   KRV-DVTKFQKAHPGGSKVFRIFQERDATEQFESYHSPKA  SEQ ID NO16 (Pavlova lutheri).pro
41   KRV-DVTKFQRTHPGGSKVFRIFQDRDATEQFESYHSKRA  SEQ ID NO76 (Pavlova salina).pro
14   GTTYDVSAWVNFHPGGAEIIENYQGRDATDAFMVMHSQEA  SEQ ID NO77 (Euglena gracilis).pro
37   KKVYDVTEFIEDHPGGAQVLLTHVGKDASDVFHAMHPESA  SEQ ID NO17 (Rhizopus stolonifer).pro
37   KKVYDVTEFIEDHPGGAQVLLTHVGKDASDVFHAMHPESA  SEQ ID NO2 (Rhizopus stolonifer).pro

         90        100       110       120
76   IKMMEGMLKKSEDAPASVPLPSRSTMGTEFKEMIERHKRA  SEQ ID NO16 (Pavlova lutheri).pro
80   IKMMEGMLKKSEDAPADTPLPSQSPMGKDFKAMIERHVAA  SEQ ID NO76 (Pavlova salina).pro
54   FDKLKR-MPKINPSSELPPQAAVNEAQEDFRKLREELIAT  SEQ ID NO77 (Euglena gracilis).pro
77   YEVLNNYFVGDVQETVVTEKSSSAQFAVEMRQLRDQLKKE  SEQ ID NO17 (Rhizopus stolonifer).pro
77   YEVLNNYFVGDVQETVVTEKSSSAQFAVEMRQLRDQLKKE  SEQ ID NO2 (Rhizopus stolonifer).pro

         130       140       150       160
116  GLYDPCPLDELFKLTIVLAPIFVGAYLV----RSGV-SPL  SEQ ID NO16 (Pavlova lutheri).pro
120  GYYDPCPLDELFKLSLVLLPTFAGMYML----KAGVGSPL  SEQ ID NO76 (Pavlova salina).pro
93   GMFDASPLWYSYKISTTLGLGVLGYFLMVQYQM-----YF  SEQ ID NO77 (Euglena gracilis).pro
117  GYFHSSKLFYAYKVLSTLAICIAGLSPLYAYGRTSTLAVV  SEQ ID NO17 (Rhizopus stolonifer).pro
117  GYFHSSKLFYAYKVLSTLAICIAGLSLLYAYGRTSTLAVV  SEQ ID NO2 (Rhizopus stolonifer).pro

         170       180       190       200
151  AGALSMGFGFYLDGWLAHDYLHHAVFKGSVNTLVKANNAM  SEQ ID NO16 (Pavlova lutheri).pro
156  CGALMVSFGWYLDGWLAHDYLHHSVFKGSVARTVGWNNAA  SEQ ID NO76 (Pavlova salina).pro
128  IGAVLLGMHYQQMGWLSHDICHHQTFKNR-----NWNNLV  SEQ ID NO77 (Euglena gracilis).pro
157  ASAITVGIFWQQCGWLAHDFGHHQCFEDR-----TWNDVL  SEQ ID NO17 (Rhizopus stolonifer).pro
157  ASAITVGIFWQQCGWLAHDFGHHQCFEDR-----TWNDVL  SEQ ID NO2 (Rhizopus stolonifer).pro

         210       220       230       240
191  GYALG-FLQGYDVAWWRARHNTHHVCTNEDGSDPDIKTAP  SEQ ID NO16 (Pavlova lutheri).pro
196  GYFLG-FVQGYAVEWWRARHNTHHVCTNEDGSDPDIKTAP  SEQ ID NO76 (Pavlova salina).pro
163  GLVFGNGLQGFSVTWWKDRHNAHHSATNVQGHDPDIDNLP  SEQ ID NO77 (Euglena gracilis).pro
192  VVFLGNFCQGFSLSWWKNKHNTHHASTNVHGQDPDIDTAP  SEQ ID NO17 (Rhizopus stolonifer).pro
192  VVFLGNFCQGFSLSWWKNKHNTHHASTNVHGQDPDIDTAP  SEQ ID NO2 (Rhizopus stolonifer).pro
```

FIG. 13B

```
                    250       260       270       280
230  LLIY-----------VRENPSIAKRL---NFFQRWQQYYY   SEQ ID NO16 (Pavlova lutheri).pro
235  LLIY-----------VRNKPSIAKRL---NAFQRYQQYYY   SEQ ID NO76 (Pavlova salina).pro
203  LLAWSE-------DDVTRASPISRKLIQFQ------QYYF   SEQ ID NO77 (Euglena gracilis).pro
232  VLLWDEYASAAYYASLDQEPTMVSRFLAEQVLPHQTRYFF   SEQ ID NO17 (Rhizopus stolonifer).pro
232  VLLWDEYASAAYYASLDQEPTMVSRFLAEQVLPHQTRYFF   SEQ ID NO2 (Rhizopus stolonifer).pro

                    290       300       310       320
256  VPTMAILDLYWRLESIAYVAVR--LPKMWMQAA-------   SEQ ID NO16 (Pavlova lutheri).pro
261  VPVMAILDLYWRLESIAYVAMR--LPKMLPQAL-------   SEQ ID NO76 (Pavlova salina).pro
230  LVICILLRFIWCFQSV---LTVRSL-KDRDNQFYRSQYKK   SEQ ID NO77 (Euglena gracilis).pro
272  FIL-AFARLSWALQSLSYSFKKESINKSRQLNLF------   SEQ ID NO17 (Rhizopus stolonifer).pro
272  FIL-AFARLSWALQSLSYSFKKESINKSRQLNLF------   SEQ ID NO2 (Rhizopus stolonifer).pro

                    330       340       350       360
287  ---------ALAAHYALLCWVFAAHLNLIPLMM--VARGF   SEQ ID NO16 (Pavlova lutheri).pro
292  ---------ALVAHYAIVAWVFAGNYHLLPLVT--VLRGF   SEQ ID NO76 (Pavlova salina).pro
268  EAIGLALHWTLKTLFHLF-FMPSILTSLLVFFVSELVGGF   SEQ ID NO77 (Euglena gracilis).pro
305  ERVCIVGHWALSA-FCIYSWCSNVYHMVLFFLVSQATTGY   SEQ ID NO17 (Rhizopus stolonifer).pro
305  ERVCIVGHWALFA-FCIYSWCSNVYHMVLFFLVSQATTGY   SEQ ID NO2 (Rhizopus stolonifer).pro

                    370       380       390       400
316  ATGIVVFATHYGEDILDREHVEGMTLVEQTAKTSRNITGG   SEQ ID NO16 (Pavlova lutheri).pro
321  GTGITVFATHYGEDILDADQVRHMTLVEQTALTSRNISGG   SEQ ID NO76 (Pavlova salina).pro
305  GIAIVVFMNHYPLEKIGDSVWDGHGFSVGQIHETMNIRRG   SEQ ID NO77 (Euglena gracilis).pro
344  TLALVFALNHNGMPVITEEKAESMEFFEIQVITGRDVTLS   SEQ ID NO17 (Rhizopus stolonifer).pro
344  TLALVFALNHNGMPVITEEKAESMEFFEIQVITGRDVTLS   SEQ ID NO2 (Rhizopus stolonifer).pro

                    410       420       430       440
356  WLVNVLTGFISLQTEHHLFPMMPTGNLMTIQPEVRDFFKK   SEQ ID NO16 (Pavlova lutheri).pro
361  WLVNVLTGFISLQTEHHLFPMMPTGNLMTIQPEVRAFFKK   SEQ ID NO76 (Pavlova salina).pro
345  IITDWFFGGLNYQIEHHLWPTLPRHNLTAVSYQVEQLCQK   SEQ ID NO77 (Euglena gracilis).pro
384  PLGDWFMGGLNYQIEHHVFPNMPRHNLPTVKPMVKSLCQK   SEQ ID NO17 (Rhizopus stolonifer).pro
384  PLGDWFMGGLNYQIEHHVFPNMPRHNLPTVKPMVKSLCQK   SEQ ID NO2 (Rhizopus stolonifer).pro

                    450       460       470
396  HGLEYREGNLFQCVHQNIKALAFEHLLH               SEQ ID NO16 (Pavlova lutheri).pro
401  HGLEYREGNLIECVRQNIRALAFEHLL                SEQ ID NO76 (Pavlova salina).pro
365  HNLPYRNPLPHEGLVILLRYLAVFARMAEKQPAGKAL      SEQ ID NO77 (Euglena gracilis).pro
424  YDINYHDTGFLKGTLEVLQTLDITSKLSL-QLSKKSF      SEQ ID NO17 (Rhizopus stolonifer).pro
424  YDINYHDTGFLKGTLEVLQTLDITSKLSL-QLSKKSF      SEQ ID NO2 (Rhizopus stolonifer).pro
```

FIG. 14

| Event | Embryos Analyzed | Fatty Acid Composition (wt.%) | | | | | | | | | | | | | | | Total delta-8 %Desat |
|---|---|---|---|---|---|---|---|---|---|---|---|---|---|---|---|---|---|
| | | 16:0 | 18:0 | 18:1 | LA | GLA | ALA | EDA | HGLA | ARA | ERA | JUN | ETA | EPA | DPA | Other | |
| 4802-1-7 | 10 | 14.3 | 2.0 | 10.9 | 33.2 | 0.9 | 11.2 | 1.8 | 4.6 | 0.3 | 2.3 | 2.7 | 4.3 | 9.9 | 0.1 | 1.5 | 73.8 |
| 4802-5-1 | 10 | 14.1 | 3.2 | 12.4 | 3.8 | 0.0 | 33.7 | 0.6 | 1.1 | 0.6 | 5.2 | 2.2 | 10.9 | 9.3 | 0.1 | 2.8 | 73.7 |
| 4802-6-1 | 10 | 17.0 | 2.1 | 16.6 | 24.2 | 0.6 | 11.1 | 3.0 | 3.4 | 0.1 | 3.2 | 4.0 | 3.6 | 8.9 | 0.0 | 2.0 | 61.1 |
| 4801-8-1 | 10 | 18.1 | 3.0 | 17.0 | 4.7 | 0.0 | 31.7 | 0.1 | 0.8 | 0.0 | 5.3 | 4.3 | 5.5 | 7.5 | 0.0 | 1.9 | 58.3 |
| 4802-1-1 | 10 | 16.3 | 5.2 | 11.0 | 32.0 | 0.3 | 19.0 | 0.5 | 1.1 | 0.1 | 1.7 | 2.3 | 1.4 | 7.4 | 0.1 | 1.9 | 69.3 |
| 4801-2-11 | 9 | 16.5 | 3.1 | 15.1 | 30.0 | 0.7 | 9.6 | 3.2 | 5.2 | 0.3 | 2.8 | 2.3 | 2.4 | 7.2 | 0.2 | 1.5 | 64.8 |
| 4801-4-9 | 10 | 16.3 | 2.8 | 16.4 | 31.9 | 0.7 | 11.2 | 1.1 | 4.3 | 0.1 | 1.6 | 1.3 | 3.4 | 7.1 | 0.1 | 1.6 | 78.8 |
| 4802-3-14 | 7 | 13.9 | 2.5 | 14.6 | 36.2 | 0.8 | 13.6 | 0.9 | 3.6 | 1.7 | 0.7 | 1.2 | 1.2 | 6.7 | 0.2 | 2.1 | 82.5 |
| 4801-1-9 | 10 | 13.8 | 2.5 | 20.3 | 2.9 | 0.0 | 42.0 | 0.0 | 0.2 | 0.0 | 1.6 | 1.7 | 5.5 | 6.6 | 0.0 | 3.0 | 79.1 |
| 4801-4-2 | 10 | 16.3 | 2.6 | 22.1 | 5.3 | 0.1 | 28.6 | 0.7 | 1.2 | 0.0 | 5.9 | 3.6 | 4.8 | 6.6 | 0.1 | 2.2 | 55.4 |

SEQUENCE LISTING

```
<160> NUMBER OF SEQ ID NOS: 78

<210> SEQ ID NO 1
<211> LENGTH: 19
<212> TYPE: DNA
<213> ORGANISM: Artificial Sequence
<220> FEATURE:
<223> OTHER INFORMATION: T7 primer

<400> SEQUENCE: 1

ggaaacagct atgaccatg                                                   19


<210> SEQ ID NO 2
<211> LENGTH: 459
<212> TYPE: PRT
<213> ORGANISM: Rhizopus stolonifer

<400> SEQUENCE: 2

Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110
```

```
Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Leu Leu
    130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
    210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
            260                 265                 270

Ile Leu Ala Phe Ala Arg Leu Ser Trp Ala Leu Gln Ser Leu Ser Tyr
        275                 280                 285

Ser Phe Lys Lys Glu Ser Ile Asn Lys Ser Arg Gln Leu Asn Leu Phe
    290                 295                 300

Glu Arg Val Cys Ile Val Gly His Trp Ala Leu Phe Ala Phe Cys Ile
305                 310                 315                 320

Tyr Ser Trp Cys Ser Asn Val Tyr His Met Val Leu Phe Phe Leu Val
                325                 330                 335

Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
        355                 360                 365

Phe Phe Glu Ile Gln Val Ile Thr Gly Arg Asp Val Thr Leu Ser Pro
    370                 375                 380

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
        435                 440                 445

Lys Leu Ser Leu Gln Leu Ser Lys Lys Ser Phe
    450                 455
```

```
<210> SEQ ID NO 3
<211> LENGTH: 695
<212> TYPE: DNA
<213> ORGANISM: Pavlova lutherii

<400> SEQUENCE: 3

agggccaagg gtgccaacca ccttccacgt gagactacac accgtaggcc gatgggcaag      60

ggtggagacg gcggcgcgca ggcggtgagc gggaccgacg cgtctctcgc tgaggtgagc     120

tccgtcgata gcaagagcgt gcacgtcgtg ctctacggca agcgcgtgga tgtcacaaag     180
```

```
ttccagggct acgacgtggc ctggtggcgc gcgcgccata acacgcacca cgtgtgcacc    240

aacgaggatg gttcggaccc ggacatcaag acggcgcccc tgctcatcta cgtgcgagag    300

aacccgtcca ttgccaagcg gctcaacttc ttccagcgct ggcagcagta ctactatgtg    360

ccgaccatgg ccatcctcga cctctactgg cgcctggagt ccatcgcgta cgtggctgtg    420

cgcctgccta agatgtggat gcaggccgcc gctcttgccg ctcactacgc gctcctgtgc    480

tgggtcttcg cagcgcatct caacctcatc cctctcatga tggttgcacg cggcttcgcg    540

acgggcatcg ttgtctttgc aacccactat ggtgaggaca tcctcgaccg cgagcacgtc    600

gagggcatga cgctcgtcga gcagaccgcc aagacctccc gtaacatcac gggcggctgg    660

ctagtgaacg tgctcacggg cttcatctcc ctgca                               695
```

<210> SEQ ID NO 4
<211> LENGTH: 1106
<212> TYPE: DNA
<213> ORGANISM: Pavlova lutherii

<400> SEQUENCE: 4

```
agggccaagg gtgccaacca ccttccacgt gagactacac accgtaggcc gatgggcaag     60

ggtggagacg gcggcgcgca ggcggtgagc gggaccgacg cgtctctcgc tgaggtgagc    120

tccgtcgata gcaagagcgt gcacgtcgtg ctctacggca agcgcgtgga tgtcacaaag    180

ttccagggct acgacgtggc ctggtggcgc gcgcgccata acacgcacca cgtgtgcacc    240

aacgaggatg gttcggaccc ggacatcaag acggcgcccc tgctcatcta cgtgcgagag    300

aacccgtcca ttgccaagcg gctcaacttc ttccagcgct ggcagcagta ctactatgtg    360

ccgaccatgg ccatcctcga cctctactgg cgcctggagt ccatcgcgta cgtggctgtg    420

cgcctgccta agatgtggat gcaggccgcc gctcttgccg ctcactacgc gctcctgtgc    480

tgggtcttcg cagcgcatct caacctcatc cctctcatga tggttgcacg cggcttcgcg    540

acgggcatcg ttgtctttgc aacccactat ggtgaggaca tcctcgaccg cgagcacgtc    600

gagggcatga cgctcgtcga gcagaccgcc aagacctccc gtaacatcac gggcggctgg    660

ctagtgaacg tgctcacggg cttcatctcc ctgcagaccg agcatcacct cttccccatg    720

atgcccaccg gcaacctaat gactatccag cccgaggtac gcgacttctt caagaagcat    780

ggcctcgagt accgcgaggg caacctcttc cagtgcgtgc accagaacat caaggctctc    840

gccttcgagc acctcctcca ctgagcgtca ccactcaagc gtcctaagtg cacaggtact    900

gtcttctgac cgatggccgc gcggctccct cggctggcag tggggccaac gagtggcctc    960

gcgggatcgg gcacgatcgg gcctccatga aacttcagtg ttcagagaca agccgacaac   1020

ctccgcatcg tgagaaatct tttaaagcag tatgttccat cacgccgctt ttgcagtcaa   1080

taacattacc caaaaaaaaa aaaaaa                                        1106
```

<210> SEQ ID NO 5
<211> LENGTH: 287
<212> TYPE: PRT
<213> ORGANISM: Pavlova lutherii

<400> SEQUENCE: 5

```
Arg Ala Lys Gly Ala Asn His Leu Pro Arg Glu Thr Thr His Arg Arg
1               5                   10                  15

Pro Met Gly Lys Gly Gly Asp Gly Gly Ala Gln Ala Val Ser Gly Thr
            20                  25                  30

Asp Ala Ser Leu Ala Glu Val Ser Ser Val Asp Ser Lys Ser Val His
```

```
        35                  40                  45

Val Val Leu Tyr Gly Lys Arg Val Asp Val Thr Lys Phe Gln Gly Tyr
    50                  55                  60

Asp Val Ala Trp Trp Arg Ala Arg His Asn Thr His His Val Cys Thr
65                  70                  75                  80

Asn Glu Asp Gly Ser Asp Pro Asp Ile Lys Thr Ala Pro Leu Leu Ile
                85                  90                  95

Tyr Val Arg Glu Asn Pro Ser Ile Ala Lys Arg Leu Asn Phe Phe Gln
            100                 105                 110

Arg Trp Gln Gln Tyr Tyr Tyr Val Pro Thr Met Ala Ile Leu Asp Leu
        115                 120                 125

Tyr Trp Arg Leu Glu Ser Ile Ala Tyr Val Ala Val Arg Leu Pro Lys
    130                 135                 140

Met Trp Met Gln Ala Ala Ala Leu Ala Ala His Tyr Ala Leu Leu Cys
145                 150                 155                 160

Trp Val Phe Ala Ala His Leu Asn Leu Ile Pro Leu Met Met Val Ala
                165                 170                 175

Arg Gly Phe Ala Thr Gly Ile Val Val Phe Ala Thr His Tyr Gly Glu
            180                 185                 190

Asp Ile Leu Asp Arg Glu His Val Glu Gly Met Thr Leu Val Glu Gln
        195                 200                 205

Thr Ala Lys Thr Ser Arg Asn Ile Thr Gly Gly Trp Leu Val Asn Val
    210                 215                 220

Leu Thr Gly Phe Ile Ser Leu Gln Thr Glu His His Leu Phe Pro Met
225                 230                 235                 240

Met Pro Thr Gly Asn Leu Met Thr Ile Gln Pro Glu Val Arg Asp Phe
                245                 250                 255

Phe Lys Lys His Gly Leu Glu Tyr Arg Glu Gly Asn Leu Phe Gln Cys
            260                 265                 270

Val His Gln Asn Ile Lys Ala Leu Ala Phe Glu His Leu Leu His
        275                 280                 285


<210> SEQ ID NO 6
<211> LENGTH: 20
<212> TYPE: DNA
<213> ORGANISM: Artificial Sequence
<220> FEATURE:
<223> OTHER INFORMATION: primer SeqE

<400> SEQUENCE: 6

cgacacactc caatctttcc                                                  20


<210> SEQ ID NO 7
<211> LENGTH: 20
<212> TYPE: DNA
<213> ORGANISM: Artificial Sequence
<220> FEATURE:
<223> OTHER INFORMATION: primer SeqW

<400> SEQUENCE: 7

ggtggctgga gttagacatc                                                  20


<210> SEQ ID NO 8
<211> LENGTH: 457
<212> TYPE: PRT
<213> ORGANISM: Mortierella alpine

<400> SEQUENCE: 8

Met Ala Ala Ala Pro Ser Val Arg Thr Phe Thr Arg Ala Glu Ile Leu
```

-continued

```
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Ala Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Phe Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Met Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Ile Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Gly Val Arg Tyr His Thr Thr Gly Met
            420                 425                 430
```

```
Ile Glu Gly Thr Ala Glu Val Phe Ser Arg Leu Asn Glu Val Ser Lys
        435                 440                 445

Ala Ala Ser Lys Met Gly Lys Ala Gln
    450                 455


<210> SEQ ID NO 9
<211> LENGTH: 22
<212> TYPE: DNA
<213> ORGANISM: Artificial Sequence
<220> FEATURE:
<223> OTHER INFORMATION: primer AP1

<400> SEQUENCE: 9

gtaatacgac tcactatagg gc                                              22


<210> SEQ ID NO 10
<211> LENGTH: 20
<212> TYPE: DNA
<213> ORGANISM: Artificial Sequence
<220> FEATURE:
<223> OTHER INFORMATION: primer GSP PvDES

<400> SEQUENCE: 10

ctgcgaagac ccagcacagg                                                 20


<210> SEQ ID NO 11
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 11

gtaatacgac tcactatagg gc                                              22


<210> SEQ ID NO 12
<211> LENGTH: 21
<212> TYPE: DNA
<213> ORGANISM: Artificial Sequence
<220> FEATURE:
<223> OTHER INFORMATION: primer PavDes seq

<400> SEQUENCE: 12

ttgtggcgct caatcatctc c                                               21


<210> SEQ ID NO 13
<211> LENGTH: 1294
<212> TYPE: DNA
<213> ORGANISM: Pavlova lutherii

<400> SEQUENCE: 13

ctttgcgagc gcggcgcaga cgattgcggc ccgtagtgat cgcggtgcgc attgctgtgt      60

ttctagtttt gctgacgccc ggcccgataa tgacaccttc tcccgtttga aatactaata     120

agtaactata ttataatatt caaaggtggc gactatggat ctccttttct aaagttcagc     180

ggaattggga atcggagaaa tttcgagata tgtcataatc acgtgctcta tctcgaatga     240

accgcggccg gtgagcgatt actcgggaag ccaattccta ttaacgagtc agggggggatc    300

tttgaggtga gtcggccacg cagagagagc aaggaatcat cctcatccgc cgttctcgag     360

aaagagccaa gggtgccaac caccttccac gtgagactac acaccgtagg ccgatgggca     420

agggtggaga cggcggcgcg caggcggcga gcgggaccga cgcatctctc gctgaggtga     480

gctccgtcga tagcaagagc gtgcgcgtcg tgctctacgg caagcgcgtg gatgtcacaa     540
```

```
agttccagag ggcacacccg ggcgggagca aggtgttccg catcttccag gagcgcgacg    600

cgacggagca gttcgagtct taccactcgc ccaaggccat caagatgatg gagggcatgc    660

tcaagaagtc ggaggatgcg cccgcttccg tgcccctgcc ctcgcggtcc accatgggca    720

cggagttcaa ggagatgatt gagcgccaca agagggctgg tctctacgac ccttgcccgt    780

tggacgagct gttcaagctc accatcgtcc ttgcgcccat cttcgtgggc gcctatctcg    840

tgcggagcgg cgtctcgccc ctcgcgggcg cgctctccat gggctttggc ttctacctcg    900

acggctggct tgctcacrac tacctgcatc acgcagtctt caagggctcg gtcaacacgc    960

tcgtcaaggc gaacaacgcc atgggatacg ccctcggctt cctccagggc tacgacgtgg   1020

cctggtggcg cgcgcgccat aacacgcacc acgtgtgcac caacgaggat ggttcggacc   1080

cggacatcaa gacggcgccc ctgctcatct acgtgcgaga gaacccgtcc attgccaagc   1140

ggctcaactt cttccagcgc tggcagcagt actactatgt gccgaccatg gccatcctcg   1200

acctctactg gcgcctggag tccatcgcgt acgtggctgt gcgcctgcct aagatgtgga   1260

tgcaggccgc cgctcttgcc gctcactacg cgct                              1294
```

```
<210> SEQ ID NO 14
<211> LENGTH: 1927
<212> TYPE: DNA
<213> ORGANISM: Pavlova lutherii

<400> SEQUENCE: 14

ctttgcgagc gcggcgcaga cgattgcggc ccgtagtgat cgcggtgcgc attgctgtgt     60

ttctagtttt gctgacgccc ggcccgataa tgacaccttc tcccgtttga aatactaata    120

agtaactata ttataatatt caaaggtggc gactatggat ctccttttct aaagttcagc    180

ggaattggga atcggagaaa tttcgagata tgtcataatc acgtgctcta tctcgaatga    240

accgcggccg gtgagcgatt actcgggaag ccaattccta ttaacgagtc aggggggatc    300

tttgaggtga gtcggccacg cagagagagc aaggaatcat cctcatccgc cgttctcgag    360

aaagagccaa gggtgccaac caccttccac gtgagactac acaccgtagg ccgatgggca    420

agggtggaga cggcggcgcg caggcggtga gcgggaccga cgcgtctctc gctgaggtga    480

gctccgtcga tagcaagagc gtgcacgtcg tgctctacgg caagcgcgtg gatgtcacaa    540

agttccagaa ggcacacccg ggcgggagca aggtgttccg catcttccag gagcgcgacg    600

cgacggagca gttcgagtct taccactcgc ccaaggccat caagatgatg gagggcatgc    660

tcaagaagtc ggaggatgcg cccgcttccg tgcccctgcc ctcgcggtcc accatgggca    720

cggagttcaa ggagatgatt gagcgccaca agagggctgg tctctacgac ccttgcccgt    780

tggacgagct gttcaagctc accatcgtcc ttgcgcccat cttcgtgggc gcctatctcg    840

tgcggagcgg cgtctcgccc ctcgcgggcg cgctctccat gggctttggc ttctacctcg    900

acggctggct tgctcacgac tacctgcatc acgcagtctt caagggctcg gtcaacacgc    960

tcgtcaaggc gaacaacgcc atgggatacg ccctcggctt cctccagggc tacgacgtgg   1020

cctggtggcg cgcgcgccat aacacgcacc acgtgtgcac caacgaggat ggttcggacc   1080

cggacatcaa gacggcgccc ctgctcatct acgtgcgaga gaacccgtcc attgccaagc   1140

ggctcaactt cttccagcgc tggcagcagt actactatgt gccgaccatg gccatcctcg   1200

acctctactg gcgcctggag tccatcgcgt acgtggctgt gcgcctgcct aagatgtgga   1260

tgcaggccgc cgctcttgcc gctcactacg cgctcctgtg ctgggtcttc gcagcgcatc   1320

tcaacctcat ccctctcatg atggttgcac gcggcttcgc gacgggcatc gttgtctttg   1380
```

```
caacccacta tggtgaggac atcctcgacc gcgagcacgt cgagggcatg acgctcgtcg   1440

agcagaccgc caagacctcc cgtaacatca cgggcggctg gctagtgaac gtgctcacgg   1500

gcttcatctc cctgcagacc gagcatcacc tcttccccat gatgcccacc ggcaacctaa   1560

tgactatcca gcccgaggta cgcgacttct tcaagaagca tggcctcgag taccgcgagg   1620

gcaacctctt ccagtgcgtg caccagaaca tcaaggctct cgccttcgag cacctcctcc   1680

actgagcgtc accactcaag cgtcctaagt gcacaggtac tgtcttctga ccgatggccg   1740

cgcggctccc tcggctggca gtggggccaa cgagtggcct cgcgggatcg ggcacgatcg   1800

ggcctccatg aaacttcagt gttcagagac aagccgacaa cctccgcatc gtgagaaatc   1860

ttttaaagca gtatgttcca tcacgccgct tttgcagtca ataacattac ccaaaaaaaa   1920

aaaaaaa                                                             1927
```

<210> SEQ ID NO 15

<400> SEQUENCE: 15

000

<210> SEQ ID NO 16
<211> LENGTH: 423
<212> TYPE: PRT
<213> ORGANISM: Pavlova lutherii

<400> SEQUENCE: 16

```
Met Gly Lys Gly Gly Asp Gly Gly Ala Gln Ala Val Ser Gly Thr Asp
1               5                   10                  15

Ala Ser Leu Ala Glu Val Ser Ser Val Asp Ser Lys Ser Val His Val
            20                  25                  30

Val Leu Tyr Gly Lys Arg Val Asp Val Thr Lys Phe Gln Lys Ala His
        35                  40                  45

Pro Gly Gly Ser Lys Val Phe Arg Ile Phe Gln Glu Arg Asp Ala Thr
    50                  55                  60

Glu Gln Phe Glu Ser Tyr His Ser Pro Lys Ala Ile Lys Met Met Glu
65                  70                  75                  80

Gly Met Leu Lys Lys Ser Glu Asp Ala Pro Ala Ser Val Pro Leu Pro
                85                  90                  95

Ser Arg Ser Thr Met Gly Thr Glu Phe Lys Glu Met Ile Glu Arg His
            100                 105                 110

Lys Arg Ala Gly Leu Tyr Asp Pro Cys Pro Leu Asp Glu Leu Phe Lys
        115                 120                 125

Leu Thr Ile Val Leu Ala Pro Ile Phe Val Gly Ala Tyr Leu Val Arg
    130                 135                 140

Ser Gly Val Ser Pro Leu Ala Gly Ala Leu Ser Met Gly Phe Gly Phe
145                 150                 155                 160

Tyr Leu Asp Gly Trp Leu Ala His Asp Tyr Leu His His Ala Val Phe
                165                 170                 175

Lys Gly Ser Val Asn Thr Leu Val Lys Ala Asn Asn Ala Met Gly Tyr
            180                 185                 190

Ala Leu Gly Phe Leu Gln Gly Tyr Asp Val Ala Trp Trp Arg Ala Arg
        195                 200                 205

His Asn Thr His His Val Cys Thr Asn Glu Asp Gly Ser Asp Pro Asp
    210                 215                 220

Ile Lys Thr Ala Pro Leu Leu Ile Tyr Val Arg Glu Asn Pro Ser Ile
225                 230                 235                 240
```

```
Ala Lys Arg Leu Asn Phe Phe Gln Arg Trp Gln Gln Tyr Tyr Tyr Val
                245                 250                 255

Pro Thr Met Ala Ile Leu Asp Leu Tyr Trp Arg Leu Glu Ser Ile Ala
            260                 265                 270

Tyr Val Ala Val Arg Leu Pro Lys Met Trp Met Gln Ala Ala Ala Leu
        275                 280                 285

Ala Ala His Tyr Ala Leu Leu Cys Trp Val Phe Ala Ala His Leu Asn
    290                 295                 300

Leu Ile Pro Leu Met Met Val Ala Arg Gly Phe Ala Thr Gly Ile Val
305                 310                 315                 320

Val Phe Ala Thr His Tyr Gly Glu Asp Ile Leu Asp Arg Glu His Val
                325                 330                 335

Glu Gly Met Thr Leu Val Glu Gln Thr Ala Lys Thr Ser Arg Asn Ile
            340                 345                 350

Thr Gly Gly Trp Leu Val Asn Val Leu Thr Gly Phe Ile Ser Leu Gln
        355                 360                 365

Thr Glu His His Leu Phe Pro Met Met Pro Thr Gly Asn Leu Met Thr
    370                 375                 380

Ile Gln Pro Glu Val Arg Asp Phe Phe Lys Lys His Gly Leu Glu Tyr
385                 390                 395                 400

Arg Glu Gly Asn Leu Phe Gln Cys Val His Gln Asn Ile Lys Ala Leu
                405                 410                 415

Ala Phe Glu His Leu Leu His
            420


<210> SEQ ID NO 17
<211> LENGTH: 459
<212> TYPE: PRT
<213> ORGANISM: Rhizopus stolonifer

<400> SEQUENCE: 17

Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Pro Leu
    130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190
```

```
Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
    210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
            260                 265                 270

Ile Leu Ala Phe Ala Arg Leu Ser Trp Ala Leu Gln Ser Leu Ser Tyr
        275                 280                 285

Ser Phe Lys Lys Glu Ser Ile Asn Lys Ser Arg Gln Leu Asn Leu Phe
    290                 295                 300

Glu Arg Val Cys Ile Val Gly His Trp Ala Leu Ser Ala Phe Cys Ile
305                 310                 315                 320

Tyr Ser Trp Cys Ser Asn Val Tyr His Met Val Leu Phe Phe Leu Val
                325                 330                 335

Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
        355                 360                 365

Phe Phe Glu Ile Gln Val Ile Thr Gly Arg Asp Val Thr Leu Ser Pro
    370                 375                 380

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
        435                 440                 445

Lys Leu Ser Leu Gln Leu Ser Lys Lys Ser Phe
    450                 455
```

<210> SEQ ID NO 18
<211> LENGTH: 30
<212> TYPE: DNA
<213> ORGANISM: Artificial Sequence
<220> FEATURE:
<223> OTHER INFORMATION: primer PvDES5'Not-1

<400> SEQUENCE: 18
gcggccgcac catgggcaag ggtggagacg 30

<210> SEQ ID NO 19
<211> LENGTH: 27
<212> TYPE: DNA
<213> ORGANISM: Artificial Sequence
<220> FEATURE:
<223> OTHER INFORMATION: primer PvDES3'Not-1

<400> SEQUENCE: 19
gcggccgctc agtggaggag gtgctcg 27

<210> SEQ ID NO 20
<211> LENGTH: 20
<212> TYPE: DNA
<213> ORGANISM: Artificial Sequence
<220> FEATURE:
<223> OTHER INFORMATION: primer GSP PvDES-2

<400> SEQUENCE: 20
gcatccacat cttaggcagg 20

<210> SEQ ID NO 21
<211> LENGTH: 8801
<212> TYPE: DNA
<213> ORGANISM: Artificial Sequence
<220> FEATURE:
<223> OTHER INFORMATION: plasmid pY121

<400> SEQUENCE: 21
ggccgcaggg cggatccccc gggctgcagg aattcgatat caagcttatc gataccgtcg 60
acctcgaggg ggggcccggt acccaattcg ccctatagtg agtcgtatta cgcgcgctca 120
ctggccgtcg ttttacaacg tcgtgactgg gaaaaccctg gcgttaccca acttaatcgc 180
cttgcagcac atcccccttt cgccagctgg cgtaatagcg aagaggcccg caccgatcgc 240
ccttcccaac agttgcgcag cctgaatggc gaatggcgcg acgcgccctg tagcggcgca 300
ttaagcgcgg cgggtgtggt ggttacgcgc agcgtgaccg ctacacttgc cagcgcccta 360
gcgcccgctc ctttcgcttt cttcccttcc tttctcgcca cgttcgccgg ctttccccgt 420
caagctctaa atcgggggct ccctttaggg ttccgattta gtgctttacg gcacctcgac 480
cccaaaaaac ttgattaggg tgatggttca cgtagtgggc catcgccctg atagacggtt 540
tttcgccctt tgacgttgga gtccacgttc tttaatagtg gactcttgtt ccaaactgga 600
acaacactca accctatctc ggtctattct tttgatttat aagggatttt gccgatttcg 660
gcctattggt taaaaaatga gctgatttaa caaaaattta acgcgaattt taacaaaata 720
ttaacgttta caatttcctg atgcggtatt ttctccttac gcatctgtgc ggtatttcac 780
accgcatatc gacggtcgag gagaacttct agtatatcca catacctaat attattgcct 840
tattaaaaat ggaatcccaa caattacatc aaaatccaca ttctcttcaa aatcaattgt 900
cctgtacttc cttgttcatg tgtgttcaaa aacgttatat ttataggata attatactct 960
atttctcaac aagtaattgg ttgtttggcc gagcggtcta aggcgcctga ttcaagaaat 1020
atcttgaccg cagttaactg tgggaatact caggtatcgt aagatgcaag agttcgaatc 1080
tcttagcaac cattattttt ttcctcaaca taacgagaac acacaggggc gctatcgcac 1140
agaatcaaat tcgatgactg gaaatttttt gttaatttca gaggtcgcct gacgcatata 1200
cctttttcaa ctgaaaaatt gggagaaaaa ggaaaggtga gaggccggaa ccggcttttc 1260
atatagaata gagaagcgtt catgactaaa tgcttgcatc acaatacttg aagttgacaa 1320
tattatttaa ggacctattg ttttttccaa taggtggtta gcaatcgtct tactttctaa 1380
cttttcttac cttttacatt tcagcaatat atatatatat ttcaaggata taccattcta 1440
atgtctgccc ctatgtctgc ccctaagaag atcgtcgttt tgccaggtga ccacgttggt 1500
caagaaatca cagccgaagc cattaaggtt cttaaagcta tttctgatgt tcgttccaat 1560
gtcaagttcg atttcgaaaa tcatttaatt ggtggtgctg ctatcgatgc tacaggtgtc 1620
ccacttccag atgaggcgct ggaagcctcc aagaaggttg atgccgtttt gttaggtgct 1680
gtggctggtc ctaaatgggg taccggtagt gttagacctg aacaaggttt actaaaaatc 1740
cgtaaagaac ttcaattgta cgccaactta agaccatgta actttgcatc cgactctctt 1800
ttagacttat ctccaatcaa gccacaattt gctaaaggta ctgacttcgt tgttgtcaga 1860
gaattagtgg gaggtattta ctttggtaag agaaaggaag acgatggtga tggtgtcgct 1920
tgggatagtg aacaatacac cgttccagaa gtgcaaagaa tcacaagaat ggccgctttc 1980
atggccctac aacatgagcc accattgcct atttggtcct tggataaagc taatcttttg 2040
gcctcttcaa gattatggag aaaaactgtg gaggaaacca tcaagaacga attccctaca 2100
ttgaaggttc aacatcaatt gattgattct gccgccatga tcctagttaa gaacccaacc 2160
cacctaaatg gtattataat caccagcaac atgtttggtg atatcatctc cgatgaagcc 2220
tccgttatcc caggttcctt gggtttgttg ccatctgcgt ccttggcctc tttgccagac 2280
aagaacaccg catttggttt gtacgaacca tgccacggtt ctgctccaga tttgccaaag 2340
aataaggttg accctatcgc cactatcttg tctgctgcaa tgatgttgaa attgtcattg 2400
aacttgcctg aagaaggtaa ggccattgaa gatgcagtta aaaaggtttt ggatgcaggt 2460
atcagaactg gtgatttagg tggttccaac agtaccaccg aagtcggtga tgctgtcgcc 2520
gaagaagtta agaaaatcct tgcttaaaaa gattctcttt ttttatgata tttgtacata 2580
aactttataa atgaaattca taatagaaac gacacgaaat tacaaaatgg aatatgttca 2640
tagggtagac gaaactatat acgcaatcta catacattta tcaagaagga gaaaaaggag 2700
gatagtaaag gaatacaggt aagcaaattg atactaatgg ctcaacgtga taaggaaaaa 2760
gaattgcact ttaacattaa tattgacaag gaggagggca ccacacaaaa agttaggtgt 2820
aacagaaaat catgaaacta cgattcctaa tttgatattg gaggattttc tctaaaaaaa 2880
aaaaaataca acaaataaaa aacactcaat gacctgacca tttgatggag tttaagtcaa 2940
taccttcttg aagcatttcc cataatggtg aaagttccct caagaatttt actctgtcag 3000
aaacggcctt acgacgtagt cgatatggtg cactctcagt acaatctgct ctgatgccgc 3060
atagttaagc cagccccgac acccgccaac acccgctgac gcgccctgac gggcttgtct 3120
gctcccggca tccgcttaca gacaagctgt gaccgtctcc gggagctgca tgtgtcagag 3180
gttttcaccg tcatcaccga aacgcgcgag acgaaagggc ctcgtgatac gcctattttt 3240
ataggttaat gtcatgataa taatggtttc ttagtatgat ccaatatcaa aggaaatgat 3300
agcattgaag gatgagacta atccaattga ggagtggcag catatagaac agctaaaggg 3360
tagtgctgaa ggaagcatac gataccccgc atggaatggg ataatatcac aggaggtact 3420
agactacctt tcatcctaca taaatagacg catataagta cgcatttaag cataaacacg 3480
cactatgccg ttcttctcat gtatatatat atacaggcaa cacgcagata taggtgcgac 3540
gtgaacagtg agctgtatgt gcgcagctcg cgttgcattt tcggaagcgc tcgttttcgg 3600
aaacgctttg aagttcctat tccgaagttc ctattctcta gaaagtatag gaacttcaga 3660
gcgcttttga aaaccaaaag cgctctgaag acgcactttc aaaaaaccaa aaacgcaccg 3720
gactgtaacg agctactaaa atattgcgaa taccgcttcc acaaacattg ctcaaaagta 3780
tctctttgct atatatctct gtgctatatc cctatataac ctacccatcc acctttcgct 3840
ccttgaactt gcatctaaac tcgacctcta catttttat gtttatctct agtattactc 3900
tttagacaaa aaaattgtag taagaactat tcatagagtg aatcgaaaac aatacgaaaa 3960
tgtaaacatt tcctatacgt agtatataga gacaaaatag aagaaaccgt tcataatttt 4020
ctgaccaatg aagaatcatc aacgctatca ctttctgttc acaaagtatg cgcaatccac 4080
atcggtatag aatataatcg gggatgcctt tatcttgaaa aaatgcaccc gcagcttcgc 4140
tagtaatcag taaacgcggg aagtggagtc aggcttttt tatggaagag aaaatagaca 4200
ccaaagtagc cttcttctaa ccttaacgga cctacagtgc aaaaagttat caagagactg 4260
cattatagag cgcacaaagg agaaaaaaag taatctaaga tgctttgtta gaaaaatagc 4320

```
gctctcggga tgcatttttg tagaacaaaa aagaagtata gattctttgt tggtaaaata   4380
gcgctctcgc gttgcatttc tgttctgtaa aaatgcagct cagattcttt gtttgaaaaa   4440
ttagcgctct cgcgttgcat ttttgtttta caaaaatgaa gcacagattc ttcgttggta   4500
aaatagcgct ttcgcgttgc atttctgttc tgtaaaaatg cagctcagat tctttgtttg   4560
aaaaattagc gctctcgcgt tgcatttttg ttctacaaaa tgaagcacag atgcttcgtt   4620
caggtggcac ttttcgggga aatgtgcgcg gaacccctat ttgtttattt ttctaaatac   4680
attcaaatat gtatccgctc atgagacaat aaccctgata aatgcttcaa taatattgaa   4740
aaaggaagag tatgagtatt caacatttcc gtgtcgccct tattcccttt tttgcggcat   4800
tttgccttcc tgtttttgct cacccagaaa cgctggtgaa agtaaaagat gctgaagatc   4860
agttgggtgc acgagtgggt tacatcgaac tggatctcaa cagcggtaag atccttgaga   4920
gttttcgccc cgaagaacgt tttccaatga tgagcacttt taaagttctg ctatgtggcg   4980
cggtattatc ccgtattgac gccgggcaag agcaactcgg tcgccgcata cactattctc   5040
agaatgactt ggttgagtac tcaccagtca cagaaaagca tcttacggat ggcatgacag   5100
taagagaatt atgcagtgct gccataacca tgagtgataa cactgcggcc aacttacttc   5160
tgacaacgat cggaggaccg aaggagctaa ccgctttttt gcacaacatg ggggatcatg   5220
taactcgcct tgatcgttgg gaaccggagc tgaatgaagc cataccaaac gacgagcgtg   5280
acaccacgat gcctgtagca atggcaacaa cgttgcgcaa actattaact ggcgaactac   5340
ttactctagc ttcccggcaa caattaatag actggatgga ggcggataaa gttgcaggac   5400
cacttctgcg ctcggccctt ccggctggct ggtttattgc tgataaatct ggagccggtg   5460
agcgtgggtc tcgcggtatc attgcagcac tggggccaga tggtaagccc tcccgtatcg   5520
tagttatcta cacgacgggg agtcaggcaa ctatggatga acgaaataga cagatcgctg   5580
agataggtgc ctcactgatt aagcattggt aactgtcaga ccaagtttac tcatatatac   5640
tttagattga tttaaaactt catttttaat ttaaaaggat ctaggtgaag atcctttttg   5700
ataatctcat gaccaaaatc ccttaacgtg agttttcgtt ccactgagcg tcagaccccg   5760
tagaaaagat caaaggatct tcttgagatc cttttttct gcgcgtaatc tgctgcttgc   5820
aaacaaaaaa accaccgcta ccagcggtgg tttgtttgcc ggatcaagag ctaccaactc   5880
tttttccgaa ggtaactggc ttcagcagag cgcagatacc aaatactgtc cttctagtgt   5940
agccgtagtt aggccaccac ttcaagaact ctgtagcacc gcctacatac ctcgctctgc   6000
taatcctgtt accagtggct gctgccagtg gcgataagtc gtgtcttacc gggttggact   6060
caagacgata gttaccggat aaggcgcagc ggtcgggctg aacggggggt tcgtgcacac   6120
agcccagctt ggagcgaacg acctacaccg aactgagata cctacagcgt gagctatgag   6180
aaagcgccac gcttcccgaa gggagaaagg cggacaggta tccggtaagc ggcagggtcg   6240
gaacaggaga gcgcacgagg gagcttccag ggggaaacgc ctggtatctt tatagtcctg   6300
tcgggtttcg ccacctctga cttgagcgtc gatttttgtg atgctcgtca ggggggcgga   6360
gcctatggaa aaacgccagc aacgcggcct ttttacggtt cctggccttt tgctggcctt   6420
ttgctcacat gttctttcct gcgttatccc ctgattctgt ggataaccgt attaccgcct   6480
ttgagtgagc tgataccgct cgccgcagcc gaacgaccga gcgcagcgag tcagtgagcg   6540
aggaagcgga agagcgccca atacgcaaac cgcctctccc cgcgcgttgg ccgattcatt   6600
aatgcagctg gcacgacagg tttcccgact ggaaagcggg cagtgagcgc aacgcaatta   6660
atgtgagtta cctcactcat taggcacccc aggctttaca ctttatgctt ccggctccta   6720
```

```
tgttgtgtgg aattgtgagc ggataacaat ttcacacagg aaacagctat gaccatgatt   6780

acgccaagcg cgcaattaac cctcactaaa gggaacaaaa gctggagctc caccgcggga   6840

tttcgaaact aagttcttgg tgttttaaaa ctaaaaaaaa gactaactat aaaagtagaa   6900

tttaagaagt ttaagaaata gatttacaga attacaatca atacctaccg tctttatata   6960

cttattagtc aagtagggga ataatttcag ggaactggtt tcaacctttt ttttcagctt   7020

tttccaaatc agagagagca gaaggtaata gaaggtgtaa gaaaatgaga tagatacatg   7080

cgtgggtcaa ttgccttgtg tcatcattta ctccaggcag gttgcatcac tccattgagg   7140

ttgtgcccgt tttttgcctg tttgtgcccc tgttctctgt agttgcgcta agagaatgga   7200

cctatgaact gatggttggt gaagaaaaca atattttggt gctgggattc tttttttttc   7260

tggatgccag cttaaaaagc gggctccatt atatttagtg gatgccagga ataaactgtt   7320

cacccagaca cctacgatgt tatatattct gtgtaacccg cccccctattt tgggcatgta   7380

cgggttacag cagaattaaa aggctaattt tttgactaaa taaagttagg aaaatcacta   7440

ctattaatta tttacgtatt ctttgaaatg gcagtattga taatgataaa ctcgaaatca   7500

ctagtggatc cgcccagcgg ccgcaccatg ggcaagggtg gagacggcgg cgcgcaggcg   7560

gtgagcggga ccgacgcgtc tctcgctgag gtgagctccg tcgatagcaa gagcgtgcac   7620

gtcgtgctct acggcaagcg cgtggatgtc acaaagttcc agaaggcaca cccgggcggg   7680

agcaaggtgt tccgcatctt ccaggagcgc gacgcgacgg agcagttcga gtcttaccac   7740

tcgcccaagg ccatcaagat gatggagggc atgctcaaga agtcggagga tgcgcccgct   7800

tccgtgcccc tgccctcgcg gtccaccatg ggcacggagt tcaaggagat gattgagcgc   7860

cacaagaggg ctggtctcta cgacccttgc ccgttggacg agctgttcaa gctcaccatc   7920

gtccttgcgc ccatcttcgt gggcgcctat ctcgtgcgga gcggcgtctc gcccctcgcg   7980

ggcgcgctct ccatgggctt tggcttctac ctcgacggct ggcttgctca cgactacctg   8040

catcacgcag tcttcaaggg ctcggtcaac acgctcgtca aggcgaacaa cgccatggga   8100

tacgccctcg gcttcctcca gggctacgac gtggcctggt ggcgcgcgcg ccataacacg   8160

caccacgtgt gcaccaacga ggatggttcg gacccggaca tcaagacggc gcccctgctc   8220

atctacgtgc gagagaaccc gtccattgcc aagcggctca acttcttcca gcgctggcag   8280

cagtactact atgtgccgac catggccatc ctcgacctct actggcgcct ggagtccatc   8340

gcgtacgtgg ctgtgcgcct gcctaagatg tggatgcagg ccgccgctct tgccgctcac   8400

tacgcgctcc tgtgctgggt cttcgcagcg catctcaacc tcatccctct catgatggtt   8460

gcacgcggct tcgcgacggg catcgttgtc tttgcaaccc actatggtga ggacatcctc   8520

gaccgcgagc acgtcgaggg catgacgctc gtcgagcaga ccgccaagac ctcccgtaac   8580

atcacgggcg gctggctagt gaacgtgctc acgggcttca tctccctgca gaccgagcat   8640

cacctcttcc ccatgatgcc caccggcaac ctaatgacta tccagcccga ggtacgcgac   8700

ttcttcaaga agcatggcct cgagtaccgc gagggcaacc tcttccagtg cgtgcaccag   8760

aacatcaagg ctctcgcctt cgagcacctc ctccactgag c                        8801
```

```
<210> SEQ ID NO 22
<211> LENGTH: 4993
<212> TYPE: DNA
<213> ORGANISM: Artificial Sequence
<220> FEATURE:
<223> OTHER INFORMATION: plasmid pKR123r
<220> FEATURE:
<221> NAME/KEY: misc_feature
```

<222> LOCATION: (1126)..(1126)
<223> OTHER INFORMATION: n is a, c, g, or t

<400> SEQUENCE: 22

```
ctagacctgc aggatataat gagccgtaaa caaagatgat taagtagtaa ttaatacgta     60
ctagtaaaag tggcaaaaga taacgagaaa gaaccaattt ctttgcattc ggccttagcg    120
gaaggcatat ataagctttg attattttat ttagtgtaat gatttcgtac aaccaaagca    180
tttatttagt actctcacac ttgtgtcgcg gccgcttggg gggctatgga agactttctt    240
agttagttgt gtgaataagc aatgttggga gaatcgggac tacttatagg ataggaataa    300
aacagaaaag tattaagtgc taatgaaata tttagactga taattaaaat cttcacgtat    360
gtccacttga tataaaaacg tcaggaataa aggaagtaca gtagaattta aaggtactct    420
ttttatatat acccgtgttc tctttttggc tagctagttg cataaaaaat aatctatatt    480
tttatcatta ttttaaatat cttatgagat ggtaaatatt tatcataatt tttttacta    540
ttatttatta tttgtgtgtg taatacatat agaagttaat tacaaatttt atttactttt    600
tcattatttt gatatgattc accattaatt tagtgttatt atttataata gttcatttta    660
atctttttgt atatattatg cgtgcagtac tttttttccta catataacta ctattacatt    720
ttatttatat aatattttta ttaatgaatt ttcgtgataa tatgtaatat tgttcattat    780
tatttcagat tttttaaaaa tatttgtgtt attatttatg aaatatgtaa ttttttttagt    840
atttgatttt atgatgataa agtgttctaa attcaaaaga agggggaaag cgtaaacatt    900
aaaaaacgtc atcaaacaaa aacaaaatct tgttaataaa gataaaactg tttgttttga    960
tcactgttat ttcgtaatat aaaaacatta tttatattta tattgttgac aaccaaattt   1020
gcctatcaaa tctaaccaat ataatgcatg cgtggcaggt aatgtactac catgaactta   1080
agtcatgaca taataaaccg tgaatctgac caatgcatgt acctanctaa attgtatttg   1140
tgacacgaag caaatgattc aattcacaat ggagatggga aacaaataat gaagaaccca   1200
gaactaagaa agcttttctg aaaaataaaa taaaggcaat gtcaaaagta tactgcatca   1260
tcagtccaga aagcacatga tattttttta tcagtatcaa tgcagctagt tttattttac   1320
aatatcgata tagctagttt aaatatattg cagctagatt tataaatatt tgtgttatta   1380
tttatcattt gtgtaatcct gtttttagta ttttagttta tatatgatga taatgtattc   1440
caaatttaaa agaagggaaa taaatttaaa caagaaaaaa agtcatcaaa caaaaaaacaa   1500
atgaaagggt ggaaagatgt taccatgtaa tgtgaatgtt acagtatttc ttttattata   1560
gagttaacaa attaactaat atgattttgt taataatgat aaaatatttt ttttattatt   1620
atttcataat ataaaaatag tttacttaat ataaaaaaaa ttctatcgtt cacaacaaag   1680
ttggccacct aatttaacca tgcatgtacc catggaccat attaggtaac catcaaacct   1740
gatgaagaga taaagagatg aagacttaag tcataacaca aaaccataaa aaacaaaaat   1800
acaatcaacc gtcaatctga ccaatgcatg aaaaagctgc aatagtgagt ggcgacacaa   1860
agcacatgat tttcttacaa cggagataaa accaaaaaaa tatttcatga acaacctaga   1920
acaaataaag cttttatata ataaatatat aaataaataa aggctatgga ataatatact   1980
tcaatatatt tggattaaat aaattgttgg cggggttgat atatttatac acacctaaag   2040
tcacttcaat ctcattttca cttaactttt attttttttt tctttttatt tatcataaag   2100
agaatattga taatatactt tttaacatat ttttatgaca ttttttattg gtgaaaactt   2160
attaaaaatc ataaattttg taagttagat ttatttaaag agttcctctt cttattttaa   2220
attttttaat aaatttttaa ataactaaaa tttgtgttaa aaatgttaaa aaatgtgtta   2280
```

```
ttaacccttc tcttcgagga cgtacgtcta gagtcgacct gcaggcatgc aagcttggcg   2340

taatcatggt catagctgtt tcctgtgtga aattgttatc cgctcacaat tccacacaac   2400

atacgagccg gaagcataaa gtgtaaagcc tggggtgcct aatgagtgag ctaactcaca   2460

ttaattgcgt tgcgctcact gcccgctttc cagtcgggaa acctgtcgtg ccagctgcat   2520

taatgaatcg gccaacgcgc ggggagaggc ggtttgcgta ttgggcgctc ttccgcttcc   2580

tcgctcactg actcgctgcg ctcggtcgtt cggctgcggc gagcggtatc agctcactca   2640

aaggcggtaa tacggttatc cacagaatca ggggataacg caggaaagaa catgtgagca   2700

aaaggccagc aaaaggccag gaaccgtaaa aaggccgcgt tgctggcgtt tttccatagg   2760

ctccgccccc ctgacgagca tcacaaaaat cgacgctcaa gtcagaggtg gcgaaacccg   2820

acaggactat aaagatacca ggcgtttccc cctggaagct ccctcgtgcg ctctcctgtt   2880

ccgaccctgc cgcttaccgg atacctgtcc gcctttctcc cttcgggaag cgtggcgctt   2940

tctcatagct cacgctgtag gtatctcagt tcggtgtagg tcgttcgctc caagctgggc   3000

tgtgtgcacg aaccccccgt tcagcccgac cgctgcgcct tatccggtaa ctatcgtctt   3060

gagtccaacc cggtaagaca cgacttatcg ccactggcag cagccactgg taacaggatt   3120

agcagagcga ggtatgtagg cggtgctaca gagttcttga agtggtggcc taactacggc   3180

tacactagaa ggacagtatt tggtatctgc gctctgctga agccagttac cttcggaaaa   3240

agagttggta gctcttgatc cggcaaacaa accaccgctg gtagcggtgg tttttttgtt   3300

tgcaagcagc agattacgcg cagaaaaaaa ggatctcaag aagatccttt gatcttttct   3360

acggggtctg acgctcagtg gaacgaaaac tcacgttaag ggattttggt catgagatta   3420

tcaaaaagga tcttcaccta gatcctttta aattaaaaat gaagttttaa atcaatctaa   3480

agtatatatg agtaaacttg gtctgacagt taccaatgct taatcagtga ggcacctatc   3540

tcagcgatct gtctatttcg ttcatccata gttgcctgac tccccgtcgt gtagataact   3600

acgatacggg agggcttacc atctggcccc agtgctgcaa tgataccgcg agacccacgc   3660

tcaccggctc cagatttatc agcaataaac cagccagccg gaagggccga gcgcagaagt   3720

ggtcctgcaa ctttatccgc ctccatccag tctattaatt gttgccggga agctagagta   3780

agtagttcgc cagttaatag tttgcgcaac gttgttgcca ttgctacagg catcgtggtg   3840

tcacgctcgt cgtttggtat ggcttcattc agctccggtt cccaacgatc aaggcgagtt   3900

acatgatccc ccatgttgtg caaaaaagcg gttagctcct tcggtcctcc gatcgttgtc   3960

agaagtaagt tggccgcagt gttatcactc atggttatgg cagcactgca taattctctt   4020

actgtcatgc catccgtaag atgcttttct gtgactggtg agtactcaac caagtcattc   4080

tgagaatagt gtatgcggcg accgagttgc tcttgcccgg cgtcaatacg ggataatacc   4140

gcgccacata gcagaacttt aaaagtgctc atcattggaa aacgttcttc ggggcgaaaa   4200

ctctcaagga tcttaccgct gttgagatcc agttcgatgt aacccactcg tgcacccaac   4260

tgatcttcag catcttttac tttcaccagc gtttctgggt gagcaaaaac aggaaggcaa   4320

aatgccgcaa aaaagggaat aagggcgaca cggaaatgtt gaatactcat actcttcctt   4380

tttcaatatt attgaagcat ttatcagggt tattgtctca tgagcggata catatttgaa   4440

tgtatttaga aaaataaaca aataggggtt ccgcgcacat ttccccgaaa agtgccacct   4500

gacgtctaag aaaccattat tatcatgaca ttaacctata aaaataggcg tatcacgagg   4560

ccctttcgtc tcgcgcgttt cggtgatgac ggtgaaaacc tctgacacat gcagctcccg   4620

gagacggtca cagcttgtct gtaagcggat gccgggagca gacaagcccg tcagggcgcg   4680
```

```
tcagcgggtg ttggcgggtg tcggggctgg cttaactatg cggcatcaga gcagattgta   4740

ctgagagtgc accatatgcg gtgtgaaata ccgcacagat gcgtaaggag aaaataccgc   4800

atcaggcgcc attcgccatt caggctgcgc aactgttggg aagggcgatc ggtgcgggcc   4860

tcttcgctat tacgccagct ggcgaaaggg ggatgtgctg caaggcgatt aagttgggta   4920

acgccagggt tttcccagtc acgacgttgt aaaacgacgg ccagtgaatt cgagctcggt   4980

acccggggat cct                                                      4993
```

<210> SEQ ID NO 23
<211> LENGTH: 6276
<212> TYPE: DNA
<213> ORGANISM: Artificial Sequence
<220> FEATURE:
<223> OTHER INFORMATION: plasmid pKR900
<220> FEATURE:
<221> NAME/KEY: misc_feature
<222> LOCATION: (4081)..(4081)
<223> OTHER INFORMATION: n is a, c, g, or t

<400> SEQUENCE: 23

```
ggccgcgaca caagtgtgag agtactaaat aaatgctttg gttgtacgaa atcattacac     60

taaataaaat aatcaaagct tatatatgcc ttccgctaag gccgaatgca aagaaattgg    120

ttctttctcg ttatcttttg ccacttttac tagtacgtat taattactac ttaatcatct    180

ttgtttacgg ctcattatat cctgcaggtc tagaggatcc ccgggtaccg agctcgaatt    240

cactggccgt cgttttacaa cgtcgtgact gggaaaaccc tggcgttacc caacttaatc    300

gccttgcagc acatccccct ttcgccagct ggcgtaatag cgaagaggcc cgcaccgatc    360

gcccttccca acagttgcgc agcctgaatg gcgaatggcg cctgatgcgg tattttctcc    420

ttacgcatct gtgcggtatt tcacaccgca tatggtgcac tctcagtaca atctgctctg    480

atgccgcata gttaagccag ccccgacacc cgccaacacc cgctgacgcg ccctgacggg    540

cttgtctgct cccggcatcc gcttacagac aagctgtgac cgtctccggg agctgcatgt    600

gtcagaggtt ttcaccgtca tcaccgaaac gcgcgagacg aaagggcctc gtgatacgcc    660

tatttttata ggttaatgtc atgataataa tggtttctta gacgtcaggt ggcacttttc    720

ggggaaatgt gcgcggaacc cctatttgtt tatttttcta aatacattca aatatgtatc    780

cgctcatgag acaataaccc tgataaatgc ttcaataata ttgaaaaagg aagagtatga    840

gtattcaaca tttccgtgtc gcccttattc ccttttttgc ggcattttgc cttcctgttt    900

ttgctcaccc agaaacgctg gtgaaagtaa aagatgctga agatcagttg ggtgcacgag    960

tgggttacat cgaactggat ctcaacagcg gtaagatcct tgagagtttt cgccccgaag   1020

aacgttttcc aatgatgagc acttttaaag ttctgctatg tggcgcggta ttatcccgta   1080

ttgacgccgg gcaagagcaa ctcggtcgcc gcatacacta ttctcagaat gacttggttg   1140

agtactcacc agtcacagaa aagcatctta cggatggcat gacagtaaga gaattatgca   1200

gtgctgccat aaccatgagt gataacactg cggccaactt acttctgaca acgatcggag   1260

gaccgaagga gctaaccgct tttttgcaca acatggggga tcatgtaact cgccttgatc   1320

gttgggaacc ggagctgaat gaagccatac caaacgacga gcgtgacacc acgatgcctg   1380

tagcaatggc aacaacgttg cgcaaactat taactggcga actacttact ctagcttccc   1440

ggcaacaatt aatagactgg atggaggcgg ataaagttgc aggaccactt ctgcgctcgg   1500

cccttccggc tggctggttt attgctgata aatctggagc cggtgagcgt gggtctcgcg   1560

gtatcattgc agcactgggg ccagatggta agccctcccg tatcgtagtt atctacacga   1620
```

```
cggggagtca ggcaactatg gatgaacgaa atagacagat cgctgagata ggtgcctcac   1680
tgattaagca ttggtaactg tcagaccaag tttactcata tatactttag attgatttaa   1740
aacttcattt ttaatttaaa aggatctagg tgaagatcct ttttgataat ctcatgacca   1800
aaatccctta acgtgagttt tcgttccact gagcgtcaga ccccgtagaa aagatcaaag   1860
gatcttcttg agatcctttt tttctgcgcg taatctgctg cttgcaaaca aaaaaaccac   1920
cgctaccagc ggtggtttgt ttgccggatc aagagctacc aactcttttt ccgaaggtaa   1980
ctggcttcag cagagcgcag ataccaaata ctgtccttct agtgtagccg tagttaggcc   2040
accacttcaa gaactctgta gcaccgccta catacctcgc tctgctaatc ctgttaccag   2100
tggctgctgc cagtggcgat aagtcgtgtc ttaccgggtt ggactcaaga cgatagttac   2160
cggataaggc gcagcggtcg ggctgaacgg ggggttcgtg cacacagccc agcttggagc   2220
gaacgaccta caccgaactg agatacctac agcgtgagct atgagaaagc gccacgcttc   2280
ccgaagggag aaaggcggac aggtatccgg taagcggcag ggtcggaaca ggagagcgca   2340
cgagggagct tccaggggga aacgcctggt atctttatag tcctgtcggg tttcgccacc   2400
tctgacttga gcgtcgattt ttgtgatgct cgtcaggggg gcggagccta tggaaaaacg   2460
ccagcaacgc ggccttttta cggttcctgg ccttttgctg gccttttgct cacatgttct   2520
ttcctgcgtt atcccctgat tctgtggata accgtattac cgcctttgag tgagctgata   2580
ccgctcgccg cagccgaacg accgagcgca gcgagtcagt gagcgaggaa gcggaagagc   2640
gcccaatacg caaaccgcct ctccccgcgc gttggccgat tcattaatgc agctggcacg   2700
acaggtttcc cgactggaaa gcgggcagtg agcgcaacgc aattaatgtg agttagctca   2760
ctcattaggc accccaggct ttacacttta tgcttccggc tcgtatgttg tgtggaattg   2820
tgagcggata acaatttcac acaggaaaca gctatgacca tgattacgcc aagcttgcat   2880
gcctgcaggt cgactctaga cgtacgtcct cgaagagaag ggttaataac acatttttta   2940
acatttttaa cacaaatttt agttatttaa aaatttatta aaaaatttaa aataagaaga   3000
ggaactcttt aaataaatct aacttacaaa atttatgatt tttaataagt tttcaccaat   3060
aaaaaatgtc ataaaaatat gttaaaaagt atattatcaa tattctcttt atgataaata   3120
aaaagaaaaa aaaaataaaa gttaagtgaa aatgagattg aagtgacttt aggtgtgtat   3180
aaatatatca accccgccaa caatttattt aatccaaata tattgaagta tattattcca   3240
tagcctttat ttatttatat atttattata taaaagcttt atttgttcta ggttgttcat   3300
gaaatatttt tttggtttta tctccgttgt aagaaaatca tgtgctttgt gtcgccactc   3360
actattgcag ctttttcatg cattggtcag attgacggtt gattgtattt ttgtttttta   3420
tggttttgtg ttatgactta agtcttcatc tctttatctc ttcatcaggt ttgatggtta   3480
cctaatatgg tccatgggta catgcatggt taaattaggt ggccaacttt gttgtgaacg   3540
atagaatttt ttttatatta agtaaactat ttttatatta tgaaataata ataaaaaaaa   3600
tattttatca ttattaacaa aatcatatta gttaatttgt taactctata ataaaagaaa   3660
tactgtaaca ttcacattac atggtaacat ctttccaccc tttcatttgt tttttgtttg   3720
atgacttttt ttcttgttta aatttatttc ccttctttta aatttggaat acattatcat   3780
catatataaa ctaaaatact aaaaacagga ttacacaaat gataaataat aacacaaata   3840
tttataaatc tagctgcaat atatttaaac tagctatatc gatattgtaa aataaaacta   3900
gctgcattga tactgataaa aaaatatcat gtgctttctg gactgatgat gcagtatact   3960
tttgacattg cctttatttt atttttcaga aaagctttct tagttctggg ttcttcatta   4020
```

```
tttgtttccc atctccattg tgaattgaat catttgcttc gtgtcacaaa tacaatttag   4080
ntaggtacat gcattggtca gattcacggt ttattatgtc atgacttaag ttcatggtag   4140
tacattacct gccacgcatg cattatattg gttagatttg ataggcaaat ttggttgtca   4200
acaatataaa tataaataat gtttttatat tacgaaataa cagtgatcaa aacaaacagt   4260
tttatcttta ttaacaagat tttgtttttg tttgatgacg ttttttaatg tttacgcttt   4320
ccccttcttt ttgaatttag aacactttat catcataaaa tcaaatacta aaaaaattac   4380
atatttcata aataataaca caaatatttt taaaaaatct gaaataataa tgaacaatat   4440
tacatattat cacgaaaatt cattaataaa aatattatat aaataaaatg taatagtagt   4500
tatatgtagg aaaaaagtac tgcacgcata atatatacaa aaagattaaa atgaactatt   4560
ataaataata acactaaatt aatggtgaat catatcaaaa taatgaaaaa gtaaataaaa   4620
tttgtaatta acttctatat gtattacaca cacaaataat aaataatagt aaaaaaaatt   4680
atgataaata tttaccatct cataagatat ttaaaataat gataaaaata tagattattt   4740
tttatgcaac tagctagcca aaaagagaac acgggtatat ataaaaagag tacctttaaa   4800
ttctactgta cttcctttat tcctgacgtt tttatatcaa gtggacatac gtgaagattt   4860
taattatcag tctaaatatt tcattagcac ttaatacttt tctgttttat tcctatccta   4920
taagtagtcc cgattctccc aacattgctt attcacacaa ctaactaaga aagtcttcca   4980
tagcccccca agcggccgca ccatgggcaa gggtggagac ggcggcgcgc aggcggtgag   5040
cgggaccgac gcgtctctcg ctgaggtgag ctccgtcgat agcaagagcg tgcacgtcgt   5100
gctctacggc aagcgcgtgg atgtcacaaa gttccagaag gcacacccgg gcgggagcaa   5160
ggtgttccgc atcttccagg agcgcgacgc gacggagcag ttcgagtctt accactcgcc   5220
caaggccatc aagatgatgg agggcatgct caagaagtcg gaggatgcgc ccgcttccgt   5280
gcccctgccc tcgcggtcca ccatgggcac ggagttcaag gagatgattg agcgccacaa   5340
gagggctggt ctctacgacc cttgcccgtt ggacgagctg ttcaagctca ccatcgtcct   5400
tgcgcccatc ttcgtgggcg cctatctcgt gcggagcggc gtctcgcccc tcgcgggcgc   5460
gctctccatg ggctttggct tctacctcga cggctggctt gctcacgact acctgcatca   5520
cgcagtcttc aagggctcgg tcaacacgct cgtcaaggcg aacaacgcca tgggatacgc   5580
cctcggcttc ctccagggct acgacgtggc ctggtggcgc gcgcgccata acacgcacca   5640
cgtgtgcacc aacgaggatg gttcggaccc ggacatcaag acggcgcccc tgctcatcta   5700
cgtgcgagag aacccgtcca ttgccaagcg gctcaacttc ttccagcgct ggcagcagta   5760
ctactatgtg ccgaccatgg ccatcctcga cctctactgg cgcctggagt ccatcgcgta   5820
cgtggctgtg cgcctgccta agatgtggat gcaggccgcc gctcttgccg ctcactacgc   5880
gctcctgtgc tgggtcttcg cagcgcatct caacctcatc cctctcatga tggttgcacg   5940
cggcttcgcg acgggcatcg ttgtctttgc aacccactat ggtgaggaca tcctcgaccg   6000
cgagcacgtc gagggcatga cgctcgtcga gcagaccgcc aagacctccc gtaacatcac   6060
gggcggctgg ctagtgaacg tgctcacggg cttcatctcc ctgcagaccg agcatcacct   6120
cttccccatg atgcccaccg gcaacctaat gactatccag cccgaggtac gcgacttctt   6180
caagaagcat ggcctcgagt accgcgaggg caacctcttc cagtgcgtgc accagaacat   6240
caaggctctc gccttcgagc acctcctcca ctgagc                             6276
```

<210> SEQ ID NO 24
<211> LENGTH: 5303

<212> TYPE: DNA
<213> ORGANISM: Artificial Sequence
<220> FEATURE:
<223> OTHER INFORMATION: primer pKR325

<400> SEQUENCE: 24

```
agcttggatc tcctgcagga tctggccggc cggatctcgt acggatccgt cgacggcgcg     60
cccgatcatc cggatatagt tcctcctttc agcaaaaaac ccctcaagac ccgtttagag    120
gccccaaggg gttatgctag ttattgctca gcggtggcag cagccaactc agcttccttt    180
cgggctttgt tagcagccgg atcgatccaa gctgtacctc actattcctt tgccctcgga    240
cgagtgctgg ggcgtcggtt tccactatcg gcgagtactt ctacacagcc atcggtccag    300
acggccgcgc ttctgcgggc gatttgtgta cgcccgacag tcccggctcc ggatcggacg    360
attgcgtcgc atcgaccctg cgcccaagct gcatcatcga aattgccgtc aaccaagctc    420
tgatagagtt ggtcaagacc aatgcggagc atatacgccc ggagccgcgg cgatcctgca    480
agctccggat gcctccgctc gaagtagcgc gtctgctgct ccatacaagc caaccacggc    540
ctccagaaga agatgttggc gacctcgtat tgggaatccc cgaacatcgc ctcgctccag    600
tcaatgaccg ctgttatgcg gccattgtcc gtcaggacat tgttggagcc gaaatccgcg    660
tgcacgaggt gccggacttc ggggcagtcc tcggcccaaa gcatcagctc atcgagagcc    720
tgcgcgacgg acgcactgac ggtgtcgtcc atcacagttt gccagtgata cacatgggga    780
tcagcaatcg cgcatatgaa atcacgccat gtagtgtatt gaccgattcc ttgcggtccg    840
aatgggccga acccgctcgt ctggctaaga tcggccgcag cgatcgcatc catagcctcc    900
gcgaccggct gcagaacagc gggcagttcg gtttcaggca ggtcttgcaa cgtgacaccc    960
tgtgcacggc gggagatgca ataggtcagg ctctcgctga attccccaat gtcaagcact   1020
tccggaatcg ggagcgcggc cgatgcaaag tgccgataaa cataacgatc tttgtagaaa   1080
ccatcggcgc agctatttac ccgcaggaca tatccacgcc ctcctacatc gaagctgaaa   1140
gcacgagatt cttcgccctc cgagagctgc atcaggtcgg agacgctgtc gaacttttcg   1200
atcagaaact tctcgacaga cgtcgcggtg agttcaggct tttccatggg tatatctcct   1260
tcttaaagtt aaacaaaatt atttctagag ggaaaccgtt gtggtctccc tatagtgagt   1320
cgtattaatt tcgcgggatc gagatcgatc caattccaat cccacaaaaa tctgagctta   1380
acagcacagt tgctcctctc agagcagaat cgggtattca acaccctcat atcaactact   1440
acgttgtgta taacggtcca catgccggta tatacgatga ctggggttgt acaaaggcgg   1500
caacaaacgg cgttcccgga gttgcacaca agaaatttgc cactattaca gaggcaagag   1560
cagcagctga cgcgtacaca acaagtcagc aaacagacag gttgaacttc atccccaaag   1620
gagaagctca actcaagccc aagagctttg ctaaggccct aacaagccca ccaaagcaaa   1680
aagcccactg gctcacgcta ggaaccaaaa ggcccagcag tgatccagcc ccaaaagaga   1740
tctcctttgc cccggagatt acaatggacg atttcctcta tctttacgat ctaggaagga   1800
agttcgaagg tgaaggtgac gacactatgt tcaccactga taatgagaag gttagcctct   1860
tcaatttcag aaagaatgct gacccacaga tggttagaga ggcctacgca gcaggtctca   1920
tcaagacgat ctacccgagt aacaatctcc aggagatcaa ataccttccc aagaaggtta   1980
aagatgcagt caaaagattc aggactaatt gcatcaagaa cacagagaaa gacatatttc   2040
tcaagatcag aagtactatt ccagtatgga cgattcaagg cttgcttcat aaaccaaggc   2100
aagtaataga gattggagtc tctaaaaagg tagttcctac tgaatctaag gccatgcatg   2160
gagtctaaga ttcaaatcga ggatctaaca gaactcgccg tgaagactgg cgaacagttc   2220
```

```
atacagagtc ttttacgact caatgacaag aagaaaatct tcgtcaacat ggtggagcac   2280
gacactctgg tctactccaa aaatgtcaaa gatacagtct cagaagacca aagggctatt   2340
gagacttttc aacaaaggat aatttcggga aacctcctcg gattccattg cccagctatc   2400
tgtcacttca tcgaaaggac agtagaaaag gaaggtggct cctacaaatg ccatcattgc   2460
gataaaggaa aggctatcat tcaagatgcc tctgccgaca gtggtcccaa agatggaccc   2520
ccacccacga ggagcatcgt ggaaaaagaa gacgttccaa ccacgtcttc aaagcaagtg   2580
gattgatgtg acatctccac tgacgtaagg gatgacgcac aatcccacta tccttcgcaa   2640
gacccttcct ctatataagg aagttcattt catttggaga ggacacgctc gagctcattt   2700
ctctattact tcagccataa caaaagaact cttttctctt cttattaaac catgaaaaag   2760
cctgaactca ccgcgacgtc tgtcgagaag tttctgatcg aaaagttcga cagcgtctcc   2820
gacctgatgc agctctcgga gggcgaagaa tctcgtgctt tcagcttcga tgtaggaggg   2880
cgtggatatg tcctgcgggt aaatagctgc gccgatggtt tctacaaaga tcgttatgtt   2940
tatcggcact ttgcatcggc cgcgctcccg attccggaag tgcttgacat tggggaattc   3000
agcgagagcc tgacctattg catctcccgc cgtgcacagg gtgtcacgtt gcaagacctg   3060
cctgaaaccg aactgcccgc tgttctgcag ccggtcgcgg aggccatgga tgcgatcgct   3120
gcggccgatc ttagccagac gagcgggttc ggcccattcg gaccgcaagg aatcggtcaa   3180
tacactacat ggcgtgattt catatgcgcg attgctgatc cccatgtgta tcactggcaa   3240
actgtgatgg acgacaccgt cagtgcgtcc gtcgcgcagg ctctcgatga gctgatgctt   3300
tgggccgagg actgccccga agtccggcac ctcgtgcacg cggatttcgg ctccaacaat   3360
gtcctgacgg acaatggccg cataacagcg gtcattgact ggagcgaggc gatgttcggg   3420
gattcccaat acgaggtcgc caacatcttc ttctggaggc cgtggttggc ttgtatggag   3480
cagcagacgc gctacttcga gcggaggcat ccggagcttg caggatcgcc gcggctccgg   3540
gcgtatatgc tccgcattgg tcttgaccaa ctctatcaga gcttggttga cggcaatttc   3600
gatgatgcag cttgggcgca gggtcgatgc gacgcaatcg tccgatccgg agccgggact   3660
gtcgggcgta cacaaatcgc ccgcagaagc gcggccgtct ggaccgatgg ctgtgtagaa   3720
gtactcgccg atagtggaaa ccgacgcccc agcactcgtc cgagggcaaa ggaatagtga   3780
ggtacctaaa gaaggagtgc gtcgaagcag atcgttcaaa catttggcaa taaagtttct   3840
taagattgaa tcctgttgcc ggtcttgcga tgattatcat ataatttctg ttgaattacg   3900
ttaagcatgt aataattaac atgtaatgca tgacgttatt tatgagatgg gtttttatga   3960
ttagagtccc gcaattatac atttaatacg cgatagaaaa caaaatatag cgcgcaaact   4020
aggataaatt atcgcgcgcg gtgtcatcta tgttactaga tcgatgtcga atcgatcaac   4080
ctgcattaat gaatcggcca acgcgcgggg agaggcggtt tgcgtattgg gcgctcttcc   4140
gcttcctcgc tcactgactc gctgcgctcg gtcgttcggc tgcggcgagc ggtatcagct   4200
cactcaaagg cggtaatacg gttatccaca gaatcagggg ataacgcagg aaagaacatg   4260
tgagcaaaag gccagcaaaa ggccaggaac cgtaaaaagg ccgcgttgct ggcgtttttc   4320
cataggctcc gcccccctga cgagcatcac aaaaatcgac gctcaagtca gaggtggcga   4380
aacccgacag gactataaag ataccaggcg tttccccctg gaagctccct cgtgcgctct   4440
cctgttccga ccctgccgct taccggatac ctgtccgcct ttctcccttc gggaagcgtg   4500
gcgctttctc aatgctcacg ctgtaggtat ctcagttcgg tgtaggtcgt tcgctccaag   4560
ctgggctgtg tgcacgaacc ccccgttcag cccgaccgct gcgccttatc cggtaactat   4620
```

```
cgtcttgagt ccaacccggt aagacacgac ttatcgccac tggcagcagc cactggtaac   4680

aggattagca gagcgaggta tgtaggcggt gctacagagt tcttgaagtg gtggcctaac   4740

tacggctaca ctagaaggac agtatttggt atctgcgctc tgctgaagcc agttaccttc   4800

ggaaaaagag ttggtagctc ttgatccggc aaacaaacca ccgctggtag cggtggtttt   4860

tttgtttgca agcagcagat tacgcgcaga aaaaaaggat ctcaagaaga tcctttgatc   4920

ttttctacgg ggtctgacgc tcagtggaac gaaaactcac gttaagggat tttggtcatg   4980

acattaacct ataaaaatag gcgtatcacg aggccctttc gtctcgcgcg tttcggtgat   5040

gacggtgaaa acctctgaca catgcagctc ccggagacgg tcacagcttg tctgtaagcg   5100

gatgccggga gcagacaagc ccgtcagggc gcgtcagcgg gtgttggcgg gtgtcggggc   5160

tggcttaact atgcggcatc agagcagatt gtactgagag tgcaccatat ggacatattg   5220

tcgttagaac gcggctacaa ttaatacata accttatgta tcatacacat acgatttagg   5280

tgacactata gaacggcgcg cca                                           5303
```

<210> SEQ ID NO 25
<211> LENGTH: 8898
<212> TYPE: DNA
<213> ORGANISM: Artificial Sequence
<220> FEATURE:
<223> OTHER INFORMATION: plasmid pKR902
<220> FEATURE:
<221> NAME/KEY: misc_feature
<222> LOCATION: (7701)..(7701)
<223> OTHER INFORMATION: n is a, c, g, or t

<400> SEQUENCE: 25

```
ggatctggcc ggccggatct cgtacggatc cgtcgacggc gcgcccgatc atccggatat     60

agttcctcct ttcagcaaaa aacccctcaa gacccgttta gaggccccaa ggggttatgc    120

tagttattgc tcagcggtgg cagcagccaa ctcagcttcc tttcgggctt tgttagcagc    180

cggatcgatc caagctgtac ctcactattc ctttgccctc ggacgagtgc tggggcgtcg    240

gtttccacta tcggcgagta cttctacaca gccatcggtc cagacggccg cgcttctgcg    300

ggcgatttgt gtacgcccga cagtcccggc tccggatcgg acgattgcgt cgcatcgacc    360

ctgcgcccaa gctgcatcat cgaaattgcc gtcaaccaag ctctgataga gttggtcaag    420

accaatgcgg agcatatacg cccggagccg cggcgatcct gcaagctccg gatgcctccg    480

ctcgaagtag cgcgtctgct gctccataca agccaaccac ggcctccaga agaagatgtt    540

ggcgacctcg tattgggaat ccccgaacat cgcctcgctc cagtcaatga ccgctgttat    600

gcggccattg tccgtcagga cattgttgga gccgaaatcc gcgtgcacga ggtgccggac    660

ttcggggcag tcctcggccc aaagcatcag ctcatcgaga gcctgcgcga cggacgcact    720

gacggtgtcg tccatcacag tttgccagtg atacacatgg ggatcagcaa tcgcgcatat    780

gaaatcacgc catgtagtgt attgaccgat tccttgcggt ccgaatgggc cgaacccgct    840

cgtctggcta agatcggccg cagcgatcgc atccatagcc tccgcgaccg gctgcagaac    900

agcgggcagt tcggtttcag gcaggtcttg caacgtgaca ccctgtgcac ggcgggagat    960

gcaataggtc aggctctcgc tgaattcccc aatgtcaagc acttccggaa tcgggagcgc   1020

ggccgatgca aagtgccgat aaacataacg atctttgtag aaaccatcgg cgcagctatt   1080

tacccgcagg acatatccac gccctcctac atcgaagctg aaagcacgag attcttcgcc   1140

ctccgagagc tgcatcaggt cggagacgct gtcgaacttt tcgatcagaa acttctcgac   1200

agacgtcgcg gtgagttcag gcttttccat gggtatatct ccttcttaaa gttaaacaaa   1260
```

```
attatttcta gagggaaacc gttgtggtct ccctatagtg agtcgtatta atttcgcggg   1320
atcgagatcg atccaattcc aatcccacaa aaatctgagc ttaacagcac agttgctcct   1380
ctcagagcag aatcgggtat tcaacaccct catatcaact actacgttgt gtataacggt   1440
ccacatgccg gtatatacga tgactggggt tgtacaaagg cggcaacaaa cggcgttccc   1500
ggagttgcac acaagaaatt tgccactatt acagaggcaa gagcagcagc tgacgcgtac   1560
acaacaagtc agcaaacaga caggttgaac ttcatcccca aaggagaagc tcaactcaag   1620
cccaagagct ttgctaaggc cctaacaagc ccaccaaagc aaaaagccca ctggctcacg   1680
ctaggaacca aaaggcccag cagtgatcca gccccaaaag agatctcctt tgccccggag   1740
attacaatgg acgatttcct ctatctttac gatctaggaa ggaagttcga aggtgaaggt   1800
gacgacacta tgttcaccac tgataatgag aaggttagcc tcttcaattt cagaaagaat   1860
gctgacccac agatggttag agaggcctac gcagcaggtc tcatcaagac gatctacccg   1920
agtaacaatc tccaggagat caaatacctt cccaagaagg ttaaagatgc agtcaaaaga   1980
ttcaggacta attgcatcaa gaacacagag aaagacatat ttctcaagat cagaagtact   2040
attccagtat ggacgattca aggcttgctt cataaaccaa ggcaagtaat agagattgga   2100
gtctctaaaa aggtagttcc tactgaatct aaggccatgc atggagtcta agattcaaat   2160
cgaggatcta acagaactcg ccgtgaagac tggcgaacag ttcatacaga gtcttttacg   2220
actcaatgac aagaagaaaa tcttcgtcaa catggtggag cacgacactc tggtctactc   2280
caaaaatgtc aaagatacag tctcagaaga ccaaagggct attgagactt ttcaacaaag   2340
gataatttcg ggaaacctcc tcggattcca ttgcccagct atctgtcact tcatcgaaag   2400
gacagtagaa aaggaaggtg gctcctacaa atgccatcat tgcgataaag gaaaggctat   2460
cattcaagat gcctctgccg acagtggtcc caaagatgga cccccaccca cgaggagcat   2520
cgtggaaaaa gaagacgttc caaccacgtc ttcaaagcaa gtggattgat gtgacatctc   2580
cactgacgta agggatgacg cacaatccca ctatccttcg caagaccctt cctctatata   2640
aggaagttca tttcatttgg agaggacacg ctcgagctca tttctctatt acttcagcca   2700
taacaaaaga actcttttct cttcttatta aaccatgaaa aagcctgaac tcaccgcgac   2760
gtctgtcgag aagtttctga tcgaaaagtt cgacagcgtc tccgacctga tgcagctctc   2820
ggagggcgaa gaatctcgtg ctttcagctt cgatgtagga gggcgtggat atgtcctgcg   2880
ggtaaatagc tgcgccgatg gtttctacaa agatcgttat gtttatcggc actttgcatc   2940
ggccgcgctc ccgattccgg aagtgcttga cattggggaa ttcagcgaga gcctgaccta   3000
ttgcatctcc cgccgtgcac agggtgtcac gttgcaagac ctgcctgaaa ccgaactgcc   3060
cgctgttctg cagccggtcg cggaggccat ggatgcgatc gctgcggccg atcttagcca   3120
gacgagcggg ttcggcccat tcggaccgca aggaatcggt caatacacta catggcgtga   3180
tttcatatgc gcgattgctg atccccatgt gtatcactgg caaactgtga tggacgacac   3240
cgtcagtgcg tccgtcgcgc aggctctcga tgagctgatg ctttgggccg aggactgccc   3300
cgaagtccgg cacctcgtgc acgcggattt cggctccaac aatgtcctga cggacaatgg   3360
ccgcataaca gcggtcattg actggagcga ggcgatgttc ggggattccc aatacgaggt   3420
cgccaacatc ttcttctgga ggccgtggtt ggcttgtatg gagcagcaga cgcgctactt   3480
cgagcggagg catccggagc ttgcaggatc gccgcggctc cgggcgtata tgctccgcat   3540
tggtcttgac caactctatc agagcttggt tgacggcaat ttcgatgatg cagcttgggc   3600
gcagggtcga tgcgacgcaa tcgtccgatc cggagccggg actgtcgggc gtacacaaat   3660
```

```
cgcccgcaga agcgcggccg tctggaccga tggctgtgta gaagtactcg ccgatagtgg   3720
aaaccgacgc cccagcactc gtccgagggc aaaggaatag tgaggtacct aaagaaggag   3780
tgcgtcgaag cagatcgttc aaacatttgg caataaagtt tcttaagatt gaatcctgtt   3840
gccggtcttg cgatgattat catataattt ctgttgaatt acgttaagca tgtaataatt   3900
aacatgtaat gcatgacgtt atttatgaga tgggttttta tgattagagt cccgcaatta   3960
tacatttaat acgcgataga aaacaaaata tagcgcgcaa actaggataa attatcgcgc   4020
gcggtgtcat ctatgttact agatcgatgt cgaatcgatc aacctgcatt aatgaatcgg   4080
ccaacgcgcg gggagaggcg gtttgcgtat tgggcgctct tccgcttcct cgctcactga   4140
ctcgctgcgc tcggtcgttc ggctgcggcg agcggtatca gctcactcaa aggcggtaat   4200
acggttatcc acagaatcag gggataacgc aggaaagaac atgtgagcaa aaggccagca   4260
aaaggccagg aaccgtaaaa aggccgcgtt gctggcgttt ttccataggc tccgcccccc   4320
tgacgagcat cacaaaaatc gacgctcaag tcagaggtgg cgaaacccga caggactata   4380
aagataccag gcgtttcccc ctggaagctc cctcgtgcgc tctcctgttc cgaccctgcc   4440
gcttaccgga tacctgtccg cctttctccc ttcgggaagc gtggcgcttt ctcaatgctc   4500
acgctgtagg tatctcagtt cggtgtaggt cgttcgctcc aagctgggct gtgtgcacga   4560
accccccgtt cagcccgacc gctgcgcctt atccggtaac tatcgtcttg agtccaaccc   4620
ggtaagacac gacttatcgc cactggcagc agccactggt aacaggatta gcagagcgag   4680
gtatgtaggc ggtgctacag agttcttgaa gtggtggcct aactacggct acactagaag   4740
gacagtattt ggtatctgcg ctctgctgaa gccagttacc ttcggaaaaa gagttggtag   4800
ctcttgatcc ggcaaacaaa ccaccgctgg tagcggtggt ttttttgttt gcaagcagca   4860
gattacgcgc agaaaaaaag gatctcaaga agatcctttg atcttttcta cggggtctga   4920
cgctcagtgg aacgaaaact cacgttaagg gattttggtc atgacattaa cctataaaaa   4980
taggcgtatc acgaggccct ttcgtctcgc gcgtttcggt gatgacggtg aaaacctctg   5040
acacatgcag ctcccggaga cggtcacagc ttgtctgtaa gcggatgccg ggagcagaca   5100
agcccgtcag ggcgcgtcag cgggtgttgg cgggtgtcgg ggctggctta actatgcggc   5160
atcagagcag attgtactga gagtgcacca tatggacata ttgtcgttag aacgcggcta   5220
caattaatac ataaccttat gtatcataca catacgattt aggtgacact atagaacggc   5280
gcgccaagct tggatctcct gcaggatata atgagccgta aacaaagatg attaagtagt   5340
aattaatacg tactagtaaa agtggcaaaa gataacgaga aagaaccaat ttctttgcat   5400
tcggccttag cggaaggcat atataagctt tgattatttt atttagtgta atgatttcgt   5460
acaaccaaag catttattta gtactctcac acttgtgtcg cggccgctca gtggaggagg   5520
tgctcgaagg cgagagcctt gatgttctgg tgcacgcact ggaagaggtt gccctcgcgg   5580
tactcgaggc catgcttctt gaagaagtcg cgtacctcgg gctggatagt cattaggttg   5640
ccggtgggca tcatggggaa gaggtgatgc tcggtctgca gggagatgaa gcccgtgagc   5700
acgttcacta gccagccgcc cgtgatgtta cgggaggtct tggcggtctg ctcgacgagc   5760
gtcatgccct cgacgtgctc gcggtcgagg atgtcctcac catagtgggt tgcaaagaca   5820
acgatgcccg tcgcgaagcc gcgtgcaacc atcatgagag ggatgaggtt gagatgcgct   5880
gcgaagaccc agcacaggag cgcgtagtga gcggcaagag cggcggcctg catccacatc   5940
ttaggcaggc gcacagccac gtacgcgatg gactccaggc gccagtagag gtcgaggatg   6000
gccatggtcg gcacatagta gtactgctgc cagcgctgga agaagttgag ccgcttggca   6060
```

```
atggacgggt tctctcgcac gtagatgagc aggggcgccg tcttgatgtc cgggtccgaa   6120
ccatcctcgt tggtgcacac gtggtgcgtg ttatggcgcg cgcgccacca ggccacgtcg   6180
tagccctgga ggaagccgag ggcgtatccc atggcgttgt tcgccttgac gagcgtgttg   6240
accgagccct tgaagactgc gtgatgcagg tagtcgtgag caagccagcc gtcgaggtag   6300
aagccaaagc ccatggagag cgcgcccgcg aggggcgaga cgccgctccg cacgagatag   6360
gcgcccacga agatgggcgc aaggacgatg gtgagcttga acagctcgtc caacgggcaa   6420
gggtcgtaga gaccagccct cttgtggcgc tcaatcatct ccttgaactc cgtgcccatg   6480
gtggaccgcg agggcagggg cacggaagcg ggcgcatcct ccgacttctt gagcatgccc   6540
tccatcatct tgatggcctt gggcgagtgg taagactcga actgctccgt cgcgtcgcgc   6600
tcctggaaga tgcggaacac cttgctcccg cccgggtgtg ccttctggaa ctttgtgaca   6660
tccacgcgct tgccgtagag cacgacgtgc acgctcttgc tatcgacgga gctcacctca   6720
gcgagagacg cgtcggtccc gctcaccgcc tgcgcgccgc cgtctccacc cttgcccatg   6780
gtgcggccgc ttggggggct atggaagact ttcttagtta gttgtgtgaa taagcaatgt   6840
tgggagaatc gggactactt ataggatagg aataaaacag aaaagtatta agtgctaatg   6900
aaatatttag actgataatt aaaatcttca cgtatgtcca cttgatataa aaacgtcagg   6960
aataaaggaa gtacagtaga atttaaaggt actcttttta tatatacccg tgttctcttt   7020
ttggctagct agttgcataa aaaataatct atatttttat cattatttta aatatcttat   7080
gagatggtaa atatttatca taattttttt tactattatt tattatttgt gtgtgtaata   7140
catatagaag ttaattacaa atttatttta ctttttcatt attttgatat gattcaccat   7200
taatttagtg ttattattta taatagttca ttttaatctt tttgtatata ttatgcgtgc   7260
agtacttttt tcctacatat aactactatt acattttatt tatataatat ttttattaat   7320
gaattttcgt gataatatgt aatattgttc attattattt cagatttttt aaaaatattt   7380
gtgttattat ttatgaaata tgtaattttt ttagtatttg attttatgat gataaagtgt   7440
tctaaattca aaagaagggg gaaagcgtaa acattaaaaa acgtcatcaa acaaaaacaa   7500
aatcttgtta ataaagataa aactgtttgt tttgatcact gttatttcgt aatataaaaa   7560
cattatttat atttatattg ttgacaacca aatttgccta tcaaatctaa ccaatataat   7620
gcatgcgtgg caggtaatgt actaccatga acttaagtca tgacataata aaccgtgaat   7680
ctgaccaatg catgtaccta nctaaattgt atttgtgaca cgaagcaaat gattcaattc   7740
acaatggaga tgggaaacaa ataatgaaga acccagaact aagaaagctt ttctgaaaaa   7800
taaaataaag gcaatgtcaa aagtatactg catcatcagt ccagaaagca catgatattt   7860
ttttatcagt atcaatgcag ctagttttat tttacaatat cgatatagct agtttaaata   7920
tattgcagct agatttataa atatttgtgt tattatttat catttgtgta atcctgtttt   7980
tagtatttta gtttatatat gatgataatg tattccaaat ttaaaagaag ggaaataaat   8040
ttaaacaaga aaaaaagtca tcaaacaaaa aacaaatgaa agggtggaaa gatgttacca   8100
tgtaatgtga atgttacagt atttctttta ttatagagtt aacaaattaa ctaatatgat   8160
tttgttaata atgataaaat atttttttta ttattatttc ataatataaa aatagtttac   8220
ttaatataaa aaaaattcta tcgttcacaa caaagttggc cacctaattt aaccatgcat   8280
gtacccatgg accatattag gtaaccatca aacctgatga agagataaag agatgaagac   8340
ttaagtcata acacaaaacc ataaaaaaca aaaatacaat caaccgtcaa tctgaccaat   8400
gcatgaaaaa gctgcaatag tgagtggcga cacaaagcac atgattttct tacaacggag   8460
```

```
ataaaaccaa aaaaatattt catgaacaac ctagaacaaa taaagctttt atataataaa   8520

tatataaata aataaaggct atggaataat atacttcaat atatttggat taaataaatt   8580

gttggcgggg ttgatatatt tatacacacc taaagtcact tcaatctcat tttcacttaa   8640

cttttatttt ttttttcttt ttatttatca taaagagaat attgataata tactttttaa   8700

catattttta tgacattttt tattggtgaa aacttattaa aaatcataaa ttttgtaagt   8760

tagatttatt taaagagttc ctcttcttat tttaaatttt ttaataaatt tttaaataac   8820

taaaatttgt gttaaaaatg ttaaaaaatg tgttattaac ccttctcttc gaggacgtac   8880

gtctagagtc gacctgca                                                  8898
```

<210> SEQ ID NO 26
<211> LENGTH: 7887
<212> TYPE: DNA
<213> ORGANISM: Artificial Sequence
<220> FEATURE:
<223> OTHER INFORMATION: plasmid pKR607

<400> SEQUENCE: 26

```
ggccgcagta tatcttaaat tctttaatac ggtgtactag gatattgaac tggttcttga     60

tgatgaaaac ctgggccgag attgcagcta tttatagtca taggtcttgt taacatgcat    120

ggacatttgg ccacggggtg gcatgcagtt tgacgggtgt tgaaataaac aaaaatgagg    180

tggcggaaga gaatacgagt ttgaggttgg gttagaaaca acaaatgtga gggctcatga    240

tgggttgagt tggtgaatgt tttgggctgc tcgattgaca cctttgtgag tacgtgttgt    300

tgtgcatggc ttttggggtc cagttttttt ttcttgacgc ggcgatcctg atcagctagt    360

ggataagtga tgtccactgt gtgtgattgc gtttttgttt gaattttatg aacttagaca    420

ttgctatgca aaggatactc tcattgtgtt ttgtcttctt ttgttccttg gctttttctt    480

atgatccaag agactagtca gtgttgtggc attcgagact accaagatta attatgatgg    540

gggaaggata agtaactgat tagtacggac tgttaccaaa ttaattaata agcggcaaat    600

gaagggcatg gatcaaaagc ttggatctcc tgcaggatct ggccggccgg atctcgtacg    660

gatccgtcga cggcgcgccc gatcatccgg atatagttcc tcctttcagc aaaaaacccc    720

tcaagacccg tttagaggcc ccaaggggtt atgctagtta ttgctcagcg gtggcagcag    780

ccaactcagc ttcctttcgg gctttgttag cagccggatc gatccaagct gtacctcact    840

attcctttgc cctcggacga gtgctggggc gtcggtttcc actatcggcg agtacttcta    900

cacagccatc ggtccagacg gccgcgcttc tgcgggcgat ttgtgtacgc ccgacagtcc    960

cggctccgga tcggacgatt gcgtcgcatc gaccctgcgc ccaagctgca tcatcgaaat   1020

tgccgtcaac caagctctga tagagttggt caagaccaat gcggagcata tacgcccgga   1080

gccgcggcga tcctgcaagc tccggatgcc tccgctcgaa gtagcgcgtc tgctgctcca   1140

tacaagccaa ccacggcctc cagaagaaga tgttggcgac ctcgtattgg gaatccccga   1200

acatcgcctc gctccagtca atgaccgctg ttatgcggcc attgtccgtc aggacattgt   1260

tggagccgaa atccgcgtgc acgaggtgcc ggacttcggg gcagtcctcg gcccaaagca   1320

tcagctcatc gagagcctgc gcgacggacg cactgacggt gtcgtccatc acagtttgcc   1380

agtgatacac atggggatca gcaatcgcgc atatgaaatc acgccatgta gtgtattgac   1440

cgattccttg cggtccgaat gggccgaacc cgctcgtctg gctaagatcg gccgcagcga   1500

tcgcatccat agcctccgcg accggctgca gaacagcggg cagttcggtt tcaggcaggt   1560

cttgcaacgt gacaccctgt gcacggcggg agatgcaata ggtcaggctc tcgctgaatt   1620
```

ccccaatgtc aagcacttcc ggaatcggga gcgcggccga tgcaaagtgc cgataaacat 1680
aacgatcttt gtagaaacca tcggcgcagc tatttacccg caggacatat ccacgccctc 1740
ctacatcgaa gctgaaagca cgagattctt cgccctccga gagctgcatc aggtcggaga 1800
cgctgtcgaa cttttcgatc agaaacttct cgacagacgt cgcggtgagt tcaggctttt 1860
ccatgggtat atctccttct taaagttaaa caaaattatt tctagaggga aaccgttgtg 1920
gtctccctat agtgagtcgt attaatttcg cgggatcgag atcgatccaa ttccaatccc 1980
acaaaaatct gagcttaaca gcacagttgc tcctctcaga gcagaatcgg gtattcaaca 2040
ccctcatatc aactactacg ttgtgtataa cggtccacat gccggtatat acgatgactg 2100 ggttgtaca aaggcggcaa caaacggcgt tcccggagtt gcacacaaga aatttgccac 2160
tattacagag gcaagagcag cagctgacgc gtacacaaca agtcagcaaa cagacaggtt 2220
gaacttcatc cccaaaggag aagctcaact caagcccaag agctttgcta aggccctaac 2280
aagcccacca aagcaaaaag cccactggct cacgctagga accaaaaggc ccagcagtga 2340
tccagcccca aaagagatct cctttgcccc ggagattaca atggacgatt tcctctatct 2400
ttacgatcta ggaaggaagt tcgaaggtga aggtgacgac actatgttca ccactgataa 2460
tgagaaggtt agcctcttca atttcagaaa gaatgctgac ccacagatgg ttagagaggc 2520
ctacgcagca ggtctcatca agacgatcta cccgagtaac aatctccagg agatcaaata 2580
ccttcccaag aaggttaaag atgcagtcaa aagattcagg actaattgca tcaagaacac 2640
agagaaagac atatttctca agatcagaag tactattcca gtatggacga ttcaaggctt 2700
gcttcataaa ccaaggcaag taatagagat tggagtctct aaaaaggtag ttcctactga 2760
atctaaggcc atgcatggag tctaagattc aaatcgagga tctaacagaa ctcgccgtga 2820
agactggcga acagttcata cagagtcttt tacgactcaa tgacaagaag aaaatcttcg 2880
tcaacatggt ggagcacgac actctggtct actccaaaaa tgtcaaagat acagtctcag 2940
aagaccaaag ggctattgag acttttcaac aaaggataat ttcgggaaac ctcctcggat 3000
tccattgccc agctatctgt cacttcatcg aaaggacagt agaaaaggaa ggtggctcct 3060
acaaatgcca tcattgcgat aaaggaaagg ctatcattca agatgcctct gccgacagtg 3120
gtcccaaaga tggaccccca cccacgagga gcatcgtgga aaaagaagac gttccaacca 3180
cgtcttcaaa gcaagtggat tgatgtgaca tctccactga cgtaagggat gacgcacaat 3240
cccactatcc ttcgcaagac ccttcctcta tataaggaag ttcatttcat ttggagagga 3300
cacgctcgag ctcatttctc tattacttca gccataacaa aagaactctt ttctcttctt 3360
attaaaccat gaaaaagcct gaactcaccg cgacgtctgt cgagaagttt ctgatcgaaa 3420
agttcgacag cgtctccgac ctgatgcagc tctcggaggg cgaagaatct cgtgctttca 3480
gcttcgatgt aggagggcgt ggatatgtcc tgcgggtaaa tagctgcgcc gatggtttct 3540
acaaagatcg ttatgtttat cggcactttg catcggccgc gctcccgatt ccggaagtgc 3600
ttgacattgg ggaattcagc gagagcctga cctattgcat ctcccgccgt gcacagggtg 3660
tcacgttgca agacctgcct gaaaccgaac tgcccgctgt tctgcagccg gtcgcggagg 3720
ccatggatgc gatcgctgcg gccgatctta gccagacgag cgggttcggc ccattcggac 3780
cgcaaggaat cggtcaatac actacatggc gtgatttcat atgcgcgatt gctgatcccc 3840
atgtgtatca ctggcaaact gtgatggacg acaccgtcag tgcgtccgtc gcgcaggctc 3900
tcgatgagct gatgctttgg gccgaggact gccccgaagt ccggcacctc gtgcacgcgg 3960
atttcggctc caacaatgtc ctgacggaca atggccgcat aacagcggtc attgactgga 4020
gcgaggcgat gttcggggat tcccaatacg aggtcgccaa catcttcttc tggaggccgt 4080
ggttggcttg tatggagcag cagacgcgct acttcgagcg gaggcatccg gagcttgcag 4140
gatcgccgcg gctccgggcg tatatgctcc gcattggtct tgaccaactc tatcagagct 4200
tggttgacgg caatttcgat gatgcagctt gggcgcaggg tcgatgcgac gcaatcgtcc 4260
gatccggagc cgggactgtc gggcgtacac aaatcgcccg cagaagcgcg gccgtctgga 4320
ccgatggctg tgtagaagta ctcgccgata gtggaaaccg acgccccagc actcgtccga 4380
gggcaaagga atagtgaggt acctaaagaa ggagtgcgtc gaagcagatc gttcaaacat 4440
ttggcaataa agtttcttaa gattgaatcc tgttgccggt cttgcgatga ttatcatata 4500
atttctgttg aattacgtta agcatgtaat aattaacatg taatgcatga cgttatttat 4560
gagatgggtt tttatgatta gagtcccgca attatacatt taatacgcga tagaaaacaa 4620
aatatagcgc gcaaactagg ataaattatc gcgcgcggtg tcatctatgt tactagatcg 4680
atgtcgaatc gatcaacctg cattaatgaa tcggccaacg cgcggggaga ggcggtttgc 4740
gtattgggcg ctcttccgct tcctcgctca ctgactcgct gcgctcggtc gttcggctgc 4800
ggcgagcggt atcagctcac tcaaaggcgg taatacggtt atccacagaa tcaggggata 4860
acgcaggaaa gaacatgtga gcaaaaggcc agcaaaaggc caggaaccgt aaaaaggccg 4920
cgttgctggc gtttttccat aggctccgcc cccctgacga gcatcacaaa aatcgacgct 4980
caagtcagag gtggcgaaac ccgacaggac tataaagata ccaggcgttt ccccctggaa 5040
gctccctcgt gcgctctcct gttccgaccc tgccgcttac cggatacctg tccgcctttc 5100
tcccttcggg aagcgtggcg ctttctcaat gctcacgctg taggtatctc agttcggtgt 5160
aggtcgttcg ctccaagctg ggctgtgtgc acgaaccccc cgttcagccc gaccgctgcg 5220
ccttatccgg taactatcgt cttgagtcca acccggtaag acacgactta tcgccactgg 5280
cagcagccac tggtaacagg attagcagag cgaggtatgt aggcggtgct acagagttct 5340
tgaagtggtg gcctaactac ggctacacta gaaggacagt atttggtatc tgcgctctgc 5400
tgaagccagt taccttcgga aaaagagttg gtagctcttg atccggcaaa caaaccaccg 5460
ctggtagcgg tggttttttt gtttgcaagc agcagattac gcgcagaaaa aaaggatctc 5520
aagaagatcc tttgatcttt tctacggggt ctgacgctca gtggaacgaa aactcacgtt 5580
aagggatttt ggtcatgaca ttaacctata aaaataggcg tatcacgagg ccctttcgtc 5640
tcgcgcgttt cggtgatgac ggtgaaaacc tctgacacat gcagctcccg gagacggtca 5700
cagcttgtct gtaagcggat gccgggagca gacaagcccg tcagggcgcg tcagcgggtg 5760
ttggcgggtg tcggggctgg cttaactatg cggcatcaga gcagattgta ctgagagtgc 5820
accatatgga catattgtcg ttagaacgcg gctacaatta atacataacc ttatgtatca 5880
tacacatacg atttaggtga cactatagaa cggcgcgcca agcttgttga aacatccctg 5940
aagtgtctca ttttatttta tttattcttt gctgataaaa aaataaaata aaagaagcta 6000
agcacacggt caaccattgc tctactgcta aaagggttat gtgtagtgtt ttactgcata 6060
aattatgcag caaacaagac aactcaaatt aaaaaatttc ctttgcttgt ttttttgttg 6120
tctctgactt gactttcttg tggaagttgg ttgtataagg attgggacac cattgtcctt 6180
cttaatttaa ttttattctt tgctgataaa aaaaaaaatt tcatatagtg ttaaataata 6240
atttgttaaa taaccaaaaa gtcaaatatg tttactctcg tttaaataat tgagattcgt 6300
ccagcaaggc taaacgattg tatagattta tgacaatatt tacttttttta tagataaatg 6360 ttatattata ataaatttat atacatatat tatatgttat ttattattat tttaaatcct 6420

```
tcaatatttt atcaaaccaa ctcataattt ttttttatc tgtaagaagc aataaaatta   6480

aatagaccca ctttaaggat gatccaacct ttatacagag taagagagtt caaatagtac   6540

cctttcatat acatatcaac taaaatatta gaaatatcat ggatcaaacc ttataaagac   6600

attaaataag tggataagta taatatataa atgggtagta tataatatat aaatggatac   6660

aaacttctct ctttataatt gttatgtctc cttaacatcc taatataata cataagtggg   6720

taatatataa tatataaatg gagacaaact tcttccatta taattgttat gtcttcttaa   6780

cacttatgtc tcgttcacaa tgctaaggtt agaattgttt agaaagtctt atagtacaca   6840

tttgtttttg tactatttga agcattccat aagccgtcac gattcagatg atttataata   6900

ataagaggaa atttatcata gaacaataag gtgcatagat agagtgttaa tatatcataa   6960

catcctttgt ttattcatag aagaagtgag atggagctca gttattatac tgttacatgg   7020

tcggatacaa tattccatgc tctccatgag ctcttacacc tacatgcatt ttagttcata   7080

cttgcggccg ctaaagctgc ttaccagcct tagcggattt cttggtggcc aggttgtcct   7140

ggtaaaagaa gtgacagaac aggagaaaga cagatccgac gtaggcgtag ttgaaagccc   7200

aggagaacag cttgcccttg tcagagttga agcagggaac gttgatgtag tcccagacca   7260

ggagaaagcc accgacgaac tggcaaatct gcatggcagt gatcagaggc ttggccttga   7320

acttgtagcc agcggcagtc agtccatagt aggtgtacat gatggtgtga atgaacgagt   7380

taaagaacat gaagatccac acaccctcgt tgtgcagtcg aatgccgagg tagacgtccc   7440

agggagctcc aaagtgatgg aaggcctgca gaaaggacac tcgcttgccc ttgaggacca   7500

gccaagcggt gtcgaggtac tccacgtact tagaatagta gaaggccttg gcagtccagg   7560

tgaacagctt ggagtcccag acaggagagg gacactgaaa gagaggctgg ggagtatcac   7620

cggtctgtct tcgcagccag gctccagtac cgtagtccca gccgagagcg gtggcagtca   7680

cgtagaagga cagggcagag aagagagcca ggaggacgtt gtaccagatc atggaggttc   7740

ggtaggctcc tttcttctcg tccacgagac cagagtttcg caggagaggc ttcaggagca   7800

ggtaggagaa ggtgccaatg aggatttcgg gatcggtgac ggcagcccag attcgctcgc   7860

cagcgtcgtt ggccagagcc atggtgc                                      7887
```

<210> SEQ ID NO 27
<211> LENGTH: 11482
<212> TYPE: DNA
<213> ORGANISM: Artificial Sequence
<220> FEATURE:
<223> OTHER INFORMATION: plasmid pKR903
<220> FEATURE:
<221> NAME/KEY: misc_feature
<222> LOCATION: (9081)..(9081)
<223> OTHER INFORMATION: n is a, c, g, or t

<400> SEQUENCE: 27

```
ggatctggcc ggccggatct cgtacggatc cgtcgacggc gcgcccgatc atccggatat     60

agttcctcct ttcagcaaaa aacccctcaa gacccgttta gaggccccaa ggggttatgc    120

tagttattgc tcagcggtgg cagcagccaa ctcagcttcc tttcgggctt tgttagcagc    180

cggatcgatc caagctgtac ctcactattc ctttgccctc ggacgagtgc tggggcgtcg    240

gtttccacta tcggcgagta cttctacaca gccatcggtc cagacggccg cgcttctgcg    300

ggcgatttgt gtacgcccga cagtcccggc tccggatcgg acgattgcgt cgcatcgacc    360

ctgcgcccaa gctgcatcat cgaaattgcc gtcaaccaag ctctgataga gttggtcaag    420

accaatgcgg agcatatacg cccggagccg cggcgatcct gcaagctccg gatgcctccg    480
```

```
ctcgaagtag cgcgtctgct gctccataca agccaaccac ggcctccaga agaagatgtt    540
ggcgacctcg tattgggaat ccccgaacat cgcctcgctc cagtcaatga ccgctgttat    600
gcggccattg tccgtcagga cattgttgga gccgaaatcc gcgtgcacga ggtgccggac    660
ttcggggcag tcctcggccc aaagcatcag ctcatcgaga gcctgcgcga cggacgcact    720
gacggtgtcg tccatcacag tttgccagtg atacacatgg ggatcagcaa tcgcgcatat    780
gaaatcacgc catgtagtgt attgaccgat tccttgcggt ccgaatgggc cgaacccgct    840
cgtctggcta agatcggccg cagcgatcgc atccatagcc tccgcgaccg gctgcagaac    900
agcgggcagt tcggtttcag gcaggtcttg caacgtgaca ccctgtgcac ggcgggagat    960
gcaataggtc aggctctcgc tgaattcccc aatgtcaagc acttccggaa tcgggagcgc   1020
ggccgatgca aagtgccgat aaacataacg atctttgtag aaaccatcgg cgcagctatt   1080
tacccgcagg acatatccac gccctcctac atcgaagctg aaagcacgag attcttcgcc   1140
ctccgagagc tgcatcaggt cggagacgct gtcgaacttt tcgatcagaa acttctcgac   1200
agacgtcgcg gtgagttcag gcttttccat gggtatatct ccttcttaaa gttaaacaaa   1260
attatttcta gagggaaacc gttgtggtct ccctatagtg agtcgtatta atttcgcggg   1320
atcgagatcg atccaattcc aatcccacaa aaatctgagc ttaacagcac agttgctcct   1380
ctcagagcag aatcgggtat tcaacaccct catatcaact actacgttgt gtataacggt   1440
ccacatgccg gtatatacga tgactggggt tgtacaaagg cggcaacaaa cggcgttccc   1500
ggagttgcac acaagaaatt tgccactatt acagaggcaa gagcagcagc tgacgcgtac   1560
acaacaagtc agcaaacaga caggttgaac ttcatcccca aaggagaagc tcaactcaag   1620
cccaagagct ttgctaaggc cctaacaagc ccaccaaagc aaaaagccca ctggctcacg   1680
ctaggaacca aaaggcccag cagtgatcca gccccaaaag agatctcctt tgccccggag   1740
attacaatgg acgatttcct ctatctttac gatctaggaa ggaagttcga aggtgaaggt   1800
gacgacacta tgttcaccac tgataatgag aaggttagcc tcttcaattt cagaaagaat   1860
gctgacccac agatggttag agaggcctac gcagcaggtc tcatcaagac gatctacccg   1920
agtaacaatc tccaggagat caaatacctt cccaagaagg ttaaagatgc agtcaaaaga   1980
ttcaggacta attgcatcaa gaacacagag aaagacatat ttctcaagat cagaagtact   2040
attccagtat ggacgattca aggcttgctt cataaaccaa ggcaagtaat agagattgga   2100
gtctctaaaa aggtagttcc tactgaatct aaggccatgc atggagtcta agattcaaat   2160
cgaggatcta acagaactcg ccgtgaagac tggcgaacag ttcatacaga gtcttttacg   2220
actcaatgac aagaagaaaa tcttcgtcaa catggtggag cacgacactc tggtctactc   2280
caaaaatgtc aaagatacag tctcagaaga ccaaagggct attgagactt ttcaacaaag   2340
gataatttcg ggaaacctcc tcggattcca ttgcccagct atctgtcact tcatcgaaag   2400
gacagtagaa aaggaaggtg gctcctacaa atgccatcat tgcgataaag gaaaggctat   2460
cattcaagat gcctctgccg acagtggtcc caaagatgga cccccaccca cgaggagcat   2520
cgtggaaaaa gaagacgttc caaccacgtc ttcaaagcaa gtggattgat gtgacatctc   2580
cactgacgta agggatgacg cacaatccca ctatccttcg caagaccctt cctctatata   2640
aggaagttca tttcatttgg agaggacacg ctcgagctca tttctctatt acttcagcca   2700
taacaaaaga actcttttct cttcttatta aaccatgaaa aagcctgaac tcaccgcgac   2760
gtctgtcgag aagtttctga tcgaaaagtt cgacagcgtc tccgacctga tgcagctctc   2820
ggagggcgaa gaatctcgtg ctttcagctt cgatgtagga gggcgtggat atgtcctgcg   2880
```

```
ggtaaatagc tgcgccgatg gtttctacaa agatcgttat gtttatcggc actttgcatc   2940
ggccgcgctc ccgattccgg aagtgcttga cattggggaa ttcagcgaga gcctgaccta   3000
ttgcatctcc cgccgtgcac agggtgtcac gttgcaagac ctgcctgaaa ccgaactgcc   3060
cgctgttctg cagccggtcg cggaggccat ggatgcgatc gctgcggccg atcttagcca   3120
gacgagcggg ttcggcccat tcggaccgca aggaatcggt caatacacta catggcgtga   3180
tttcatatgc gcgattgctg atccccatgt gtatcactgg caaactgtga tggacgacac   3240
cgtcagtgcg tccgtcgcgc aggctctcga tgagctgatg ctttgggccg aggactgccc   3300
cgaagtccgg cacctcgtgc acgcggattt cggctccaac aatgtcctga cggacaatgg   3360
ccgcataaca gcggtcattg actggagcga ggcgatgttc ggggattccc aatacgaggt   3420
cgccaacatc ttcttctgga ggccgtggtt ggcttgtatg gagcagcaga cgcgctactt   3480
cgagcggagg catccggagc ttgcaggatc gccgcggctc cgggcgtata tgctccgcat   3540
tggtcttgac caactctatc agagcttggt tgacggcaat ttcgatgatg cagcttgggc   3600
gcagggtcga tgcgacgcaa tcgtccgatc cggagccggg actgtcgggc gtacacaaat   3660
cgcccgcaga agcgcggccg tctggaccga tggctgtgta gaagtactcg ccgatagtgg   3720
aaaccgacgc cccagcactc gtccgagggc aaaggaatag tgaggtacct aaagaaggag   3780
tgcgtcgaag cagatcgttc aaacatttgg caataaagtt tcttaagatt gaatcctgtt   3840
gccggtcttg cgatgattat catataattt ctgttgaatt acgttaagca tgtaataatt   3900
aacatgtaat gcatgacgtt atttatgaga tgggttttta tgattagagt cccgcaatta   3960
tacatttaat acgcgataga aaacaaaata tagcgcgcaa actaggataa attatcgcgc   4020
gcggtgtcat ctatgttact agatcgatgt cgaatcgatc aacctgcatt aatgaatcgg   4080
ccaacgcgcg gggagaggcg gtttgcgtat tgggcgctct tccgcttcct cgctcactga   4140
ctcgctgcgc tcggtcgttc ggctgcggcg agcggtatca gctcactcaa aggcggtaat   4200
acggttatcc acagaatcag gggataacgc aggaaagaac atgtgagcaa aaggccagca   4260
aaaggccagg aaccgtaaaa aggccgcgtt gctggcgttt ttccataggc tccgcccccc   4320
tgacgagcat cacaaaaatc gacgctcaag tcagaggtgg cgaaacccga caggactata   4380
aagataccag gcgtttcccc ctggaagctc cctcgtgcgc tctcctgttc cgaccctgcc   4440
gcttaccgga tacctgtccg cctttctccc ttcgggaagc gtggcgcttt ctcaatgctc   4500
acgctgtagg tatctcagtt cggtgtaggt cgttcgctcc aagctgggct gtgtgcacga   4560
accccccgtt cagcccgacc gctgcgcctt atccggtaac tatcgtcttg agtccaaccc   4620
ggtaagacac gacttatcgc cactggcagc agccactggt aacaggatta gcagagcgag   4680
gtatgtaggc ggtgctacag agttcttgaa gtggtggcct aactacggct acactagaag   4740
gacagtattt ggtatctgcg ctctgctgaa gccagttacc ttcggaaaaa gagttggtag   4800
ctcttgatcc ggcaaacaaa ccaccgctgg tagcggtggt ttttttgttt gcaagcagca   4860
gattacgcgc agaaaaaaag gatctcaaga agatcctttg atcttttcta cggggtctga   4920
cgctcagtgg aacgaaaact cacgttaagg gattttggtc atgacattaa cctataaaaa   4980
taggcgtatc acgaggccct ttcgtctcgc gcgtttcggt gatgacggtg aaaacctctg   5040
acacatgcag ctcccggaga cggtcacagc ttgtctgtaa gcggatgccg ggagcagaca   5100
agcccgtcag ggcgcgtcag cgggtgttgg cgggtgtcgg ggctggctta actatgcggc   5160
atcagagcag attgtactga gagtgcacca tatggacata ttgtcgttag aacgcggcta   5220
caattaatac ataaccttat gtatcataca catacgattt aggtgacact atagaacggc   5280
```

```
gcgccaagct tgttgaaaca tccctgaagt gtctcatttt attttattta ttctttgctg   5340
ataaaaaaat aaaataaaag aagctaagca cacggtcaac cattgctcta ctgctaaaag   5400
ggttatgtgt agtgttttac tgcataaatt atgcagcaaa caagacaact caaattaaaa   5460
aatttccttt gcttgttttt ttgttgtctc tgacttgact ttcttgtgga agttggttgt   5520
ataaggattg ggacaccatt gtccttctta atttaatttt attctttgct gataaaaaaa   5580
aaaatttcat atagtgttaa ataataattt gttaaataac caaaaagtca aatatgttta   5640
ctctcgttta aataattgag attcgtccag caaggctaaa cgattgtata gatttatgac   5700
aatatttact tttttataga taaatgttat attataataa atttatatac atatattata   5760
tgttatttat tattatttta aatccttcaa tattttatca aaccaactca taattttttt   5820
tttatctgta agaagcaata aaattaaata gacccacttt aaggatgatc caacctttat   5880
acagagtaag agagttcaaa tagtaccctt tcatatacat atcaactaaa atattagaaa   5940
tatcatggat caaaccttat aaagacatta aataagtgga taagtataat atataaatgg   6000
gtagtatata atatataaat ggatacaaac ttctctcttt ataattgtta tgtctcctta   6060
acatcctaat ataatacata agtgggtaat atataatata taaatggaga caaacttctt   6120
ccattataat tgttatgtct tcttaacact tatgtctcgt tcacaatgct aaggttagaa   6180
ttgtttagaa agtcttatag tacacatttg tttttgtact atttgaagca ttccataagc   6240
cgtcacgatt cagatgattt ataataataa gaggaaattt atcatagaac aataaggtgc   6300
atagatagag tgttaatata tcataacatc ctttgtttat tcatagaaga agtgagatgg   6360
agctcagtta ttatactgtt acatggtcgg atacaatatt ccatgctctc catgagctct   6420
tacacctaca tgcattttag ttcatacttg cggccgctaa agctgcttac cagccttagc   6480
ggatttcttg gtggccaggt tgtcctggta aaagaagtga cagaacagga gaaagacaga   6540
tccgacgtag gcgtagttga aagcccagga gaacagcttg cccttgtcag agttgaagca   6600
gggaacgttg atgtagtccc agaccaggag aaagccaccg acgaactggc aaatctgcat   6660
ggcagtgatc agaggcttgg ccttgaactt gtagccagcg gcagtcagtc catagtaggt   6720
gtacatgatg gtgtgaatga acgagttaaa gaacatgaag atccacacac cctcgttgtg   6780
cagtcgaatg ccgaggtaga cgtcccaggg agctccaaag tgatggaagg cctgcagaaa   6840
ggacactcgc ttgcccttga ggaccagcca agcggtgtcg aggtactcca cgtacttaga   6900
atagtagaag gccttggcag tccaggtgaa cagcttggag tcccagacag gagagggaca   6960
ctgaaagaga ggctggggag tatcaccggt ctgtcttcgc agccaggctc cagtaccgta   7020
gtcccagccg agagcggtgg cagtcacgta gaaggacagg gcagagaaga gagccaggag   7080
gacgttgtac cagatcatgg aggttcggta ggctcctttc ttctcgtcca cgagaccaga   7140
gtttcgcagg agaggcttca ggagcaggta ggagaaggtg ccaatgagga tttcgggatc   7200
ggtgacggca gcccagattc gctcgccagc gtcgttggcc agagccatgg tgcggccgca   7260
gtatatctta aattctttaa tacggtgtac taggatattg aactggttct tgatgatgaa   7320
aacctgggcc gagattgcag ctatttatag tcataggtct tgttaacatg catggacatt   7380
tggccacggg gtggcatgca gtttgacggg tgttgaaata aacaaaaatg aggtggcgga   7440
agagaatacg agtttgaggt tgggttagaa acaacaaatg tgagggctca tgatgggttg   7500
agttggtgaa tgttttgggc tgctcgattg acacctttgt gagtacgtgt tgttgtgcat   7560
ggcttttggg gtccagtttt tttttcttga cgcggcgatc ctgatcagct agtggataag   7620
tgatgtccac tgtgtgtgat tgcgtttttg tttgaatttt atgaacttag acattgctat   7680
```

```
gcaaaggata ctctcattgt gttttgtctt cttttgttcc ttggcttttt cttatgatcc   7740
aagagactag tcagtgttgt ggcattcgag actaccaaga ttaattatga tgggggaagg   7800
ataagtaact gattagtacg gactgttacc aaattaatta ataagcggca aatgaagggc   7860
atggatcaaa agcttggatc tcctgcaggt cgactctaga cgtacgtcct cgaagagaag   7920
ggttaataac acatttttta acatttttaa cacaaatttt agttatttaa aaatttatta   7980
aaaaatttaa aataagaaga ggaactcttt aaataaatct aacttacaaa atttatgatt   8040
tttaataagt tttcaccaat aaaaaatgtc ataaaaatat gttaaaaagt atattatcaa   8100
tattctcttt atgataaata aaaagaaaaa aaaaataaaa gttaagtgaa aatgagattg   8160
aagtgacttt aggtgtgtat aaatatatca accccgccaa caatttattt aatccaaata   8220
tattgaagta tattattcca tagcctttat ttatttatat atttattata taaaagcttt   8280
atttgttcta ggttgttcat gaaatatttt tttggtttta tctccgttgt aagaaaatca   8340
tgtgctttgt gtcgccactc actattgcag ctttttcatg cattggtcag attgacggtt   8400
gattgtattt ttgtttttta tggttttgtg ttatgactta agtcttcatc tctttatctc   8460
ttcatcaggt ttgatggtta cctaatatgg tccatgggta catgcatggt taaattaggt   8520
ggccaacttt gttgtgaacg atagaatttt ttttatatta agtaaactat ttttatatta   8580
tgaaataata ataaaaaaaa tattttatca ttattaacaa aatcatatta gttaatttgt   8640
taactctata ataaaagaaa tactgtaaca ttcacattac atggtaacat ctttccaccc   8700
tttcatttgt tttttgtttg atgacttttt ttcttgttta aatttatttc ccttctttta   8760
aatttggaat acattatcat catatataaa ctaaaatact aaaaacagga ttacacaaat   8820
gataaataat aacacaaata tttataaatc tagctgcaat atatttaaac tagctatatc   8880
gatattgtaa aataaaacta gctgcattga tactgataaa aaaatatcat gtgctttctg   8940
gactgatgat gcagtatact tttgacattg cctttatttt atttttcaga aaagctttct   9000
tagttctggg ttcttcatta tttgtttccc atctccattg tgaattgaat catttgcttc   9060
gtgtcacaaa tacaatttag ntaggtacat gcattggtca gattcacggt ttattatgtc   9120
atgacttaag ttcatggtag tacattacct gccacgcatg cattatattg gttagatttg   9180
ataggcaaat ttggttgtca acaatataaa tataaataat gtttttatat tacgaaataa   9240
cagtgatcaa aacaaacagt tttatcttta ttaacaagat tttgtttttg tttgatgacg   9300
ttttttaatg tttacgcttt ccccccttctt ttgaatttag aacactttat catcataaaa   9360
tcaaatacta aaaaaattac atatttcata aataataaca caaatatttt taaaaaatct   9420
gaaataataa tgaacaatat tacatattat cacgaaaatt cattaataaa aatattatat   9480
aaataaaatg taatagtagt tatatgtagg aaaaaagtac tgcacgcata atatatacaa   9540
aaagattaaa atgaactatt ataaataata acactaaatt aatggtgaat catatcaaaa   9600
taatgaaaaa gtaaataaaa tttgtaatta acttctatat gtattacaca cacaaataat   9660
aaataatagt aaaaaaaatt atgataaata tttaccatct cataagatat ttaaaataat   9720
gataaaaata tagattattt tttatgcaac tagctagcca aaaagagaac acgggtatat   9780
ataaaaagag tacctttaaa ttctactgta cttcctttat tcctgacgtt tttatatcaa   9840
gtggacatac gtgaagattt taattatcag tctaaatatt tcattagcac ttaatacttt   9900
tctgttttat tcctatccta taagtagtcc cgattctccc aacattgctt attcacacaa   9960
ctaactaaga aagtcttcca tagcccccca agcggccgca ccatgggcaa gggtggagac  10020
ggcggcgcgc aggcggtgag cgggaccgac gcgtctctcg ctgaggtgag ctccgtcgat  10080
```

agcaagagcg tgcacgtcgt gctctacggc aagcgcgtgg atgtcacaaa gttccagaag 10140
gcacacccgg gcgggagcaa ggtgttccgc atcttccagg agcgcgacgc gacggagcag 10200
ttcgagtctt accactcgcc caaggccatc aagatgatgg agggcatgct caagaagtcg 10260
gaggatgcgc ccgcttccgt gcccctgccc tcgcggtcca ccatgggcac ggagttcaag 10320
gagatgattg agcgccacaa gagggctggt ctctacgacc cttgcccgtt ggacgagctg 10380
ttcaagctca ccatcgtcct tgcgcccatc ttcgtgggcg cctatctcgt gcggagcggc 10440
gtctcgcccc tcgcgggcgc gctctccatg ggctttggct tctacctcga cggctggctt 10500
gctcacgact acctgcatca cgcagtcttc aagggctcgg tcaacacgct cgtcaaggcg 10560
aacaacgcca tgggatacgc cctcggcttc ctccagggct acgacgtggc ctggtggcgc 10620
gcgcgccata acacgcacca cgtgtgcacc aacgaggatg gttcggaccc ggacatcaag 10680
acggcgcccc tgctcatcta cgtgcgagag aacccgtcca ttgccaagcg gctcaacttc 10740
ttccagcgct ggcagcagta ctactatgtg ccgaccatgg ccatcctcga cctctactgg 10800
cgcctggagt ccatcgcgta cgtggctgtg cgcctgccta agatgtggat gcaggccgcc 10860
gctcttgccg ctcactacgc gctcctgtgc tgggtcttcg cagcgcatct caacctcatc 10920
cctctcatga tggttgcacg cggcttcgcg acgggcatcg ttgtctttgc aacccactat 10980
ggtgaggaca tcctcgaccg cgagcacgtc gagggcatga cgctcgtcga gcagaccgcc 11040
aagacctccc gtaacatcac gggcggctgg ctagtgaacg tgctcacggg cttcatctcc 11100
ctgcagaccg agcatcacct cttccccatg atgcccaccg gcaacctaat gactatccag 11160
cccgaggtac gcgacttctt caagaagcat ggcctcgagt accgcgaggg caacctcttc 11220
cagtgcgtgc accagaacat caaggctctc gccttcgagc acctcctcca ctgagcggcc 11280
gcgacacaag tgtgagagta ctaaataaat gctttggttg tacgaaatca ttacactaaa 11340
taaaataatc aaagcttata tatgccttcc gctaaggccg aatgcaaaga aattggttct 11400
ttctcgttat cttttgccac ttttactagt acgtattaat tactacttaa tcatctttgt 11460
ttacggctca ttatatcctg ca 11482

<210> SEQ ID NO 28
<211> LENGTH: 18
<212> TYPE: DNA
<213> ORGANISM: Artificial Sequence
<220> FEATURE:
<223> OTHER INFORMATION: GPDsense primer

<400> SEQUENCE: 28
atacgagatc gtcaaggg 18

<210> SEQ ID NO 29
<211> LENGTH: 26
<212> TYPE: DNA
<213> ORGANISM: Artificial Sequence
<220> FEATURE:
<223> OTHER INFORMATION: GPDantisense primer

<400> SEQUENCE: 29
gcggccgcgg attgatgtgt gtttaa 26

<210> SEQ ID NO 30
<211> LENGTH: 6970
<212> TYPE: DNA
<213> ORGANISM: Artificial Sequence
<220> FEATURE:
<223> OTHER INFORMATION: plasmid pY5-22GPD

<400> SEQUENCE: 30

```
tcgacgcagt aggatgtcct gcacgggtct ttttgtgggg tgtggagaaa ggggtgcttg     60
gagatggaag ccggtagaac cgggctgctt gtgcttggag atggaagccg gtagaaccgg    120
gctgcttggg gggatttggg gccgctgggc tccaaagagg ggtaggcatt tcgttggggt    180
tacgtaattg cggcatttgg gtcctgcgcg catgtcccat tggtcagaat tagtccggat    240
aggagactta tcagccaatc acagcgccgg atccacctgt aggttgggtt gggtgggagc    300
acccctccac agagtagagt caaacagcag cagcaacatg atagttgggg gtgtgcgtgt    360
taaaggaaaa aaaagaagct tgggttatat tcccgctcta tttagaggtt gcgggataga    420
cgccgacgga gggcaatggc gccatggaac cttgcggata tcgatacgcc gcggcggact    480
gcgtccgaac cagctccagc agcgtttttt ccgggccatt gagccgactg cgaccccgcc    540
aacgtgtctt ggcccacgca ctcatgtcat gttggtgttg ggaggccact tttaagtag     600
cacaaggcac ctagctcgca gcaaggtgtc cgaaccaaag aagcggctgc agtggtgcaa    660
acggggcgga aacggcggga aaaagccacg ggggcacgaa ttgaggcacg ccctcgaatt    720
tgagacgagt cacggcccca ttcgcccgcg caatggctcg ccaacgcccg gtcttttgca    780
ccacatcagg ttaccccaag ccaaaccttt gtgttaaaaa gcttaacata ttataccgaa    840
cgtaggtttg ggcgggcttg ctccgtctgt ccaaggcaac atttatataa gggtctgcat    900
cgccggctca attgaatctt ttttcttctt ctcttctcta tattcattct tgaattaaac    960
acacatcaat ccgcggccgc caccgcggcc cgagattccg gcctcttcgg ccgccaagcg   1020
acccgggtgg acgtctagag gtacctagca attaacagat agtttgccgg tgataattct   1080
cttaacctcc cacactcctt tgacataacg atttatgtaa cgaaactgaa atttgaccag   1140
atattgtgtc cgcggtggag ctccagcttt tgttcccttt agtgagggtt aatttcgagc   1200
ttggcgtaat catggtcata gctgtttcct gtgtgaaatt gttatccgct cacaattcca   1260
cacaacgtac gagccggaag cataaagtgt aaagcctggg gtgcctaatg agtgagctaa   1320
ctcacattaa ttgcgttgcg ctcactgccc gctttccagt cgggaaacct gtcgtgccag   1380
ctgcattaat gaatcggcca acgcgcgggg agaggcggtt tgcgtattgg gcgctcttcc   1440
gcttcctcgc tcactgactc gctgcgctcg gtcgttcggc tgcggcgagc ggtatcagct   1500
cactcaaagg cggtaatacg gttatccaca gaatcagggg ataacgcagg aaagaacatg   1560
tgagcaaaag gccagcaaaa ggccaggaac cgtaaaaagg ccgcgttgct ggcgtttttc   1620
cataggctcc gcccccctga cgagcatcac aaaaatcgac gctcaagtca gaggtggcga   1680
aacccgacag gactataaag ataccaggcg tttccccctg gaagctccct cgtgcgctct   1740
cctgttccga ccctgccgct taccggatac ctgtccgcct ttctcccttc gggaagcgtg   1800
gcgctttctc atagctcacg ctgtaggtat ctcagttcgg tgtaggtcgt tcgctccaag   1860
ctgggctgtg tgcacgaacc ccccgttcag cccgaccgct gcgccttatc cggtaactat   1920
cgtcttgagt ccaacccggt aagacacgac ttatcgccac tggcagcagc cactggtaac   1980
aggattagca gagcgaggta tgtaggcggt gctacagagt tcttgaagtg gtggcctaac   2040
tacggctaca ctagaaggac agtatttggt atctgcgctc tgctgaagcc agttaccttc   2100
ggaaaaagag ttggtagctc ttgatccggc aaacaaacca ccgctggtag cggtggtttt   2160
tttgtttgca agcagcagat tacgcgcaga aaaaaaggat ctcaagaaga tcctttgatc   2220
ttttctacgg ggtctgacgc tcagtggaac gaaaactcac gttaagggat tttggtcatg   2280
agattatcaa aaggatcttc acctagatcc ttttaaatt aaaaatgaag ttttaaatca    2340
```

```
atctaaagta tatatgagta aacttggtct gacagttacc aatgcttaat cagtgaggca   2400

cctatctcag cgatctgtct atttcgttca tccatagttg cctgactccc cgtcgtgtag   2460

ataactacga tacgggaggg cttaccatct ggccccagtg ctgcaatgat accgcgagac   2520

ccacgctcac cggctccaga tttatcagca ataaaccagc cagccggaag ggccgagcgc   2580

agaagtggtc ctgcaacttt atccgcctcc atccagtcta ttaattgttg ccgggaagct   2640

agagtaagta gttcgccagt taatagtttg cgcaacgttg ttgccattgc tacaggcatc   2700

gtggtgtcac gctcgtcgtt tggtatggct tcattcagct ccggttccca acgatcaagg   2760

cgagttacat gatcccccat gttgtgcaaa aaagcggtta gctccttcgg tcctccgatc   2820

gttgtcagaa gtaagttggc cgcagtgtta tcactcatgg ttatggcagc actgcataat   2880

tctcttactg tcatgccatc cgtaagatgc ttttctgtga ctggtgagta ctcaaccaag   2940

tcattctgag aatagtgtat gcggcgaccg agttgctctt gcccggcgtc aatacgggat   3000

aataccgcgc cacatagcag aactttaaaa gtgctcatca ttggaaaacg ttcttcgggg   3060

cgaaaactct caaggatctt accgctgttg agatccagtt cgatgtaacc cactcgtgca   3120

cccaactgat cttcagcatc ttttactttc accagcgttt ctgggtgagc aaaaacagga   3180

aggcaaaatg ccgcaaaaaa gggaataagg gcgacacgga aatgttgaat actcatactc   3240

ttcctttttc aatattattg aagcatttat cagggttatt gtctcatgag cggatacata   3300

tttgaatgta tttagaaaaa taaacaaata ggggttccgc gcacatttcc ccgaaaagtg   3360

ccacctgacg cgccctgtag cggcgcatta agcgcggcgg gtgtggtggt tacgcgcagc   3420

gtgaccgcta cacttgccag cgccctagcg cccgctcctt tcgctttctt cccttccttt   3480

ctcgccacgt tcgccggctt tccccgtcaa gctctaaatc gggggctccc tttagggttc   3540

cgatttagtg ctttacggca cctcgacccc aaaaaacttg attagggtga tggttcacgt   3600

agtgggccat cgccctgata gacggttttt cgccctttga cgttggagtc cacgttcttt   3660

aatagtggac tcttgttcca aactggaaca acactcaacc ctatctcggt ctattctttt   3720

gatttataag ggattttgcc gatttcggcc tattggttaa aaaatgagct gatttaacaa   3780

aaatttaacg cgaattttaa caaaatatta acgcttacaa tttccattcg ccattcaggc   3840

tgcgcaactg ttgggaaggg cgatcggtgc gggcctcttc gctattacgc cagctggcga   3900

aagggggatg tgctgcaagg cgattaagtt gggtaacgcc agggttttcc cagtcacgac   3960

gttgtaaaac gacggccagt gaattgtaat acgactcact atagggcgaa ttgggtaccg   4020

ggcccccccct cgaggtcgat ggtgtcgata agcttgatat cgaattcatg tcacacaaac   4080

cgatcttcgc ctcaaggaaa cctaattcta catccgagag actgccgaga tccagtctac   4140

actgattaat tttcgggcca ataatttaaa aaaatcgtgt tatataatat tatatgtatt   4200

atatatatac atcatgatga tactgacagt catgtcccat tgctaaatag acagactcca   4260

tctgccgcct ccaactgatg ttctcaatat ttaaggggtc atctcgcatt gtttaataat   4320

aaacagactc catctaccgc ctccaaatga tgttctcaaa atatattgta tgaacttatt   4380

tttattactt agtattatta gacaacttac ttgctttatg aaaaacactt cctatttagg   4440

aaacaattta taatggcagt tcgttcattt aacaatttat gtagaataaa tgttataaat   4500

gcgtatggga aatcttaaat atggatagca taaatgatat ctgcattgcc taattcgaaa   4560

tcaacagcaa cgaaaaaaat cccttgtaca acataaatag tcatcgagaa atatcaacta   4620

tcaaagaaca gctattcaca cgttactatt gagattatta ttggacgaga atcacacact   4680

caactgtctt tctctcttct agaaatacag gtacaagtat gtactattct cattgttcat   4740
```

```
acttctagtc atttcatccc acatattcct tggatttctc tccaatgaat gacattctat   4800
cttgcaaatt caacaattat aataagatat accaaagtag cggtatagtg gcaatcaaaa   4860
agcttctctg gtgtgcttct cgtatttatt tttattctaa tgatccatta aaggtatata   4920
tttatttctt gttatataat ccttttgttt attacatggg ctggatacat aaaggtattt   4980
tgatttaatt ttttgcttaa attcaatccc ccctcgttca gtgtcaactg taatggtagg   5040
aaattaccat acttttgaag aagcaaaaaa aatgaaagaa aaaaaaaatc gtatttccag   5100
gttagacgtt ccgcagaatc tagaatgcgg tatgcggtac attgttcttc gaacgtaaaa   5160
gttgcgctcc ctgagatatt gtacattttt gcttttacaa gtacaagtac atcgtacaac   5220
tatgtactac tgttgatgca tccacaacag tttgttttgt tttttttgt ttttttttt      5280
tctaatgatt cattaccgct atgtatacct acttgtactt gtagtaagcc gggttattgg   5340
cgttcaatta atcatagact tatgaatctg cacggtgtgc gctgcgagtt acttttagct   5400
tatgcatgct acttgggtgt aatattggga tctgttcgga aatcaacgga tgctcaaccg   5460
atttcgacag taattaatta agtcatacac aagtcagctt tcttcgagcc tcatataagt   5520
ataagtagtt caacgtatta gcactgtacc cagcatctcc gtatcgagaa acacaacaac   5580
atgccccatt ggacagatca tgcggataca caggttgtgc agtatcatac atactcgatc   5640
agacaggtcg tctgaccatc atacaagctg aacaagcgct ccatacttgc acgctctcta   5700
tatacacagt taaattacat atccatagtc taacctctaa cagttaatct tctggtaagc   5760
ctcccagcca gccttctggt atcgcttggc ctcctcaata ggatctcggt tctggccgta   5820
cagacctcgg ccgacaatta tgatatccgt tccggtagac atgacatcct caacagttcg   5880
gtactgctgt ccgagagcgt ctcccttgtc gtcaagaccc accccggggg tcagaataag   5940
ccagtcctca gagtcgccct taggtcggtt ctgggcaatg aagccaacca caaactcggg   6000
gtcggatcgg gcaagctcaa tggtctgctt ggagtactcg ccagtggcca gagagccctt   6060
gcaagacagc tcggccagca tgagcagacc tctggccagc ttctcgttgg gagaggggac   6120
taggaactcc ttgtactggg agttctcgta gtcagagacg tcctccttct tctgttcaga   6180
gacagtttcc tcggcaccag ctcgcaggcc agcaatgatt ccggttccgg gtacaccgtg   6240
ggcgttggtg atatcggacc actcggcgat tcggtgacac cggtactggt gcttgacagt   6300
gttgccaata tctgcgaact ttctgtcctc gaacaggaag aaaccgtgct taagagcaag   6360
ttccttgagg gggagcacag tgccggcgta ggtgaagtcg tcaatgatgt cgatatgggt   6420
tttgatcatg cacacataag gtccgacctt atcggcaagc tcaatgagct ccttggtggt   6480
ggtaacatcc agagaagcac acaggttggt tttcttggct gccacgagct tgagcactcg   6540
agcggcaaag gcggacttgt ggacgttagc tcgagcttcg taggagggca ttttggtggt   6600
gaagaggaga ctgaaataaa tttagtctgc agaacttttt atcggaacct tatctggggc   6660
agtgaagtat atgttatggt aatagttacg agttagttga acttatagat agactggact   6720
atacggctat cggtccaaat tagaaagaac gtcaatggct ctctgggcgt cgcctttgcc   6780
gacaaaaatg tgatcatgat gaaagccagc aatgacgttg cagctgatat tgttgtcggc   6840
caaccgcgcc gaaaacgcag ctgtcagacc cacagcctcc aacgaagaat gtatcgtcaa   6900
agtgatccaa gcacactcat agttggagtc gtactccaaa ggcggcaatg acgagtcaga   6960
cagatactcg                                                           6970
```

<210> SEQ ID NO 31
<211> LENGTH: 8253

<212> TYPE: DNA
<213> ORGANISM: Artificial Sequence
<220> FEATURE:
<223> OTHER INFORMATION: plasmid pY118

<400> SEQUENCE: 31

```
ggccgccacc gcggcccgag attccggcct cttcggccgc caagcgaccc gggtggacgt      60
ctagaggtac ctagcaatta acagatagtt tgccggtgat aattctctta acctcccaca     120
ctcctttgac ataacgattt atgtaacgaa actgaaattt gaccagatat tgtgtccgcg     180
gtggagctcc agcttttgtt ccctttagtg agggttaatt tcgagcttgg cgtaatcatg     240
gtcatagctg tttcctgtgt gaaattgtta tccgctcaca attccacaca acgtacgagc     300
cggaagcata aagtgtaaag cctggggtgc ctaatgagtg agctaactca cattaattgc     360
gttgcgctca ctgcccgctt tccagtcggg aaacctgtcg tgccagctgc attaatgaat     420
cggccaacgc gcggggagag gcggtttgcg tattgggcgc tcttccgctt cctcgctcac     480
tgactcgctg cgctcggtcg ttcggctgcg gcgagcggta tcagctcact caaaggcggt     540
aatacggtta tccacagaat caggggataa cgcaggaaag aacatgtgag caaaaggcca     600
gcaaaaggcc aggaaccgta aaaaggccgc gttgctggcg tttttccata ggctccgccc     660
ccctgacgag catcacaaaa atcgacgctc aagtcagagg tggcgaaacc cgacaggact     720
ataaagatac caggcgtttc cccctggaag ctccctcgtg cgctctcctg ttccgaccct     780
gccgcttacc ggatacctgt ccgcctttct cccttcggga agcgtggcgc tttctcatag     840
ctcacgctgt aggtatctca gttcggtgta ggtcgttcgc tccaagctgg gctgtgtgca     900
cgaacccccc gttcagcccg accgctgcgc cttatccggt aactatcgtc ttgagtccaa     960
cccggtaaga cacgacttat cgccactggc agcagccact ggtaacagga ttagcagagc    1020
gaggtatgta ggcggtgcta cagagttctt gaagtggtgg cctaactacg gctacactag    1080
aaggacagta tttggtatct gcgctctgct gaagccagtt accttcggaa aaagagttgg    1140
tagctcttga tccggcaaac aaaccaccgc tggtagcggt ggtttttttg tttgcaagca    1200
gcagattacg cgcagaaaaa aaggatctca agaagatcct ttgatctttt ctacggggtc    1260
tgacgctcag tggaacgaaa actcacgtta agggattttg gtcatgagat tatcaaaaag    1320
gatcttcacc tagatccttt taaattaaaa atgaagtttt aaatcaatct aaagtatata    1380
tgagtaaact tggtctgaca gttaccaatg cttaatcagt gaggcaccta tctcagcgat    1440
ctgtctattt cgttcatcca tagttgcctg actccccgtc gtgtagataa ctacgatacg    1500
ggagggctta ccatctggcc ccagtgctgc aatgataccg cgagacccac gctcaccggc    1560
tccagattta tcagcaataa accagccagc cggaagggcc gagcgcagaa gtggtcctgc    1620
aactttatcc gcctccatcc agtctattaa ttgttgccgg gaagctagag taagtagttc    1680
gccagttaat agtttgcgca acgttgttgc cattgctaca ggcatcgtgg tgtcacgctc    1740
gtcgtttggt atggcttcat tcagctccgg ttcccaacga tcaaggcgag ttacatgatc    1800
ccccatgttg tgcaaaaaag cggttagctc cttcggtcct ccgatcgttg tcagaagtaa    1860
gttggccgca gtgttatcac tcatggttat ggcagcactg cataattctc ttactgtcat    1920
gccatccgta agatgctttt ctgtgactgg tgagtactca accaagtcat tctgagaata    1980
gtgtatgcgg cgaccgagtt gctcttgccc ggcgtcaata cgggataata ccgcgccaca    2040
tagcagaact ttaaaagtgc tcatcattgg aaaacgttct tcggggcgaa aactctcaag    2100
gatcttaccg ctgttgagat ccagttcgat gtaacccact cgtgcaccca actgatcttc    2160
agcatctttt actttcacca gcgtttctgg gtgagcaaaa acaggaaggc aaaatgccgc    2220
```

```
aaaaaaggga ataagggcga cacggaaatg ttgaatactc atactcttcc tttttcaata   2280
ttattgaagc atttatcagg gttattgtct catgagcgga tacatatttg aatgtattta   2340
gaaaaataaa caaatagggg ttccgcgcac atttccccga aaagtgccac ctgacgcgcc   2400
ctgtagcggc gcattaagcg cggcgggtgt ggtggttacg cgcagcgtga ccgctacact   2460
tgccagcgcc ctagcgcccg ctcctttcgc tttcttccct tcctttctcg ccacgttcgc   2520
cggctttccc cgtcaagctc taaatcgggg gctcccttta gggttccgat ttagtgcttt   2580
acggcacctc gaccccaaaa aacttgatta gggtgatggt tcacgtagtg ggccatcgcc   2640
ctgatagacg gtttttcgcc ctttgacgtt ggagtccacg ttctttaata gtggactctt   2700
gttccaaact ggaacaacac tcaaccctat ctcggtctat tcttttgatt tataagggat   2760
tttgccgatt tcggcctatt ggttaaaaaa tgagctgatt taacaaaaat ttaacgcgaa   2820
ttttaacaaa atattaacgc ttacaatttc cattcgccat tcaggctgcg caactgttgg   2880
gaagggcgat cggtgcgggc ctcttcgcta ttacgccagc tggcgaaagg gggatgtgct   2940
gcaaggcgat taagttgggt aacgccaggg ttttcccagt cacgacgttg taaaacgacg   3000
gccagtgaat tgtaatacga ctcactatag ggcgaattgg gtaccgggcc ccccctcgag   3060
gtcgatggtg tcgataagct tgatatcgaa ttcatgtcac acaaaccgat cttcgcctca   3120
aggaaaccta attctacatc cgagagactg ccgagatcca gtctacactg attaattttc   3180
gggccaataa tttaaaaaaa tcgtgttata taatattata tgtattatat atatacatca   3240
tgatgatact gacagtcatg tcccattgct aaatagacag actccatctg ccgcctccaa   3300
ctgatgttct caatatttaa ggggtcatct cgcattgttt aataataaac agactccatc   3360
taccgcctcc aaatgatgtt ctcaaaatat attgtatgaa cttattttta ttacttagta   3420
ttattagaca acttacttgc tttatgaaaa acacttccta tttaggaaac aatttataat   3480
ggcagttcgt tcatttaaca atttatgtag aataaatgtt ataaatgcgt atgggaaatc   3540
ttaaatatgg atagcataaa tgatatctgc attgcctaat tcgaaatcaa cagcaacgaa   3600
aaaaatccct tgtacaacat aaatagtcat cgagaaatat caactatcaa agaacagcta   3660
ttcacacgtt actattgaga ttattattgg acgagaatca cacactcaac tgtctttctc   3720
tcttctagaa atacaggtac aagtatgtac tattctcatt gttcatactt ctagtcattt   3780
catcccacat attccttgga tttctctcca atgaatgaca ttctatcttg caaattcaac   3840
aattataata agatatacca aagtagcggt atagtggcaa tcaaaaagct tctctggtgt   3900
gcttctcgta tttattttta ttctaatgat ccattaaagg tatatattta tttcttgtta   3960
tataatcctt ttgtttatta catgggctgg atacataaag gtattttgat ttaatttttt   4020
gcttaaattc aatcccccct cgttcagtgt caactgtaat ggtaggaaat taccatactt   4080
ttgaagaagc aaaaaaaatg aaagaaaaaa aaaatcgtat ttccaggtta gacgttccgc   4140
agaatctaga atgcggtatg cggtacattg ttcttcgaac gtaaaagttg cgctccctga   4200
gatattgtac atttttgctt ttacaagtac aagtacatcg tacaactatg tactactgtt   4260
gatgcatcca caacagtttg ttttgttttt ttttgttttt tttttttcta atgattcatt   4320
accgctatgt atacctactt gtacttgtag taagccgggt tattggcgtt caattaatca   4380
tagacttatg aatctgcacg gtgtgcgctg cgagttactt ttagcttatg catgctactt   4440
gggtgtaata ttgggatctg ttcggaaatc aacggatgct caaccgattt cgacagtaat   4500
taattaagtc atacacaagt cagctttctt cgagcctcat ataagtataa gtagttcaac   4560
gtattagcac tgtacccagc atctccgtat cgagaaacac aacaacatgc cccattggac   4620
```

```
agatcatgcg gatacacagg ttgtgcagta tcatacatac tcgatcagac aggtcgtctg   4680
accatcatac aagctgaaca agcgctccat acttgcacgc tctctatata cacagttaaa   4740
ttacatatcc atagtctaac ctctaacagt taatcttctg gtaagcctcc cagccagcct   4800
tctggtatcg cttggcctcc tcaataggat ctcggttctg gccgtacaga cctcggccga   4860
caattatgat atccgttccg gtagacatga catcctcaac agttcggtac tgctgtccga   4920
gagcgtctcc cttgtcgtca agacccaccc cgggggtcag aataagccag tcctcagagt   4980
cgcccttagg tcggttctgg gcaatgaagc caaccacaaa ctcggggtcg gatcgggcaa   5040
gctcaatggt ctgcttggag tactcgccag tggccagaga gcccttgcaa gacagctcgg   5100
ccagcatgag cagacctctg gccagcttct cgttgggaga ggggactagg aactccttgt   5160
actgggagtt ctcgtagtca gagacgtcct ccttcttctg ttcagagaca gtttcctcgg   5220
caccagctcg caggccagca atgattccgg ttccgggtac accgtgggcg ttggtgatat   5280
cggaccactc ggcgattcgg tgacaccggt actggtgctt gacagtgttg ccaatatctg   5340
cgaactttct gtcctcgaac aggaagaaac cgtgcttaag agcaagttcc ttgaggggga   5400
gcacagtgcc ggcgtaggtg aagtcgtcaa tgatgtcgat atgggttttg atcatgcaca   5460
cataaggtcc gaccttatcg gcaagctcaa tgagctcctt ggtggtggta acatccagag   5520
aagcacacag gttggttttc ttggctgcca cgagcttgag cactcgagcg gcaaaggcgg   5580
acttgtggac gttagctcga gcttcgtagg agggcatttt ggtggtgaag aggagactga   5640
aataaattta gtctgcagaa ctttttatcg gaaccttatc tggggcagtg aagtatatgt   5700
tatggtaata gttacgagtt agttgaactt atagatagac tggactatac ggctatcggt   5760
ccaaattaga aagaacgtca atggctctct gggcgtcgcc tttgccgaca aaaatgtgat   5820
catgatgaaa gccagcaatg acgttgcagc tgatattgtt gtcggccaac cgcgccgaaa   5880
acgcagctgt cagacccaca gcctccaacg aagaatgtat cgtcaaagtg atccaagcac   5940
actcatagtt ggagtcgtac tccaaaggcg gcaatgacga gtcagacaga tactcgtcga   6000
cgcagtagga tgtcctgcac gggtcttttt gtggggtgtg gagaaagggg tgcttggaga   6060
tggaagccgg tagaaccggg ctgcttgtgc ttggagatgg aagccggtag aaccgggctg   6120
cttgggggga tttggggccg ctgggctcca aagaggggta ggcatttcgt tggggttacg   6180
taattgcggc atttgggtcc tgcgcgcatg tcccattggt cagaattagt ccggatagga   6240
gacttatcag ccaatcacag cgccggatcc acctgtaggt tgggttgggt gggagcaccc   6300
ctccacagag tagagtcaaa cagcagcagc aacatgatag ttgggggtgt gcgtgttaaa   6360
ggaaaaaaaa gaagcttggg ttatattccc gctctattta gaggttgcgg gatagacgcc   6420
gacggagggc aatggcgcca tggaaccttg cggatatcga tacgccgcgg cggactgcgt   6480
ccgaaccagc tccagcagcg ttttttccgg gccattgagc cgactgcgac cccgccaacg   6540
tgtcttggcc cacgcactca tgtcatgttg gtgttgggag gccacttttt aagtagcaca   6600
aggcacctag ctcgcagcaa ggtgtccgaa ccaaagaagc ggctgcagtg gtgcaaacgg   6660
ggcggaaacg gcgggaaaaa gccacggggg cacgaattga ggcacgccct cgaatttgag   6720
acgagtcacg gccccattcg cccgcgcaat ggctcgccaa cgcccggtct tttgcaccac   6780
atcaggttac cccaagccaa acctttgtgt taaaaagctt aacatattat accgaacgta   6840
ggtttgggcg ggcttgctcc gtctgtccaa ggcaacattt atataagggt ctgcatcgcc   6900
ggctcaattg aatctttttt cttcttctct tctctatatt cattcttgaa ttaaacacac   6960
atcaatccgc ggccgcacca tgggcaaggg tggagacggc ggcgcgcagg cggtgagcgg   7020
```

```
gaccgacgcg tctctcgctg aggtgagctc cgtcgatagc aagagcgtgc acgtcgtgct   7080

ctacggcaag cgcgtggatg tcacaaagtt ccagaaggca cacccgggcg ggagcaaggt   7140

gttccgcatc ttccaggagc gcgacgcgac ggagcagttc gagtcttacc actcgcccaa   7200

ggccatcaag atgatggagg gcatgctcaa gaagtcggag gatgcgcccg cttccgtgcc   7260

cctgccctcg cggtccacca tgggcacgga gttcaaggag atgattgagc gccacaagag   7320

ggctggtctc tacgaccctt gcccgttgga cgagctgttc aagctcacca tcgtccttgc   7380

gcccatcttc gtgggcgcct atctcgtgcg gagcggcgtc tcgcccctcg cgggcgcgct   7440

ctccatgggc tttggcttct acctcgacgg ctggcttgct cacgactacc tgcatcacgc   7500

agtcttcaag ggctcggtca acacgctcgt caaggcgaac aacgccatgg gatacgccct   7560

cggcttcctc cagggctacg acgtggcctg gtggcgcgcg cgccataaca cgcaccacgt   7620

gtgcaccaac gaggatggtt cggacccgga catcaagacg gcgcccctgc tcatctacgt   7680

gcgagagaac ccgtccattg ccaagcggct caacttcttc cagcgctggc agcagtacta   7740

ctatgtgccg accatggcca tcctcgacct ctactggcgc ctggagtcca tcgcgtacgt   7800

ggctgtgcgc ctgcctaaga tgtggatgca ggccgccgct cttgccgctc actacgcgct   7860

cctgtgctgg gtcttcgcag cgcatctcaa cctcatccct ctcatgatgg ttgcacgcgg   7920

cttcgcgacg ggcatcgttg tctttgcaac ccactatggt gaggacatcc tcgaccgcga   7980

gcacgtcgag ggcatgacgc tcgtcgagca gaccgccaag acctcccgta acatcacggg   8040

cggctggcta gtgaacgtgc tcacgggctt catctccctg cagaccgagc atcacctctt   8100

ccccatgatg cccaccggca acctaatgac tatccagccc gaggtacgcg acttcttcaa   8160

gaagcatggc ctcgagtacc gcgagggcaa cctcttccag tgcgtgcacc agaacatcaa   8220

ggctctcgcc ttcgagcacc tcctccactg agc                                8253
```

<210> SEQ ID NO 32
<211> LENGTH: 777
<212> TYPE: DNA
<213> ORGANISM: Euglena gracilis

<400> SEQUENCE: 32

```
atggaggtgg tgaatgaaat agtctcaatt gggcaggaag ttttacccaa agttgattat     60

gcccaactct ggagtgatgc cagtcactgt gaggtgcttt acttgtccat cgcatttgtc    120

atcttgaagt tcactcttgg ccccccttggt ccaaaaggtc agtctcgtat gaagtttgtt    180

ttcaccaatt acaaccttct catgtccatt tattcgttgg gatcattcct ctcaatggca    240

tatgccatgt acaccatcgg tgttatgtct gacaactgcg agaaggcttt tgacaacaac    300

gtcttcagga tcaccacgca gttgttctat ttgagcaagt tcctggagta tattgactcc    360

ttctatttgc cactgatggg caagcctctg acctggttgc aattcttcca tcatttgggg    420

gcaccgatgg atatgtggct gttctataat taccgaaatg aagctgtttg gatttttgtg    480

ctgttgaatg gtttcatcca ctggatcatg tacggttatt attggaccag attgatcaag    540

ctgaagttcc ccatgccaaa atccctgatt acatcaatgc agatcattca attcaatgtt    600

ggtttctaca ttgtctggaa gtacaggaac attccctgtt atcgccaaga tgggatgagg    660

atgtttggct ggttcttcaa ttacttttat gttggcacag tcttgtgttt gttcttgaat    720

ttctatgtgc aaacgtatat cgtcaggaag cacaagggag ccaaaaagat tcagtga       777
```

<210> SEQ ID NO 33
<211> LENGTH: 30

<212> TYPE: DNA
<213> ORGANISM: Artificial Sequence
<220> FEATURE:
<223> OTHER INFORMATION: sense oligonucleotide oEugEL1-1 primer

<400> SEQUENCE: 33
agcggccgca ccatggaggt ggtgaatgaa 30

<210> SEQ ID NO 34
<211> LENGTH: 30
<212> TYPE: DNA
<213> ORGANISM: Artificial Sequence
<220> FEATURE:
<223> OTHER INFORMATION: sense oligonucleotide oEugEL1-2 primer

<400> SEQUENCE: 34
tgcggccgct cactgaatct tttggctcc 30

<210> SEQ ID NO 35
<211> LENGTH: 4311
<212> TYPE: DNA
<213> ORGANISM: Artificial Sequence
<220> FEATURE:
<223> OTHER INFORMATION: plasmid pKR906

<400> SEQUENCE: 35
agcggccgca ccatggaggt ggtgaatgaa atagtctcaa ttgggcagga agttttaccc 60
aaagttgatt atgcccaact ctggagtgat gccagtcact gtgaggtgct ttacttgtcc 120
atcgcatttg tcatcttgaa gttcactctt ggcccccttg gtccaaaagg tcagtctcgt 180
atgaagtttg ttttcaccaa ttacaacctt ctcatgtcca tttattcgtt gggatcattc 240
ctctcaatgg catatgccat gtacaccatc ggtgttatgt ctgacaactg cgagaaggct 300
tttgacaaca acgtcttcag gatcaccacg cagttgttct atttgagcaa gttcctggag 360
tatattgact ccttctattt gccactgatg ggcaagcctc tgacctggtt gcaattcttc 420
catcatttgg gggcaccgat ggatatgtgg ctgttctata attaccgaaa tgaagctgtt 480
tggatttttg tgctgttgaa tggtttcatc cactggatca tgtacggtta ttattggacc 540
agattgatca agctgaagtt ccccatgcca aaatccctga ttacatcaat gcagatcatt 600
caattcaatg ttggtttcta cattgtctgg aagtacagga acattccctg ttatcgccaa 660
gatgggatga ggatgtttgg ctggttcttc aattactttt atgttggcac agtcttgtgt 720
ttgttcttga atttctatgt gcaaacgtat atcgtcagga agcacaaggg agccaaaaag 780
attcagtgag cggccgcacc tgaattccag cacactggcg gccgttacta gtggatccga 840
gctcggtacc aagcttgatg catagcttga gtattctaac gcgtcaccta aatagcttgg 900
cgtaatcatg gtcatagctg tttcctgtgt gaaattgtta tccgctcaca attccacaca 960
acatacgagc cggaagcata aagtgtaaag cctggggtgc ctaatgagtg agctaactca 1020
cattaattgc gttgcgctca ctgcccgctt tccagtcggg aaacctgtcg tgccagctgc 1080
attaatgaat cggccaacgc gcggggagag gcggtttgcg tattgggcgc tcttccgctt 1140
cctcgctcac tgactcgctg cgctcggtcg ttcggctgcg gcgagcggta tcagctcact 1200
caaaggcggt aatacggtta tccacagaat caggggataa cgcaggaaag aacatgtgag 1260
caaaaggcca gcaaaagccc aggaaccgta aaaaggccgc gttgctggcg tttttccata 1320
ggctccgccc ccctgacgag catcacaaaa atcgacgctc aagtcagagg tggcgaaacc 1380
cgacaggact ataaagatac caggcgtttc cccctggaag ctccctcgtg cgctctcctg 1440
ttccgaccct gccgcttacc ggatacctgt ccgcctttct cccttcggga agcgtggcgc 1500

```
tttctcatag ctcacgctgt aggtatctca gttcggtgta ggtcgttcgc tccaagctgg   1560
gctgtgtgca cgaacccccc gttcagcccg accgctgcgc cttatccggt aactatcgtc   1620
ttgagtccaa cccggtaaga cacgacttat cgccactggc agcagccact ggtaacagga   1680
ttagcagagc gaggtatgta ggcggtgcta cagagttctt gaagtggtgg cctaactacg   1740
gctacactag aaggacagta tttggtatct gcgctctgct gaagccagtt accttcggaa   1800
aaagagttgg tagctcttga tccggcaaac aaaccaccgc tggtagcggt ggtttttttg   1860
tttgcaagca gcagattacg cgcagaaaaa aaggatctca agaagatcct ttgatctttt   1920
ctacggggtc tgacgctcag tggaacgaaa actcacgtta agggattttg gtcatgagat   1980
tatcaaaaag gatcttcacc tagatccttt taaattaaaa atgaagtttt agcacgtgtc   2040
agtcctgctc ctcggccacg aagtgcacgc agttgccggc cgggtcgcgc agggcgaact   2100
cccgccccca cggctgctcg ccgatctcgg tcatggccgg cccggaggcg tcccggaagt   2160
tcgtggacac gacctccgac cactcggcgt acagctcgtc caggccgcgc acccacaccc   2220
aggccagggt gttgtccggc accacctggt cctggaccgc gctgatgaac agggtcacgt   2280
cgtcccggac cacaccggcg aagtcgtcct ccacgaagtc ccgggagaac ccgagccggt   2340
cggtccagaa ctcgaccgct ccggcgacgt cgcgcgcggt gagcaccgga acggcactgg   2400
tcaacttggc catggtggcc ctcctcacgt gctattattg aagcatttat cagggttatt   2460
gtctcatgag cggatacata tttgaatgta tttagaaaaa taaacaaata ggggttccgc   2520
gcacatttcc ccgaaaagtg ccacctgtat gcggtgtgaa ataccgcaca gatgcgtaag   2580
gagaaaatac cgcatcagga aattgtaagc gttaataatt cagaagaact cgtcaagaag   2640
gcgatagaag gcgatgcgct gcgaatcggg agcggcgata ccgtaaagca cgaggaagcg   2700
gtcagcccat tcgccgccaa gctcttcagc aatatcacgg gtagccaacg ctatgtcctg   2760
atagcggtcc gccacaccca gccggccaca gtcgatgaat ccagaaaagc ggccattttc   2820
caccatgata ttcggcaagc aggcatcgcc atgggtcacg acgagatcct cgccgtcggg   2880
catgctcgcc ttgagcctgg cgaacagttc ggctggcgcg agcccctgat gctcttcgtc   2940
cagatcatcc tgatcgacaa gaccggcttc catccgagta cgtgctcgct cgatgcgatg   3000
tttcgcttgg tggtcgaatg ggcaggtagc cggatcaagc gtatgcagcc gccgcattgc   3060
atcagccatg atggatactt tctcggcagg agcaaggtga gatgacagga gatcctgccc   3120
cggcacttcg cccaatagca gccagtccct tcccgcttca gtgacaacgt cgagcacagc   3180
tgcgcaagga acgcccgtcg tggccagcca cgatagccgc gctgcctcgt cttgcagttc   3240
attcagggca ccggacaggt cggtcttgac aaaaagaacc gggcgcccct gcgctgacag   3300
ccggaacacg gcggcatcag agcagccgat tgtctgttgt gcccagtcat agccgaatag   3360
cctctccacc caagcggccg gagaacctgc gtgcaatcca tcttgttcaa tcatgcgaaa   3420
cgatcctcat cctgtctctt gatcagagct tgatcccctg cgccatcaga tccttggcgg   3480
cgagaaagcc atccagttta ctttgcaggg cttcccaacc ttaccagagg gcgccccagc   3540
tggcaattcc ggttcgcttg ctgtccataa aaccgcccag tctagctatc gccatgtaag   3600
cccactgcaa gctacctgct ttctctttgc gcttgcgttt tcccttgtcc agatagccca   3660
gtagctgaca ttcatccggg gtcagcaccg tttctgcgga ctggctttct acgtgaaaag   3720
gatctaggtg aagatccttt ttgataatct catgcctgac atttatattc cccagaacat   3780
caggttaatg gcgtttttga tgtcattttc gcggtggctg agatcagcca cttcttcccc   3840
gataacggag accggcacac tggccatatc ggtggtcatc atgcgccagc tttcatcccc   3900
```

```
gatatgcacc accgggtaaa gttcacggga gactttatct gacagcagac gtgcactggc   3960

caggggggatc accatccgtc gccccggcgt gtcaataata tcactctgta catccacaaa   4020

cagacgataa cggctctctc ttttataggt gtaaacctta aactgccgta cgtataggct   4080

gcgcaactgt tgggaagggc gatcggtgcg ggcctcttcg ctattacgcc agctggcgaa   4140

agggggatgt gctgcaaggc gattaagttg ggtaacgcca gggttttccc agtcacgacg   4200

ttgtaaaacg acggccagtg aattgtaata cgactcacta tagggcgaat tgggccctct   4260

agatgcatgc tcgagcggcc gccagtgtga tggatatctg cagaattcag g            4311
```

```
<210> SEQ ID NO 36
<211> LENGTH: 3983
<212> TYPE: DNA
<213> ORGANISM: Artificial Sequence
<220> FEATURE:
<223> OTHER INFORMATION: plasmid pKR132

<400> SEQUENCE: 36

ctagagtcga cctgcaggca tgcaagcttg gcgtaatcat ggtcatagct gtttcctgtg     60

tgaaattgtt atccgctcac aattccacac aacatacgag ccggaagcat aaagtgtaaa    120

gcctggggtg cctaatgagt gagctaactc acattaattg cgttgcgctc actgcccgct    180

ttccagtcgg gaaacctgtc gtgccagctg cattaatgaa tcggccaacg cgcggggaga    240

ggcggtttgc gtattgggcg ctcttccgct tcctcgctca ctgactcgct gcgctcggtc    300

gttcggctgc ggcgagcggt atcagctcac tcaaaggcgg taatacggtt atccacagaa    360

tcaggggata acgcaggaaa gaacatgtga gcaaaaggcc agcaaaaggc caggaaccgt    420

aaaaaggccg cgttgctggc gtttttccat aggctccgcc cccctgacga gcatcacaaa    480

aatcgacgct caagtcagag gtggcgaaac ccgacaggac tataaagata ccaggcgttt    540

ccccctggaa gctccctcgt gcgctctcct gttccgaccc tgccgcttac cggatacctg    600

tccgcctttc tcccttcggg aagcgtggcg ctttctcata gctcacgctg taggtatctc    660

agttcggtgt aggtcgttcg ctccaagctg ggctgtgtgc acgaaccccc cgttcagccc    720

gaccgctgcg ccttatccgg taactatcgt cttgagtcca acccggtaag acacgactta    780

tcgccactgg cagcagccac tggtaacagg attagcagag cgaggtatgt aggcggtgct    840

acagagttct tgaagtggtg gcctaactac ggctacacta gaaggacagt atttggtatc    900

tgcgctctgc tgaagccagt taccttcgga aaaagagttg gtagctcttg atccggcaaa    960

caaaccaccg ctggtagcgg tggttttttt gtttgcaagc agcagattac gcgcagaaaa   1020

aaaggatctc aagaagatcc tttgatcttt tctacggggt ctgacgctca gtggaacgaa   1080

aactcacgtt aagggatttt ggtcatgaga ttatcaaaaa ggatcttcac ctagatcctt   1140

ttaaattaaa aatgaagttt taaatcaatc taaagtatat atgagtaaac ttggtctgac   1200

agttaccaat gcttaatcag tgaggcacct atctcagcga tctgtctatt tcgttcatcc   1260

atagttgcct gactccccgt cgtgtagata actacgatac gggagggctt accatctggc   1320

cccagtgctg caatgatacc gcgagaccca cgctcaccgg ctccagattt atcagcaata   1380

aaccagccag ccggaagggc cgagcgcaga agtggtcctg caactttatc cgcctccatc   1440

cagtctatta attgttgccg ggaagctaga gtaagtagtt cgccagttaa tagtttgcgc   1500

aacgttgttg ccattgctac aggcatcgtg gtgtcacgct cgtcgtttgg tatggcttca   1560

ttcagctccg gttcccaacg atcaaggcga gttacatgat cccccatgtt gtgcaaaaaa   1620

gcggttagct ccttcggtcc tccgatcgtt gtcagaagta agttggccgc agtgttatca   1680
```

```
ctcatggtta tggcagcact gcataattct cttactgtca tgccatccgt aagatgcttt   1740
tctgtgactg gtgagtactc aaccaagtca ttctgagaat agtgtatgcg gcgaccgagt   1800
tgctcttgcc cggcgtcaat acgggataat accgcgccac atagcagaac tttaaaagtg   1860
ctcatcattg gaaaacgttc ttcggggcga aaactctcaa ggatcttacc gctgttgaga   1920
tccagttcga tgtaacccac tcgtgcaccc aactgatctt cagcatcttt tactttcacc   1980
agcgtttctg ggtgagcaaa aacaggaagg caaaatgccg caaaaaaggg aataagggcg   2040
acacggaaat gttgaatact catactcttc ctttttcaat attattgaag catttatcag   2100
ggttattgtc tcatgagcgg atacatattt gaatgtattt agaaaaataa acaaataggg   2160
gttccgcgca catttccccg aaaagtgcca cctgacgtct aagaaaccat tattatcatg   2220
acattaacct ataaaaatag gcgtatcacg aggccctttc gtctcgcgcg tttcggtgat   2280
gacggtgaaa acctctgaca catgcagctc ccggagacgg tcacagcttg tctgtaagcg   2340
gatgccggga gcagacaagc ccgtcagggc gcgtcagcgg gtgttggcgg gtgtcggggc   2400
tggcttaact atgcggcatc agagcagatt gtactgagag tgcaccatat gcggtgtgaa   2460
ataccgcaca gatgcgtaag gagaaaatac cgcatcaggc gccattcgcc attcaggctg   2520
cgcaactgtt gggaagggcg atcggtgcgg gcctcttcgc tattacgcca gctggcgaaa   2580
gggggatgtg ctgcaaggcg attaagttgg gtaacgccag ggttttccca gtcacgacgt   2640
tgtaaaacga cggccagtga attcgagctc ggtacccggg gatcctctag acctgcaggc   2700
caactgcgtt tggggctcca gattaaacga cgccgtttcg ttcctttcgc ttcacggctt   2760
aacgatgtcg tttctgtctg tgcccaaaaa ataaaggcat ttgttatttg caccagatat   2820
ttactaagtg caccctagtt tgacaagtag gcgataatta caaatagatg cggtgcaaat   2880
aataaatttt gaaggaaata attacaaaag aacagaactt atatttactt tattttaaaa   2940
aactaaaatg aaagaacaaa aaaagtaaaa aatacaaaaa atgtgcttta accactttca   3000
ttatttgtta cagaaagtat gattctactc aaattgatct gttgtatctg gtgctgcctt   3060
gtcacactgg cgatttcaat cccctaaaga tatggtgcaa actgcgaagt gatcaatatc   3120
tgctcggtta atttagatta attaataata ttcaacgtga tgtaccaaaa aaagacaatt   3180
ttttgctcca ttgacaaatt aaacctcatc aaggtaattt ccaaacctat aagcaaaaaa   3240
atttcacatt aattggcccg caatcctatt agtcttatta tactagagta ggaaaaaaaa   3300
caattacaca acttgtctta ttattctcta tgctaatgaa tatttttccc ttttgttaga   3360
aatcagtgtt tcctaattta ttgagtatta attccactca ccgcatatat ttaccgttga   3420
ataagaaaat tttacacata attcttttta agataaataa tttttttata ctagatctta   3480
tatgattacg tgaagccaag tgggttatac taatgatata taatgtttga tagtaatcag   3540
tttataaacc aaatgcatgg aaatgttacg tggaagcacg taaattaaca agcattgaag   3600
caaatgcagc caccgcacca aaaccacccc acttcacttc cacgtaccat attccatgca   3660
actacaacac cctaaaactt caataaatgc ccccaccttc acttcacttc acccatcaat   3720
agcaagcggc cgcgaagtta aaagcaatgt tgtcacttgt cgtactaaca catgatgtga   3780
tagtttatgc tagctagcta taacataagc tgtctctgag tgtgttgtat attaataaag   3840
atcatcactg gtgaatggtg atcgtgtacg taccctactt agtaggcaat ggaagcactt   3900
agagtgtgct ttgtgcatgg ccttgcctct gttttgagac ttttgtaatg ttttcgagtt   3960
taaatctttg cctttgcgta cgt                                           3983
```

<210> SEQ ID NO 37
<211> LENGTH: 4771
<212> TYPE: DNA
<213> ORGANISM: Artificial Sequence
<220> FEATURE:
<223> OTHER INFORMATION: plasmid pKR953

<400> SEQUENCE: 37

```
ggccgcgaag ttaaaagcaa tgttgtcact tgtcgtacta acacatgatg tgatagttta     60
tgctagctag ctataacata agctgtctct gagtgtgttg tatattaata aagatcatca    120
ctggtgaatg gtgatcgtgt acgtacccta cttagtaggc aatggaagca cttagagtgt    180
gctttgtgca tggccttgcc tctgttttga gacttttgta atgttttcga gtttaaatct    240
ttgcctttgc gtacgtctag agtcgacctg caggcatgca agcttggcgt aatcatggtc    300
atagctgttt cctgtgtgaa attgttatcc gctcacaatt ccacacaaca tacgagccgg    360
aagcataaag tgtaaagcct ggggtgccta atgagtgagc taactcacat taattgcgtt    420
gcgctcactg cccgctttcc agtcgggaaa cctgtcgtgc cagctgcatt aatgaatcgg    480
ccaacgcgcg gggagaggcg gtttgcgtat tgggcgctct tccgcttcct cgctcactga    540
ctcgctgcgc tcggtcgttc ggctgcggcg agcggtatca gctcactcaa aggcggtaat    600
acggttatcc acagaatcag gggataacgc aggaaagaac atgtgagcaa aaggccagca    660
aaaggccagg aaccgtaaaa aggccgcgtt gctggcgttt ttccataggc tccgcccccc    720
tgacgagcat cacaaaaatc gacgctcaag tcagaggtgg cgaaacccga caggactata    780
aagataccag gcgtttcccc ctggaagctc cctcgtgcgc tctcctgttc cgaccctgcc    840
gcttaccgga tacctgtccg cctttctccc ttcgggaagc gtggcgcttt ctcatagctc    900
acgctgtagg tatctcagtt cggtgtaggt cgttcgctcc aagctgggct gtgtgcacga    960
accccccgtt cagcccgacc gctgcgcctt atccggtaac tatcgtcttg agtccaaccc   1020
ggtaagacac gacttatcgc cactggcagc agccactggt aacaggatta gcagagcgag   1080
gtatgtaggc ggtgctacag agttcttgaa gtggtggcct aactacggct acactagaag   1140
gacagtattt ggtatctgcg ctctgctgaa gccagttacc ttcggaaaaa gagttggtag   1200
ctcttgatcc ggcaaacaaa ccaccgctgg tagcggtggt ttttttgttt gcaagcagca   1260
gattacgcgc agaaaaaaag gatctcaaga agatcctttg atcttttcta cggggtctga   1320
cgctcagtgg aacgaaaact cacgttaagg gattttggtc atgagattat caaaaaggat   1380
cttcacctag atccttttaa attaaaaatg aagttttaaa tcaatctaaa gtatatatga   1440
gtaaacttgg tctgacagtt accaatgctt aatcagtgag gcacctatct cagcgatctg   1500
tctatttcgt tcatccatag ttgcctgact ccccgtcgtg tagataacta cgatacggga   1560
gggcttacca tctggcccca gtgctgcaat gataccgcga gacccacgct caccggctcc   1620
agatttatca gcaataaacc agccagccgg aagggccgag cgcagaagtg gtcctgcaac   1680
tttatccgcc tccatccagt ctattaattg ttgccgggaa gctagagtaa gtagttcgcc   1740
agttaatagt ttgcgcaacg ttgttgccat tgctacaggc atcgtggtgt cacgctcgtc   1800
gtttggtatg gcttcattca gctccggttc ccaacgatca aggcgagtta catgatcccc   1860
catgttgtgc aaaaaagcgg ttagctcctt cggtcctccg atcgttgtca gaagtaagtt   1920
ggccgcagtg ttatcactca tggttatggc agcactgcat aattctctta ctgtcatgcc   1980
atccgtaaga tgcttttctg tgactggtga gtactcaacc aagtcattct gagaatagtg   2040
tatgcggcga ccgagttgct cttgcccggc gtcaatacgg gataataccg cgccacatag   2100
cagaacttta aaagtgctca tcattggaaa acgttcttcg gggcgaaaac tctcaaggat   2160
```

```
cttaccgctg ttgagatcca gttcgatgta acccactcgt gcacccaact gatcttcagc   2220
atcttttact ttcaccagcg tttctgggtg agcaaaaaca ggaaggcaaa atgccgcaaa   2280
aaagggaata agggcgacac ggaaatgttg aatactcata ctcttccttt ttcaatatta   2340
ttgaagcatt tatcagggtt attgtctcat gagcggatac atatttgaat gtatttagaa   2400
aaataaacaa ataggggttc cgcgcacatt tccccgaaaa gtgccacctg acgtctaaga   2460
aaccattatt atcatgacat taacctataa aaataggcgt atcacgaggc cctttcgtct   2520
cgcgcgtttc ggtgatgacg gtgaaaacct ctgacacatg cagctcccgg agacggtcac   2580
agcttgtctg taagcggatg ccgggagcag acaagcccgt cagggcgcgt cagcgggtgt   2640
tggcgggtgt cggggctggc ttaactatgc ggcatcagag cagattgtac tgagagtgca   2700
ccatatgcgg tgtgaaatac cgcacagatg cgtaaggaga aaataccgca tcaggcgcca   2760
ttcgccattc aggctgcgca actgttggga agggcgatcg gtgcgggcct cttcgctatt   2820
acgccagctg gcgaaagggg gatgtgctgc aaggcgatta agttgggtaa cgccagggtt   2880
ttcccagtca cgacgttgta aaacgacggc cagtgaattc gagctcggta cccggggatc   2940
ctctagacct gcaggccaac tgcgtttggg gctccagatt aaacgacgcc gtttcgttcc   3000
tttcgcttca cggcttaacg atgtcgtttc tgtctgtgcc caaaaaataa aggcatttgt   3060
tatttgcacc agatatttac taagtgcacc ctagtttgac aagtaggcga taattacaaa   3120
tagatgcggt gcaaataata aattttgaag gaaataatta caaaagaaca gaacttatat   3180
ttactttatt ttaaaaaact aaaatgaaag aacaaaaaaa gtaaaaaata caaaaaatgt   3240
gctttaacca ctttcattat ttgttacaga aagtatgatt ctactcaaat tgatctgttg   3300
tatctggtgc tgccttgtca cactggcgat ttcaatcccc taaagatatg gtgcaaactg   3360
cgaagtgatc aatatctgct cggttaattt agattaatta ataatattca acgtgatgta   3420
ccaaaaaaag acaatttttt gctccattga caaattaaac ctcatcaagg taatttccaa   3480
acctataagc aaaaaaattt cacattaatt ggcccgcaat cctattagtc ttattatact   3540
agagtaggaa aaaaaacaat tacacaactt gtcttattat tctctatgct aatgaatatt   3600
tttccctttt gttagaaatc agtgtttcct aatttattga gtattaattc cactcaccgc   3660
atatatttac cgttgaataa gaaaatttta cacataattc tttttaagat aaataatttt   3720
tttatactag atcttatatg attacgtgaa gccaagtggg ttatactaat gatatataat   3780
gtttgatagt aatcagttta taaaccaaat gcatggaaat gttacgtgga agcacgtaaa   3840
ttaacaagca ttgaagcaaa tgcagccacc gcaccaaaac caccccactt cacttccacg   3900
taccatattc catgcaacta caacacccta aaacttcaat aaatgccccc accttcactt   3960
cacttcaccc atcaatagca agcggccgca ccatggaggt ggtgaatgaa atagtctcaa   4020
ttgggcagga agttttaccc aaagttgatt atgcccaact ctggagtgat gccagtcact   4080
gtgaggtgct ttacttgtcc atcgcatttg tcatcttgaa gttcactctt ggcccccttg   4140
gtccaaaagg tcagtctcgt atgaagtttg ttttcaccaa ttacaacctt ctcatgtcca   4200
tttattcgtt gggatcattc ctctcaatgg catatgccat gtacaccatc ggtgttatgt   4260
ctgacaactg cgagaaggct tttgacaaca acgtcttcag gatcaccacg cagttgttct   4320
atttgagcaa gttcctggag tatattgact ccttctattt gccactgatg ggcaagcctc   4380
tgacctggtt gcaattcttc catcatttgg gggcaccgat ggatatgtgg ctgttctata   4440
attaccgaaa tgaagctgtt tggatttttg tgctgttgaa tggtttcatc cactggatca   4500
tgtacggtta ttattggacc agattgatca agctgaagtt ccccatgcca aaatccctga   4560
```

```
ttacatcaat gcagatcatt caattcaatg ttggtttcta cattgtctgg aagtacagga   4620

acattccctg ttatcgccaa gatgggatga ggatgtttgg ctggttcttc aattactttt   4680

atgttggcac agtcttgtgt ttgttcttga atttctatgt gcaaacgtat atcgtcagga   4740

agcacaaggg agccaaaaag attcagtgag c                                  4771
```

<210> SEQ ID NO 38
<211> LENGTH: 5492
<212> TYPE: DNA
<213> ORGANISM: Artificial Sequence
<220> FEATURE:
<223> OTHER INFORMATION: plasmid pKR287

<400> SEQUENCE: 38

```
ggccgcattt cgcaccaaat caatgaaagt aataatgaaa agtctgaata agaatactta     60

ggcttagatg cctttgttac ttgtgtaaaa taacttgagt catgtacctt tggcggaaac    120

agaataaata aaaggtgaaa ttccaatgct ctatgtataa gttagtaata cttaatgtgt    180

tctacggttg tttcaatatc atcaaactct aattgaaact ttagaaccac aaatctcaat    240

cttttcttaa tgaaatgaaa aatcttaatt gtaccatgtt tatgttaaac accttacaat    300

tggttggaga ggaggaccaa ccgatgggac aacattggga gaaagagatt caatggagat    360

ttggatagga gaacaacatt ctttttcact tcaatacaag atgagtgcaa cactaaggat    420

atgtatgaga ctttcagaag ctacgacaac atagatgagt gaggtggtga ttcctagcaa    480

gaaagacatt agaggaagcc aaaatcgaac aaggaagaca tcaagggcaa gagacaggac    540

catccatctc aggaaaagga gctttgggat agtccgagaa gttgtacaag aaattttttg    600

gagggtgagt gatgcattgc tggtgacttt aactcaatca aaattgagaa agaaagaaaa    660

gggagggggc tcacatgtga atagaaggga aacgggagaa ttttacagtt ttgatctaat    720

gggcatccca gctagtggta acatattcac catgtttaac cttcacgtac gtctagagga    780

tccccgggta ccgagctcga attcactggc cgtcgtttta caacgtcgtg actgggaaaa    840

ccctggcgtt acccaactta atcgccttgc agcacatccc cctttcgcca gctggcgtaa    900

tagcgaagag gcccgcaccg atcgcccttc ccaacagttg cgcagcctga atggcgaatg    960

gcgcctgatg cggtattttc tccttacgca tctgtgcggt atttcacacc gcatatggtg   1020

cactctcagt acaatctgct ctgatgccgc atagttaagc cagccccgac acccgccaac   1080

acccgctgac gcgccctgac gggcttgtct gctcccggca tccgcttaca gacaagctgt   1140

gaccgtctcc gggagctgca tgtgtcagag gttttcaccg tcatcaccga aacgcgcgag   1200

acgaaagggc ctcgtgatac gcctattttt ataggttaat gtcatgataa taatggtttc   1260

ttagacgtca ggtggcactt ttcggggaaa tgtgcgcgga acccctattt gtttattttt   1320

ctaaatacat tcaaatatgt atccgctcat gagacaataa ccctgataaa tgcttcaata   1380

atattgaaaa aggaagagta tgagtattca acatttccgt gtcgccctta ttcccttttt   1440

tgcggcattt tgccttcctg tttttgctca cccagaaacg ctggtgaaag taaaagatgc   1500

tgaagatcag ttgggtgcac gagtgggtta catcgaactg gatctcaaca gcggtaagat   1560

ccttgagagt tttcgccccg aagaacgttt tccaatgatg agcactttta aagttctgct   1620

atgtggcgcg gtattatccc gtattgacgc cgggcaagag caactcggtc gccgcataca   1680

ctattctcag aatgacttgg ttgagtactc accagtcaca gaaaagcatc ttacggatgg   1740

catgacagta agagaattat gcagtgctgc cataaccatg agtgataaca ctgcggccaa   1800

cttacttctg acaacgatcg gaggaccgaa ggagctaacc gcttttttgc acaacatggg   1860
```

```
ggatcatgta actcgccttg atcgttggga accggagctg aatgaagcca taccaaacga   1920
cgagcgtgac accacgatgc ctgtagcaat ggcaacaacg ttgcgcaaac tattaactgg   1980
cgaactactt actctagctt cccggcaaca attaatagac tggatggagg cggataaagt   2040
tgcaggacca cttctgcgct cggcccttcc ggctggctgg tttattgctg ataaatctgg   2100
agccggtgag cgtgggtctc gcggtatcat tgcagcactg gggccagatg gtaagccctc   2160
ccgtatcgta gttatctaca cgacggggag tcaggcaact atggatgaac gaaatagaca   2220
gatcgctgag ataggtgcct cactgattaa gcattggtaa ctgtcagacc aagtttactc   2280
atatatactt tagattgatt taaaacttca tttttaattt aaaaggatct aggtgaagat   2340
cctttttgat aatctcatga ccaaaatccc ttaacgtgag ttttcgttcc actgagcgtc   2400
agaccccgta gaaaagatca aaggatcttc ttgagatcct ttttttctgc gcgtaatctg   2460
ctgcttgcaa acaaaaaaac caccgctacc agcggtggtt tgtttgccgg atcaagagct   2520
accaactctt tttccgaagg taactggctt cagcagagcg cagataccaa atactgtcct   2580
tctagtgtag ccgtagttag gccaccactt caagaactct gtagcaccgc ctacatacct   2640
cgctctgcta atcctgttac cagtggctgc tgccagtggc gataagtcgt gtcttaccgg   2700
gttggactca agacgatagt taccggataa ggcgcagcgg tcgggctgaa cggggggttc   2760
gtgcacacag cccagcttgg agcgaacgac ctacaccgaa ctgagatacc tacagcgtga   2820
gctatgagaa agcgccacgc ttcccgaagg gagaaaggcg gacaggtatc cggtaagcgg   2880
cagggtcgga acaggagagc gcacgaggga gcttccaggg ggaaacgcct ggtatcttta   2940
tagtcctgtc gggtttcgcc acctctgact tgagcgtcga tttttgtgat gctcgtcagg   3000
ggggcggagc ctatggaaaa acgccagcaa cgcggccttt ttacggttcc tggccttttg   3060
ctggcctttt gctcacatgt tctttcctgc gttatcccct gattctgtgg ataaccgtat   3120
taccgccttt gagtgagctg ataccgctcg ccgcagccga acgaccgagc gcagcgagtc   3180
agtgagcgag gaagcggaag agcgcccaat acgcaaaccg cctctccccg cgcgttggcc   3240
gattcattaa tgcagctggc acgacaggtt tcccgactgg aaagcgggca gtgagcgcaa   3300
cgcaattaat gtgagttagc tcactcatta ggcaccccag gctttacact ttatgcttcc   3360
ggctcgtatg ttgtgtggaa ttgtgagcgg ataacaattt cacacaggaa acagctatga   3420
ccatgattac gccaagcttg catgcctgca ggctagccta agtacgtact caaaatgcca   3480
acaaataaaa aaaaagttgc tttaataatg ccaaaacaaa ttaataaaac acttacaaca   3540
ccggattttt tttaattaaa atgtgccatt taggataaat agttaatatt tttaataatt   3600
atttaaaaag ccgtatctac taaaatgatt tttatttggt tgaaaatatt aatatgttta   3660
aatcaacaca atctatcaaa attaaactaa aaaaaaaata agtgtacgtg gttaacatta   3720
gtacagtaat ataagaggaa aatgagaaat taagaaattg aaagcgagtc taatttttaa   3780
attatgaacc tgcatatata aaaggaaaga aagaatccag gaagaaaaga aatgaaacca   3840
tgcatggtcc cctcgtcatc acgagtttct gccatttgca atagaaacac tgaaacacct   3900
ttctctttgt cacttaattg agatgccgaa gccacctcac accatgaact tcatgaggtg   3960
tagcacccaa ggcttccata gccatgcata ctgaagaatg tctcaagctc agcaccctac   4020
ttctgtgacg tgtccctcat tcaccttcct ctcttcccta taaataacca cgcctcaggt   4080
tctccgcttc acaactcaaa cattctctcc attggtcctt aaacactcat cagtcatcac   4140
cgcggccgca tgggaacgga ccaaggaaaa accttcacct gggaagagct ggcggcccat   4200
aacaccaagg acgacctact cttggccatc cgcggcaggg tgtacgatgt cacaaagttc   4260
```

```
ttgagccgcc atcctggtgg agtggacact ctcctgctcg gagctggccg agatgttact   4320

ccggtctttg agatgtatca cgcgtttggg gctgcagatg ccattatgaa gaagtactat   4380

gtcggtacac tggtctcgaa tgagctgccc atcttcccgg agccaacggt gttccacaaa   4440

accatcaaga cgagagtcga gggctacttt acggatcgga acattgatcc caagaataga   4500

ccagagatct ggggacgata cgctcttatc tttggatcct tgatcgcttc ctactacgcg   4560

cagctctttg tgcctttcgt tgtcgaacgc acatggcttc aggtggtgtt tgcaatcatc   4620

atgggatttg cgtgcgcaca agtcggactc aaccctcttc atgatgcgtc tcacttttca   4680

gtgacccaca accccactgt ctggaagatt ctgggagcca cgcacgactt tttcaacgga   4740

gcatcgtacc tggtgtggat gtaccaacat atgctcggcc atcaccccta caccaacatt   4800

gctggagcag atcccgacgt gtcgacgtct gagcccgatg ttcgtcgtat caagcccaac   4860

caaaagtggt ttgtcaacca catcaaccag cacatgtttg ttcctttcct gtacggactg   4920

ctggcgttca aggtgcgcat tcaggacatc aacattttgt actttgtcaa gaccaatgac   4980

gctattcgtg tcaatcccat ctcgacatgg cacactgtga tgttctgggg cggcaaggct   5040

ttctttgtct ggtatcgcct gattgttccc ctgcagtatc tgcccctggg caaggtgctg   5100

ctcttgttca cggtcgcgga catggtgtcg tcttactggc tggcgctgac cttccaggcg   5160

aaccacgttg ttgaggaagt tcagtggccg ttgcctgacg agaacgggat catccaaaag   5220

gactgggcag ctatgcaggt cgagactacg caggattacg cacacgattc gcacctctgg   5280

accagcatca ctggcagctt gaactaccag gctgtgcacc atctgttccc caacgtgtcg   5340

cagcaccatt atcccgatat tctggccatc atcaagaaca cctgcagcga gtacaaggtt   5400

ccataccttg tcaaggatac gttttggcaa gcatttgctt cacatttgga gcacttgcgt   5460

gttcttggac tccgtcccaa ggaagagtag gc                                 5492
```

<210> SEQ ID NO 39
<211> LENGTH: 1338
<212> TYPE: DNA
<213> ORGANISM: Mortierella alpine

<400> SEQUENCE: 39

```
atgggaacgg accaaggaaa aaccttcacc tgggaagagc tggcggccca taacaccaag     60

gacgacctac tcttggccat ccgcggcagg gtgtacgatg tcacaaagtt cttgagccgc    120

catcctggtg gagtggacac tctcctgctc ggagctggcc gagatgttac tccggtcttt    180

gagatgtatc acgcgtttgg ggctgcagat gccattatga agaagtacta tgtcggtaca    240

ctggtctcga atgagctgcc catcttcccg gagccaacgg tgttccacaa aaccatcaag    300

acgagagtcg agggctactt tacggatcgg aacattgatc ccaagaatag accagagatc    360

tggggacgat acgctcttat ctttggatcc ttgatcgctt cctactacgc gcagctcttt    420

gtgcctttcg ttgtcgaacg cacatggctt caggtggtgt ttgcaatcat catgggattt    480

gcgtgcgcac aagtcggact caaccctctt catgatgcgt ctcacttttc agtgacccac    540

aaccccactg tctggaagat tctgggagcc acgcacgact ttttcaacgg agcatcgtac    600

ctggtgtgga tgtaccaaca tatgctcggc catcacccct acaccaacat tgctggagca    660

gatcccgacg tgtcgacgtc tgagcccgat gttcgtcgta tcaagcccaa ccaaaagtgg    720

tttgtcaacc acatcaacca gcacatgttt gttcctttcc tgtacggact gctggcgttc    780

aaggtgcgca ttcaggacat caacattttg tactttgtca agaccaatga cgctattcgt    840

gtcaatccca tctcgacatg gcacactgtg atgttctggg gcggcaaggc tttctttgtc    900
```

```
tggtatcgcc tgattgttcc cctgcagtat ctgcccctgg gcaaggtgct gctcttgttc     960
acggtcgcgg acatggtgtc gtcttactgg ctggcgctga ccttccaggc gaaccacgtt    1020
gttgaggaag ttcagtggcc gttgcctgac gagaacggga tcatccaaaa ggactgggca    1080
gctatgcagg tcgagactac gcaggattac gcacacgatt cgcacctctg gaccagcatc    1140
actggcagct tgaactacca ggctgtgcac catctgttcc ccaacgtgtc gcagcaccat    1200
tatcccgata ttctggccat catcaagaac acctgcagcg agtacaaggt tccatacctt    1260
gtcaaggata cgttttggca agcatttgct tcacatttgg agcacttgcg tgttcttgga    1320
ctccgtccca aggaagag                                                   1338
```

<210> SEQ ID NO 40
<211> LENGTH: 2577
<212> TYPE: DNA
<213> ORGANISM: Artificial Sequence
<220> FEATURE:
<223> OTHER INFORMATION: plasmid pKR277

<400> SEQUENCE: 40

```
agcttggatc tcctgcagga tctggccggc cggatctcgt acggatccgt cgacggcgcg      60
cccgatcatc cggatatagt tcctcctttc agcaaaaaac ccctcaagac ccgtttagag     120
gccccaaggg gttatgctag ttattgctca gcggtggcag cagccaactc agcttccttt     180
cgggctttgt tagcagccgg atcgatccaa gctgtacctc actattcctt tgccctcgga     240
cgagtgctgg ggcgtcggtt tccactatcg gcgagtactt ctacacagcc atcggtccag     300
acggccgcgc ttctgcgggc gatttgtgta cgcccgacag tcccggctcc ggatcggacg     360
attgcgtcgc atcgaccctg cgcccaagct gcatcatcga aattgccgtc aaccaagctc     420
tgatagagtt ggtcaagacc aatgcggagc atatacgccc ggagccgcgg cgatcctgca     480
agctccggat gcctccgctc gaagtagcgc gtctgctgct ccatacaagc caaccacggc     540
ctccagaaga agatgttggc gacctcgtat tgggaatccc cgaacatcgc ctcgctccag     600
tcaatgaccg ctgttatgcg gccattgtcc gtcaggacat tgttggagcc gaaatccgcg     660
tgcacgaggt gccggacttc ggggcagtcc tcggcccaaa gcatcagctc atcgagagcc     720
tgcgcgacgg acgcactgac ggtgtcgtcc atcacagttt gccagtgata cacatgggga     780
tcagcaatcg cgcatatgaa atcacgccat gtagtgtatt gaccgattcc ttgcggtccg     840
aatgggccga acccgctcgt ctggctaaga tcggccgcag cgatcgcatc catagcctcc     900
gcgaccggct gcagaacagc gggcagttcg gtttcaggca ggtcttgcaa cgtgacaccc     960
tgtgcacggc gggagatgca ataggtcagg ctctcgctga attccccaat gtcaagcact    1020
tccggaatcg ggagcgcggc cgatgcaaag tgccgataaa cataacgatc tttgtagaaa    1080
ccatcggcgc agctatttac ccgcaggaca tatccacgcc ctcctacatc gaagctgaaa    1140
gcacgagatt cttcgccctc cgagagctgc atcaggtcgg agacgctgtc gaacttttcg    1200
atcagaaact tctcgacaga cgtcgcggtg agttcaggct ttttccatggg tatatctcct    1260
tcttaaagtt aaacaaaatt atttctagag ggaaaccgtt gtggtctccc tatagtgagt    1320
cgtattaatt tcgcgggatc gagatctgat caacctgcat taatgaatcg gccaacgcgc    1380
ggggagaggc ggtttgcgta ttgggcgctc ttccgcttcc tcgctcactg actcgctgcg    1440
ctcggtcgtt cggctgcggc gagcggtatc agctcactca aaggcggtaa tacggttatc    1500
cacagaatca ggggataacg caggaaagaa catgtgagca aaaggccagc aaaaggccag    1560
gaaccgtaaa aaggccgcgt tgctggcgtt tttccatagg ctccgccccc ctgacgagca    1620
```

```
tcacaaaaat cgacgctcaa gtcagaggtg gcgaaacccg acaggactat aaagatacca   1680

ggcgtttccc cctggaagct ccctcgtgcg ctctcctgtt ccgaccctgc cgcttaccgg   1740

atacctgtcc gcctttctcc cttcgggaag cgtggcgctt tctcaatgct cacgctgtag   1800

gtatctcagt tcggtgtagg tcgttcgctc caagctgggc tgtgtgcacg aaccccccgt   1860

tcagcccgac cgctgcgcct tatccggtaa ctatcgtctt gagtccaacc cggtaagaca   1920

cgacttatcg ccactggcag cagccactgg taacaggatt agcagagcga ggtatgtagg   1980

cggtgctaca gagttcttga agtggtggcc taactacggc tacactagaa ggacagtatt   2040

tggtatctgc gctctgctga agccagttac cttcggaaaa agagttggta gctcttgatc   2100

cggcaaacaa accaccgctg gtagcggtgg tttttttgtt tgcaagcagc agattacgcg   2160

cagaaaaaaa ggatctcaag aagatccttt gatcttttct acggggtctg acgctcagtg   2220

gaacgaaaac tcacgttaag ggattttggt catgacatta acctataaaa ataggcgtat   2280

cacgaggccc tttcgtctcg cgcgtttcgg tgatgacggt gaaaacctct gacacatgca   2340

gctcccggag acggtcacag cttgtctgta agcggatgcc gggagcagac aagcccgtca   2400

gggcgcgtca gcgggtgttg gcgggtgtcg gggctggctt aactatgcgg catcagagca   2460

gattgtactg agagtgcacc atatggacat attgtcgtta gaacgcggct acaattaata   2520

cataacctta tgtatcatac acatacgatt taggtgacac tatagaacgg cgcgcca      2577
```

<210> SEQ ID NO 41
<211> LENGTH: 5364
<212> TYPE: DNA
<213> ORGANISM: Artificial Sequence
<220> FEATURE:
<223> OTHER INFORMATION: plasmid pKR952

<400> SEQUENCE: 41

```
ggctagccta agtacgtact caaaatgcca acaaataaaa aaaaagttgc tttaataatg     60

ccaaaacaaa ttaataaaac acttacaaca ccggattttt tttaattaaa atgtgccatt    120

taggataaat agttaatatt tttaataatt atttaaaaag ccgtatctac taaaatgatt    180

tttatttggt tgaaaatatt aatatgttta aatcaacaca atctatcaaa attaaactaa    240

aaaaaaaata agtgtacgtg gttaacatta gtacagtaat ataagaggaa aatgagaaat    300

taagaaattg aaagcgagtc taatttttaa attatgaacc tgcatatata aaaggaaaga    360

aagaatccag gaagaaaaga aatgaaacca tgcatggtcc cctcgtcatc acgagtttct    420

gccatttgca atagaaacac tgaaacacct ttctctttgt cacttaattg agatgccgaa    480

gccacctcac accatgaact tcatgaggtg tagcacccaa ggcttccata gccatgcata    540

ctgaagaatg tctcaagctc agcaccctac ttctgtgacg tgtccctcat tcaccttcct    600

ctcttcccta taaataacca cgcctcaggt tctccgcttc acaactcaaa cattctctcc    660

attggtcctt aaacactcat cagtcatcac cgcggccgca tgggaacgga ccaaggaaaa    720

accttcacct gggaagagct ggcggcccat aacaccaagg acgacctact cttggccatc    780

cgcggcaggg tgtacgatgt cacaaagttc ttgagccgcc atcctggtgg agtggacact    840

ctcctgctcg gagctggccg agatgttact ccggtctttg agatgtatca cgcgtttggg    900

gctgcagatg ccattatgaa gaagtactat gtcggtacac tggtctcgaa tgagctgccc    960

atcttcccgg agccaacggt gttccacaaa accatcaaga cgagagtcga gggctacttt   1020

acggatcgga acattgatcc caagaataga ccagagatct ggggacgata cgctcttatc   1080

tttggatcct tgatcgcttc ctactacgcg cagctctttg tgcctttcgt tgtcgaacgc   1140
```

```
acatggcttc aggtggtgtt tgcaatcatc atgggatttg cgtgcgcaca agtcggactc   1200
aaccctcttc atgatgcgtc tcacttttca gtgacccaca accccactgt ctggaagatt   1260
ctgggagcca cgcacgactt tttcaacgga gcatcgtacc tggtgtggat gtaccaacat   1320
atgctcggcc atcaccccta caccaacatt gctggagcag atcccgacgt gtcgacgtct   1380
gagcccgatg ttcgtcgtat caagcccaac caaaagtggt ttgtcaacca catcaaccag   1440
cacatgtttg ttcctttcct gtacggactg ctggcgttca aggtgcgcat tcaggacatc   1500
aacattttgt actttgtcaa gaccaatgac gctattcgtg tcaatcccat ctcgacatgg   1560
cacactgtga tgttctgggg cggcaaggct ttctttgtct ggtatcgcct gattgttccc   1620
ctgcagtatc tgcccctggg caaggtgctg ctcttgttca cggtcgcgga catggtgtcg   1680
tcttactggc tggcgctgac cttccaggcg aaccacgttg ttgaggaagt tcagtggccg   1740
ttgcctgacg agaacgggat catccaaaag gactgggcag ctatgcaggt cgagactacg   1800
caggattacg cacacgattc gcacctctgg accagcatca ctggcagctt gaactaccag   1860
gctgtgcacc atctgttccc caacgtgtcg cagcaccatt atcccgatat tctggccatc   1920
atcaagaaca cctgcagcga gtacaaggtt ccataccttg tcaaggatac gttttggcaa   1980
gcatttgctt cacatttgga gcacttgcgt gttcttggac tccgtcccaa ggaagagtag   2040
gcggccgcat ttcgcaccaa atcaatgaaa gtaataatga aaagtctgaa taagaatact   2100
taggcttaga tgcctttgtt acttgtgtaa aataacttga gtcatgtacc tttggcggaa   2160
acagaataaa taaaaggtga aattccaatg ctctatgtat aagttagtaa tacttaatgt   2220
gttctacggt tgtttcaata tcatcaaact ctaattgaaa ctttagaacc acaaatctca   2280
atcttttctt aatgaaatga aaaatcttaa ttgtaccatg tttatgttaa acaccttaca   2340
attggttgga gaggaggacc aaccgatggg acaacattgg gagaaagaga ttcaatggag   2400
atttggatag gagaacaaca ttcttttttca cttcaataca agatgagtgc aacactaagg   2460
atatgtatga gactttcaga agctacgaca acatagatga gtgaggtggt gattcctagc   2520
aagaaagaca ttagaggaag ccaaaatcga acaaggaaga catcaagggc aagagacagg   2580
accatccatc tcaggaaaag gagctttggg atagtccgag aagttgtaca agaaattttt   2640
tggagggtga gtgatgcatt gctggtgact ttaactcaat caaaattgag aaagaaagaa   2700
aagggagggg gctcacatgt gaatagaagg gaaacgggag aattttacag ttttgatcta   2760
atgggcatcc cagctagtgg taacatattc accatgttta accttcacgt acggatccgt   2820
cgacggcgcg cccgatcatc cggatatagt tcctcctttc agcaaaaaac ccctcaagac   2880
ccgtttagag gccccaaggg gttatgctag ttattgctca gcggtggcag cagccaactc   2940
agcttccttt cgggctttgt tagcagccgg atcgatccaa gctgtacctc actattcctt   3000
tgccctcgga cgagtgctgg ggcgtcggtt tccactatcg gcgagtactt ctacacagcc   3060
atcggtccag acggccgcgc ttctgcgggc gatttgtgta cgcccgacag tcccggctcc   3120
ggatcggacg attgcgtcgc atcgaccctg cgcccaagct gcatcatcga aattgccgtc   3180
aaccaagctc tgatagagtt ggtcaagacc aatgcggagc atatacgccc ggagccgcgg   3240
cgatcctgca agctccggat gcctccgctc gaagtagcgc gtctgctgct ccatacaagc   3300
caaccacggc ctccagaaga agatgttggc gacctcgtat tgggaatccc cgaacatcgc   3360
ctcgctccag tcaatgaccg ctgttatgcg gccattgtcc gtcaggacat tgttggagcc   3420
gaaatccgcg tgcacgaggt gccggacttc ggggcagtcc tcggcccaaa gcatcagctc   3480
atcgagagcc tgcgcgacgg acgcactgac ggtgtcgtcc atcacagttt gccagtgata   3540
```

```
cacatgggga tcagcaatcg cgcatatgaa atcacgccat gtagtgtatt gaccgattcc   3600
ttgcggtccg aatgggccga acccgctcgt ctggctaaga tcggccgcag cgatcgcatc   3660
catagcctcc gcgaccggct gcagaacagc gggcagttcg gtttcaggca ggtcttgcaa   3720
cgtgacaccc tgtgcacggc gggagatgca ataggtcagg ctctcgctga attccccaat   3780
gtcaagcact tccggaatcg ggagcgcggc cgatgcaaag tgccgataaa cataacgatc   3840
tttgtagaaa ccatcggcgc agctatttac ccgcaggaca tatccacgcc ctcctacatc   3900
gaagctgaaa gcacgagatt cttcgccctc cgagagctgc atcaggtcgg agacgctgtc   3960
gaacttttcg atcagaaact tctcgacaga cgtcgcggtg agttcaggct tttccatggg   4020
tatatctcct tcttaaagtt aaacaaaatt atttctagag ggaaaccgtt gtggtctccc   4080
tatagtgagt cgtattaatt tcgcgggatc gagatctgat caacctgcat taatgaatcg   4140
gccaacgcgc ggggagaggc ggtttgcgta ttgggcgctc ttccgcttcc tcgctcactg   4200
actcgctgcg ctcggtcgtt cggctgcggc gagcggtatc agctcactca aaggcggtaa   4260
tacggttatc cacagaatca ggggataacg caggaaagaa catgtgagca aaaggccagc   4320
aaaaggccag gaaccgtaaa aaggccgcgt tgctggcgtt tttccatagg ctccgccccc   4380
ctgacgagca tcacaaaaat cgacgctcaa gtcagaggtg gcgaaacccg acaggactat   4440
aaagatacca ggcgtttccc cctggaagct ccctcgtgcg ctctcctgtt ccgaccctgc   4500
cgcttaccgg atacctgtcc gcctttctcc cttcgggaag cgtggcgctt tctcaatgct   4560
cacgctgtag gtatctcagt tcggtgtagg tcgttcgctc caagctgggc tgtgtgcacg   4620
aaccccccgt tcagcccgac cgctgcgcct tatccggtaa ctatcgtctt gagtccaacc   4680
cggtaagaca cgacttatcg ccactggcag cagccactgg taacaggatt agcagagcga   4740
ggtatgtagg cggtgctaca gagttcttga agtggtggcc taactacggc tacactagaa   4800
ggacagtatt tggtatctgc gctctgctga agccagttac cttcggaaaa agagttggta   4860
gctcttgatc cggcaaacaa accaccgctg gtagcggtgg tttttttgtt tgcaagcagc   4920
agattacgcg cagaaaaaaa ggatctcaag aagatccttt gatcttttct acggggtctg   4980
acgctcagtg gaacgaaaac tcacgttaag ggattttggt catgacatta acctataaaa   5040
ataggcgtat cacgaggccc tttcgtctcg cgcgtttcgg tgatgacggt gaaaacctct   5100
gacacatgca gctcccggag acggtcacag cttgtctgta agcggatgcc gggagcagac   5160
aagcccgtca gggcgcgtca gcgggtgttg gcgggtgtcg gggctggctt aactatgcgg   5220
catcagagca gattgtactg agagtgcacc atatggacat attgtcgtta gaacgcggct   5280
acaattaata cataacctta tgtatcatac acatacgatt taggtgacac tatagaacgg   5340
cgcgccaagc ttggatctcc tgca                                           5364
```

<210> SEQ ID NO 42
<211> LENGTH: 5252
<212> TYPE: DNA
<213> ORGANISM: Artificial Sequence
<220> FEATURE:
<223> OTHER INFORMATION: plasmid pKR457
<220> FEATURE:
<221> NAME/KEY: misc_feature
<222> LOCATION: (3872)..(3872)
<223> OTHER INFORMATION: n is a, c, g, or t

<400> SEQUENCE: 42

```
gtacgtgggc ggatcccccg ggctgcagga attcactggc cgtcgtttta caacgtcgtg     60
actgggaaaa ccctggcgtt acccaactta atcgccttgc agcacatccc cctttcgcca    120
```

```
gctggcgtaa tagcgaagag gcccgcaccg atcgcccttc ccaacagttg cgcagcctga    180
atggcgaatg gcgcctgatg cggtattttc tccttacgca tctgtgcggt atttcacacc    240
gcatatggtg cactctcagt acaatctgct ctgatgccgc atagttaagc cagccccgac    300
acccgccaac acccgctgac gcgccctgac gggcttgtct gctcccggca tccgcttaca    360
gacaagctgt gaccgtctcc gggagctgca tgtgtcagag gttttcaccg tcatcaccga    420
aacgcgcgag acgaaagggc ctcgtgatac gcctattttt ataggttaat gtcatgataa    480
taatggtttc ttagacgtca ggtggcactt ttcggggaaa tgtgcgcgga acccctattt    540
gtttattttt ctaaatacat tcaaatatgt atccgctcat gagacaataa ccctgataaa    600
tgcttcaata atattgaaaa aggaagagta tgagtattca acatttccgt gtcgccctta    660
ttcccttttt tgcggcattt tgccttcctg tttttgctca cccagaaacg ctggtgaaag    720
taaaagatgc tgaagatcag ttgggtgcac gagtgggtta catcgaactg gatctcaaca    780
gcggtaagat ccttgagagt tttcgccccg aagaacgttt tccaatgatg agcactttta    840
aagttctgct atgtggcgcg gtattatccc gtattgacgc cgggcaagag caactcggtc    900
gccgcataca ctattctcag aatgacttgg ttgagtactc accagtcaca gaaaagcatc    960
ttacggatgg catgacagta agagaattat gcagtgctgc cataaccatg agtgataaca   1020
ctgcggccaa cttacttctg acaacgatcg gaggaccgaa ggagctaacc gcttttttgc   1080
acaacatggg ggatcatgta actcgccttg atcgttggga accggagctg aatgaagcca   1140
taccaaacga cgagcgtgac accacgatgc ctgtagcaat ggcaacaacg ttgcgcaaac   1200
tattaactgg cgaactactt actctagctt cccggcaaca attaatagac tggatggagg   1260
cggataaagt tgcaggacca cttctgcgct cggcccttcc ggctggctgg tttattgctg   1320
ataaatctgg agccggtgag cgtgggtctc gcggtatcat tgcagcactg gggccagatg   1380
gtaagccctc ccgtatcgta gttatctaca cgacggggag tcaggcaact atggatgaac   1440
gaaatagaca gatcgctgag ataggtgcct cactgattaa gcattggtaa ctgtcagacc   1500
aagtttactc atatatactt tagattgatt taaaacttca tttttaattt aaaaggatct   1560
aggtgaagat cctttttgat aatctcatga ccaaaatccc ttaacgtgag ttttcgttcc   1620
actgagcgtc agaccccgta gaaaagatca aaggatcttc ttgagatcct ttttttctgc   1680
gcgtaatctg ctgcttgcaa acaaaaaaac caccgctacc agcggtggtt tgtttgccgg   1740
atcaagagct accaactctt tttccgaagg taactggctt cagcagagcg cagataccaa   1800
atactgtcct tctagtgtag ccgtagttag gccaccactt caagaactct gtagcaccgc   1860
ctacatacct cgctctgcta atcctgttac cagtggctgc tgccagtggc gataagtcgt   1920
gtcttaccgg gttggactca agacgatagt taccggataa ggcgcagcgg tcgggctgaa   1980
cggggggttc gtgcacacag cccagcttgg agcgaacgac ctacaccgaa ctgagatacc   2040
tacagcgtga gctatgagaa agcgccacgc ttcccgaagg gagaaaggcg gacaggtatc   2100
cggtaagcgg cagggtcgga acaggagagc gcacgaggga gcttccaggg ggaaacgcct   2160
ggtatcttta tagtcctgtc gggtttcgcc acctctgact tgagcgtcga tttttgtgat   2220
gctcgtcagg ggggcggagc ctatggaaaa acgccagcaa cgcggccttt ttacggttcc   2280
tggccttttg ctggcctttt gctcacatgt tctttcctgc gttatcccct gattctgtgg   2340
ataaccgtat taccgccttt gagtgagctg ataccgctcg ccgcagccga acgaccgagc   2400
gcagcgagtc agtgagcgag gaagcggaag agcgcccaat acgcaaaccg cctctccccg   2460
cgcgttggcc gattcattaa tgcagctggc acgacaggtt tcccgactgg aaagcgggca   2520
```

```
gtgagcgcaa cgcaattaat gtgagttagc tcactcatta ggcaccccag gctttacact   2580

ttatgcttcc ggctcgtatg ttgtgtggaa ttgtgagcgg ataacaattt cacacaggaa   2640

acagctatga ccatgattac gccaagcttg catgcctgca ggtcgactcg acgtacgtcc   2700

tcgaagagaa gggttaataa cacatttttt aacattttta acacaaattt tagttattta   2760

aaaatttatt aaaaaattta aaataagaag aggaactctt taaataaatc taacttacaa   2820

aatttatgat tttaataag ttttcaccaa taaaaaatgt cataaaaata tgttaaaaag   2880

tatattatca atattctctt tatgataaat aaaaagaaaa aaaaaataaa agttaagtga   2940

aaatgagatt gaagtgactt taggtgtgta taaatatatc aaccccgcca acaatttatt   3000

taatccaaat atattgaagt atattattcc atagccttta tttatttata tatttattat   3060

ataaaagctt tatttgttct aggttgttca tgaaatattt ttttggtttt atctccgttg   3120

taagaaaatc atgtgctttg tgtcgccact cactattgca gctttttcat gcattggtca   3180

gattgacggt tgattgtatt tttgtttttt atggttttgt gttatgactt aagtcttcat   3240

ctctttatct cttcatcagg tttgatggtt acctaatatg gtccatgggt acatgcatgg   3300

ttaaattagg tggccaactt tgttgtgaac gatagaattt tttttatatt aagtaaacta   3360

tttttatatt atgaaataat aataaaaaaa atattttatc attattaaca aaatcatatt   3420

agttaatttg ttaactctat aataaaagaa atactgtaac attcacatta catggtaaca   3480

tctttccacc ctttcatttg ttttttgttt gatgactttt tttcttgttt aaatttattt   3540

cccttctttt aaatttggaa tacattatca tcatatataa actaaaatac taaaaacagg   3600

attacacaaa tgataaataa taacacaaat atttataaat ctagctgcaa tatatttaaa   3660

ctagctatat cgatattgta aaataaaact agctgcattg atactgataa aaaaatatca   3720

tgtgctttct ggactgatga tgcagtatac ttttgacatt gcctttattt tatttttcag   3780

aaaagctttc ttagttctgg gttcttcatt atttgtttcc catctccatt gtgaattgaa   3840

tcatttgctt cgtgtcacaa atacaattta gntaggtaca tgcattggtc agattcacgg   3900

tttattatgt catgacttaa gttcatggta gtacattacc tgccacgcat gcattatatt   3960

ggttagattt gataggcaaa tttggttgtc aacaatataa atataaataa tgtttttata   4020

ttacgaaata acagtgatca aaacaaacag ttttatcttt attaacaaga ttttgttttt   4080

gtttgatgac gttttttaat gtttacgctt tccccccttct tttgaattta gaacacttta   4140

tcatcataaa atcaaatact aaaaaaatta catatttcat aaataataac acaaatattt   4200

ttaaaaaatc tgaaataata atgaacaata ttacatatta tcacgaaaat tcattaataa   4260

aaatattata taaataaaat gtaatagtag ttatatgtag gaaaaaagta ctgcacgcat   4320

aatatataca aaaagattaa aatgaactat tataaataat aacactaaat taatggtgaa   4380

tcatatcaaa ataatgaaaa agtaaataaa atttgtaatt aacttctata tgtattacac   4440

acacaaataa taaataatag taaaaaaaat tatgataaat atttaccatc tcataagata   4500

tttaaaataa tgataaaaat atagattatt ttttatgcaa ctagctagcc aaaaagagaa   4560

cacgggtata tataaaaaga gtacctttaa attctactgt acttccttta ttcctgacgt   4620

ttttatatca agtggacata cgtgaagatt ttaattatca gtctaaatat ttcattagca   4680

cttaatactt ttctgtttta ttcctatcct ataagtagtc ccgattctcc caacattgct   4740

tattcacaca actaactaag aaagtcttcc atagcccccc aagcggccgc gacacaagtg   4800

tgagagtact aaataaatgc tttggttgta cgaaatcatt acactaaata aaataatcaa   4860

agcttatata tgccttccgc taaggccgaa tgcaaagaaa ttggttcttt ctcgttatct   4920
```

```
tttgccactt ttactagtac gtattaatta ctacttaatc atctttgttt acggctcatt   4980

atatccggtc tagaggatcc aaggccgcga agttaaaagc aatgttgtca cttgtcgtac   5040

taacacatga tgtgatagtt tatgctagct agctataaca taagctgtct ctgagtgtgt   5100

tgtatattaa taaagatcat cactggtgaa tggtgatcgt gtacgtaccc tacttagtag   5160

gcaatggaag cacttagagt gtgctttgtg catggccttg cctctgtttt gagacttttg   5220

taatgttttc gagtttaaat ctttgccttt gc                                 5252
```

```
<210> SEQ ID NO 43
<211> LENGTH: 2635
<212> TYPE: DNA
<213> ORGANISM: Artificial Sequence
<220> FEATURE:
<223> OTHER INFORMATION: modified Kti/NotI/Kti3'Salb3' cassette
<220> FEATURE:
<221> NAME/KEY: misc_feature
<222> LOCATION: (1229)..(1229)
<223> OTHER INFORMATION: n is a, c, g, or t

<400> SEQUENCE: 43

ggtaccgggc ccccccctcga ggtcgcccgg gggatccgcc ctaagcttcg tacgtcctcg     60

aagagaaggg ttaataacac attttttaac atttttaaca caaattttag ttatttaaaa    120

atttattaaa aaatttaaaa taagaagagg aactctttaa ataaatctaa cttacaaaat    180

ttatgatttt taataagttt tcaccaataa aaaatgtcat aaaaatatgt taaaaagtat    240

attatcaata ttctctttat gataaataaa aagaaaaaaa aaataaaagt taagtgaaaa    300

tgagattgaa gtgactttag gtgtgtataa atatatcaac cccgccaaca atttatttaa    360

tccaaatata ttgaagtata ttattccata gcctttattt atttatatat ttattatata    420

aaagctttat ttgttctagg ttgttcatga aatatttttt tggttttatc tccgttgtaa    480

gaaaatcatg tgctttgtgt cgccactcac tattgcagct ttttcatgca ttggtcagat    540

tgacggttga ttgtattttt gttttttatg gttttgtgtt atgacttaag tcttcatctc    600

tttatctctt catcaggttt gatggttacc taatatggtc catgggtaca tgcatggtta    660

aattaggtgg ccaactttgt tgtgaacgat agaatttttt ttatattaag taaactattt    720

ttatattatg aaataataat aaaaaaaata ttttatcatt attaacaaaa tcatattagt    780

taatttgtta actctataat aaaagaaata ctgtaacatt cacattacat ggtaacatct    840

ttccaccctt tcatttgttt tttgtttgat gacttttttt cttgtttaaa tttatttccc    900

ttcttttaaa tttggaatac attatcatca tatataaact aaaatactaa aaacaggatt    960

acacaaatga taaataataa cacaaatatt tataaatcta gctgcaatat atttaaacta   1020

gctatatcga tattgtaaaa taaaactagc tgcattgata ctgataaaaa aatatcatgt   1080

gctttctgga ctgatgatgc agtatacttt tgacattgcc tttattttat ttttcagaaa   1140

agctttctta gttctgggtt cttcattatt tgtttcccat ctccattgtg aattgaatca   1200

tttgcttcgt gtcacaaata caatttagnt aggtacatgc attggtcaga ttcacggttt   1260

attatgtcat gacttaagtt catggtagta cattacctgc cacgcatgca ttatattggt   1320

tagatttgat aggcaaattt ggttgtcaac aatataaata taaataatgt ttttatatta   1380

cgaaataaca gtgatcaaaa caaacagttt tatctttatt aacaagattt tgtttttgtt   1440

tgatgacgtt ttttaatgtt tacgctttcc cccttctttt gaatttagaa cactttatca   1500

tcataaaatc aaatactaaa aaaattacat atttcataaa taataacaca aatattttta   1560

aaaaatctga aataataatg aacaatatta catattatca cgaaaattca ttaataaaaa   1620
```

```
tattatataa ataaaatgta atagtagtta tatgtaggaa aaaagtactg cacgcataat   1680

atatacaaaa agattaaaat gaactattat aaataataac actaaattaa tggtgaatca   1740

tatcaaaata atgaaaaagt aaataaaatt tgtaattaac ttctatatgt attacacaca   1800

caaataataa ataatagtaa aaaaaattat gataaatatt taccatctca taagatattt   1860

aaaataatga taaaaatata gattattttt tatgcaacta gctagccaaa aagagaacac   1920

gggtatatat aaaaagagta cctttaaatt ctactgtact tcctttattc ctgacgtttt   1980

tatatcaagt ggacatacgt gaagatttta attatcagtc taaatatttc attagcactt   2040

aatacttttc tgttttattc ctatcctata agtagtcccg attctcccaa cattgcttat   2100

tcacacaact aactaagaaa gtcttccata gcccccaag cggccgcgac acaagtgtga    2160

gagtactaaa taaatgcttt ggttgtacga aatcattaca ctaaataaaa taatcaaagc   2220

ttatatatgc cttccgctaa ggccgaatgc aaagaaattg gttctttctc gttatctttt   2280

gccactttta ctagtacgta ttaattacta cttaatcatc tttgtttacg gctcattata   2340

tccggtctag aggatccaag gccgcgaagt taaaagcaat gttgtcactt gtcgtactaa   2400

cacatgatgt gatagtttat gctagctagc tataacataa gctgtctctg agtgtgttgt   2460

atattaataa agatcatcac tggtgaatgg tgatcgtgta cgtaccctac ttagtaggca   2520

atggaagcac ttagagtgtg ctttgtgcat ggccttgcct ctgttttgag acttttgtaa   2580

tgttttcgag tttaaatctt tgcctttgcg tacgtctaga ggatccccgg gtacc        2635
```

<210> SEQ ID NO 44
<211> LENGTH: 9276
<212> TYPE: DNA
<213> ORGANISM: Artificial Sequence
<220> FEATURE:
<223> OTHER INFORMATION: plasmid pKR970
<220> FEATURE:
<221> NAME/KEY: misc_feature
<222> LOCATION: (6592)..(6592)
<223> OTHER INFORMATION: n is a, c, g, or t

<400> SEQUENCE: 44

```
gtacggatcc gtcgacggcg cgcccgatca tccggatata gttcctcctt tcagcaaaaa     60

acccctcaag acccgtttag aggccccaag gggttatgct agttattgct cagcggtggc    120

agcagccaac tcagcttcct ttcgggcttt gttagcagcc ggatcgatcc aagctgtacc    180

tcactattcc tttgccctcg gacgagtgct ggggcgtcgg tttccactat cggcgagtac    240

ttctacacag ccatcggtcc agacggccgc gcttctgcgg gcgatttgtg tacgcccgac    300

agtcccggct ccggatcgga cgattgcgtc gcatcgaccc tgcgcccaag ctgcatcatc    360

gaaattgccg tcaaccaagc tctgatagag ttggtcaaga ccaatgcgga gcatatacgc    420

ccggagccgc ggcgatcctg caagctccgg atgcctccgc tcgaagtagc gcgtctgctg    480

ctccatacaa gccaaccacg gcctccagaa gaagatgttg gcgacctcgt attgggaatc    540

cccgaacatc gcctcgctcc agtcaatgac cgctgttatg cggccattgt ccgtcaggac    600

attgttggag ccgaaatccg cgtgcacgag gtgccggact tcggggcagt cctcggccca    660

aagcatcagc tcatcgagag cctgcgcgac ggacgcactg acggtgtcgt ccatcacagt    720

ttgccagtga tacacatggg gatcagcaat cgcgcatatg aaatcacgcc atgtagtgta    780

ttgaccgatt ccttgcggtc cgaatgggcc gaacccgctc gtctggctaa gatcggccgc    840

agcgatcgca tccatagcct ccgcgaccgg ctgcagaaca gcgggcagtt cggtttcagg    900

caggtcttgc aacgtgacac cctgtgcacg gcgggagatg caataggtca ggctctcgct    960
```

```
gaattcccca atgtcaagca cttccggaat cgggagcgcg gccgatgcaa agtgccgata   1020
aacataacga tctttgtaga aaccatcggc gcagctattt acccgcagga catatccacg   1080
ccctcctaca tcgaagctga aagcacgaga ttcttcgccc tccgagagct gcatcaggtc   1140
ggagacgctg tcgaactttt cgatcagaaa cttctcgaca gacgtcgcgg tgagttcagg   1200
cttttccatg ggtatatctc cttcttaaag ttaaacaaaa ttatttctag agggaaaccg   1260
ttgtggtctc cctatagtga gtcgtattaa tttcgcggga tcgagatctg atcaacctgc   1320
attaatgaat cggccaacgc gcggggagag gcggtttgcg tattgggcgc tcttccgctt   1380
cctcgctcac tgactcgctg cgctcggtcg ttcggctgcg gcgagcggta tcagctcact   1440
caaaggcggt aatacggtta tccacagaat caggggataa cgcaggaaag aacatgtgag   1500
caaaaggcca gcaaaaggcc aggaaccgta aaaaggccgc gttgctggcg tttttccata   1560
ggctccgccc ccctgacgag catcacaaaa atcgacgctc aagtcagagg tggcgaaacc   1620
cgacaggact ataaagatac caggcgtttc cccctggaag ctccctcgtg cgctctcctg   1680
ttccgaccct gccgcttacc ggatacctgt ccgcctttct cccttcggga agcgtggcgc   1740
tttctcaatg ctcacgctgt aggtatctca gttcggtgta ggtcgttcgc tccaagctgg   1800
gctgtgtgca cgaacccccc gttcagcccg accgctgcgc cttatccggt aactatcgtc   1860
ttgagtccaa cccggtaaga cacgacttat cgccactggc agcagccact ggtaacagga   1920
ttagcagagc gaggtatgta ggcggtgcta cagagttctt gaagtggtgg cctaactacg   1980
gctacactag aaggacagta tttggtatct gcgctctgct gaagccagtt accttcggaa   2040
aaagagttgg tagctcttga tccggcaaac aaaccaccgc tggtagcggt ggtttttttg   2100
tttgcaagca gcagattacg cgcagaaaaa aaggatctca agaagatcct ttgatctttt   2160
ctacggggtc tgacgctcag tggaacgaaa actcacgtta agggattttg gtcatgacat   2220
taacctataa aaataggcgt atcacgaggc cctttcgtct cgcgcgtttc ggtgatgacg   2280
gtgaaaacct ctgacacatg cagctcccgg agacggtcac agcttgtctg taagcggatg   2340
ccgggagcag acaagcccgt cagggcgcgt cagcgggtgt tggcgggtgt cggggctggc   2400
ttaactatgc ggcatcagag cagattgtac tgagagtgca ccatatggac atattgtcgt   2460
tagaacgcgg ctacaattaa tacataacct tatgtatcat acacatacga tttaggtgac   2520
actatagaac ggcgcgccaa gcttggatct cctgcaggct agcctaagta cgtactcaaa   2580
atgccaacaa ataaaaaaaa agttgcttta ataatgccaa aacaaattaa taaaacactt   2640
acaacaccgg attttttta attaaaatgt gccatttagg ataaatagtt aatattttta   2700
ataattattt aaaaagccgt atctactaaa atgattttta tttggttgaa aatattaata   2760
tgtttaaatc aacacaatct atcaaaatta aactaaaaaa aaaataagtg tacgtggtta   2820
acattagtac agtaatataa gaggaaaatg agaaattaag aaattgaaag cgagtctaat   2880
ttttaaatta tgaacctgca tatataaaag gaaagaaaga atccaggaag aaaagaaatg   2940
aaaccatgca tggtcccctc gtcatcacga gtttctgcca tttgcaatag aaacactgaa   3000
acacctttct ctttgtcact taattgagat gccgaagcca cctcacacca tgaacttcat   3060
gaggtgtagc acccaaggct tccatagcca tgcatactga agaatgtctc aagctcagca   3120
ccctacttct gtgacgtgtc cctcattcac cttcctctct tccctataaa taaccacgcc   3180
tcaggttctc cgcttcacaa ctcaaacatt ctctccattg gtccttaaac actcatcagt   3240
catcaccgcg gccgcatggg aacggaccaa ggaaaaacct tcacctggga agagctggcg   3300
gcccataaca ccaaggacga cctactcttg gccatccgcg gcagggtgta cgatgtcaca   3360
```

```
aagttcttga gccgccatcc tggtggagtg gacactctcc tgctcggagc tggccgagat   3420
gttactccgg tctttgagat gtatcacgcg tttggggctg cagatgccat tatgaagaag   3480
tactatgtcg gtacactggt ctcgaatgag ctgcccatct tcccggagcc aacggtgttc   3540
cacaaaacca tcaagacgag agtcgagggc tactttacgg atcggaacat tgatcccaag   3600
aatagaccag agatctgggg acgatacgct cttatctttg gatccttgat cgcttcctac   3660
tacgcgcagc tctttgtgcc tttcgttgtc gaacgcacat ggcttcaggt ggtgtttgca   3720
atcatcatgg gatttgcgtg cgcacaagtc ggactcaacc ctcttcatga tgcgtctcac   3780
ttttcagtga cccacaaccc cactgtctgg aagattctgg gagccacgca cgactttttc   3840
aacggagcat cgtacctggt gtggatgtac caacatatgc tcggccatca cccctacacc   3900
aacattgctg gagcagatcc cgacgtgtcg acgtctgagc ccgatgttcg tcgtatcaag   3960
cccaaccaaa agtggtttgt caaccacatc aaccagcaca tgtttgttcc tttcctgtac   4020
ggactgctgg cgttcaaggt gcgcattcag gacatcaaca ttttgtactt tgtcaagacc   4080
aatgacgcta ttcgtgtcaa tcccatctcg acatggcaca ctgtgatgtt ctggggcggc   4140
aaggctttct ttgtctggta tcgcctgatt gttcccctgc agtatctgcc cctgggcaag   4200
gtgctgctct tgttcacggt cgcggacatg gtgtcgtctt actggctggc gctgaccttc   4260
caggcgaacc acgttgttga ggaagttcag tggccgttgc ctgacgagaa cgggatcatc   4320
caaaaggact gggcagctat gcaggtcgag actacgcagg attacgcaca cgattcgcac   4380
ctctggacca gcatcactgg cagcttgaac taccaggctg tgcaccatct gttccccaac   4440
gtgtcgcagc accattatcc cgatattctg gccatcatca agaacacctg cagcgagtac   4500
aaggttccat accttgtcaa ggatacgttt tggcaagcat ttgcttcaca tttggagcac   4560
ttgcgtgttc ttggactccg tcccaaggaa gagtaggcgg ccgcatttcg caccaaatca   4620
atgaaagtaa taatgaaaag tctgaataag aatacttagg cttagatgcc tttgttactt   4680
gtgtaaaata acttgagtca tgtacctttg gcggaaacag aataaataaa aggtgaaatt   4740
ccaatgctct atgtataagt tagtaatact taatgtgttc tacggttgtt tcaatatcat   4800
caaactctaa ttgaaacttt agaaccacaa atctcaatct tttcttaatg aaatgaaaaa   4860
tcttaattgt accatgttta tgttaaacac cttacaattg gttggagagg aggaccaacc   4920
gatgggacaa cattgggaga aagagattca atggagattt ggataggaga acaacattct   4980
ttttcacttc aatacaagat gagtgcaaca ctaaggatat gtatgagact ttcagaagct   5040
acgacaacat agatgagtga ggtggtgatt cctagcaaga aagacattag aggaagccaa   5100
aatcgaacaa ggaagacatc aagggcaaga gacaggacca tccatctcag gaaaaggagc   5160
tttgggatag tccgagaagt tgtacaagaa attttttgga gggtgagtga tgcattgctg   5220
gtgactttaa ctcaatcaaa attgagaaag aaagaaaagg gagggggctc acatgtgaat   5280
agaagggaaa cgggagaatt ttacagtttt gatctaatgg gcatcccagc tagtggtaac   5340
atattcacca tgtttaacct tcacgtaccg ggccccccct cgaggtcgcc cgggggatcc   5400
gccctaagct tcgtacgtcc tcgaagagaa gggttaataa cacatttttt aacattttta   5460
acacaaattt tagttattta aaaatttatt aaaaaattta aaataagaag aggaactctt   5520
taaataaatc taacttacaa aatttatgat tttaataag ttttcaccaa taaaaaatgt    5580
cataaaaata tgttaaaaag tatattatca atattctctt tatgataaat aaaaagaaaa   5640
aaaaaataaa agttaagtga aaatgagatt gaagtgactt taggtgtgta taaatatatc   5700
aaccccgcca acaatttatt taatccaaat atattgaagt atattattcc atagccttta   5760
```

```
tttatttata tatttattat ataaaagctt tatttgttct aggttgttca tgaaatattt   5820
ttttggtttt atctccgttg taagaaaatc atgtgctttg tgtcgccact cactattgca   5880
gctttttcat gcattggtca gattgacggt tgattgtatt tttgtttttt atggttttgt   5940
gttatgactt aagtcttcat ctctttatct cttcatcagg tttgatggtt acctaatatg   6000
gtccatgggt acatgcatgg ttaaattagg tggccaactt tgttgtgaac gatagaattt   6060
tttttatatt aagtaaacta tttttatatt atgaaataat aataaaaaaa atattttatc   6120
attattaaca aaatcatatt agttaatttg ttaactctat aataaaagaa atactgtaac   6180
attcacatta catggtaaca tctttccacc ctttcatttg tttttgttt gatgactttt    6240
tttcttgttt aaatttattt cccttctttt aaatttggaa tacattatca tcatatataa   6300
actaaaatac taaaaacagg attacacaaa tgataaataa taacacaaat atttataaat   6360
ctagctgcaa tatatttaaa ctagctatat cgatattgta aaataaaact agctgcattg   6420
atactgataa aaaaatatca tgtgctttct ggactgatga tgcagtatac ttttgacatt   6480
gcctttattt tatttttcag aaaagctttc ttagttctgg gttcttcatt atttgtttcc   6540
catctccatt gtgaattgaa tcatttgctt cgtgtcacaa atacaattta gntaggtaca   6600
tgcattggtc agattcacgg tttattatgt catgacttaa gttcatggta gtacattacc   6660
tgccacgcat gcattatatt ggttagattt gataggcaaa tttggttgtc aacaatataa   6720
atataaataa tgtttttata ttacgaaata acagtgatca aaacaaacag ttttatcttt   6780
attaacaaga ttttgttttt gtttgatgac gtttttaat gtttacgctt tccccttct     6840
tttgaattta gaacacttta tcatcataaa atcaaatact aaaaaaatta catatttcat   6900
aaataataac acaaatattt ttaaaaaatc tgaaataata atgaacaata ttacatatta   6960
tcacgaaaat tcattaataa aaatattata taaataaaat gtaatagtag ttatatgtag   7020
gaaaaaagta ctgcacgcat aatatataca aaaagattaa aatgaactat tataaataat   7080
aacactaaat taatggtgaa tcatatcaaa ataatgaaaa agtaaataaa atttgtaatt   7140
aacttctata tgtattacac acacaaataa taaataatag taaaaaaaat tatgataaat   7200
atttaccatc tcataagata tttaaaataa tgataaaaat atagattatt ttttatgcaa   7260
ctagctagcc aaaaagagaa cacgggtata tataaaaaga gtacctttaa attctactgt   7320
acttccttta ttcctgacgt ttttatatca agtggacata cgtgaagatt ttaattatca   7380
gtctaaatat ttcattagca cttaatactt ttctgtttta ttcctatcct ataagtagtc   7440
ccgattctcc caacattgct tattcacaca actaactaag aaagtcttcc atagcccccc   7500
aagcggccgc accatgggca agggtggaga cggcggcgcg caggcggtga gcgggaccga   7560
cgcgtctctc gctgaggtga gctccgtcga tagcaagagc gtgcacgtcg tgctctacgg   7620
caagcgcgtg gatgtcacaa agttccagaa ggcacacccg ggcgggagca aggtgttccg   7680
catcttccag gagcgcgacg cgacggagca gttcgagtct taccactcgc ccaaggccat   7740
caagatgatg gagggcatgc tcaagaagtc ggaggatgcg cccgcttccg tgcccctgcc   7800
ctcgcggtcc accatgggca cggagttcaa ggagatgatt gagcgccaca agagggctgg   7860
tctctacgac ccttgcccgt tggacgagct gttcaagctc accatcgtcc ttgcgcccat   7920
cttcgtgggc gcctatctcg tgcggagcgg cgtctcgccc ctcgcgggcg cgctctccat   7980
gggctttggc ttctacctcg acggctggct tgctcacgac tacctgcatc acgcagtctt   8040
caagggctcg gtcaacacgc tcgtcaaggc gaacaacgcc atgggatacg ccctcggctt   8100
cctccagggc tacgacgtgg cctggtggcg cgcgcgccat aacacgcacc acgtgtgcac   8160
```

```
caacgaggat ggttcggacc cggacatcaa gacggcgccc ctgctcatct acgtgcgaga   8220
gaacccgtcc attgccaagc ggctcaactt cttccagcgc tggcagcagt actactatgt   8280
gccgaccatg gccatcctcg acctctactg gcgcctggag tccatcgcgt acgtggctgt   8340
gcgcctgcct aagatgtgga tgcaggccgc cgctcttgcc gctcactacg cgctcctgtg   8400
ctgggtcttc gcagcgcatc tcaacctcat ccctctcatg atggttgcac gcggcttcgc   8460
gacgggcatc gttgtctttg caacccacta tggtgaggac atcctcgacc gcgagcacgt   8520
cgagggcatg acgctcgtcg agcagaccgc caagacctcc cgtaacatca cgggcggctg   8580
gctagtgaac gtgctcacgg gcttcatctc cctgcagacc gagcatcacc tcttccccat   8640
gatgcccacc ggcaacctaa tgactatcca gcccgaggta cgcgacttct tcaagaagca   8700
tggcctcgag taccgcgagg gcaacctctt ccagtgcgtg caccagaaca tcaaggctct   8760
cgccttcgag cacctcctcc actgagcggc cgcgacacaa gtgtgagagt actaaataaa   8820
tgctttggtt gtacgaaatc attacactaa ataaaataat caaagcttat atatgccttc   8880
cgctaaggcc gaatgcaaag aaattggttc tttctcgtta tcttttgcca cttttactag   8940
tacgtattaa ttactactta atcatctttg tttacggctc attatatccg gtctagagga   9000
tccaaggccg cgaagttaaa agcaatgttg tcacttgtcg tactaacaca tgatgtgata   9060
gtttatgcta gctagctata acataagctg tctctgagtg tgttgtatat taataaagat   9120
catcactggt gaatggtgat cgtgtacgta ccctacttag taggcaatgg aagcacttag   9180
agtgtgcttt gtgcatggcc ttgcctctgt tttgagactt ttgtaatgtt ttcgagttta   9240
aatctttgcc tttgcgtacg tctagaggat ccccgg                              9276
```

<210> SEQ ID NO 45
<211> LENGTH: 11366
<212> TYPE: DNA
<213> ORGANISM: Artificial Sequence
<220> FEATURE:
<223> OTHER INFORMATION: plasmid pKR973
<220> FEATURE:
<221> NAME/KEY: misc_feature
<222> LOCATION: (5237)..(5237)
<223> OTHER INFORMATION: n is a, c, g, or t

<400> SEQUENCE: 45

```
ggagatccaa gcttggcgcg ccgttctata gtgtcaccta aatcgtatgt gtatgataca     60
taaggttatg tattaattgt agccgcgttc taacgacaat atgtccatat ggtgcactct    120
cagtacaatc tgctctgatg ccgcatagtt aagccagccc cgacacccgc caacacccgc    180
tgacgcgccc tgacgggctt gtctgctccc ggcatccgct tacagacaag ctgtgaccgt    240
ctccgggagc tgcatgtgtc agaggttttc accgtcatca ccgaaacgcg cgagacgaaa    300
gggcctcgtg atacgcctat ttttataggt taatgtcatg accaaaatcc cttaacgtga    360
gttttcgttc cactgagcgt cagaccccgt agaaaagatc aaaggatctt cttgagatcc    420
tttttttctg cgcgtaatct gctgcttgca aacaaaaaaa ccaccgctac cagcggtggt    480
ttgtttgccg gatcaagagc taccaactct ttttccgaag gtaactggct tcagcagagc    540
gcagatacca aatactgtcc ttctagtgta gccgtagtta ggccaccact tcaagaactc    600
tgtagcaccg cctacatacc tcgctctgct aatcctgtta ccagtggctg ctgccagtgg    660
cgataagtcg tgtcttaccg ggttggactc aagacgatag ttaccggata aggcgcagcg    720
gtcgggctga acggggggtt cgtgcacaca gcccagcttg gagcgaacga cctacaccga    780
actgagatac ctacagcgtg agcattgaga aagcgccacg cttcccgaag ggagaaaggc    840
```

```
ggacaggtat ccggtaagcg gcagggtcgg aacaggagag cgcacgaggg agcttccagg    900
gggaaacgcc tggtatcttt atagtcctgt cgggtttcgc cacctctgac ttgagcgtcg    960
atttttgtga tgctcgtcag gggggcggag cctatggaaa aacgccagca acgcggcctt   1020
tttacggttc ctggcctttt gctggccttt tgctcacatg ttctttcctg cgttatcccc   1080
tgattctgtg gataaccgta ttaccgcctt tgagtgagct gataccgctc gccgcagccg   1140
aacgaccgag cgcagcgagt cagtgagcga ggaagcggaa gagcgcccaa tacgcaaacc   1200
gcctctcccc gcgcgttggc cgattcatta atgcaggttg atcagatctc gatcccgcga   1260
aattaatacg actcactata gggagaccac aacggtttcc ctctagaaat aattttgttt   1320
aactttaaga aggagatata cccatggaaa agcctgaact caccgcgacg tctgtcgaga   1380
agtttctgat cgaaaagttc gacagcgtct ccgacctgat gcagctctcg gagggcgaag   1440
aatctcgtgc tttcagcttc gatgtaggag ggcgtggata tgtcctgcgg gtaaatagct   1500
gcgccgatgg tttctacaaa gatcgttatg tttatcggca ctttgcatcg gccgcgctcc   1560
cgattccgga agtgcttgac attggggaat tcagcgagag cctgacctat tgcatctccc   1620
gccgtgcaca gggtgtcacg ttgcaagacc tgcctgaaac cgaactgccc gctgttctgc   1680
agccggtcgc ggaggctatg gatgcgatcg ctgcggccga tcttagccag acgagcgggt   1740
tcggcccatt cggaccgcaa ggaatcggtc aatacactac atggcgtgat ttcatatgcg   1800
cgattgctga tccccatgtg tatcactggc aaactgtgat ggacgacacc gtcagtgcgt   1860
ccgtcgcgca ggctctcgat gagctgatgc tttgggccga ggactgcccc gaagtccggc   1920
acctcgtgca cgcggatttc ggctccaaca atgtcctgac ggacaatggc cgcataacag   1980
cggtcattga ctggagcgag gcgatgttcg gggattccca atacgaggtc gccaacatct   2040
tcttctggag gccgtggttg gcttgtatgg agcagcagac gcgctacttc gagcggaggc   2100
atccggagct tgcaggatcg ccgcggctcc gggcgtatat gctccgcatt ggtcttgacc   2160
aactctatca gagcttggtt gacggcaatt tcgatgatgc agcttgggcg cagggtcgat   2220
gcgacgcaat cgtccgatcc ggagccggga ctgtcgggcg tacacaaatc gcccgcagaa   2280
gcgcggccgt ctggaccgat ggctgtgtag aagtactcgc cgatagtgga aaccgacgcc   2340
ccagcactcg tccgagggca aaggaatagt gaggtacagc ttggatcgat ccggctgcta   2400
acaaagcccg aaaggaagct gagttggctg ctgccaccgc tgagcaataa ctagcataac   2460
cccttggggc ctctaaacgg gtcttgaggg gttttttgct gaaaggagga actatatccg   2520
gatgatcggg cgcgccgtcg acggatccgt acccggggat cctctagacg tacgcaaagg   2580
caaagattta aactcgaaaa cattacaaaa gtctcaaaac agaggcaagg ccatgcacaa   2640
agcacactct aagtgcttcc attgcctact aagtagggta cgtacacgat caccattcac   2700
cagtgatgat ctttattaat atacaacaca ctcagagaca gcttatgtta tagctagcta   2760
gcataaacta tcacatcatg tgttagtacg acaagtgaca acattgcttt taacttcgcg   2820
gccttggatc ctctagaccg gatataatga gccgtaaaca aagatgatta agtagtaatt   2880
aatacgtact agtaaaagtg gcaaaagata acgagaaaga accaatttct ttgcattcgg   2940
ccttagcgga aggcatatat aagctttgat tattttattt agtgtaatga tttcgtacaa   3000
ccaaagcatt tatttagtac tctcacactt gtgtcgcggc cgctcagtgg aggaggtgct   3060
cgaaggcgag agccttgatg ttctggtgca cgcactggaa gaggttgccc tcgcggtact   3120
cgaggccatg cttcttgaag aagtcgcgta cctcgggctg gatagtcatt aggttgccgg   3180
tgggcatcat ggggaagagg tgatgctcgg tctgcaggga gatgaagccc gtgagcacgt   3240
```

```
tcactagcca gccgcccgtg atgttacggg aggtcttggc ggtctgctcg acgagcgtca   3300
tgccctcgac gtgctcgcgg tcgaggatgt cctcaccata gtgggttgca aagacaacga   3360
tgcccgtcgc gaagccgcgt gcaaccatca tgagagggat gaggttgaga tgcgctgcga   3420
agacccagca caggagcgcg tagtgagcgg caagagcggc ggcctgcatc cacatcttag   3480
gcaggcgcac agccacgtac gcgatggact ccaggcgcca gtagaggtcg aggatggcca   3540
tggtcggcac atagtagtac tgctgccagc gctggaagaa gttgagccgc ttggcaatgg   3600
acgggttctc tcgcacgtag atgagcaggg gcgccgtctt gatgtccggg tccgaaccat   3660
cctcgttggt gcacacgtgg tgcgtgttat ggcgcgcgcg ccaccaggcc acgtcgtagc   3720
cctggaggaa gccgagggcg tatcccatgg cgttgttcgc cttgacgagc gtgttgaccg   3780
agcccttgaa gactgcgtga tgcaggtagt cgtgagcaag ccagccgtcg aggtagaagc   3840
caaagcccat ggagagcgcg cccgcgaggg gcgagacgcc gctccgcacg agataggcgc   3900
ccacgaagat gggcgcaagg acgatggtga gcttgaacag ctcgtccaac gggcaagggt   3960
cgtagagacc agccctcttg tggcgctcaa tcatctcctt gaactccgtg cccatggtgg   4020
accgcgaggg caggggcacg gaagcgggcg catcctccga cttcttgagc atgccctcca   4080
tcatcttgat ggccttgggc gagtggtaag actcgaactg ctccgtcgcg tcgcgctcct   4140
ggaagatgcg gaacaccttg ctcccgcccg ggtgtgcctt ctggaacttt gtgacatcca   4200
cgcgcttgcc gtagagcacg acgtgcacgc tcttgctatc gacggagctc acctcagcga   4260
gagacgcgtc ggtcccgctc accgcctgcg cgccgccgtc tccacccttg cccatggtgc   4320
ggccgcttgg ggggctatgg aagactttct tagttagttg tgtgaataag caatgttggg   4380
agaatcggga ctacttatag gataggaata aaacagaaaa gtattaagtg ctaatgaaat   4440
atttagactg ataattaaaa tcttcacgta tgtccacttg atataaaaac gtcaggaata   4500
aaggaagtac agtagaattt aaaggtactc tttttatata tacccgtgtt ctctttttgg   4560
ctagctagtt gcataaaaaa taatctatat ttttatcatt attttaaata tcttatgaga   4620
tggtaaatat ttatcataat ttttttact attatttatt atttgtgtgt gtaatacata   4680
tagaagttaa ttacaaattt tatttacttt ttcattattt tgatatgatt caccattaat   4740
ttagtgttat tatttataat agttcatttt aatctttttg tatatattat gcgtgcagta   4800
ctttttttcct acatataact actattacat tttatttata taatattttt attaatgaat   4860
tttcgtgata atatgtaata ttgttcatta ttatttcaga ttttttaaaa atatttgtgt   4920
tattatttat gaaatatgta atttttttag tatttgattt tatgatgata aagtgttcta   4980
aattcaaaag aagggggaaa gcgtaaacat taaaaaacgt catcaaacaa aaacaaaatc   5040
ttgttaataa agataaaact gtttgttttg atcactgtta tttcgtaata taaaaacatt   5100
atttatattt atattgttga caaccaaatt tgcctatcaa atctaaccaa tataatgcat   5160
gcgtggcagg taatgtacta ccatgaactt aagtcatgac ataataaacc gtgaatctga   5220
ccaatgcatg tacctancta aattgtattt gtgacacgaa gcaaatgatt caattcacaa   5280
tggagatggg aaacaaataa tgaagaaccc agaactaaga aagcttttct gaaaaataaa   5340
ataaaggcaa tgtcaaaagt atactgcatc atcagtccag aaagcacatg atattttttt   5400
atcagtatca atgcagctag ttttatttta caatatcgat atagctagtt taaatatatt   5460
gcagctagat ttataaatat ttgtgttatt atttatcatt tgtgtaatcc tgtttttagt   5520
attttagttt atatatgatg ataatgtatt ccaaatttaa aagaagggaa ataaatttaa   5580
acaagaaaaa aagtcatcaa acaaaaaaca aatgaaaggg tggaaagatg ttaccatgta   5640
```

```
atgtgaatgt tacagtattt cttttattat agagttaaca aattaactaa tatgattttg   5700
ttaataatga taaaatattt tttttattat tatttcataa tataaaaata gtttacttaa   5760
tataaaaaaa attctatcgt tcacaacaaa gttggccacc taatttaacc atgcatgtac   5820
ccatggacca tattaggtaa ccatcaaacc tgatgaagag ataaagagat gaagacttaa   5880
gtcataacac aaaaccataa aaaacaaaaa tacaatcaac cgtcaatctg accaatgcat   5940
gaaaaagctg caatagtgag tggcgacaca aagcacatga ttttcttaca acggagataa   6000
aaccaaaaaa atatttcatg aacaacctag aacaaataaa gcttttatat aataaatata   6060
taaataaata aaggctatgg aataatatac ttcaatatat ttggattaaa taaattgttg   6120
gcggggttga tatatttata cacacctaaa gtcacttcaa tctcatttc acttaacttt    6180
tattttttt ttctttttat ttatcataaa gagaatattg ataatatact ttttaacata    6240
tttttatgac atttttattt ggtgaaaact tattaaaaat cataaatttt gtaagttaga   6300
tttatttaaa gagttcctct tcttatttta aatttttaa taaattttta aataactaaa    6360
atttgtgtta aaaatgttaa aaaatgtgtt attaaccctt ctcttcgagg acgtacgaag   6420
cttagggcgg atcccccggg cgacctcgag ggggggcccg gtacgtgaag gttaaacatg   6480
gtgaatatgt taccactagc tgggatgccc attagatcaa aactgtaaaa ttctcccgtt   6540
tcccttctat tcacatgtga gccccctccc ttttctttct ttctcaattt tgattgagtt   6600
aaagtcacca gcaatgcatc actcaccctc caaaaaattt cttgtacaac ttctcggact   6660
atcccaaagc tccttttcct gagatggatg gtcctgtctc ttgcccttga tgtcttcctt   6720
gttcgatttt ggcttcctct aatgtctttc ttgctaggaa tcaccacctc actcatctat   6780
gttgtcgtag cttctgaaag tctcatacat atccttagtg ttgcactcat cttgtattga   6840
agtgaaaaag aatgttgttc tcctatccaa atctccattg aatctctttc tcccaatgtt   6900
gtcccatcgg ttggtcctcc tctccaacca attgtaaggt gtttaacata aacatggtac   6960
aattaagatt tttcatttca ttaagaaaag attgagattt gtggttctaa agtttcaatt   7020
agagtttgat gatattgaaa caaccgtaga acacattaag tattactaac ttatacatag   7080
agcattggaa tttcaccttt tatttattct gtttccgcca aaggtacatg actcaagtta   7140
ttttacacaa gtaacaaagg catctaagcc taagtattct tattcagact tttcattatt   7200
actttcattg atttggtgcg aaatgcggcc gcctactctt ccttgggacg gagtccaaga   7260
acacgcaagt gctccaaatg tgaagcaaat gcttgccaaa acgtatcctt gacaaggtat   7320
ggaaccttgt actcgctgca ggtgttcttg atgatggcca gaatatcggg ataatggtgc   7380
tgcgacacgt tggggaacag atggtgcaca gcctggtagt tcaagctgcc agtgatgctg   7440
gtccagaggt gcgaatcgtg tgcgtaatcc tgcgtagtct cgacctgcat agctgcccag   7500
tccttttgga tgatcccgtt ctcgtcaggc aacggccact gaacttcctc aacaacgtgg   7560
ttcgcctgga aggtcagcgc cagccagtaa gacgacacca tgtccgcgac cgtgaacaag   7620
agcagcacct tgcccagggg cagatactgc aggggaacaa tcaggcgata ccagacaaag   7680
aaagccttgc cgccccagaa catcacagtg tgccatgtcg agatgggatt gacacgaata   7740
gcgtcattgg tcttgacaaa gtacaaaatg ttgatgtcct gaatgcgcac cttgaacgcc   7800
agcagtccgt acaggaaagg aacaaacatg tgctggttga tgtggttgac aaaccacttt   7860
tggttgggct tgatacgacg aacatcgggc tcagacgtcg acacgtcggg atctgctcca   7920
gcaatgttgg tgtaggggtg atggccgagc atatgttggt acatccacac caggtacgat   7980
gctccgttga aaaagtcgtg cgtggctccc agaatcttcc agacagtggg gttgtgggtc   8040
```

```
actgaaaagt gagacgcatc atgaagaggg ttgagtccga cttgtgcgca cgcaaatccc   8100
atgatgattg caaacaccac ctgaagccat gtgcgttcga caacgaaagg cacaaagagc   8160
tgcgcgtagt aggaagcgat caaggatcca aagataagag cgtatcgtcc ccagatctct   8220
ggtctattct tgggatcaat gttccgatcc gtaaagtagc cctcgactct cgtcttgatg   8280
gttttgtgga acaccgttgg ctccgggaag atgggcagct cattcgagac cagtgtaccg   8340
acatagtact tcttcataat ggcatctgca gccccaaacg cgtgatacat ctcaaagacc   8400
ggagtaacat ctcggccagc tccgagcagg agagtgtcca ctccaccagg atggcggctc   8460
aagaactttg tgacatcgta caccctgccg cggatggcca agagtaggtc gtccttggtg   8520
ttatgggccg ccagctcttc ccaggtgaag gtttttcctt ggtccgttcc catgcggccg   8580
cggtgatgac tgatgagtgt ttaaggacca atggagagaa tgtttgagtt gtgaagcgga   8640
gaacctgagg cgtggttatt tatagggaag agaggaaggt gaatgaggga cacgtcacag   8700
aagtagggtg ctgagcttga gacattcttc agtatgcatg gctatggaag ccttgggtgc   8760
tacacctcat gaagttcatg gtgtgaggtg gcttcggcat ctcaattaag tgacaaagag   8820
aaaggtgttt cagtgtttct attgcaaatg gcagaaactc gtgatgacga ggggaccatg   8880
catggtttca tttcttttct tcctggattc tttctttcct tttatatatg caggttcata   8940
atttaaaaat tagactcgct ttcaatttct taatttctca ttttcctctt atattactgt   9000
actaatgtta accacgtaca cttatttttt ttttagttta attttgatag attgtgttga   9060
tttaaacata ttaatatttt caaccaaata aaaatcattt tagtagatac ggctttttaa   9120
ataattatta aaaatattaa ctatttatcc taaatggcac attttaatta aaaaaaatcc   9180
ggtgttgtaa gtgttttatt aatttgtttt ggcattatta aagcaacttt tttttttattt   9240
gttggcattt tgagtacgta cttaggctag cctgcaggcc aactgcgttt ggggctccag   9300
attaaacgac gccgtttcgt tcctttcgct tcacggctta acgatgtcgt ttctgtctgt   9360
gcccaaaaaa taaaggcatt tgttatttgc accagatatt tactaagtgc accctagttt   9420
gacaagtagg cgataattac aaatagatgc ggtgcaaata ataaattttg aaggaaataa   9480
ttacaaaaga acagaactta tatttacttt attttaaaaa actaaaatga aagaacaaaa   9540
aaagtaaaaa atacaaaaaa tgtgctttaa ccactttcat tatttgttac agaaagtatg   9600
attctactca aattgatctg ttgtatctgg tgctgccttg tcacactggc gatttcaatc   9660
ccctaaagat atggtgcaaa ctgcgaagtg atcaatatct gctcggttaa tttagattaa   9720
ttaataatat tcaacgtgat gtaccaaaaa aagacaattt tttgctccat tgacaaatta   9780
aacctcatca aggtaatttc caaacctata agcaaaaaaa tttcacatta attggcccgc   9840
aatcctatta gtcttattat actagagtag gaaaaaaaac aattacacaa cttgtcttat   9900
tattctctat gctaatgaat atttttccct tttgttagaa atcagtgttt cctaatttat   9960
tgagtattaa ttccactcac cgcatatatt taccgttgaa taagaaaatt ttacacataa  10020
ttctttttaa gataaataat ttttttatac tagatcttat atgattacgt gaagccaagt  10080
gggttatact aatgatatat aatgtttgat agtaatcagt ttataaacca aatgcatgga  10140
aatgttacgt ggaagcacgt aaattaacaa gcattgaagc aaatgcagcc accgcaccaa  10200
aaccacccca cttcacttcc acgtaccata ttccatgcaa ctacaacacc ctaaaacttc  10260
aataaatgcc cccaccttca cttcacttca cccatcaata gcaagcggcc gcaccatgga  10320
ggtggtgaat gaaatagtct caattgggca ggaagtttta cccaaagttg attatgccca  10380
actctggagt gatgccagtc actgtgaggt gctttacttg tccatcgcat ttgtcatctt  10440
```

```
gaagttcact cttggccccc ttggtccaaa aggtcagtct cgtatgaagt ttgttttcac  10500

caattacaac cttctcatgt ccatttattc gttgggatca ttcctctcaa tggcatatgc  10560

catgtacacc atcggtgtta tgtctgacaa ctgcgagaag gcttttgaca acaacgtctt  10620

caggatcacc acgcagttgt tctatttgag caagttcctg gagtatattg actccttcta  10680

tttgccactg atgggcaagc ctctgacctg gttgcaattc ttccatcatt tgggggcacc  10740

gatggatatg tggctgttct ataattaccg aaatgaagct gtttggattt ttgtgctgtt  10800

gaatggtttc atccactgga tcatgtacgg ttattattgg accagattga tcaagctgaa  10860

gttccccatg ccaaaatccc tgattacatc aatgcagatc attcaattca atgttggttt  10920

ctacattgtc tggaagtaca ggaacattcc ctgttatcgc caagatggga tgaggatgtt  10980

tggctggttc ttcaattact ttatgttgg cacagtcttg tgtttgttct tgaatttcta  11040

tgtgcaaacg tatatcgtca ggaagcacaa gggagccaaa aagattcagt gagcggccgc  11100

gaagttaaaa gcaatgttgt cacttgtcgt actaacacat gatgtgatag tttatgctag  11160

ctagctataa cataagctgt ctctgagtgt gttgtatatt aataaagatc atcactggtg  11220

aatggtgatc gtgtacgtac cctacttagt aggcaatgga agcacttaga gtgtgctttg  11280

tgcatggcct tgcctctgtt ttgagacttt tgtaatgttt tcgagtttaa atctttgcct  11340

ttgcgtacgt ctagagtcga cctgca                                        11366


<210> SEQ ID NO 46
<211> LENGTH: 7085
<212> TYPE: DNA
<213> ORGANISM: Artificial Sequence
<220> FEATURE:
<223> OTHER INFORMATION: plasmid pKR72

<400> SEQUENCE: 46

gtacggatcc gtcgacggcg cgcccgatca tccggatata gttcctcctt tcagcaaaaa     60

acccctcaag acccgtttag aggccccaag gggttatgct agttattgct cagcggtggc    120

agcagccaac tcagcttcct ttcgggcttt gttagcagcc ggatcgatcc aagctgtacc    180

tcactattcc tttgccctcg gacgagtgct ggggcgtcgg tttccactat cggcgagtac    240

ttctacacag ccatcggtcc agacggccgc gcttctgcgg gcgatttgtg tacgcccgac    300

agtcccggct ccggatcgga cgattgcgtc gcatcgaccc tgcgcccaag ctgcatcatc    360

gaaattgccg tcaaccaagc tctgatagag ttggtcaaga ccaatgcgga gcatatacgc    420

ccggagccgc ggcgatcctg caagctccgg atgcctccgc tcgaagtagc gcgtctgctg    480

ctccatacaa gccaaccacg gcctccagaa gaagatgttg gcgacctcgt attgggaatc    540

cccgaacatc gcctcgctcc agtcaatgac cgctgttatg cggccattgt ccgtcaggac    600

attgttggag ccgaaatccg cgtgcacgag gtgccggact tcggggcagt cctcggccca    660

aagcatcagc tcatcgagag cctgcgcgac ggacgcactg acggtgtcgt ccatcacagt    720

ttgccagtga tacacatggg gatcagcaat cgcgcatatg aaatcacgcc atgtagtgta    780

ttgaccgatt ccttgcggtc cgaatgggcc gaacccgctc gtctggctaa gatcggccgc    840

agcgatcgca tccatagcct ccgcgaccgg ctgcagaaca gcgggcagtt cggtttcagg    900

caggtcttgc aacgtgacac cctgtgcacg gcgggagatg caataggtca ggctctcgct    960

gaattcccca atgtcaagca cttccggaat cgggagcgcg gccgatgcaa agtgccgata   1020

aacataacga tctttgtaga aaccatcggc gcagctattt acccgcagga catatccacg   1080

ccctcctaca tcgaagctga aagcacgaga ttcttcgccc tccgagagct gcatcaggtc   1140
```

```
ggagacgctg tcgaactttt cgatcagaaa cttctcgaca gacgtcgcgg tgagttcagg   1200
cttttccatg ggtatatctc cttcttaaag ttaaacaaaa ttatttctag agggaaaccg   1260
ttgtggtctc cctatagtga gtcgtattaa tttcgcggga tcgagatcga tccaattcca   1320
atcccacaaa aatctgagct taacagcaca gttgctcctc tcagagcaga atcgggtatt   1380
caacaccctc atatcaacta ctacgttgtg tataacggtc cacatgccgg tatatacgat   1440
gactggggtt gtacaaaggc ggcaacaaac ggcgttcccg gagttgcaca caagaaattt   1500
gccactatta cagaggcaag agcagcagct gacgcgtaca caacaagtca gcaaacagac   1560
aggttgaact tcatccccaa aggagaagct caactcaagc ccaagagctt tgctaaggcc   1620
ctaacaagcc caccaaagca aaaagcccac tggctcacgc taggaaccaa aaggcccagc   1680
agtgatccag ccccaaaaga gatctccttt gccccggaga ttacaatgga cgatttcctc   1740
tatctttacg atctaggaag gaagttcgaa ggtgaaggtg acgacactat gttcaccact   1800
gataatgaga aggttagcct cttcaatttc agaaagaatg ctgacccaca gatggttaga   1860
gaggcctacg cagcaggtct catcaagacg atctacccga gtaacaatct ccaggagatc   1920
aaataccttc ccaagaaggt taaagatgca gtcaaaagat tcaggactaa ttgcatcaag   1980
aacacagaga aagacatatt tctcaagatc agaagtacta ttccagtatg gacgattcaa   2040
ggcttgcttc ataaaccaag gcaagtaata gagattggag tctctaaaaa ggtagttcct   2100
actgaatcta aggccatgca tggagtctaa gattcaaatc gaggatctaa cagaactcgc   2160
cgtgaagact ggcgaacagt tcatacagag tcttttacga ctcaatgaca agaagaaaat   2220
cttcgtcaac atggtggagc acgacactct ggtctactcc aaaaatgtca aagatacagt   2280
ctcagaagac caaagggcta ttgagacttt tcaacaaagg ataatttcgg gaaacctcct   2340
cggattccat tgcccagcta tctgtcactt catcgaaagg acagtagaaa aggaaggtgg   2400
ctcctacaaa tgccatcatt gcgataaagg aaaggctatc attcaagatg cctctgccga   2460
cagtggtccc aaagatggac ccccacccac gaggagcatc gtggaaaaag aagacgttcc   2520
aaccacgtct tcaaagcaag tggattgatg tgacatctcc actgacgtaa gggatgacgc   2580
acaatcccac tatccttcgc aagacccttc ctctatataa ggaagttcat ttcatttgga   2640
gaggacacgc tcgagctcat ttctctatta cttcagccat aacaaaagaa ctcttttctc   2700
ttcttattaa accatgaaaa agcctgaact caccgcgacg tctgtcgaga agtttctgat   2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca ctttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
cggaccgcaa ggaatcggtc aatacactac atggcgtgat ttcatatgcg cgattgctga   3180
tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
```

```
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aaggaatagt gaggtaccta aagaaggagt gcgtcgaagc agatcgttca   3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggtttttat gattagagtc ccgcaattat acatttaata cgcgatagaa   3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgacattaac ctataaaaat aggcgtatca cgaggccctt   4980
tcgtctcgcg cgtttcggtg atgacggtga aaacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt gttgaaacat   5280
ccctgaagtg tctcatttta ttttatttat tctttgctga taaaaaaata aaataaaaga   5340
agctaagcac acggtcaacc attgctctac tgctaaaagg gttatgtgta gtgttttact   5400
gcataaatta tgcagcaaac aagacaactc aaattaaaaa atttcctttg cttgtttttt   5460
tgttgtctct gacttgactt tcttgtggaa gttggttgta taaggattgg gacaccattg   5520
tccttcttaa tttaatttta ttctttgctg ataaaaaaaa aaatttcata tagtgttaaa   5580
taataatttg ttaaataacc aaaaagtcaa atatgtttac tctcgtttaa ataattgaga   5640
ttcgtccagc aaggctaaac gattgtatag atttatgaca atatttactt ttttatagat   5700
aaatgttata ttataataaa tttatataca tatattatat gttatttatt attattttaa   5760
atccttcaat attttatcaa accaactcat aatttttttt ttatctgtaa gaagcaataa   5820
aattaaatag acccacttta aggatgatcc aacctttata cagagtaaga gagttcaaat   5880
agtacccttt catatacata tcaactaaaa tattagaaat atcatggatc aaaccttata   5940
```

```
aagacattaa ataagtggat aagtataata tataaatggg tagtatataa tatataaatg   6000

gatacaaact tctctcttta taattgttat gtctccttaa catcctaata taatacataa   6060

gtgggtaata tataatatat aaatggagac aaacttcttc cattataatt gttatgtctt   6120

cttaacactt atgtctcgtt cacaatgcta aggttagaat tgtttagaaa gtcttatagt   6180

acacatttgt ttttgtacta tttgaagcat tccataagcc gtcacgattc agatgattta   6240

taataataag aggaaattta tcatagaaca ataaggtgca tagatagagt gttaatatat   6300

cataacatcc tttgtttatt catagaagaa gtgagatgga gctcagttat tatactgtta   6360

catggtcgga tacaatattc catgctctcc atgagctctt acacctacat gcattttagt   6420

tcatacttgc ggccgcagta tatcttaaat tctttaatac ggtgtactag gatattgaac   6480

tggttcttga tgatgaaaac ctgggccgag attgcagcta tttatagtca taggtcttgt   6540

taacatgcat ggacatttgg ccacggggtg gcatgcagtt tgacgggtgt tgaaataaac   6600

aaaaatgagg tggcggaaga gaatacgagt ttgaggttgg gttagaaaca acaaatgtga   6660

gggctcatga tgggttgagt tggtgaatgt tttgggctgc tcgattgaca cctttgtgag   6720

tacgtgttgt tgtgcatggc ttttggggtc cagttttttt ttcttgacgc ggcgatcctg   6780

atcagctagt ggataagtga tgtccactgt gtgtgattgc gtttttgttt gaattttatg   6840

aacttagaca ttgctatgca aaggatactc tcattgtgtt ttgtcttctt ttgttccttg   6900

gctttttctt atgatccaag agactagtca gtgttgtggc attcgagact accaagatta   6960

attatgatgg gggaaggata agtaactgat tagtacggac tgttaccaaa ttaattaata   7020

agcggcaaat gaagggcatg gatcaaaagc ttggatctcc tgcaggatct ggccggccgg   7080

atctc                                                               7085
```

<210> SEQ ID NO 47
<211> LENGTH: 7873
<212> TYPE: DNA
<213> ORGANISM: Artificial Sequence
<220> FEATURE:
<223> OTHER INFORMATION: plasmid pKR912

<400> SEQUENCE: 47

```
ggccgcaagt atgaactaaa atgcatgtag gtgtaagagc tcatggagag catggaatat     60

tgtatccgac catgtaacag tataataact gagctccatc tcacttcttc tatgaataaa    120

caaaggatgt tatgatatat taacactcta tctatgcacc ttattgttct atgataaatt    180

tcctcttatt attataaatc atctgaatcg tgacggctta tggaatgctt caaatagtac    240

aaaaacaaat gtgtactata agactttcta aacaattcta accttagcat tgtgaacgag    300

acataagtgt taagaagaca taacaattat aatggaagaa gtttgtctcc atttatatat    360

tatatattac ccacttatgt attatattag gatgttaagg agacataaca attataaaga    420

gagaagtttg tatccattta tatattatat actacccatt tatatattat acttatccac    480

ttatttaatg tctttataag gtttgatcca tgatatttct aatattttag ttgatatgta    540

tatgaaaggg tactatttga actctcttac tctgtataaa ggttggatca tccttaaagt    600

gggtctattt aattttattg cttcttacag ataaaaaaaa aattatgagt tggtttgata    660

aaatattgaa ggatttaaaa taataataaa taacatataa tatatgtata taaatttatt    720

ataaatataac atttatctat aaaaaagtaa atattgtcat aaatctatac aatcgtttag    780

ccttgctgga cgaatctcaa ttatttaaac gagagtaaac atatttgact ttttggttat    840

ttaacaaatt attatttaac actatatgaa attttttttt ttatcagcaa agaataaaat    900
```

```
taaattaaga aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taaccctttt agcagtagag caatggttga   1080
ccgtgtgctt agcttctttt attttatttt tttatcagca aagaataaat aaaataaaat   1140
gagacacttc agggatgttt caacaagctt ggcgcgccgt tctatagtgt cacctaaatc   1200
gtatgtgtat gatacataag gttatgtatt aattgtagcc gcgttctaac gacaatatgt   1260
ccatatggtg cactctcagt acaatctgct ctgatgccgc atagttaagc cagccccgac   1320
acccgccaac acccgctgac gcgccctgac gggcttgtct gctcccggca tccgcttaca   1380
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
accacttcaa gaactctgta gcaccgccta catacctcgc tctgctaatc ctgttaccag   1800
tggctgctgc cagtggcgat aagtcgtgtc ttaccgggtt ggactcaaga cgatagttac   1860
cggataaggc gcagcggtcg ggctgaacgg ggggttcgtg cacacagccc agcttggagc   1920
gaacgaccta caccgaactg agatacctac agcgtgagca ttgagaaagc gccacgcttc   1980
ccgaagggag aaaggcggac aggtatccgg taagcggcag ggtcggaaca ggagagcgca   2040
cgagggagct tccaggggga aacgcctggt atctttatag tcctgtcggg tttcgccacc   2100
tctgacttga gcgtcgattt ttgtgatgct cgtcaggggg gcggagccta tggaaaaacg   2160
ccagcaacgc ggccttttta cggttcctgg ccttttgctg gccttttgct cacatgttct   2220
ttcctgcgtt atcccctgat tctgtggata accgtattac cgcctttgag tgagctgata   2280
ccgctcgccg cagccgaacg accgagcgca gcgagtcagt gagcgaggaa gcggaagagc   2340
gcccaatacg caaaccgcct ctccccgcgc gttggccgat tcattaatgc aggttgatcg   2400
attcgacatc gatctagtaa catagatgac accgcgcgcg ataatttatc ctagtttgcg   2460
cgctatattt tgttttctat cgcgtattaa atgtataatt gcgggactct aatcataaaa   2520
acccatctca taaataacgt catgcattac atgttaatta ttacatgctt aacgtaattc   2580
aacagaaatt atatgataat catcgcaaga ccggcaacag gattcaatct taagaaactt   2640
tattgccaaa tgtttgaacg atctgcttcg acgcactcct tctttaggta cctcactatt   2700
cctttgccct cggacgagtg ctggggcgtc ggtttccact atcggcgagt acttctacac   2760
agccatcggt ccagacggcc gcgcttctgc gggcgatttg tgtacgcccg acagtcccgg   2820
ctccggatcg gacgattgcg tcgcatcgac cctgcgccca agctgcatca tcgaaattgc   2880
cgtcaaccaa gctctgatag agttggtcaa gaccaatgcg gagcatatac gcccggagcc   2940
gcggcgatcc tgcaagctcc ggatgcctcc gctcgaagta gcgcgtctgc tgctccatac   3000
aagccaacca cggcctccag aagaagatgt tggcgacctc gtattgggaa tccccgaaca   3060
tcgcctcgct ccagtcaatg accgctgtta tgcggccatt gtccgtcagg acattgttgg   3120
agccgaaatc cgcgtgcacg aggtgccgga cttcggggca gtcctcggcc caaagcatca   3180
gctcatcgag agcctgcgcg acggacgcac tgacggtgtc gtccatcaca gtttgccagt   3240
gatacacatg ggatcagcaa atcgcgcata tgaaatcacg ccatgtagtg tattgaccga   3300
```

```
ttccttgcgg tccgaatggg ccgaacccgc tcgtctggct aagatcggcc gcagcgatcg   3360
catccatggc ctccgcgacc ggctgcagaa cagcgggcag ttcggtttca ggcaggtctt   3420
gcaacgtgac accctgtgca cggcgggaga tgcaataggt caggctctcg ctgaattccc   3480
caatgtcaag cacttccgga atcgggagcg cggccgatgc aaagtgccga taaacataac   3540
gatctttgta gaaaccatcg gcgcagctat ttacccgcag gacatatcca cgccctccta   3600
catcgaagct gaaagcacga gattcttcgc cctccgagag ctgcatcagg tcggagacgc   3660
tgtcgaactt ttcgatcaga aacttctcga cagacgtcgc ggtgagttca ggctttttca   3720
tggtttaata agaagagaaa agagttcttt tgttatggct gaagtaatag agaaatgagc   3780
tcgagcgtgt cctctccaaa tgaaatgaac ttccttatat agaggaaggg tcttgcgaag   3840
gatagtggga ttgtgcgtca tcccttacgt cagtggagat gtcacatcaa tccacttgct   3900
ttgaagacgt ggttggaacg tcttcttttt ccacgatgct cctcgtgggt gggggtccat   3960
ctttgggacc actgtcggca gaggcatctt gaatgatagc ctttccttta tcgcaatgat   4020
ggcatttgta ggagccacct tccttttcta ctgtcctttc gatgaagtga cagatagctg   4080
ggcaatggaa tccgaggagg tttcccgaaa ttatcctttg ttgaaaagtc tcaatagccc   4140
tttggtcttc tgagactgta tctttgacat ttttggagta gaccagagtg tcgtgctcca   4200
ccatgttgac gaagattttc ttcttgtcat tgagtcgtaa aagactctgt atgaactgtt   4260
cgccagtctt cacggcgagt tctgttagat cctcgatttg aatcttagac tccatgcatg   4320
gccttagatt cagtaggaac taccttttta gagactccaa tctctattac ttgccttggt   4380
ttatgaagca agccttgaat cgtccatact ggaatagtac ttctgatctt gagaaatatg   4440
tctttctctg tgttcttgat gcaattagtc ctgaatcttt tgactgcatc tttaaccttc   4500
ttgggaaggt atttgatctc ctggagattg ttactcgggt agatcgtctt gatgagacct   4560
gctgcgtagg cctctctaac catctgtggg tcagcattct ttctgaaatt gaagaggcta   4620
accttctcat tatcagtggt gaacatagtg tcgtcacctt caccttcgaa cttccttcct   4680
agatcgtaaa gatagaggaa atcgtccatt gtaatctccg gggcaaagga gatctctttt   4740
ggggctggat cactgctggg ccttttggtt cctagcgtga gccagtgggc tttttgcttt   4800
ggtgggcttg ttagggcctt agcaaagctc ttgggcttga gttgagcttc tcctttgggg   4860
atgaagttca acctgtctgt ttgctgactt gttgtgtacg cgtcagctgc tgctcttgcc   4920
tctgtaatag tggcaaattt cttgtgtgca actccgggaa cgccgtttgt tgccgccttt   4980
gtacaacccc agtcatcgta tataccggca tgtggaccgt tatacacaac gtagtagttg   5040
atatgagggt gttgaatacc cgattctgct ctgagaggag caactgtgct gttaagctca   5100
gatttttgtg ggattggaat tggatcgatc tcgatcccgc gaaattaata cgactcacta   5160
tagggagacc acaacggttt ccctctagaa ataattttgt ttaactttaa gaaggagata   5220
tacccatgga aaagcctgaa ctcaccgcga cgtctgtcga gaagtttctg atcgaaaagt   5280
tcgacagcgt ctccgacctg atgcagctct cggagggcga agaatctcgt gctttcagct   5340
tcgatgtagg agggcgtgga tatgtcctgc gggtaaatag ctgcgccgat ggtttctaca   5400
aagatcgtta tgtttatcgg cactttgcat cggccgcgct cccgattccg gaagtgcttg   5460
acattgggga attcagcgag agcctgacct attgcatctc ccgccgtgca cagggtgtca   5520
cgttgcaaga cctgcctgaa accgaactgc ccgctgttct gcagccggtc gcggaggcta   5580
tggatgcgat cgctgcggcc gatcttagcc agacgagcgg gttcggccca ttcggaccgc   5640
aaggaatcgg tcaatacact acatggcgtg atttcatatg cgcgattgct gatccccatg   5700
```

tgtatcactg gcaaactgtg atggacgaca ccgtcagtgc gtccgtcgcg caggctctcg 5760
atgagctgat gctttgggcc gaggactgcc ccgaagtccg gcacctcgtg cacgcggatt 5820
tcggctccaa caatgtcctg acggacaatg gccgcataac agcggtcatt gactggagcg 5880
aggcgatgtt cggggattcc caatacgagg tcgccaacat cttcttctgg aggccgtggt 5940
tggcttgtat ggagcagcag acgcgctact tcgagcggag gcatccggag cttgcaggat 6000
cgccgcggct ccgggcgtat atgctccgca ttggtcttga ccaactctat cagagcttgg 6060
ttgacggcaa tttcgatgat gcagcttggg cgcagggtcg atgcgacgca atcgtccgat 6120
ccggagccgg gactgtcggg cgtacacaaa tcgcccgcag aagcgcggcc gtctggaccg 6180
atggctgtgt agaagtactc gccgatagtg gaaaccgacg ccccagcact cgtccgaggg 6240
caaaggaata gtgaggtaca gcttggatcg atccggctgc taacaaagcc cgaaaggaag 6300
ctgagttggc tgctgccacc gctgagcaat aactagcata accccttggg gcctctaaac 6360
gggtcttgag gggttttttg ctgaaaggag gaactatatc cggatgatcg ggcgcgccgt 6420
cgacggatcc gtacgagatc cggccggcca gatcctgcag gagatccaag cttttgatcc 6480
atgcccttca tttgccgctt attaattaat ttggtaacag tccgtactaa tcagttactt 6540
atccttcccc catcataatt aatcttggta gtctcgaatg ccacaacact gactagtctc 6600
ttggatcata agaaaaagcc aaggaacaaa agaagacaaa acacaatgag agtatccttt 6660
gcatagcaat gtctaagttc ataaaattca aacaaaaacg caatcacaca cagtggacat 6720
cacttatcca ctagctgatc aggatcgccg cgtcaagaaa aaaaaactgg accccaaaag 6780
ccatgcacaa caacacgtac tcacaaaggt gtcaatcgag cagcccaaaa cattcaccaa 6840
ctcaacccat catgagccct cacatttgtt gtttctaacc caacctcaaa ctcgtattct 6900
cttccgccac ctcatttttg tttatttcaa cacccgtcaa actgcatgcc accccgtggc 6960
caaatgtcca tgcatgttaa caagacctat gactataaat agctgcaatc tcggcccagg 7020
ttttcatcat caagaaccag ttcaatatcc tagtacaccg tattaaagaa tttaagatat 7080
actgcggccg caccatggag gtggtgaatg aaatagtctc aattgggcag gaagttttac 7140
ccaaagttga ttatgcccaa ctctggagtg atgccagtca ctgtgaggtg ctttacttgt 7200
ccatcgcatt tgtcatcttg aagttcactc ttggccccct tggtccaaaa ggtcagtctc 7260
gtatgaagtt tgttttcacc aattacaacc ttctcatgtc catttattcg ttgggatcat 7320
tcctctcaat ggcatatgcc atgtacacca tcggtgttat gtctgacaac tgcgagaagg 7380
cttttgacaa caacgtcttc aggatcacca cgcagttgtt ctatttgagc aagttcctgg 7440
agtatattga ctccttctat ttgccactga tgggcaagcc tctgacctgg ttgcaattct 7500
tccatcattt gggggcaccg atggatatgt ggctgttcta taattaccga aatgaagctg 7560
tttggatttt tgtgctgttg aatggtttca tccactggat catgtacggt tattattgga 7620
ccagattgat caagctgaag ttccccatgc caaaatccct gattacatca atgcagatca 7680
ttcaattcaa tgttggtttc tacattgtct ggaagtacag gaacattccc tgttatcgcc 7740
aagatgggat gaggatgttt ggctggttct tcaattactt ttatgttggc acagtcttgt 7800
gtttgttctt gaatttctat gtgcaaacgt atatcgtcag gaagcacaag ggagccaaaa 7860
agattcagtg agc 7873

<210> SEQ ID NO 48
<211> LENGTH: 9892
<212> TYPE: DNA
<213> ORGANISM: Artificial Sequence
<220> FEATURE:
<223> OTHER INFORMATION: plasmid pKR886r

<400> SEQUENCE: 48

```
ggtcgactcg acgtacgtct agaggatccg tcgacggcgc gcccgatcat ccggatatag     60

ttcctccttt cagcaaaaaa cccctcaaga cccgtttaga ggccccaagg ggttatgcta    120

gttattgctc agcggtggca gcagccaact cagcttcctt tcgggctttg ttagcagccg    180

gatcgatcca agctgtacct cactattcct ttgccctcgg acgagtgctg gggcgtcggt    240

ttccactatc ggcgagtact tctacacagc catcggtcca gacggccgcg cttctgcggg    300

cgatttgtgt acgcccgaca gtcccggctc cggatcggac gattgcgtcg catcgaccct    360

gcgcccaagc tgcatcatcg aaattgccgt caaccaagct ctgatagagt tggtcaagac    420

caatgcggag catatacgcc cggagccgcg gcgatcctgc aagctccgga tgcctccgct    480

cgaagtagcg cgtctgctgc tccatacaag ccaaccacgg cctccagaag aagatgttgg    540

cgacctcgta ttgggaatcc ccgaacatcg cctcgctcca gtcaatgacc gctgttatgc    600

ggccattgtc cgtcaggaca ttgttggagc cgaaatccgc gtgcacgagg tgccggactt    660

cggggcagtc ctcggcccaa agcatcagct catcgagagc ctgcgcgacg gacgcactga    720

cggtgtcgtc catcacagtt tgccagtgat acacatgggg atcagcaatc gcgcatatga    780

aatcacgcca tgtagtgtat tgaccgattc cttgcggtcc gaatgggccg aacccgctcg    840

tctggctaag atcggccgca gcgatcgcat ccatagcctc cgcgaccggc tgcagaacag    900

cgggcagttc ggtttcaggc aggtcttgca acgtgacacc ctgtgcacgg cgggagatgc    960

aataggtcag gctctcgctg aattccccaa tgtcaagcac ttccggaatc gggagcgcgg   1020

ccgatgcaaa gtgccgataa acataacgat ctttgtagaa accatcggcg cagctattta   1080

cccgcaggac atatccacgc cctcctacat cgaagctgaa agcacgagat tcttcgccct   1140

ccgagagctg catcaggtcg gagacgctgt cgaacttttc gatcagaaac ttctcgacag   1200

acgtcgcggt gagttcaggc ttttccatgg gtatatctcc ttcttaaagt taaacaaaat   1260

tatttctaga gggaaaccgt tgtggtctcc ctatagtgag tcgtattaat ttcgcgggat   1320

cgagatctga tcaacctgca ttaatgaatc ggccaacgcg cggggagagg cggtttgcgt   1380

attgggcgct cttccgcttc ctcgctcact gactcgctgc gctcggtcgt tcggctgcgg   1440

cgagcggtat cagctcactc aaaggcggta atacggttat ccacagaatc aggggataac   1500

gcaggaaaga acatgtgagc aaaaggccag caaaaggcca ggaaccgtaa aaaggccgcg   1560

ttgctggcgt ttttccatag gctccgcccc cctgacgagc atcacaaaaa tcgacgctca   1620

agtcagaggt ggcgaaaccc gacaggacta taaagatacc aggcgtttcc ccctggaagc   1680

tccctcgtgc gctctcctgt tccgaccctg ccgcttaccg gatacctgtc cgcctttctc   1740

ccttcgggaa gcgtggcgct ttctcaatgc tcacgctgta ggtatctcag ttcggtgtag   1800

gtcgttcgct ccaagctggg ctgtgtgcac gaaccccccg ttcagcccga ccgctgcgcc   1860

ttatccggta actatcgtct tgagtccaac ccggtaagac acgacttatc gccactggca   1920

gcagccactg gtaacaggat tagcagagcg aggtatgtag gcggtgctac agagttcttg   1980

aagtggtggc ctaactacgg ctacactaga aggacagtat ttggtatctg cgctctgctg   2040

aagccagtta ccttcggaaa aagagttggt agctcttgat ccggcaaaca aaccaccgct   2100

ggtagcggtg gtttttttgt ttgcaagcag cagattacgc gcagaaaaaa aggatctcaa   2160

gaagatcctt tgatcttttc tacggggtct gacgctcagt ggaacgaaaa ctcacgttaa   2220

gggattttgg tcatgacatt aacctataaa aataggcgta tcacgaggcc ctttcgtctc   2280
```

```
gcgcgtttcg gtgatgacgg tgaaaacctc tgacacatgc agctcccgga gacggtcaca   2340

gcttgtctgt aagcggatgc cgggagcaga caagcccgtc agggcgcgtc agcgggtgtt   2400

ggcgggtgtc ggggctggct taactatgcg gcatcagagc agattgtact gagagtgcac   2460

catatggaca tattgtcgtt agaacgcggc tacaattaat acataacctt atgtatcata   2520

cacatacgat ttaggtgaca ctatagaacg gcgcgccaag ctgggtctag aactagaaac   2580

gtgatgccac ttgttattga agtcgattac agcatctatt ctgttttact atttataact   2640

ttgccatttc tgacttttga aaactatctc tggatttcgg tatcgctttg tgaagatcga   2700

gcaaaagaga cgttttgtgg acgcaatggt ccaaatccgt tctacatgaa caaattggtc   2760

acaatttcca ctaaaagtaa ataaatggca agttaaaaaa ggaatatgca ttttactgat   2820

tgcctaggtg agctccaaga gaagttgaat ctacacgtct accaaccgct aaaaaaagaa   2880

aaacattgat atgtaacctg attccattag cttttgactt cttcaacaga ttctctactt   2940

agatttctaa cagaaatatt attactagca catcattttc agtctcacta cagcaaaaaa   3000

tccaacggca caatacagac aacaggagat atcagactac agagatagat agatgctact   3060

gcatgtagta agttaaataa aaggaaaata aaatgtcttg ctaccaaaac tactacagac   3120

tatgatgctc accacaggcc aaatcctgca actaggacag cattatctta tatatattgt   3180

acaaaacaag catcaaggaa catttggtct aggcaatcag tacctcgttc taccatcacc   3240

ctcagttatc acatccttga aggatccatt actgggaatc atcggcaaca catgctcctg   3300

atggggcaca atgacatcaa gaaggtaggg gccaggggtg tccaacattc tctgaattgc   3360

cgctctaagc tcttccttct tcgtcactcg cgctgccggt atcccacaag catcagcaaa   3420

cttgagcatg tttgggaata tctcgctctc gctagacgga tctccaagat aggtgtgagc   3480

tctattggac ttgtagaacc tatcctccaa ctgaaccacc atacccaaat gctgattgtt   3540

caacaacaat atcttaactg ggagattctc cactcttata gtggccaact cctgaacatt   3600

catgatgaaa ctaccatccc catcaatgtc aaccacaaca gccccagggt tagcaacagc   3660

agcaccaata gccgcaggca atccaaaacc catggctcca agacccccctg aggtcaacca   3720

ctgcctcggt ctcttgtact tgtaaaactg cgcagcccac atttgatgct gcccaacccc   3780

agtactaaca atagcatctc cattagtcaa ctcatcaaga acctcgatag catgctgcgg   3840

agaaatcgcg tcctggaatg tcttgtaacc caatggaaac ttgtgtttct gcacattaat   3900

ctcttctctc caacctccaa gatcaaactt accctccact cctttctcct ccaaaatcat   3960

attaattccc ttcaaggcca acttcaaatc cgcgcaaacc gacacgtgcg cctgcttgtt   4020

cttcccaatc tcggcagaat caatatcaat gtgaacaatc ttagccctac tagcaaaagc   4080

ctcaagcttc ccagtaacac ggtcatcaaa ccttacccca aaggcaagca acaaatcact   4140

attgtcaaca gcatagttag cataaacagt accatgcata cccagcatct gaagggaata   4200

ttcatcacca ataggaaaag ttccaagacc cattaaagtg ctagcaacgg gaataccagt   4260

gagttcaaca aagcgcctca attcagcact ggaattcaaa ctgccaccgc cgacgtagag   4320

aacgggcttt tgggcctcca tgatgagtct gacaatgtgt tccaattggg cctcggcggg   4380

gggcctgggc agcctggcga ggtaaccggg gaggttaacg ggctcgtccc aattaggcac   4440

ggcgagttgc tgctgaacgt ctttgggaat gtcgatgagg accggaccgg ggcggccgga   4500

ggtggcgacg aagaaagcct cggcgacgac gcgggggatg tcgtcgacgt cgaggatgag   4560

gtagttgtgc ttcgtgatgg atctgctcac ctccacgatc ggggtttctt ggaaggcgtc   4620

ggtgccgatc atccggcggg cgacctggcc ggtgatggcg acgactggga cgctgtccat   4680
```

```
taaagcgtcg gcgaggccgc tcacgaggtt ggtggcgccg gggccggagg tggcaatgca   4740
gacgccgggg aggccggagg aacgcgcgta gccttcggcg gcgaagacgc cgccctgctc   4800
gtggcgcggg agcacgttgc ggatggcggc ggagcgcgtg agcgcctggt ggatctccat   4860
cgacgcaccg ccggggtacg cgaacaccgt cgtcacgccc tgcctctcca gcgcctccac   4920
aaggatgtcc gcgcccttgc gaggttcgcc ggaggcgaac cgtgacacga agggctccgt   4980
ggtcggcgct tccttggtga agggcgccgc cgtgggggt ttggagatgg aacatttgat    5040
tttgagagcg tggttgggtt tggtgagggt ttgatgagag agagggaggg tggatctagt   5100
aatgcgtttg gggaaggtgg ggtgtgaaga ggaagaagag aatcgggtgg ttctggaagc   5160
ggtggccgcc attgtgttgt gtggcatggt tatacttcaa aaactgcaca acaagcctag   5220
agttagtacc taaacagtaa atttacaaca gagagcaaag acacatgcaa aaatttcagc   5280
cataaaaaaa gttataatag aatttaaagc aaaagtttca tttttaaac atatatacaa    5340
acaaactgga tttgaaggaa gggattaatt cccctgctca aagtttgaat tcctattgtg   5400
acctatactc gaataaaatt gaagcctaag gaatgtatga gaaacaagaa aacaaaacaa   5460
aactacagac aaacaagtac aattacaaaa ttcgctaaaa ttctgtaatc accaaacccc   5520
atctcagtca gcacaaggcc caaggtttat tttgaaataa aaaaaaagtg attttatttc   5580
tcataagcta aaagaaagaa aggcaattat gaaatgattt cgactagatc tgaaagtcca   5640
acgcgtattc cgcagatatt aaagaaagag tagagtttca catggatcct agatggaccc   5700
agttgaggaa aaagcaaggc aaagcaaacc agaagtgcaa gatccgaaat tgaaccacgg   5760
aatctaggat ttggtagagg gagaagaaaa gtaccttgag aggtagaaga gaagagaaga   5820
gcagagagat atatgaacga gtgtgtcttg gtctcaactc tgaagcgata cgagtttaga   5880
ggggagcatt gagttccaat ttatagggaa accgggtggc aggggtgagt taatgacgga   5940
aaagcccta agtaacgaga ttggattgtg ggttagattc aaccgtttgc atccgcggct    6000
tagattgggg aagtcagagt gaatctcaac cgttgactga gttgaaaatt gaatgtagca   6060
accaattgag ccaaccccag cctttgccct ttgattttga tttgtttgtt gcatactttt   6120
tatttgtctt ctggttctga ctctctttct ctcgtttcaa tgccaggttg cctactccca   6180
caccactcac aagaagattc tactgttagt attaaatatt ttttaatgta ttaaatgatg   6240
aatgcttttg taaacagaac aagactatgt ctaataagtg tcttgcaaca ttttttaaga   6300
aattaaaaaa aatatattta ttatcaaaat caaatgtatg aaaaatcatg aataatataa   6360
ttttatacat ttttttaaaa aatcttttaa tttcttaatt aatatcttaa aaataatgat   6420
taatatttaa cccaaaataa ttagtatgat tggtaaggaa gatatccatg ttatgtttgg   6480
atgtgagttt gatctagagc aaagcttact agagtcgacc tgcagcccgg gggatccgcc   6540
cacgtacggt accatctgct aatattttaa atcacatgca agagaggagg catggttcca   6600
ttttctacct tcacattatt tgagaaaaac gaacttgttc tgtgttttat ttttgccctt   6660
cacattagta caacgtggaa gactcatggt tacacagaat catacataag tacaatgctt   6720
gtccctaaga aaacaagcac tcgttgtatt gaacctttac ggctcatgcg gccgcgaatt   6780
cactagtgat tgaattcgcg gccgcttagt ccgacttggc cttggcggcc gcggccgact   6840
ctttgagcgt gaagatctgc gccgtctcgg gcacagcgcc gtagttgaca aagaggtgcg   6900
cggtcttgaa gaaggccgtg atgatgggct cgtcgttcct gcgcacgagg tgcgggtacg   6960
cggccgcaaa gtgcttggtg gcttcgttga gcttgtagtg cggaatgatc gggaacaagt   7020
ggtggacctg gtgcgtgcca atgtggtggc tcaggttgtc cacgaacgcg ccgtacgagc   7080
```

```
ggtcgacgct cgagaggttg cccttgacgt acgtccactc cgagtcgccg taccacggcg   7140
tcgcttcgtc gttgtggtgc aagaaggtcg taatgacgag gaacgaagca aagacaaaga   7200
gcggcgcata gtagtagagg cccatgacgg caaagccgag cgagtatgtg aggtacgcgt   7260
acgcggcgaa gaaggcggcc cagacgccga gcgacacgat gacggccgac gcgcggcgaa   7320
ggaggagcgg gtcccacggg tcaaagtggc tcatcgtgcg cggggcatac ccgaccttca   7380
agtagacaaa ccacgcaccg ccgagcgtgt agacccattg gcgcacgtcc tggaggtcct   7440
tgaccgaccg gtgcgggtaa aagatctcgt ccttatcaat gttgcccgtg ttcttgtggt   7500
ggtggcggtg cgtcacgcgc cagctctcga acggcgtcaa aatcgcagag tgcatgatgc   7560
agccgatgat aaagttgacg ctgtggtagc gcgagaaggc cgagtggccg cagtcgtggc   7620
cgaccgtgaa gaagccccag aagatgacgc cctgcacgta gatgtaggtg gcgcaaacga   7680
gcgcgtggag cagaacgtta tcggcaatga acggcgtcga gcgcgccgcg tagagcagcg   7740
ccgccgaggc cgacgcgttg aagatcgcgc gggccgtgta gtagagcgag aggccgaggt   7800
tcgactcaaa gcacgcgttc gggatcgagt gcttgagctc cgtgagcgtc gggaactcga   7860
ccttcgtctt atcctcagtc atgcggccgc tgaagtattg cttcttagtt aacctttcct   7920
ttctctctca gctatgtgaa ttcattttgc tttcgtcaca atttatatag tgaaattgga   7980
tctttggagt taacgccttc acaggattat cgtgttagaa caatgctttt tcatgttcta   8040
attagtagta cattacaaat gtgcactcta ttcaataagc atctttttggc acgttaataa   8100
atcatgtgaa aaaaaaatac tactatttca aagaaagtgt tgtaaaaaga aacggaaaga   8160
gagctggctt cagttgttga gacttgtttg ctagtaaaaa tggtgtgaag agtgattcat   8220
ggtgaggtgg tttttcgtcc ctttctgttt gcatgaaaaa caaatggcaa gagatgacgt   8280
aggattcctt cccttaacga ttatctgttt ttaatttcaa atatacatat aggaatttat   8340
gaattactaa ggttgtaaaa tatgctggtc atttatttat ggctaaaata ttttttttc   8400
tcgtaaatat aaaaatattt aaaatttatt tttatcatat tttttatcct tataaaatta   8460
tgtgtacaac ctatataaaa aaatatcata tttaatattg attatatgtt taatcaatat   8520
aaaaaatcat tatcatatat ttagatttat tcgaatatac atctaaacaa aaaataacat   8580
attttaattt tatgaagaaa aaaaaatatt ttatccttta tttatttaag attaattaat   8640
agttatgtat tgtggaaaga cttttacaca tgcaatagat atactgaatc aattagatgc   8700
caatgctgag ttggaaatca cttgaggagg ggaggagact tgccaatgct tttcagtttc   8760
atttaaatga tttagtggag gagatagagt agtgataaag gcatgcccca attttggagt   8820
gtatatatga gtggaaataa gagagggata gagagaaaaa ataaagagag taaaaataat   8880
taatgtgaaa tgatatgata aaaaaataaa gaaagagata aagagaaaaa tgaaatgaga   8940
gatagatgaa atagagagta gatacatgtt tgtttaggtt ttttttagga aataacacat   9000
ttttttctca tcacttatta ctcactgtca atttcctctc tttcaatcat aatgatatga   9060
tttgtttaac aaaaaatgtga aaaaacatat aaagtaaaat atttttataa attgataaat   9120
aaaaatttac aaaatttatt tcttattaaa ttgaatagaa aatgaaagaa aagaaaagaa   9180
aaagtatata taaaatgata tagctttaaa aagaataaat ttttcatatc agtctttttt   9240
taataattta gaaatattta agtatatagc aaaaatataa tgtactttac atatgcataa   9300
ataataattt gaaaatagaa ctaatagaat agagaaaaaa gtaatataat aattaactat   9360
atgaaaattt agaagggaca atatttttaa ttaagaatat aaacaatatt tcttttcatg   9420
taatgaggga cggatgtacg gggccagtgt tggagtcaaa gccaaaatag tcacggggaa   9480
```

```
attaatgcac tgcatgacta ttcgaaaaaa ttcactagcc ttacttagat gttagattaa   9540

tagctagggg gtgcagataa ttttgaaagg catgaaaaac attaatttgt acattgcaag   9600

cttttgatga caagctttgc aattgttcac actaccttat gccatttata aatagagtga   9660

ttggcatatg aaggaaatca tgagagtcga agcgaaaaac aaagcttgag agtgtaggaa   9720

aaatacagtt tttttggtaa aaatacagta tttgaatagg agcgaaaaat atcctttcaa   9780

aatgatcctt ttcttttttt ttttttttct tgttgttctt ggtcagttat tcaaaggaaa   9840

agggattgaa ataaaaactt gcatgtggga tcgtacgtcg agtcgacctg ca           9892
```

<210> SEQ ID NO 49
<211> LENGTH: 6021
<212> TYPE: DNA
<213> ORGANISM: Artificial Sequence
<220> FEATURE:
<223> OTHER INFORMATION: plasmid pKR271

<400> SEQUENCE: 49

```
ggccgcgaat tcaatcacta gtgaattcgc ggccgcatga gccgtaaagg ttcaatacaa     60

cgagtgcttg ttttcttagg gacaagcatt gtacttatgt atgattctgt gtaaccatga    120

gtcttccacg ttgtactaat gtgaagggca aaaataaaac acagaacaag ttcgtttttc    180

tcaaataatg tgaaggtaga aaatggaacc atgcctcctc tcttgcatgt gatttaaaat    240

attagcagat ggtaccgtac gtgggcggat cccccgggct gcaggaattc actggccgtc    300

gttttacaac gtcgtgactg ggaaaaccct ggcgttaccc aacttaatcg ccttgcagca    360

catccccctt tcgccagctg gcgtaatagc gaagaggccc gcaccgatcg cccttcccaa    420

cagttgcgca gcctgaatgg cgaatggcgc ctgatgcggt attttctcct tacgcatctg    480

tgcggtattt cacaccgcat atggtgcact ctcagtacaa tctgctctga tgccgcatag    540

ttaagccagc cccgacaccc gccaacaccc gctgacgcgc cctgacgggc ttgtctgctc    600

ccggcatccg cttacagaca agctgtgacc gtctccggga gctgcatgtg tcagaggttt    660

tcaccgtcat caccgaaacg cgcgagacga aagggcctcg tgatacgcct atttttatag    720

gttaatgtca tgataataat ggtttcttag acgtcaggtg gcacttttcg gggaaatgtg    780

cgcggaaccc ctatttgttt atttttctaa atacattcaa atatgtatcc gctcatgaga    840

caataaccct gataaatgct tcaataatat tgaaaaagga agagtatgag tattcaacat    900

ttccgtgtcg cccttattcc cttttttgcg gcattttgcc ttcctgtttt tgctcaccca    960

gaaacgctgg tgaaagtaaa agatgctgaa gatcagttgg gtgcacgagt gggttacatc   1020

gaactggatc tcaacagcgg taagatcctt gagagttttc gccccgaaga acgttttcca   1080

atgatgagca cttttaaagt tctgctatgt ggcgcggtat tatcccgtat tgacgccggg   1140

caagagcaac tcggtcgccg catacactat tctcagaatg acttggttga gtactcacca   1200

gtcacagaaa agcatcttac ggatggcatg acagtaagag aattatgcag tgctgccata   1260

accatgagtg ataacactgc ggccaactta cttctgacaa cgatcggagg accgaaggag   1320

ctaaccgctt ttttgcacaa catgggggat catgtaactc gccttgatcg ttgggaaccg   1380

gagctgaatg aagccatacc aaacgacgag cgtgacacca cgatgcctgt agcaatggca   1440

acaacgttgc gcaaactatt aactggcgaa ctacttactc tagcttcccg gcaacaatta   1500

atagactgga tggaggcgga taaagttgca ggaccacttc tgcgctcggc ccttccggct   1560

ggctggttta ttgctgataa atctggagcc ggtgagcgtg ggtctcgcgg tatcattgca   1620

gcactggggc cagatggtaa gccctcccgt atcgtagtta tctacacgac ggggagtcag   1680
```

```
gcaactatgg atgaacgaaa tagacagatc gctgagatag gtgcctcact gattaagcat   1740
tggtaactgt cagaccaagt ttactcatat atactttaga ttgatttaaa acttcatttt   1800
taatttaaaa ggatctaggt gaagatcctt tttgataatc tcatgaccaa aatcccttaa   1860
cgtgagtttt cgttccactg agcgtcagac cccgtagaaa agatcaaagg atcttcttga   1920
gatccttttt ttctgcgcgt aatctgctgc ttgcaaacaa aaaaaccacc gctaccagcg   1980
gtggtttgtt tgccggatca agagctacca actctttttc cgaaggtaac tggcttcagc   2040
agagcgcaga taccaaatac tgtccttcta gtgtagccgt agttaggcca ccacttcaag   2100
aactctgtag caccgcctac atacctcgct ctgctaatcc tgttaccagt ggctgctgcc   2160
agtggcgata agtcgtgtct taccgggttg gactcaagac gatagttacc ggataaggcg   2220
cagcggtcgg gctgaacggg gggttcgtgc acacagccca gcttggagcg aacgacctac   2280
accgaactga gatacctaca gcgtgagcta tgagaaagcg ccacgcttcc cgaagggaga   2340
aaggcggaca ggtatccggt aagcggcagg gtcggaacag gagagcgcac gagggagctt   2400
ccagggggaa acgcctggta tctttatagt cctgtcgggt ttcgccacct ctgacttgag   2460
cgtcgatttt tgtgatgctc gtcagggggg cggagcctat ggaaaaacgc cagcaacgcg   2520
gcctttttac ggttcctggc cttttgctgg ccttttgctc acatgttctt tcctgcgtta   2580
tcccctgatt ctgtggataa ccgtattacc gcctttgagt gagctgatac cgctcgccgc   2640
agccgaacga ccgagcgcag cgagtcagtg agcgaggaag cggaagagcg cccaatacgc   2700
aaaccgcctc tccccgcgcg ttggccgatt cattaatgca gctggcacga caggtttccc   2760
gactggaaag cgggcagtga gcgcaacgca attaatgtga gttagctcac tcattaggca   2820
ccccaggctt tacactttat gcttccggct cgtatgttgt gtggaattgt gagcggataa   2880
caatttcaca caggaaacag ctatgaccat gattacgcca agcttgcatg cctgcaggtc   2940
gactcgacgt acgatcccac atgcaagttt ttatttcaat ccctttttcct ttgaataact   3000
gaccaagaac aacaagaaaa aaaaaaaaaa agaaaaggat cattttgaaa ggatattttt   3060
cgctcctatt caaatactgt atttttacca aaaaaactgt atttttccta cactctcaag   3120
ctttgttttt cgcttcgact ctcatgattt ccttcatatg ccaatcactc tatttataaa   3180
tggcataagg tagtgtgaac aattgcaaag cttgtcatca aaagcttgca atgtacaaat   3240
taatgttttt catgcctttc aaaattatct gcacccccta gctattaatc taacatctaa   3300
gtaaggctag tgaatttttt cgaatagtca tgcagtgcat taatttcccc gtgactattt   3360
tggctttgac tccaacactg gccccgtaca tccgtccctc attacatgaa aagaaatatt   3420
gtttatattc ttaattaaaa atattgtccc ttctaaattt tcatatagtt aattattata   3480
ttactttttt ctctattcta ttagttctat tttcaaatta ttatttatgc atatgtaaag   3540
tacattatat ttttgctata tacttaaata tttctaaatt attaaaaaaa gactgatatg   3600
aaaaatttat tctttttaaa gctatatcat tttatatata ctttttcttt tcttttcttt   3660
cattttctat tcaatttaat aagaaataaa ttttgtaaat ttttatttat caatttataa   3720
aaatatttta ctttatatgt tttttcacat ttttgttaaa caaatcatat cattatgatt   3780
gaaagagagg aaattgacag tgagtaataa gtgatgagaa aaaaatgtgt tatttcctaa   3840
aaaaaaccta aacaaacatg tatctactct ctatttcatc tatctctcat ttcatttttc   3900
tctttatctc tttctttatt tttttatcat atcatttcac attaattatt tttactctct   3960
ttatttttc tctctatccc tctcttattt ccactcatat atacactcca aaattggggc   4020
atgcctttat cactactcta tctcctccac taaatcattt aaatgaaact gaaaagcatt   4080
```

ggcaagtctc ctcccctcct caagtgattt ccaactcagc attggcatct aattgattca 4140
gtatatctat tgcatgtgta aaagtctttc cacaatacat aactattaat taatcttaaa 4200
taaataaagg ataaaatatt tttttttctt cataaaatta aaatatgtta ttttttgttt 4260
agatgtatat tcgaataaat ctaaatatat gataatgatt ttttatattg attaaacata 4320
taatcaatat taaatatgat attttttttat ataggttgta cacataattt tataaggata 4380
aaaaatatga taaaaataaa ttttaaatat ttttatattt acgagaaaaa aaaatatttt 4440
agccataaat aaatgaccag catattttac aaccttagta attcataaat tcctatatgt 4500
atatttgaaa ttaaaaacag ataatcgtta agggaaggaa tcctacgtca tctcttgcca 4560
tttgtttttc atgcaaacag aaagggacga aaaaccacct caccatgaat cactcttcac 4620 accatttta ctagcaaaca agtctcaaca actgaagcca gctctctttc cgtttctttt 4680
tacaacactt tctttgaaat agtagtattt tttttcaca tgatttatta acgtgccaaa 4740
agatgcttat tgaatagagt gcacatttgt aatgtactac taattagaac atgaaaaagc 4800
attgttctaa cacgataatc ctgtgaaggc gttaactcca aagatccaat ttcactatat 4860
aaattgtgac gaaagcaaaa tgaattcaca tagctgagag agaaaggaaa ggttaactaa 4920
gaagcaatac ttcagcggcc gcatgactga ggataagacg aaggtcgagt tcccgacgct 4980
cacggagctc aagcactcga tcccgaacgc gtgctttgag tcgaacctcg gcctctcgct 5040
ctactacacg gcccgcgcga tcttcaacgc gtcggcctcg gcggcgctgc tctacgcggc 5100
gcgctcgacg ccgttcattg ccgataacgt tctgctccac gcgctcgttt gcgccaccta 5160
catctacgtg cagggcgtca tcttctgggg cttcttcacg gtcggccacg actgcggcca 5220
ctcggccttc tcgcgctacc acagcgtcaa ctttatcatc ggctgcatca tgcactctgc 5280
gattttgacg ccgttcgaga gctggcgcgt gacgcaccgc caccaccaca agaacacggg 5340
caacattgat aaggacgaga tcttttaccc gcaccggtcg gtcaaggacc tccaggacgt 5400
gcgccaatgg gtctacacgc tcggcggtgc gtggtttgtc tacttgaagg tcgggtatgc 5460
cccgcgcacg atgagccact ttgacccgtg ggacccgctc ctccttcgcc gcgcgtcggc 5520
cgtcatcgtg tcgctcggcg tctgggccgc cttcttcgcc gcgtacgcgt acctcacata 5580
ctcgctcggc tttgccgtca tgggcctcta ctactatgcg ccgctctttg tctttgcttc 5640
gttcctcgtc attacgacct tcttgcacca caacgacgaa gcgacgccgt ggtacggcga 5700
ctcggagtgg acgtacgtca agggcaacct ctcgagcgtc gaccgctcgt acggcgcgtt 5760
cgtggacaac ctgagccacc acattggcac gcaccaggtc caccacttgt tcccgatcat 5820
tccgcactac aagctcaacg aagccaccaa gcactttgcg gccgcgtacc cgcacctcgt 5880
gcgcaggaac gacgagccca tcatcacggc cttcttcaag accgcgcacc tctttgtcaa 5940
ctacggcgct gtgcccgaga cggcgcagat cttcacgctc aaagagtcgg ccgcggccgc 6000
caaggccaag tcggactaag c 6021

<210> SEQ ID NO 50
<211> LENGTH: 6524
<212> TYPE: DNA
<213> ORGANISM: Artificial Sequence
<220> FEATURE:
<223> OTHER INFORMATION: plasmid pKR226

<400> SEQUENCE: 50
gtacgtctag aggatccgtc gacggcgcgc ccgatcatcc ggatatagtt cctcctttca 60
gcaaaaaacc cctcaagacc cgtttagagg ccccaagggg ttatgctagt tattgctcag 120

```
cggtggcagc agccaactca gcttcctttc gggctttgtt agcagccgga tcgatccaag    180
ctgtacctca ctattccttt gccctcggac gagtgctggg gcgtcggttt ccactatcgg    240
cgagtacttc tacacagcca tcggtccaga cggccgcgct tctgcgggcg atttgtgtac    300
gcccgacagt cccggctccg gatcggacga ttgcgtcgca tcgaccctgc gcccaagctg    360
catcatcgaa attgccgtca accaagctct gatagagttg gtcaagacca atgcggagca    420
tatacgcccg gagccgcggc gatcctgcaa gctccggatg cctccgctcg aagtagcgcg    480
tctgctgctc catacaagcc aaccacggcc tccagaagaa gatgttggcg acctcgtatt    540
gggaatcccc gaacatcgcc tcgctccagt caatgaccgc tgttatgcgg ccattgtccg    600
tcaggacatt gttggagccg aaatccgcgt gcacgaggtg ccggacttcg gggcagtcct    660
cggcccaaag catcagctca tcgagagcct gcgcgacgga cgcactgacg gtgtcgtcca    720
tcacagtttg ccagtgatac acatggggat cagcaatcgc gcatatgaaa tcacgccatg    780
tagtgtattg accgattcct tgcggtccga atgggccgaa cccgctcgtc tggctaagat    840
cggccgcagc gatcgcatcc atagcctccg cgaccggctg cagaacagcg ggcagttcgg    900
tttcaggcag gtcttgcaac gtgacaccct gtgcacggcg ggagatgcaa taggtcaggc    960
tctcgctgaa ttccccaatg tcaagcactt ccggaatcgg gagcgcggcc gatgcaaagt   1020
gccgataaac ataacgatct ttgtagaaac catcggcgca gctatttacc cgcaggacat   1080
atccacgccc tcctacatcg aagctgaaag cacgagattc ttcgccctcc gagagctgca   1140
tcaggtcgga gacgctgtcg aacttttcga tcagaaactt ctcgacagac gtcgcggtga   1200
gttcaggctt ttccatgggt atatctcctt cttaaagtta aacaaaatta tttctagagg   1260
gaaaccgttg tggtctccct atagtgagtc gtattaattt cgcgggatcg agatctgatc   1320
aacctgcatt aatgaatcgg ccaacgcgcg gggagaggcg gtttgcgtat tgggcgctct   1380
tccgcttcct cgctcactga ctcgctgcgc tcggtcgttc ggctgcggcg agcggtatca   1440
gctcactcaa aggcggtaat acggttatcc acagaatcag gggataacgc aggaaagaac   1500
atgtgagcaa aaggccagca aaaggccagg aaccgtaaaa aggccgcgtt gctggcgttt   1560
ttccataggc tccgcccccc tgacgagcat cacaaaaatc gacgctcaag tcagaggtgg   1620
cgaaacccga caggactata aagataccag gcgtttcccc ctggaagctc cctcgtgcgc   1680
tctcctgttc cgaccctgcc gcttaccgga tacctgtccg cctttctccc ttcgggaagc   1740
gtggcgcttt ctcaatgctc acgctgtagg tatctcagtt cggtgtaggt cgttcgctcc   1800
aagctgggct gtgtgcacga accccccgtt cagcccgacc gctgcgcctt atccggtaac   1860
tatcgtcttg agtccaaccc ggtaagacac gacttatcgc cactggcagc agccactggt   1920
aacaggatta gcagagcgag gtatgtaggc ggtgctacag agttcttgaa gtggtggcct   1980
aactacggct acactagaag gacagtattt ggtatctgcg ctctgctgaa gccagttacc   2040
ttcggaaaaa gagttggtag ctcttgatcc ggcaaacaaa ccaccgctgg tagcggtggt   2100
tttttgttt gcaagcagca gattacgcgc agaaaaaaag gatctcaaga agatcctttg   2160
atcttttcta cggggtctga cgctcagtgg aacgaaaact cacgttaagg gattttggtc   2220
atgacattaa cctataaaaa taggcgtatc acgaggccct ttcgtctcgc gcgtttcggt   2280
gatgacggtg aaaacctctg acacatgcag ctcccggaga cggtcacagc ttgtctgtaa   2340
gcggatgccg ggagcagaca agcccgtcag ggcgcgtcag cgggtgttgg cgggtgtcgg   2400
ggctggctta actatgcggc atcagagcag attgtactga gagtgcacca tatggacata   2460
ttgtcgttag aacgcggcta caattaatac ataaccttat gtatcataca catacgattt   2520
```

```
aggtgacact atagaacggc gcgccaagct gggtctagaa ctagaaacgt gatgccactt   2580
gttattgaag tcgattacag catctattct gttttactat ttataacttt gccatttctg   2640
acttttgaaa actatctctg gatttcggta tcgctttgtg aagatcgagc aaaagagacg   2700
ttttgtggac gcaatggtcc aaatccgttc tacatgaaca aattggtcac aatttccact   2760
aaaagtaaat aaatggcaag ttaaaaaagg aatatgcatt ttactgattg cctaggtgag   2820
ctccaagaga agttgaatct acacgtctac caaccgctaa aaaaagaaaa acattgatat   2880
gtaacctgat tccattagct tttgacttct tcaacagatt ctctacttag atttctaaca   2940
gaaatattat tactagcaca tcattttcag tctcactaca gcaaaaaatc caacggcaca   3000
atacagacaa caggagatat cagactacag agatagatag atgctactgc atgtagtaag   3060
ttaaataaaa ggaaaataaa atgtcttgct accaaaacta ctacagacta tgatgctcac   3120
cacaggccaa atcctgcaac taggacagca ttatcttata tatattgtac aaaacaagca   3180
tcaaggaaca tttggtctag gcaatcagta cctcgttcta ccatcaccct cagttatcac   3240
atccttgaag gatccattac tgggaatcat cggcaacaca tgctcctgat ggggcacaat   3300
gacatcaaga aggtaggggc caggggtgtc caacattctc tgaattgccg ctctaagctc   3360
ttccttcttc gtcactcgcg ctgccggtat cccacaagca tcagcaaact tgagcatgtt   3420
tgggaatatc tcgctctcgc tagacggatc tccaagatag gtgtgagctc tattggactt   3480
gtagaaccta tcctccaact gaaccaccat acccaaatgc tgattgttca acaacaatat   3540
cttaactggg agattctcca ctcttatagt ggccaactcc tgaacattca tgatgaaact   3600
accatcccca tcaatgtcaa ccacaacagc cccagggtta gcaacagcag caccaatagc   3660
cgcaggcaat ccaaaaccca tggctccaag acccccctgag gtcaaccact gcctcggtct   3720
cttgtacttg taaaactgcg cagcccacat ttgatgctgc ccaaccccag tactaacaat   3780
agcatctcca ttagtcaact catcaagaac ctcgatagca tgctgcggag aaatcgcgtc   3840
ctggaatgtc ttgtaaccca atggaaactt gtgtttctgc acattaatct cttctctcca   3900
acctccaaga tcaaacttac cctccactcc tttctcctcc aaaatcatat taattccctt   3960
caaggccaac ttcaaatccg cgcaaaccga cacgtgcgcc tgcttgttct tcccaatctc   4020
ggcagaatca atatcaatgt gaacaatctt agccctacta gcaaaagcct caagcttccc   4080
agtaacacgg tcatcaaacc ttaccccaaa ggcaagcaac aaatcactat tgtcaacagc   4140
atagttagca taaacagtac catgcatacc cagcatctga agggaatatt catcaccaat   4200
aggaaaagtt ccaagaccca ttaaagtgct agcaacggga ataccagtga gttcaacaaa   4260
gcgcctcaat tcagcactgg aattcaaact gccaccgccg acgtagagaa cgggcttttg   4320
ggcctccatg atgagtctga caatgtgttc caattgggcc tcggcggggg gcctgggcag   4380
cctggcgagg taaccgggga ggttaacggg ctcgtcccaa ttaggcacgg cgagttgctg   4440
ctgaacgtct ttgggaatgt cgatgaggac cggaccgggg cggccggagg tggcgacgaa   4500
gaaagcctcg gcgacgacgc gggggatgtc gtcgacgtcg aggatgaggt agttgtgctt   4560
cgtgatggat ctgctcacct ccacgatcgg ggtttcttgg aaggcgtcgg tgccgatcat   4620
ccggcgggcg acctggccgg tgatggcgac gactgggacg ctgtccatta aagcgtcggc   4680
gaggccgctc acgaggttgg tggcgccggg gccggaggtg gcaatgcaga cgccggggag   4740
gccggaggaa cgcgcgtagc cttcggcggc gaagacgccg ccctgctcgt ggcgcgggag   4800
cacgttgcgg atggcggcgg agcgcgtgag cgcctggtgg atctccatcg acgcaccgcc   4860
ggggtacgcg aacaccgtcg tcacgccctg cctctccagc gcctccacaa ggatgtccgc   4920
```

```
gcccttgcga ggttcgccgg aggcgaaccg tgacacgaag ggctccgtgg tcggcgcttc   4980
cttggtgaag ggcgccgccg tggggggttt ggagatggaa catttgattt tgagagcgtg   5040
gttgggtttg gtgagggttt gatgagagag agggagggtg gatctagtaa tgcgtttggg   5100
gaaggtgggg tgtgaagagg aagaagagaa tcgggtggtt ctggaagcgg tggccgccat   5160
tgtgttgtgt ggcatggtta tacttcaaaa actgcacaac aagcctagag ttagtaccta   5220
aacagtaaat ttacaacaga gagcaaagac acatgcaaaa atttcagcca taaaaaaagt   5280
tataatagaa tttaaagcaa aagtttcatt ttttaaacat atatacaaac aaactggatt   5340
tgaaggaagg gattaattcc cctgctcaaa gtttgaattc ctattgtgac ctatactcga   5400
ataaaattga agcctaagga atgtatgaga aacaagaaaa caaaacaaaa ctacagacaa   5460
acaagtacaa ttacaaaatt cgctaaaatt ctgtaatcac caaaccccat ctcagtcagc   5520
acaaggccca aggtttattt tgaaataaaa aaaaagtgat tttatttctc ataagctaaa   5580
agaaagaaag gcaattatga aatgatttcg actagatctg aaagtccaac gcgtattccg   5640
cagatattaa agaaagagta gagtttcaca tggatcctag atggacccag ttgaggaaaa   5700
agcaaggcaa agcaaaccag aagtgcaaga tccgaaattg aaccacggaa tctaggattt   5760
ggtagaggga gaagaaaagt accttgagag gtagaagaga agagaagagc agagagatat   5820
atgaacgagt gtgtcttggt ctcaactctg aagcgatacg agtttagagg ggagcattga   5880
gttccaattt atagggaaac cgggtggcag gggtgagtta atgacggaaa agcccctaag   5940
taacgagatt ggattgtggg ttagattcaa ccgtttgcat ccgcggctta gattggggaa   6000
gtcagagtga atctcaaccg ttgactgagt tgaaaattga atgtagcaac caattgagcc   6060
aaccccagcc tttgcccttt gattttgatt tgtttgttgc atactttta tttgtcttct    6120
ggttctgact ctctttctct cgtttcaatg ccaggttgcc tactcccaca ccactcacaa   6180
gaagattcta ctgttagtat taaatatttt ttaatgtatt aaatgatgaa tgcttttgta   6240
aacagaacaa gactatgtct aataagtgtc ttgcaacatt ttttaagaaa ttaaaaaaaa   6300
tatatttatt atcaaaatca aatgtatgaa aaatcatgaa taatataatt ttatacattt   6360
ttttaaaaaa tcttttaatt tcttaattaa tatcttaaaa ataatgatta atatttaacc   6420
caaaataatt agtatgattg gtaaggaaga tatccatgtt atgtttggat gtgagtttga   6480
tctagagcaa agcttactag agtcgacctg caggtcgact cgac                    6524
```

<210> SEQ ID NO 51
<211> LENGTH: 32
<212> TYPE: DNA
<213> ORGANISM: Artificial Sequence
<220> FEATURE:
<223> OTHER INFORMATION: oCon-1 primer

<400> SEQUENCE: 51

```
aatctagacc tgcaggatcc atgcccttca tt                                   32
```

<210> SEQ ID NO 52
<211> LENGTH: 33
<212> TYPE: DNA
<213> ORGANISM: Artificial Sequence
<220> FEATURE:
<223> OTHER INFORMATION: oCon-2 primer

<400> SEQUENCE: 52

```
tttctagacc tgcaggttga aacatccctg aag                                  33
```

<210> SEQ ID NO 53
<211> LENGTH: 4480
<212> TYPE: DNA
<213> ORGANISM: Artificial Sequence
<220> FEATURE:
<223> OTHER INFORMATION: plasmid pKR179

<400> SEQUENCE: 53

```
ctagacctgc aggatccatg cccttcattt gccgcttatt aattaatttg gtaacagtcc     60
gtactaatca gttacttatc cttcccccat cataattaat cttggtagtc tcgaatgcca    120
caacactgac tagtctcttg gatcataaga aaaagccaag gaacaaaaga agacaaaaca    180
caatgagagt atcctttgca tagcaatgtc taagttcata aaattcaaac aaaaacgcaa    240
tcacacacag tggacatcac ttatccacta gctgatcagg atcgccgcgt caagaaaaaa    300
aaactggacc ccaaaagcca tgcacaacaa cacgtactca caaaggtgtc aatcgagcag    360
cccaaaacat tcaccaactc aacccatcat gagccctcac atttgttgtt tctaacccaa    420
cctcaaactc gtattctctt ccgccacctc atttttgttt atttcaacac ccgtcaaact    480
gcatgccacc ccgtggccaa atgtccatgc atgttaacaa gacctatgac tataaatagc    540
tgcaatctcg gcccaggttt tcatcatcaa gaaccagttc aatatcctag tacaccgtat    600
taaagaattt aagatatact gcggccgcaa gtatgaacta aaatgcatgt aggtgtaaga    660
gctcatggag agcatggaat attgtatccg accatgtaac agtataataa ctgagctcca    720
tctcacttct tctatgaata aacaaaggat gttatgatat attaacactc tatctatgca    780
ccttattgtt ctatgataaa tttcctctta ttattataaa tcatctgaat cgtgacggct    840
tatggaatgc ttcaaatagt acaaaaacaa atgtgtacta taagactttc taaacaattc    900
taaccttagc attgtgaacg agacataagt gttaagaaga cataacaatt ataatggaag    960
aagtttgtct ccatttatat attatatatt acccacttat gtattatatt aggatgttaa   1020
ggagacataa caattataaa gagagaagtt tgtatccatt tatatattat atactaccca   1080
tttatatatt atacttatcc acttatttaa tgtctttata aggtttgatc catgatattt   1140
ctaatatttt agttgatatg tatatgaaag ggtactattt gaactctctt actctgtata   1200
aaggttggat catccttaaa gtgggtctat ttaattttat tgcttcttac agataaaaaa   1260
aaaattatga gttggtttga taaaatattg aaggatttaa aataataata aataacatat   1320
aatatatgta tataaattta ttataatata acatttatct ataaaaaagt aaatattgtc   1380
ataaatctat acaatcgttt agccttgctg gacgaatctc aattatttaa acgagagtaa   1440
acatatttga ctttttggtt atttaacaaa ttattattta acactatatg aaattttttt   1500
ttttatcagc aaagaataaa attaaattaa gaaggacaat ggtgtcccaa tccttataca   1560
accaacttcc acaagaaagt caagtcagag acaacaaaaa aacaagcaaa ggaaattttt   1620
taatttgagt tgtcttgttt gctgcataat ttatgcagta aaacactaca cataaccctt   1680
ttagcagtag agcaatggtt gaccgtgtgc ttagcttctt ttattttatt tttttatcag   1740
caaagaataa ataaaataaa atgagacact tcagggatgt ttcaacctgc aggtctagag   1800
gatccccggg taccgagctc gaattcactg gccgtcgttt tacaacgtcg tgactgggaa   1860
aaccctggcg ttacccaact taatcgcctt gcagcacatc ccccttttcgc cagctggcgt   1920
aatagcgaag aggcccgcac cgatcgccct tcccaacagt tgcgcagcct gaatggcgaa   1980
tggcgcctga tgcggtattt tctccttacg catctgtgcg gtatttcaca ccgcatatgg   2040
tgcactctca gtacaatctg ctctgatgcc gcatagttaa gccagccccg acacccgcca   2100
acacccgctg acgcgccctg acgggcttgt ctgctcccgg catccgctta cagacaagct   2160
```

```
gtgaccgtct ccgggagctg catgtgtcag aggttttcac cgtcatcacc gaaacgcgcg   2220
agacgaaagg gcctcgtgat acgcctattt ttataggtta atgtcatgat aataatggtt   2280
tcttagacgt caggtggcac ttttcgggga aatgtgcgcg gaacccctat ttgtttattt   2340
ttctaaatac attcaaatat gtatccgctc atgagacaat aaccctgata aatgcttcaa   2400
taatattgaa aaaggaagag tatgagtatt caacatttcc gtgtcgccct tattcccttt   2460
tttgcggcat tttgccttcc tgtttttgct cacccagaaa cgctggtgaa agtaaaagat   2520
gctgaagatc agttgggtgc acgagtgggt tacatcgaac tggatctcaa cagcggtaag   2580
atccttgaga gttttcgccc cgaagaacgt tttccaatga tgagcacttt taaagttctg   2640
ctatgtggcg cggtattatc ccgtattgac gccgggcaag agcaactcgg tcgccgcata   2700
cactattctc agaatgactt ggttgagtac tcaccagtca cagaaaagca tcttacggat   2760
ggcatgacag taagagaatt atgcagtgct gccataacca tgagtgataa cactgcggcc   2820
aacttacttc tgacaacgat cggaggaccg aaggagctaa ccgctttttt gcacaacatg   2880
ggggatcatg taactcgcct tgatcgttgg gaaccggagc tgaatgaagc cataccaaac   2940
gacgagcgtg acaccacgat gcctgtagca atggcaacaa cgttgcgcaa actattaact   3000
ggcgaactac ttactctagc ttcccggcaa caattaatag actggatgga ggcggataaa   3060
gttgcaggac cacttctgcg ctcggccctt ccggctggct ggtttattgc tgataaatct   3120
ggagccggtg agcgtgggtc tcgcggtatc attgcagcac tggggccaga tggtaagccc   3180
tcccgtatcg tagttatcta cacgacgggg agtcaggcaa ctatggatga acgaaataga   3240
cagatcgctg agataggtgc ctcactgatt aagcattggt aactgtcaga ccaagtttac   3300
tcatatatac tttagattga tttaaaactt catttttaat ttaaaaggat ctaggtgaag   3360
atcctttttg ataatctcat gaccaaaatc ccttaacgtg agttttcgtt ccactgagcg   3420
tcagaccccg tagaaaagat caaaggatct tcttgagatc ctttttttct gcgcgtaatc   3480
tgctgcttgc aaacaaaaaa accaccgcta ccagcggtgg tttgtttgcc ggatcaagag   3540
ctaccaactc tttttccgaa ggtaactggc ttcagcagag cgcagatacc aaatactgtc   3600
cttctagtgt agccgtagtt aggccaccac ttcaagaact ctgtagcacc gcctacatac   3660
ctcgctctgc taatcctgtt accagtggct gctgccagtg gcgataagtc gtgtcttacc   3720
gggttggact caagacgata gttaccggat aaggcgcagc ggtcgggctg aacggggggt   3780
tcgtgcacac agcccagctt ggagcgaacg acctacaccg aactgagata cctacagcgt   3840
gagctatgag aaagcgccac gcttcccgaa gggagaaagg cggacaggta tccggtaagc   3900
ggcagggtcg gaacaggaga gcgcacgagg gagcttccag ggggaaacgc ctggtatctt   3960
tatagtcctg tcgggtttcg ccacctctga cttgagcgtc gatttttgtg atgctcgtca   4020
ggggggcgga gcctatggaa aaacgccagc aacgcggcct ttttacggtt cctggccttt   4080
tgctggcctt ttgctcacat gttctttcct gcgttatccc ctgattctgt ggataaccgt   4140
attaccgcct ttgagtgagc tgataccgct cgccgcagcc gaacgaccga gcgcagcgag   4200
tcagtgagcg aggaagcgga agagcgccca atacgcaaac cgcctctccc cgcgcgttgg   4260
ccgattcatt aatgcagctg gcacgacagg tttcccgact ggaaagcggg cagtgagcgc   4320
aacgcaatta atgtgagtta gctcactcat taggcacccc aggctttaca ctttatgctt   4380
ccggctcgta tgttgtgtgg aattgtgagc ggataacaat ttcacacagg aaacagctat   4440
gaccatgatt acgccaagct tgcatgcctg caggtcgact                         4480
```

<210> SEQ ID NO 54
<211> LENGTH: 9088
<212> TYPE: DNA
<213> ORGANISM: Artificial Sequence
<220> FEATURE:
<223> OTHER INFORMATION: plasmid pKR578
<220> FEATURE:
<221> NAME/KEY: misc_feature
<222> LOCATION: (6951)..(6951)
<223> OTHER INFORMATION: n is a, c, g, or t

<400> SEQUENCE: 54

```
ggccgcgaca caagtgtgag agtactaaat aaatgctttg gttgtacgaa atcattacac     60
taaataaaat aatcaaagct tatatatgcc ttccgctaag gccgaatgca aagaaattgg    120
ttctttctcg ttatcttttg ccacttttac tagtacgtat taattactac ttaatcatct    180
ttgtttacgg ctcattatat ccggtctaga ggatccaagg ccgcgaagtt aaaagcaatg    240
ttgtcacttg tcgtactaac acatgatgtg atagtttatg ctagctagct ataacataag    300
ctgtctctga gtgtgttgta tattaataaa gatcatcact ggtgaatggt gatcgtgtac    360
gtaccctact tagtaggcaa tggaagcact tagagtgtgc tttgtgcatg gccttgcctc    420
tgttttgaga cttttgtaat gttttcgagt ttaaatcttt gcctttgcgt acggatccgt    480
cgacggcgcg cccgatcatc cggatatagt tcctcctttc agcaaaaaac ccctcaagac    540
ccgtttagag gccccaaggg gttatgctag ttattgctca gcggtggcag cagccaactc    600
agcttccttt cgggctttgt tagcagccgg atcgatccaa gctgtacctc actattcctt    660
tgccctcgga cgagtgctgg ggcgtcggtt tccactatcg gcgagtactt ctacacagcc    720
atcggtccag acggccgcgc ttctgcgggc gatttgtgta cgcccgacag tcccggctcc    780
ggatcggacg attgcgtcgc atcgaccctg cgcccaagct gcatcatcga aattgccgtc    840
aaccaagctc tgatagagtt ggtcaagacc aatgcggagc atatacgccc ggagccgcgg    900
cgatcctgca agctccggat gcctccgctc gaagtagcgc gtctgctgct ccatacaagc    960
caaccacggc ctccagaaga agatgttggc gacctcgtat tgggaatccc cgaacatcgc   1020
ctcgctccag tcaatgaccg ctgttatgcg gccattgtcc gtcaggacat tgttggagcc   1080
gaaatccgcg tgcacgaggt gccggacttc ggggcagtcc tcggcccaaa gcatcagctc   1140
atcgagagcc tgcgcgacgg acgcactgac ggtgtcgtcc atcacagttt gccagtgata   1200
cacatgggga tcagcaatcg cgcatatgaa atcacgccat gtagtgtatt gaccgattcc   1260
ttgcggtccg aatgggccga acccgctcgt ctggctaaga tcggccgcag cgatcgcatc   1320
catagcctcc gcgaccggct gcagaacagc gggcagttcg gtttcaggca ggtcttgcaa   1380
cgtgacaccc tgtgcacggc gggagatgca ataggtcagg ctctcgctga attccccaat   1440
gtcaagcact tccggaatcg ggagcgcggc cgatgcaaag tgccgataaa cataacgatc   1500
tttgtagaaa ccatcggcgc agctatttac ccgcaggaca tatccacgcc ctcctacatc   1560
gaagctgaaa gcacgagatt cttcgccctc cgagagctgc atcaggtcgg agacgctgtc   1620
gaacttttcg atcagaaact tctcgacaga cgtcgcggtg agttcaggct tttccatggg   1680
tatatctcct tcttaaagtt aaacaaaatt atttctagag ggaaaccgtt gtggtctccc   1740
tatagtgagt cgtattaatt tcgcgggatc gagatcgatc caattccaat cccacaaaaa   1800
tctgagctta acagcacagt tgctcctctc agagcagaat cgggtattca acaccctcat   1860
atcaactact acgttgtgta taacggtcca catgccggta tatacgatga ctggggttgt   1920
acaaaggcgg caacaaacgg cgttcccgga gttgcacaca agaaatttgc cactattaca   1980
gaggcaagag cagcagctga cgcgtacaca acaagtcagc aaacagacag gttgaacttc   2040
```

```
atccccaaag gagaagctca actcaagccc aagagctttg ctaaggccct aacaagccca   2100
ccaaagcaaa aagcccactg gctcacgcta ggaaccaaaa ggcccagcag tgatccagcc   2160
ccaaaagaga tctcctttgc cccggagatt acaatggacg atttcctcta tctttacgat   2220
ctaggaagga agttcgaagg tgaaggtgac gacactatgt tcaccactga taatgagaag   2280
gttagcctct tcaatttcag aaagaatgct gacccacaga tggttagaga ggcctacgca   2340
gcaggtctca tcaagacgat ctacccgagt aacaatctcc aggagatcaa ataccttccc   2400
aagaaggtta aagatgcagt caaaagattc aggactaatt gcatcaagaa cacagagaaa   2460
gacatatttc tcaagatcag aagtactatt ccagtatgga cgattcaagg cttgcttcat   2520
aaaccaaggc aagtaataga gattggagtc tctaaaaagg tagttcctac tgaatctaag   2580
gccatgcatg gagtctaaga ttcaaatcga ggatctaaca gaactcgccg tgaagactgg   2640
cgaacagttc atacagagtc ttttacgact caatgacaag aagaaaatct tcgtcaacat   2700
ggtggagcac gacactctgg tctactccaa aaatgtcaaa gatacagtct cagaagacca   2760
aagggctatt gagacttttc aacaaaggat aatttcggga aacctcctcg gattccattg   2820
cccagctatc tgtcacttca tcgaaaggac agtagaaaag gaaggtggct cctacaaatg   2880
ccatcattgc gataaaggaa aggctatcat tcaagatgcc tctgccgaca gtggtcccaa   2940
agatggaccc ccacccacga ggagcatcgt ggaaaaagaa gacgttccaa ccacgtcttc   3000
aaagcaagtg gattgatgtg acatctccac tgacgtaagg gatgacgcac aatcccacta   3060
tccttcgcaa gacccttcct ctatataagg aagttcattt catttggaga ggacacgctc   3120
gagctcattt ctctattact tcagccataa caaaagaact cttttctctt cttattaaac   3180
catgaaaaag cctgaactca ccgcgacgtc tgtcgagaag tttctgatcg aaaagttcga   3240
cagcgtctcc gacctgatgc agctctcgga gggcgaagaa tctcgtgctt tcagcttcga   3300
tgtaggaggg cgtggatatg tcctgcgggt aaatagctgc gccgatggtt tctacaaaga   3360
tcgttatgtt tatcggcact ttgcatcggc cgcgctcccg attccggaag tgcttgacat   3420
tggggaattc agcgagagcc tgacctattg catctcccgc cgtgcacagg gtgtcacgtt   3480
gcaagacctg cctgaaaccg aactgcccgc tgttctgcag ccggtcgcgg aggccatgga   3540
tgcgatcgct gcggccgatc ttagccagac gagcgggttc ggcccattcg gaccgcaagg   3600
aatcggtcaa tacactacat ggcgtgattt catatgcgcg attgctgatc cccatgtgta   3660
tcactggcaa actgtgatgg acgacaccgt cagtgcgtcc gtcgcgcagg ctctcgatga   3720
gctgatgctt tgggccgagg actgccccga agtccggcac ctcgtgcacg cggatttcgg   3780
ctccaacaat gtcctgacgg acaatggccg cataacagcg gtcattgact ggagcgaggc   3840
gatgttcggg gattcccaat acgaggtcgc caacatcttc ttctggaggc cgtggttggc   3900
ttgtatggag cagcagacgc gctacttcga gcggaggcat ccggagcttg caggatcgcc   3960
gcggctccgg gcgtatatgc tccgcattgg tcttgaccaa ctctatcaga gcttggttga   4020
cggcaatttc gatgatgcag cttgggcgca gggtcgatgc gacgcaatcg tccgatccgg   4080
agccgggact gtcgggcgta cacaaatcgc ccgcagaagc gcggccgtct ggaccgatgg   4140
ctgtgtagaa gtactcgccg atagtggaaa ccgacgcccc agcactcgtc cgagggcaaa   4200
ggaatagtga ggtacctaaa gaaggagtgc gtcgaagcag atcgttcaaa catttggcaa   4260
taaagtttct taagattgaa tcctgttgcc ggtcttgcga tgattatcat ataatttctg   4320
ttgaattacg ttaagcatgt aataattaac atgtaatgca tgacgttatt tatgagatgg   4380
gtttttatga ttagagtccc gcaattatac atttaatacg cgatagaaaa caaaatatag   4440
```

cgcgcaaact aggataaatt atcgcgcgcg gtgtcatcta tgttactaga tcgatgtcga 4500
atcgatcaac ctgcattaat gaatcggcca acgcgcgggg agaggcggtt tgcgtattgg 4560
gcgctcttcc gcttcctcgc tcactgactc gctgcgctcg gtcgttcggc tgcggcgagc 4620
ggtatcagct cactcaaagg cggtaatacg gttatccaca gaatcagggg ataacgcagg 4680
aaagaacatg tgagcaaaag gccagcaaaa ggccaggaac cgtaaaaagg ccgcgttgct 4740
ggcgtttttc cataggctcc gcccccctga cgagcatcac aaaaatcgac gctcaagtca 4800
gaggtggcga aacccgacag gactataaag ataccaggcg tttccccctg gaagctccct 4860
cgtgcgctct cctgttccga ccctgccgct taccggatac ctgtccgcct ttctcccttc 4920
gggaagcgtg gcgctttctc aatgctcacg ctgtaggtat ctcagttcgg tgtaggtcgt 4980
tcgctccaag ctgggctgtg tgcacgaacc ccccgttcag cccgaccgct gcgccttatc 5040
cggtaactat cgtcttgagt ccaacccggt aagacacgac ttatcgccac tggcagcagc 5100
cactggtaac aggattagca gagcgaggta tgtaggcggt gctacagagt tcttgaagtg 5160
gtggcctaac tacggctaca ctagaaggac agtatttggt atctgcgctc tgctgaagcc 5220
agttaccttc ggaaaaagag ttggtagctc ttgatccggc aaacaaacca ccgctggtag 5280
cggtggtttt tttgtttgca agcagcagat tacgcgcaga aaaaaaggat ctcaagaaga 5340
tcctttgatc ttttctacgg ggtctgacgc tcagtggaac gaaaactcac gttaagggat 5400
tttggtcatg acattaacct ataaaaatag gcgtatcacg aggccctttc gtctcgcgcg 5460
tttcggtgat gacggtgaaa acctctgaca catgcagctc ccggagacgg tcacagcttg 5520
tctgtaagcg gatgccggga gcagacaagc ccgtcagggc gcgtcagcgg gtgttggcgg 5580
gtgtcggggc tggcttaact atgcggcatc agagcagatt gtactgagag tgcaccatat 5640
ggacatattg tcgttagaac gcggctacaa ttaatacata accttatgta tcatacacat 5700
acgatttagg tgacactata gaacggcgcg ccaagcttgg atctcctgca ggatctggcc 5760
ggccggatct cgtacgtcct cgaagagaag ggttaataac acatttttta acatttttaa 5820
cacaaatttt agttatttaa aaatttatta aaaaatttaa aataagaaga ggaactcttt 5880
aaataaatct aacttacaaa atttatgatt tttaataagt tttcaccaat aaaaaatgtc 5940
ataaaaatat gttaaaaagt atattatcaa tattctcttt atgataaata aaaagaaaaa 6000
aaaaataaaa gttaagtgaa aatgagattg aagtgacttt aggtgtgtat aaatatatca 6060
accccgccaa caatttattt aatccaaata tattgaagta tattattcca tagcctttat 6120
ttatttatat atttattata taaaagcttt atttgttcta ggttgttcat gaaatatttt 6180
tttggtttta tctccgttgt aagaaaatca tgtgctttgt gtcgccactc actattgcag 6240
ctttttcatg cattggtcag attgacggtt gattgtattt ttgtttttta tggttttgtg 6300
ttatgactta agtcttcatc tctttatctc ttcatcaggt ttgatggtta cctaatatgg 6360
tccatgggta catgcatggt taaattaggt ggccaacttt gttgtgaacg atagaatttt 6420
ttttatatta agtaaactat ttttatatta tgaaataata ataaaaaaaa tattttatca 6480
ttattaacaa aatcatatta gttaatttgt taactctata ataaaagaaa tactgtaaca 6540
ttcacattac atggtaacat ctttccaccc tttcatttgt tttttgtttg atgacttttt 6600
ttcttgttta aatttatttc ccttctttta aatttggaat acattatcat catatataaa 6660
ctaaaatact aaaaacagga ttacacaaat gataaataat aacacaaata tttataaatc 6720
tagctgcaat atatttaaac tagctatatc gatattgtaa aataaaacta gctgcattga 6780
tactgataaa aaaatatcat gtgctttctg gactgatgat gcagtatact tttgacattg 6840

```
cctttatttt atttttcaga aaagctttct tagttctggg ttcttcatta tttgtttccc   6900
atctccattg tgaattgaat catttgcttc gtgtcacaaa tacaatttag ntaggtacat   6960
gcattggtca gattcacggt ttattatgtc atgacttaag ttcatggtag tacattacct   7020
gccacgcatg cattatattg gttagatttg ataggcaaat ttggttgtca acaatataaa   7080
tataaataat gtttttatat tacgaaataa cagtgatcaa aacaaacagt tttatcttta   7140
ttaacaagat tttgtttttg tttgatgacg ttttttaatg tttacgcttt ccccccttctt  7200
ttgaatttag aacactttat catcataaaa tcaaatacta aaaaaattac atatttcata   7260
aataataaca caaatatttt taaaaaatct gaaataataa tgaacaatat tacatattat   7320
cacgaaaatt cattaataaa aatattatat aaataaaatg taatagtagt tatatgtagg   7380
aaaaaagtac tgcacgcata atatatacaa aaagattaaa atgaactatt ataaataata   7440
acactaaatt aatggtgaat catatcaaaa taatgaaaaa gtaaataaaa tttgtaatta   7500
acttctatat gtattacaca cacaaataat aaataatagt aaaaaaaatt atgataaata   7560
tttaccatct cataagatat ttaaaataat gataaaaata tagattattt tttatgcaac   7620
tagctagcca aaaagagaac acgggtatat ataaaaagag tacctttaaa ttctactgta   7680
cttcctttat tcctgacgtt tttatatcaa gtggacatac gtgaagattt taattatcag   7740
tctaaatatt tcattagcac ttaatacttt tctgttttat tcctatccta taagtagtcc   7800
cgattctccc aacattgctt attcacacaa ctaactaaga aagtcttcca tagcccccca   7860
agcggccgca caatggcgac tcgacagcga actgccacca ctgttgtggt cgaggacctt   7920
cccaaggtca ctcttgaggc caagtctgaa cctgtgttcc ccgatatcaa gaccatcaag   7980
gatgccattc ccgcgcactg cttccagccc tcgctcgtca cctcattcta ctacgtcttc   8040
cgcgattttg ccatggtctc tgccctcgtc tgggctgctc tcacctacat ccccagcatc   8100
cccgaccaga ccctccgcgt cgcagcttgg atggtctacg gcttcgtcca gggtctgttc   8160
tgcaccggtg tctggattct cggccatgag tgcggccacg gtgctttctc tctccacgga   8220
aaggtcaaca atgtgaccgg ctggttcctc cactcgttcc tcctcgtccc ctacttcagc   8280
tggaagtact ctcaccaccg ccaccaccgc ttcaccggcc acatggatct cgacatggct   8340
ttcgtcccca agactgagcc caagccctcc aagtcgctca tgattgctgg cattgacgtc   8400
gccgagcttg ttgaggacac ccccgctgct cagatggtca agctcatctt ccaccagctt   8460
ttcggatggc aggcgtacct cttcttcaac gctagctctg gcaagggcag caagcagtgg   8520
gagcccaaga ctggcctctc caagtggttc cgagtcagtc acttcgagcc taccagcgct   8580
gtcttccgcc ccaacgaggc catcttcatc ctcatctccg atatcggtct tgctctaatg   8640
ggaactgctc tgtactttgc ttccaagcaa gttggtgttt cgaccattct cttcctctac   8700
cttgttccct acctgtgggt tcaccactgg ctcgttgcca ttacctacct ccaccaccac   8760
cacaccgagc tccctcacta caccgctgag ggctggacct acgtcaaggg agctctcgcc   8820
actgtcgacc gtgagtttgg cttcatcgga aagcacctct tccacggtat cattgagaag   8880
cacgttgttc accatctctt ccctaagatc cccttctaca aggctgacga ggccaccgag   8940
gccatcaagc ccgtcattgg cgaccactac tgccacgacg accgaagctt cctgggccag   9000
ctgtggacca tcttcggcac gctcaagtac gtcgagcacg accctgcccg acccggtgcc   9060
atgcgatgga acaaggacta ggctaggc                                      9088
```

<210> SEQ ID NO 55
<211> LENGTH: 5705

<212> TYPE: DNA
<213> ORGANISM: Artificial Sequence
<220> FEATURE:
<223> OTHER INFORMATION: plasmid pKR582

<400> SEQUENCE: 55

```
ggccgcacaa tggcgactcg acagcgaact gccaccactg ttgtggtcga ggaccttccc     60

aaggtcactc ttgaggccaa gtctgaacct gtgttccccg atatcaagac catcaaggat    120

gccattcccg cgcactgctt ccagccctcg ctcgtcacct cattctacta cgtcttccgc    180

gattttgcca tggtctctgc cctcgtctgg gctgctctca cctacatccc cagcatcccc    240

gaccagaccc tccgcgtcgc agcttggatg gtctacggct tcgtccaggg tctgttctgc    300

accggtgtct ggattctcgg ccatgagtgc ggccacggtg ctttctctct ccacggaaag    360

gtcaacaatg tgaccggctg gttcctccac tcgttcctcc tcgtccccta cttcagctgg    420

aagtactctc accaccgcca ccaccgcttc accggccaca tggatctcga catggctttc    480

gtccccaaga ctgagcccaa gccctccaag tcgctcatga ttgctggcat tgacgtcgcc    540

gagcttgttg aggacacccc cgctgctcag atggtcaagc tcatcttcca ccagcttttc    600

ggatggcagg cgtacctctt cttcaacgct agctctggca agggcagcaa gcagtgggag    660

cccaagactg gcctctccaa gtggttccga gtcagtcact tcgagcctac cagcgctgtc    720

ttccgcccca acgaggccat cttcatcctc atctccgata tcggtcttgc tctaatggga    780

actgctctgt actttgcttc caagcaagtt ggtgtttcga ccattctctt cctctacctt    840

gttccctacc tgtgggttca ccactggctc gttgccatta cctacctcca ccaccaccac    900

accgagctcc ctcactacac cgctgagggc tggacctacg tcaagggagc tctcgccact    960

gtcgaccgtg agtttggctt catcggaaag cacctcttcc acggtatcat tgagaagcac   1020

gttgttcacc atctcttccc taagatcccc ttctacaagg ctgacgaggc caccgaggcc   1080

atcaagcccg tcattggcga ccactactgc cacgacgacc gaagcttcct gggccagctg   1140

tggaccatct tcggcacgct caagtacgtc gagcacgacc ctgcccgacc cggtgccatg   1200

cgatggaaca aggactaggc taggcggccg caagtatgaa ctaaaatgca tgtaggtgta   1260

agagctcatg gagagcatgg aatattgtat ccgaccatgt aacagtataa taactgagct   1320

ccatctcact tcttctatga ataaacaaag gatgttatga tatattaaca ctctatctat   1380

gcaccttatt gttctatgat aaatttcctc ttattattat aaatcatctg aatcgtgacg   1440

gcttatggaa tgcttcaaat agtacaaaaa caaatgtgta ctataagact ttctaaacaa   1500

ttctaacctt agcattgtga acgagacata agtgttaaga agacataaca attataatgg   1560

aagaagtttg tctccattta tatattatat attacccact tatgtattat attaggatgt   1620

taaggagaca taacaattat aaagagagaa gtttgtatcc atttatatat tatatactac   1680

ccatttatat attatactta tccacttatt taatgtcttt ataaggtttg atccatgata   1740

tttctaatat tttagttgat atgtatatga aagggtacta tttgaactct cttactctgt   1800

ataaaggttg gatcatcctt aaagtgggtc tatttaattt tattgcttct tacagataaa   1860

aaaaaaatta tgagttggtt tgataaaata ttgaaggatt taaaataata ataaataaca   1920

tataatatat gtatataaat ttattataat ataacattta tctataaaaa agtaaatatt   1980

gtcataaatc tatacaatcg tttagccttg ctggacgaat ctcaattatt taaacgagag   2040

taaacatatt tgactttttg gttatttaac aaattattat ttaacactat atgaaatttt   2100

tttttttatc agcaaagaat aaaattaaat taagaaggac aatggtgtcc caatccttat   2160

acaaccaact tccacaagaa agtcaagtca gagacaacaa aaaaacaagc aaaggaaatt   2220
```

```
ttttaatttg agttgtcttg tttgctgcat aatttatgca gtaaaacact acacataacc   2280
cttttagcag tagagcaatg gttgaccgtg tgcttagctt cttttatttt atttttttat   2340
cagcaaagaa taaataaaat aaaatgagac acttcaggga tgtttcaacc tgcaggtcta   2400
gaggatcccc gggtaccgag ctcgaattca ctggccgtcg ttttacaacg tcgtgactgg   2460
gaaaaccctg gcgttaccca acttaatcgc cttgcagcac atcccccttt cgccagctgg   2520
cgtaatagcg aagaggcccg caccgatcgc ccttcccaac agttgcgcag cctgaatggc   2580
gaatggcgcc tgatgcggta ttttctcctt acgcatctgt gcggtatttc acaccgcata   2640
tggtgcactc tcagtacaat ctgctctgat gccgcatagt taagccagcc ccgacacccg   2700
ccaacacccg ctgacgcgcc ctgacgggct tgtctgctcc cggcatccgc ttacagacaa   2760
gctgtgaccg tctccgggag ctgcatgtgt cagaggtttt caccgtcatc accgaaacgc   2820
gcgagacgaa agggcctcgt gatacgccta tttttatagg ttaatgtcat gataataatg   2880
gtttcttaga cgtcaggtgg cacttttcgg ggaaatgtgc gcggaacccc tatttgttta   2940
tttttctaaa tacattcaaa tatgtatccg ctcatgagac aataaccctg ataaatgctt   3000
caataatatt gaaaaaggaa gagtatgagt attcaacatt tccgtgtcgc ccttattccc   3060
ttttttgcgg cattttgcct tcctgttttt gctcacccag aaacgctggt gaaagtaaaa   3120
gatgctgaag atcagttggg tgcacgagtg ggttacatcg aactggatct caacagcggt   3180
aagatccttg agagttttcg ccccgaagaa cgttttccaa tgatgagcac ttttaaagtt   3240
ctgctatgtg gcgcggtatt atcccgtatt gacgccgggc aagagcaact cggtcgccgc   3300
atacactatt ctcagaatga cttggttgag tactcaccag tcacagaaaa gcatcttacg   3360
gatggcatga cagtaagaga attatgcagt gctgccataa ccatgagtga taacactgcg   3420
gccaacttac ttctgacaac gatcggagga ccgaaggagc taaccgcttt tttgcacaac   3480
atgggggatc atgtaactcg ccttgatcgt tgggaaccgg agctgaatga agccatacca   3540
aacgacgagc gtgacaccac gatgcctgta gcaatggcaa caacgttgcg caaactatta   3600
actggcgaac tacttactct agcttcccgg caacaattaa tagactggat ggaggcggat   3660
aaagttgcag gaccacttct gcgctcggcc cttccggctg gctggtttat tgctgataaa   3720
tctggagccg gtgagcgtgg gtctcgcggt atcattgcag cactggggcc agatggtaag   3780
ccctcccgta tcgtagttat ctacacgacg gggagtcagg caactatgga tgaacgaaat   3840
agacagatcg ctgagatagg tgcctcactg attaagcatt ggtaactgtc agaccaagtt   3900
tactcatata tactttagat tgatttaaaa cttcattttt aatttaaaag gatctaggtg   3960
aagatccttt ttgataatct catgaccaaa atcccttaac gtgagttttc gttccactga   4020
gcgtcagacc ccgtagaaaa gatcaaagga tcttcttgag atcctttttt tctgcgcgta   4080
atctgctgct tgcaaacaaa aaaaccaccg ctaccagcgg tggtttgttt gccggatcaa   4140
gagctaccaa ctctttttcc gaaggtaact ggcttcagca gagcgcagat accaaatact   4200
gtccttctag tgtagccgta gttaggccac cacttcaaga actctgtagc accgcctaca   4260
tacctcgctc tgctaatcct gttaccagtg gctgctgcca gtggcgataa gtcgtgtctt   4320
accgggttgg actcaagacg atagttaccg gataaggcgc agcggtcggg ctgaacgggg   4380
ggttcgtgca cacagcccag cttggagcga acgacctaca ccgaactgag atacctacag   4440
cgtgagctat gagaaagcgc cacgcttccc gaagggagaa aggcggacag gtatccggta   4500
agcggcaggg tcggaacagg agagcgcacg agggagcttc cagggggaaa cgcctggtat   4560
ctttatagtc ctgtcgggtt tcgccacctc tgacttgagc gtcgattttt gtgatgctcg   4620
```

```
tcagggggc ggagcctatg gaaaaacgcc agcaacgcgg cctttttacg gttcctggcc   4680
ttttgctggc cttttgctca catgttcttt cctgcgttat cccctgattc tgtggataac   4740
cgtattaccg cctttgagtg agctgatacc gctcgccgca gccgaacgac cgagcgcagc   4800
gagtcagtga gcgaggaagc ggaagagcgc ccaatacgca aaccgcctct ccccgcgcgt   4860
tggccgattc attaatgcag ctggcacgac aggtttcccg actggaaagc gggcagtgag   4920
cgcaacgcaa ttaatgtgag ttagctcact cattaggcac cccaggcttt acactttatg   4980
cttccggctc gtatgttgtg tggaattgtg agcggataac aatttcacac aggaaacagc   5040
tatgaccatg attacgccaa gcttgcatgc ctgcaggtcg actctagacc tgcaggatcc   5100
atgcccttca tttgccgctt attaattaat ttggtaacag tccgtactaa tcagttactt   5160
atccttcccc catcataatt aatcttggta gtctcgaatg ccacaacact gactagtctc   5220
ttggatcata agaaaaagcc aaggaacaaa agaagacaaa acacaatgag agtatccttt   5280
gcatagcaat gtctaagttc ataaaattca aacaaaaacg caatcacaca cagtggacat   5340
cacttatcca ctagctgatc aggatcgccg cgtcaagaaa aaaaaactgg accccaaaag   5400
ccatgcacaa caacacgtac tcacaaaggt gtcaatcgag cagcccaaaa cattcaccaa   5460
ctcaacccat catgagccct cacatttgtt gtttctaacc caacctcaaa ctcgtattct   5520
cttccgccac ctcatttttg tttatttcaa cacccgtcaa actgcatgcc accccgtggc   5580
caaatgtcca tgcatgttaa caagacctat gactataaat agctgcaatc tcggcccagg   5640
ttttcatcat caagaaccag ttcaatatcc tagtacaccg tattaaagaa tttaagatat   5700
actgc                                                               5705
```

<210> SEQ ID NO 56
<211> LENGTH: 12897
<212> TYPE: DNA
<213> ORGANISM: Artificial Sequence
<220> FEATURE:
<223> OTHER INFORMATION: plasmid pKR983

<400> SEQUENCE: 56

```
ggtcgactcg acgtacgtct agaggatccg tcgacggcgc gcccgatcat ccggatatag     60
ttcctccttt cagcaaaaaa cccctcaaga cccgtttaga ggccccaagg ggttatgcta    120
gttattgctc agcggtggca gcagccaact cagcttcctt tcgggctttg ttagcagccg    180
gatcgatcca agctgtacct cactattcct ttgccctcgg acgagtgctg gggcgtcggt    240
ttccactatc ggcgagtact tctacacagc catcggtcca gacggccgcg cttctgcggg    300
cgatttgtgt acgcccgaca gtcccggctc cggatcggac gattgcgtcg catcgaccct    360
gcgcccaagc tgcatcatcg aaattgccgt caaccaagct ctgatagagt tggtcaagac    420
caatgcggag catatacgcc cggagccgcg gcgatcctgc aagctccgga tgcctccgct    480
cgaagtagcg cgtctgctgc tccatacaag ccaaccacgg cctccagaag aagatgttgg    540
cgacctcgta ttgggaatcc ccgaacatcg cctcgctcca gtcaatgacc gctgttatgc    600
ggccattgtc cgtcaggaca ttgttggagc cgaaatccgc gtgcacgagg tgccggactt    660
cggggcagtc ctcggcccaa agcatcagct catcgagagc ctgcgcgacg gacgcactga    720
cggtgtcgtc catcacagtt tgccagtgat acacatgggg atcagcaatc gcgcatatga    780
aatcacgcca tgtagtgtat tgaccgattc cttgcggtcc gaatgggccg aacccgctcg    840
tctggctaag atcggccgca gcgatcgcat ccatagcctc cgcgaccggc tgcagaacag    900
cgggcagttc ggtttcaggc aggtcttgca acgtgacacc ctgtgcacgg cgggagatgc    960
```

```
aataggtcag gctctcgctg aattccccaa tgtcaagcac ttccggaatc gggagcgcgg   1020

ccgatgcaaa gtgccgataa acataacgat ctttgtagaa accatcggcg cagctattta   1080

cccgcaggac atatccacgc cctcctacat cgaagctgaa agcacgagat tcttcgccct   1140

ccgagagctg catcaggtcg gagacgctgt cgaacttttc gatcagaaac ttctcgacag   1200

acgtcgcggt gagttcaggc ttttccatgg gtatatctcc ttcttaaagt taaacaaaat   1260

tatttctaga gggaaaccgt tgtggtctcc ctatagtgag tcgtattaat ttcgcgggat   1320

cgagatctga tcaacctgca ttaatgaatc ggccaacgcg cggggagagg cggtttgcgt   1380

attgggcgct cttccgcttc ctcgctcact gactcgctgc gctcggtcgt tcggctgcgg   1440

cgagcggtat cagctcactc aaaggcggta atacggttat ccacagaatc aggggataac   1500

gcaggaaaga acatgtgagc aaaaggccag caaaaggcca ggaaccgtaa aaaggccgcg   1560

ttgctggcgt ttttccatag gctccgcccc cctgacgagc atcacaaaaa tcgacgctca   1620

agtcagaggt ggcgaaaccc gacaggacta taaagatacc aggcgtttcc ccctggaagc   1680

tccctcgtgc gctctcctgt tccgaccctg ccgcttaccg gatacctgtc cgcctttctc   1740

ccttcgggaa gcgtggcgct ttctcaatgc tcacgctgta ggtatctcag ttcggtgtag   1800

gtcgttcgct ccaagctggg ctgtgtgcac gaaccccccg ttcagcccga ccgctgcgcc   1860

ttatccggta actatcgtct tgagtccaac ccggtaagac acgacttatc gccactggca   1920

gcagccactg gtaacaggat tagcagagcg aggtatgtag gcggtgctac agagttcttg   1980

aagtggtggc ctaactacgg ctacactaga aggacagtat ttggtatctg cgctctgctg   2040

aagccagtta ccttcggaaa aagagttggt agctcttgat ccggcaaaca aaccaccgct   2100

ggtagcggtg gtttttttgt ttgcaagcag cagattacgc gcagaaaaaa aggatctcaa   2160

gaagatcctt tgatcttttc tacggggtct gacgctcagt ggaacgaaaa ctcacgttaa   2220

gggattttgg tcatgacatt aacctataaa aataggcgta tcacgaggcc ctttcgtctc   2280

gcgcgtttcg gtgatgacgg tgaaaacctc tgacacatgc agctcccgga gacggtcaca   2340

gcttgtctgt aagcggatgc cgggagcaga caagcccgtc agggcgcgtc agcgggtgtt   2400

ggcgggtgtc ggggctggct taactatgcg gcatcagagc agattgtact gagagtgcac   2460

catatggaca tattgtcgtt agaacgcggc tacaattaat acataacctt atgtatcata   2520

cacatacgat ttaggtgaca ctatagaacg gcgcgccaag ctgggtctag aactagaaac   2580

gtgatgccac ttgttattga agtcgattac agcatctatt ctgttttact atttataact   2640

ttgccatttc tgacttttga aaactatctc tggatttcgg tatcgctttg tgaagatcga   2700

gcaaaagaga cgttttgtgg acgcaatggt ccaaatccgt tctacatgaa caaattggtc   2760

acaatttcca ctaaaagtaa ataaatggca agttaaaaaa ggaatatgca ttttactgat   2820

tgcctaggtg agctccaaga gaagttgaat ctacacgtct accaaccgct aaaaaaagaa   2880

aaacattgat atgtaacctg attccattag cttttgactt cttcaacaga ttctctactt   2940

agatttctaa cagaaatatt attactagca catcattttc agtctcacta cagcaaaaaa   3000

tccaacggca caatacagac aacaggagat atcagactac agagatagat agatgctact   3060

gcatgtagta agttaaataa aaggaaaata aaatgtcttg ctaccaaaac tactacagac   3120

tatgatgctc accacaggcc aaatcctgca actaggacag cattatctta tatatattgt   3180

acaaaacaag catcaaggaa catttggtct aggcaatcag tacctcgttc taccatcacc   3240

ctcagttatc acatccttga aggatccatt actgggaatc atcggcaaca catgctcctg   3300

atggggcaca atgacatcaa gaaggtaggg gccaggggtg tccaacattc tctgaattgc   3360
```

```
cgctctaagc tcttccttct tcgtcactcg cgctgccggt atcccacaag catcagcaaa   3420
cttgagcatg tttgggaata tctcgctctc gctagacgga tctccaagat aggtgtgagc   3480
tctattggac ttgtagaacc tatcctccaa ctgaaccacc atacccaaat gctgattgtt   3540
caacaacaat atcttaactg ggagattctc cactcttata gtggccaact cctgaacatt   3600
catgatgaaa ctaccatccc catcaatgtc aaccacaaca gccccagggt tagcaacagc   3660
agcaccaata gccgcaggca atccaaaacc catggctcca agaccccctg aggtcaacca   3720
ctgcctcggt ctcttgtact tgtaaaactg cgcagcccac atttgatgct gcccaacccc   3780
agtactaaca atagcatctc cattagtcaa ctcatcaaga acctcgatag catgctgcgg   3840
agaaatcgcg tcctggaatg tcttgtaacc caatggaaac ttgtgtttct gcacattaat   3900
ctcttctctc caacctccaa gatcaaactt accctccact cctttctcct ccaaaatcat   3960
attaattccc ttcaaggcca acttcaaatc cgcgcaaacc gacacgtgcg cctgcttgtt   4020
cttcccaatc tcggcagaat caatatcaat gtgaacaatc ttagccctac tagcaaaagc   4080
ctcaagcttc ccagtaacac ggtcatcaaa ccttacccca aaggcaagca acaaatcact   4140
attgtcaaca gcatagttag cataaacagt accatgcata cccagcatct gaagggaata   4200
ttcatcacca ataggaaaag ttccaagacc cattaaagtg ctagcaacgg gaataccagt   4260
gagttcaaca aagcgcctca attcagcact ggaattcaaa ctgccaccgc cgacgtagag   4320
aacgggcttt tgggcctcca tgatgagtct gacaatgtgt tccaattggg cctcggcggg   4380
gggcctgggc agcctggcga ggtaaccggg gaggttaacg ggctcgtccc aattaggcac   4440
ggcgagttgc tgctgaacgt ctttgggaat gtcgatgagg accggaccgg ggcggccgga   4500
ggtggcgacg aagaaagcct cggcgacgac gcgggggatg tcgtcgacgt cgaggatgag   4560
gtagttgtgc ttcgtgatgg atctgctcac ctccacgatc ggggtttctt ggaaggcgtc   4620
ggtgccgatc atccggcggg cgacctggcc ggtgatggcg acgactggga cgctgtccat   4680
taaagcgtcg gcgaggccgc tcacgaggtt ggtggcgccg gggccggagg tggcaatgca   4740
gacgccgggg aggccggagg aacgcgcgta gccttcggcg gcgaagacgc cgccctgctc   4800
gtggcgcggg agcacgttgc ggatggcggc ggagcgcgtg agcgcctggt ggatctccat   4860
cgacgcaccg ccggggtacg cgaacaccgt cgtcacgccc tgcctctcca gcgcctccac   4920
aaggatgtcc gcgcccttgc gaggttcgcc ggaggcgaac cgtgacacga agggctccgt   4980
ggtcggcgct tccttggtga agggcgccgc cgtggggggt ttggagatgg aacatttgat   5040
tttgagagcg tggttgggtt tggtgagggt ttgatgagag agagggaggg tggatctagt   5100
aatgcgtttg gggaaggtgg ggtgtgaaga ggaagaagag aatcgggtgg ttctggaagc   5160
ggtggccgcc attgtgttgt gtggcatggt tatacttcaa aaactgcaca acaagcctag   5220
agttagtacc taaacagtaa atttacaaca gagagcaaag acacatgcaa aaatttcagc   5280
cataaaaaaa gttataatag aatttaaagc aaaagtttca ttttttaaac atatatacaa   5340
acaaactgga tttgaaggaa gggattaatt cccctgctca aagtttgaat tcctattgtg   5400
acctatactc gaataaaatt gaagcctaag gaatgtatga gaaacaagaa aacaaaacaa   5460
aactacagac aaacaagtac aattacaaaa ttcgctaaaa ttctgtaatc accaaacccc   5520
atctcagtca gcacaaggcc caaggtttat tttgaaataa aaaaaaagtg attttatttc   5580
tcataagcta aaagaaagaa aggcaattat gaaatgattt cgactagatc tgaaagtcca   5640
acgcgtattc cgcagatatt aaagaaagag tagagtttca catggatcct agatggaccc   5700
agttgaggaa aaagcaaggc aaagcaaacc agaagtgcaa gatccgaaat tgaaccacgg   5760
```

```
aatctaggat ttggtagagg gagaagaaaa gtaccttgag aggtagaaga gaagagaaga   5820
gcagagagat atatgaacga gtgtgtcttg gtctcaactc tgaagcgata cgagtttaga   5880
ggggagcatt gagttccaat ttatagggaa accgggtggc aggggtgagt taatgacgga   5940
aaagccccta agtaacgaga ttggattgtg ggttagattc aaccgtttgc atccgcggct   6000
tagattgggg aagtcagagt gaatctcaac cgttgactga gttgaaaatt gaatgtagca   6060
accaattgag ccaaccccag cctttgccct ttgattttga tttgtttgtt gcatactttt   6120
tatttgtctt ctggttctga ctctctttct ctcgtttcaa tgccaggttg cctactccca   6180
caccactcac aagaagattc tactgttagt attaaatatt ttttaatgta ttaaatgatg   6240
aatgcttttg taaacagaac aagactatgt ctaataagtg tcttgcaaca ttttttaaga   6300
aattaaaaaa aatatattta ttatcaaaat caaatgtatg aaaaatcatg aataatataa   6360
ttttatacat ttttttaaaa aatcttttaa tttcttaatt aatatcttaa aaataatgat   6420
taatatttaa cccaaaataa ttagtatgat tggtaaggaa gatatccatg ttatgtttgg   6480
atgtgagttt gatctagagc aaagcttact agagtcgacc tgcagcccgg gggatccgcc   6540
cacgtacggt accatctgct aatattttaa atcacatgca agagaggagg catggttcca   6600
ttttctacct tcacattatt tgagaaaaac gaacttgttc tgtgttttat ttttgccctt   6660
cacattagta caacgtggaa gactcatggt tacacagaat catacataag tacaatgctt   6720
gtccctaaga aaacaagcac tcgttgtatt gaacctttac ggctcatgcg gccgcgaatt   6780
cactagtgat tgaattcgcg gccgcttagt ccgacttggc cttggcggcc gcggccgact   6840
ctttgagcgt gaagatctgc gccgtctcgg gcacagcgcc gtagttgaca aagaggtgcg   6900
cggtcttgaa gaaggccgtg atgatgggct cgtcgttcct gcgcacgagg tgcgggtacg   6960
cggccgcaaa gtgcttggtg gcttcgttga gcttgtagtg cggaatgatc gggaacaagt   7020
ggtggacctg gtgcgtgcca atgtggtggc tcaggttgtc cacgaacgcg ccgtacgagc   7080
ggtcgacgct cgagaggttg cccttgacgt acgtccactc cgagtcgccg taccacggcg   7140
tcgcttcgtc gttgtggtgc aagaaggtcg taatgacgag gaacgaagca aagacaaaga   7200
gcggcgcata gtagtagagg cccatgacgg caaagccgag cgagtatgtg aggtacgcgt   7260
acgcggcgaa gaaggcggcc cagacgccga gcgacacgat gacggccgac gcgcggcgaa   7320
ggaggagcgg gtcccacggg tcaaagtggc tcatcgtgcg cggggcatac ccgaccttca   7380
agtagacaaa ccacgcaccg ccgagcgtgt agacccattg gcgcacgtcc tggaggtcct   7440
tgaccgaccg gtgcgggtaa aagatctcgt ccttatcaat gttgcccgtg ttcttgtggt   7500
ggtggcggtg cgtcacgcgc cagctctcga acggcgtcaa aatcgcagag tgcatgatgc   7560
agccgatgat aaagttgacg ctgtggtagc gcgagaaggc cgagtggccg cagtcgtggc   7620
cgaccgtgaa gaagccccag aagatgacgc cctgcacgta gatgtaggtg gcgcaaacga   7680
gcgcgtggag cagaacgtta tcggcaatga acggcgtcga gcgcgccgcg tagagcagcg   7740
ccgccgaggc cgacgcgttg aagatcgcgc gggccgtgta gtagagcgag aggccgaggt   7800
tcgactcaaa gcacgcgttc gggatcgagt gcttgagctc cgtgagcgtc gggaactcga   7860
ccttcgtctt atcctcagtc atgcggccgc tgaagtattg cttcttagtt aacctttcct   7920
ttctctctca gctatgtgaa ttcattttgc tttcgtcaca atttatatag tgaaattgga   7980
tctttggagt taacgccttc acaggattat cgtgttagaa caatgctttt tcatgttcta   8040
attagtagta cattacaaat gtgcactcta ttcaataagc atcttttggc acgttaataa   8100
atcatgtgaa aaaaaaatac tactatttca aagaaagtgt tgtaaaaaga aacggaaaga   8160
```

```
gagctggctt cagttgttga gacttgtttg ctagtaaaaa tggtgtgaag agtgattcat   8220
ggtgaggtgg tttttcgtcc ctttctgttt gcatgaaaaa caaatggcaa gagatgacgt   8280
aggattcctt cccttaacga ttatctgttt ttaatttcaa atatacatat aggaatttat   8340
gaattactaa ggttgtaaaa tatgctggtc atttatttat ggctaaaata ttttttttc   8400
tcgtaaatat aaaaatattt aaaatttatt tttatcatat tttttatcct tataaaatta   8460
tgtgtacaac ctatataaaa aaatatcata tttaatattg attatatgtt taatcaatat   8520
aaaaaatcat tatcatatat ttagatttat tcgaatatac atctaaacaa aaaataacat   8580
attttaattt tatgaagaaa aaaaaatatt ttatccttta tttatttaag attaattaat   8640
agttatgtat tgtggaaaga cttttacaca tgcaatagat atactgaatc aattagatgc   8700
caatgctgag ttggaaatca cttgaggagg ggaggagact tgccaatgct tttcagtttc   8760
atttaaatga tttagtggag gagatagagt agtgataaag gcatgcccca attttggagt   8820
gtatatatga gtggaaataa gagagggata gagagaaaaa ataaagagag taaaaataat   8880
taatgtgaaa tgatatgata aaaaaataaa gaaagagata aagagaaaaa tgaaatgaga   8940
gatagatgaa atagagagta gatacatgtt tgtttaggtt ttttttagga aataacacat   9000
tttttctca tcacttatta ctcactgtca atttcctctc tttcaatcat aatgatatga   9060
tttgtttaac aaaaatgtga aaaaacatat aaagtaaaat atttttataa attgataaat   9120
aaaaatttac aaaatttatt tcttattaaa ttgaatagaa aatgaaagaa aagaaaagaa   9180
aaagtatata taaaatgata tagctttaaa aagaataaat ttttcatatc agtctttttt   9240
taataattta gaaatattta agtatatagc aaaaatataa tgtactttac atatgcataa   9300
ataataattt gaaaatagaa ctaatagaat agagaaaaaa gtaatataat aattaactat   9360
atgaaaattt agaagggaca atatttttaa ttaagaatat aaacaatatt tcttttcatg   9420
taatgaggga cggatgtacg gggccagtgt tggagtcaaa gccaaaatag tcacggggaa   9480
attaatgcac tgcatgacta ttcgaaaaaa ttcactagcc ttacttagat gttagattaa   9540
tagctagggg gtgcagataa ttttgaaagg catgaaaaac attaatttgt acattgcaag   9600
cttttgatga caagctttgc aattgttcac actaccttat gccatttata aatagagtga   9660
ttggcatatg aaggaaatca tgagagtcga agcgaaaaac aaagcttgag agtgtaggaa   9720
aaatacagtt tttttggtaa aaatacagta tttgaatagg agcgaaaaat atcctttcaa   9780
aatgatcctt ttcttttttt ttttttttct tgttgttctt ggtcagttat tcaaaggaaa   9840
agggattgaa ataaaaactt gcatgtggga tcgtacgtcg agtcgacctg caggatccat   9900
gcccttcatt tgccgcttat taattaattt ggtaacagtc cgtactaatc agttacttat   9960
ccttcccccca tcataattaa tcttggtagt ctcgaatgcc acaacactga ctagtctctt  10020
ggatcataag aaaaagccaa ggaacaaaag aagacaaaac acaatgagag tatcctttgc  10080
atagcaatgt ctaagttcat aaaattcaaa caaaaacgca atcacacaca gtggacatca  10140
cttatccact agctgatcag gatcgccgcg tcaagaaaaa aaaactggac cccaaaagcc  10200
atgcacaaca acacgtactc acaaaggtgt caatcgagca gcccaaaaca ttcaccaact  10260
caacccatca tgagccctca catttgttgt ttctaaccca acctcaaact cgtattctct  10320
tccgccacct catttttgtt tatttcaaca cccgtcaaac tgcatgccac cccgtggcca  10380
aatgtccatg catgttaaca agacctatga ctataaatag ctgcaatctc ggcccaggtt  10440
ttcatcatca agaaccagtt caatatccta gtacaccgta ttaaagaatt taagatatac  10500
tgcggccgca caatggcgac tcgacagcga actgccacca ctgttgtggt cgaggacctt  10560
```

-continued

```
cccaaggtca ctcttgaggc caagtctgaa cctgtgttcc ccgatatcaa gaccatcaag  10620
gatgccattc ccgcgcactg cttccagccc tcgctcgtca cctcattcta ctacgtcttc  10680
cgcgattttg ccatggtctc tgccctcgtc tgggctgctc tcacctacat ccccagcatc  10740
cccgaccaga ccctccgcgt cgcagcttgg atggtctacg gcttcgtcca gggtctgttc  10800
tgcaccggtg tctggattct cggccatgag tgcggccacg gtgctttctc tctccacgga  10860
aaggtcaaca atgtgaccgg ctggttcctc cactcgttcc tcctcgtccc ctacttcagc  10920
tggaagtact ctcaccaccg ccaccaccgc ttcaccggcc acatggatct cgacatggct  10980
ttcgtcccca agactgagcc caagccctcc aagtcgctca tgattgctgg cattgacgtc  11040
gccgagcttg ttgaggacac ccccgctgct cagatggtca agctcatctt ccaccagctt  11100
ttcggatggc aggcgtacct cttcttcaac gctagctctg gcaagggcag caagcagtgg  11160
gagcccaaga ctggcctctc caagtggttc cgagtcagtc acttcgagcc taccagcgct  11220
gtcttccgcc ccaacgaggc catcttcatc ctcatctccg atatcggtct tgctctaatg  11280
ggaactgctc tgtactttgc ttccaagcaa gttggtgttt cgaccattct cttcctctac  11340
cttgttccct acctgtgggt tcaccactgg ctcgttgcca ttacctacct ccaccaccac  11400
cacaccgagc tccctcacta caccgctgag ggctggacct acgtcaaggg agctctcgcc  11460
actgtcgacc gtgagtttgg cttcatcgga aagcacctct tccacggtat cattgagaag  11520
cacgttgttc accatctctt ccctaagatc cccttctaca aggctgacga ggccaccgag  11580
gccatcaagc ccgtcattgg cgaccactac tgccacgacg accgaagctt cctgggccag  11640
ctgtggacca tcttcggcac gctcaagtac gtcgagcacg accctgcccg acccggtgcc  11700
atgcgatgga acaaggacta ggctaggcgg ccgcaagtat gaactaaaat gcatgtaggt  11760
gtaagagctc atggagagca tggaatattg tatccgacca tgtaacagta taataactga  11820
gctccatctc acttcttcta tgaataaaca aaggatgtta tgatatatta acactctatc  11880
tatgcacctt attgttctat gataaatttc ctcttattat tataaatcat ctgaatcgtg  11940
acggcttatg gaatgcttca aatagtacaa aaacaaatgt gtactataag actttctaaa  12000
caattctaac cttagcattg tgaacgagac ataagtgtta agaagacata acaattataa  12060
tggaagaagt ttgtctccat ttatatatta tatattaccc acttatgtat tatattagga  12120
tgttaaggag acataacaat tataaagaga gaagtttgta tccatttata tattatatac  12180
tacccattta tatattatac ttatccactt atttaatgtc tttataaggt ttgatccatg  12240
atatttctaa tattttagtt gatatgtata tgaaagggta ctatttgaac tctcttactc  12300
tgtataaagg ttggatcatc cttaaagtgg gtctatttaa ttttattgct tcttacagat  12360
aaaaaaaaaa ttatgagttg gtttgataaa atattgaagg atttaaaata ataataaata  12420
acatataata tatgtatata aatttattat aatataacat ttatctataa aaaagtaaat  12480
attgtcataa atctatacaa tcgtttagcc ttgctggacg aatctcaatt atttaaacga  12540
gagtaaacat atttgacttt ttggttattt aacaaattat tatttaacac tatatgaaat  12600
tttttttttt atcagcaaag aataaaatta aattaagaag gacaatggtg tcccaatcct  12660
tatacaacca acttccacaa gaaagtcaag tcagagacaa caaaaaaaca agcaaaggaa  12720
attttttaat ttgagttgtc ttgtttgctg cataatttat gcagtaaaac actacacata  12780
acccttttag cagtagagca atggttgacc gtgtgcttag cttcttttat tttatttttt  12840
tatcagcaaa gaataaataa aataaaatga gacacttcag ggatgtttca acctgca     12897
```

<210> SEQ ID NO 57
<211> LENGTH: 1272
<212> TYPE: DNA
<213> ORGANISM: Artificial Sequence
<220> FEATURE:
<223> OTHER INFORMATION: synthetic delta-8 desaturase (codon-optimized for Yarrowia lipolytica)

<400> SEQUENCE: 57

```
atgggcaagg gtggagacgg tggagcacag gctgtgtctg gcaccgatgc ctccctcgct     60

gaggtctcct ctgtggacag caagtccgtc cacgtggttc tgtacggcaa gcgagtggat    120

gtcaccaagt tccagaaggc tcaccctgga ggttcgaagg tgttccgaat ctttcaggag    180

cgagacgcca cagaacagtt cgagtcctac cactctccca aggccatcaa gatgatggaa    240

ggtatgctca aaaagtcgga ggatgctccc gcttccgtgc ctcttccctc tcgatccact    300

atgggcaccg agttcaagga gatgatcgaa cgacacaaga gagccggtct ctacgaccct    360

tgtcccttgg acgagctgtt caagctcacc attgtccttg ctcctatctt tgtgggagcc    420

tatctcgttc gatccggtgt ctctcctctt gctggagccc tgtcgatggg cttcggattc    480

tacctcgacg gctggcttgc tcacgactac ctgcatcacg cagtgttcaa gggctccgtc    540

aacacactcg tcaaggccaa caacgctatg ggatacgcct tgggcttcct ccagggttac    600

gacgttgctt ggtggcgagc cagacacaac actcatcacg tgtgcaccaa cgaggacggc    660

tccgatcccg acatcaagac ggctcctctg ctcatttacg tgcgagagaa tccctccatt    720

gccaagcggc tcaacttctt tcagcgatgg caacagtact actatgttcc tactatggcc    780

attctggatc tctactggcg actggagtct atcgcatacg tcgctgtgcg actgcccaag    840

atgtggatgc aggctgccgc tcttgccgct cactacgcac tcctgtgttg ggtcttcgct    900

gcccatctca acctgattcc tctcatgatg gttgcacgag gtttcgcgac cggaatcgtg    960

gtctttgcca cccactatgg cgaggacatt ctcgaccgag agcacgtcga aggcatgact   1020

ctggtcgagc agaccgccaa gacctcccga aacatcactg gtggatggct tgtcaacgtg   1080

ctcaccggct tcatttctct gcagaccgag catcatctgt ttcccatgat gcctactgga   1140

aacctcatga ccattcaacc cgaggttcga gactttttca aaaagcacgg tctcgagtac   1200

cgagaaggaa acctgtttca gtgcgtgcat cagaacatca aggctctcgc cttcgagcac   1260

ctgcttcact aa                                                       1272
```

<210> SEQ ID NO 58
<211> LENGTH: 3992
<212> TYPE: DNA
<213> ORGANISM: Artificial Sequence
<220> FEATURE:
<223> OTHER INFORMATION: plasmid pPiD8S

<400> SEQUENCE: 58

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acctcgcgaa    420

tgcatctaga tccatgggca agggtggaga cggtggagca caggctgtgt ctggcaccga    480
```

```
tgcctccctc gctgaggtct cctctgtgga cagcaagtcc gtccacgtgg ttctgtacgg    540
caagcgagtg gatgtcacca agttccagaa ggctcaccct ggaggttcga aggtgttccg    600
aatctttcag gagcgagacg ccacagaaca gttcgagtcc taccactctc ccaaggccat    660
caagatgatg gaaggtatgc tcaaaaagtc ggaggatgct cccgcttccg tgcctcttcc    720
ctctcgatcc actatgggca ccgagttcaa ggagatgatc gaacgacaca agagagccgg    780
tctctacgac ccttgtccct tggacgagct gttcaagctc accattgtcc ttgctcctat    840
ctttgtggga gcctatctcg ttcgatccgg tgtctctcct cttgctggag ccctgtcgat    900
gggcttcgga ttctacctcg acggctggct tgctcacgac tacctgcatc acgcagtgtt    960
caagggctcc gtcaacacac tcgtcaaggc caacaacgct atgggatacg ccttgggctt   1020
cctccagggt tacgacgttg cttggtggcg agccagacac aacactcatc acgtgtgcac   1080
caacgaggac ggctccgatc ccgacatcaa gacggctcct ctgctcattt acgtgcgaga   1140
gaatccctcc attgccaagc ggctcaactt ctttcagcga tggcaacagt actactatgt   1200
tcctactatg gccattctgg atctctactg gcgactggag tctatcgcat acgtcgctgt   1260
gcgactgccc aagatgtgga tgcaggctgc cgctcttgcc gctcactacg cactcctgtg   1320
ttgggtcttc gctgcccatc tcaacctgat tcctctcatg atggttgcac gaggtttcgc   1380
gaccggaatc gtggtctttg ccacccacta tggcgaggac attctcgacc gagagcacgt   1440
cgaaggcatg actctggtcg agcagaccgc caagacctcc cgaaacatca ctggtggatg   1500
gcttgtcaac gtgctcaccg gcttcatttc tctgcagacc gagcatcatc tgtttcccat   1560
gatgcctact ggaaacctca tgaccattca acccgaggtt cgagactttt tcaaaaagca   1620
cggtctcgag taccgagaag gaaacctgtt tcagtgcgtg catcagaaca tcaaggctct   1680
cgccttcgag cacctgcttc actaagcggc cgcatcggat cccgggcccg tcgactgcag   1740
aggcctgcat gcaagcttgg cgtaatcatg gtcatagctg tttcctgtgt gaaattgtta   1800
tccgctcaca attccacaca acatacgagc cggaagcata aagtgtaaag cctggggtgc   1860
ctaatgagtg agctaactca cattaattgc gttgcgctca ctgcccgctt tccagtcggg   1920
aaacctgtcg tgccagctgc attaatgaat cggccaacgc gcggggagag gcggtttgcg   1980
tattgggcgc tcttccgctt cctcgctcac tgactcgctg cgctcggtcg ttcggctgcg   2040
gcgagcggta tcagctcact caaaggcggt aatacggtta tccacagaat caggggataa   2100
cgcaggaaag aacatgtgag caaaaggcca gcaaaaggcc aggaaccgta aaaaggccgc   2160
gttgctggcg tttttccata ggctccgccc ccctgacgag catcacaaaa atcgacgctc   2220
aagtcagagg tggcgaaacc cgacaggact ataaagatac caggcgtttc cccctggaag   2280
ctccctcgtg cgctctcctg ttccgaccct gccgcttacc ggatacctgt ccgcctttct   2340
cccttcggga agcgtggcgc tttctcatag ctcacgctgt aggtatctca gttcggtgta   2400
ggtcgttcgc tccaagctgg gctgtgtgca cgaacccccc gttcagcccg accgctgcgc   2460
cttatccggt aactatcgtc ttgagtccaa cccggtaaga cacgacttat cgccactggc   2520
agcagccact ggtaacagga ttagcagagc gaggtatgta ggcggtgcta cagagttctt   2580
gaagtggtgg cctaactacg gctacactag aagaacagta tttggtatct gcgctctgct   2640
gaagccagtt accttcggaa aaagagttgg tagctcttga tccggcaaac aaaccaccgc   2700
tggtagcggt ggtttttttg tttgcaagca gcagattacg cgcagaaaaa aaggatctca   2760
agaagatcct ttgatctttt ctacggggtc tgacgctcag tggaacgaaa actcacgtta   2820
agggattttg gtcatgagat tatcaaaaag gatcttcacc tagatccttt taaattaaaa   2880
```

```
atgaagtttt aaatcaatct aaagtatata tgagtaaact tggtctgaca gttaccaatg   2940

cttaatcagt gaggcaccta tctcagcgat ctgtctattt cgttcatcca tagttgcctg   3000

actccccgtc gtgtagataa ctacgatacg ggagggctta ccatctggcc ccagtgctgc   3060

aatgataccg cgagacccac gctcaccggc tccagattta tcagcaataa accagccagc   3120

cggaagggcc gagcgcagaa gtggtcctgc aactttatcc gcctccatcc agtctattaa   3180

ttgttgccgg gaagctagag taagtagttc gccagttaat agtttgcgca acgttgttgc   3240

cattgctaca ggcatcgtgg tgtcacgctc gtcgtttggt atggcttcat tcagctccgg   3300

ttcccaacga tcaaggcgag ttacatgatc ccccatgttg tgcaaaaaag cggttagctc   3360

cttcggtcct ccgatcgttg tcagaagtaa gttggccgca gtgttatcac tcatggttat   3420

ggcagcactg cataattctc ttactgtcat gccatccgta agatgctttt ctgtgactgg   3480

tgagtactca accaagtcat tctgagaata gtgtatgcgg cgaccgagtt gctcttgccc   3540

ggcgtcaata cgggataata ccgcgccaca tagcagaact ttaaaagtgc tcatcattgg   3600

aaaacgttct tcggggcgaa aactctcaag gatcttaccg ctgttgagat ccagttcgat   3660

gtaacccact cgtgcaccca actgatcttc agcatctttt actttcacca gcgtttctgg   3720

gtgagcaaaa acaggaaggc aaaatgccgc aaaaaaggga ataagggcga cacggaaatg   3780

ttgaatactc atactcttcc tttttcaata ttattgaagc atttatcagg gttattgtct   3840

catgagcgga tacatatttg aatgtattta gaaaaataaa caaatagggg ttccgcgcac   3900

atttccccga aaagtgccac ctgacgtcta agaaaccatt attatcatga cattaaccta   3960

taaaaatagg cgtatcacga ggccctttcg tc                                 3992
```

<210> SEQ ID NO 59
<211> LENGTH: 792
<212> TYPE: DNA
<213> ORGANISM: Isochrysis galbana

<400> SEQUENCE: 59

```
atggccctcg caaacgacgc gggagagcgc atctgggcgg ctgtgaccga cccggaaatc     60

ctcattggca ccttctcgta cttgctactc aaaccgctgc tccgcaattc cgggctggtg    120

gatgagaaga agggcgcata caggacgtcc atgatctggt acaacgttct gctggcgctc    180

ttctctgcgc tgagcttcta cgtgacggcg accgccctcg gctgggacta tggtacgggc    240

gcgtggctgc gcaggcaaac cggcgacaca ccgcagccgc tcttccagtg cccgtccccg    300

gtttgggact cgaagctctt cacatggacc gccaaggcat tctattactc caagtacgtg    360

gagtacctcg acacggcctg gctggtgctc aagggcaaga gggtctcctt tctccaggcc    420

ttccaccact ttggcgcgcc gtgggatgtg tacctcggca ttcggctgca caacgagggc    480

gtatggatct tcatgttttt caactcgttc attcacacca tcatgtacac ctactacggc    540

ctcaccgccg ccgggtataa gttcaaggcc aagccgctca tcaccgcgat gcagatctgc    600

cagttcgtgg gcggcttcct gttggtctgg gactacatca acgtcccctg cttcaactcg    660

gacaaaggga agttgttcag ctgggctttc aactatgcat acgtcggctc ggtcttcttg    720

ctcttctgcc actttttcta ccaggacaac ttggcaacga agaaatcggc caaggcgggc    780

aagcagctct ag                                                       792
```

<210> SEQ ID NO 60
<211> LENGTH: 757
<212> TYPE: DNA
<213> ORGANISM: Euglena gracilis
<220> FEATURE:

```
<221> NAME/KEY: misc_feature
<222> LOCATION: (677)..(677)
<223> OTHER INFORMATION: n is a, c, g, or t

<400> SEQUENCE: 60

ttttttttcg aacacttaat ggaggtggtg aatgaaatag tctcaattgg gcaggaagtt     60

ttacccaaag ttgattatgc ccaactctgg agtgatgcca gtcactgtga ggtgctttac    120

ttgtccatcg catttgtcat cttgaagttc actcttggcc cccttggtcc aaaaggtcag    180

tctcgtatga agtttgtttt caccaattac aaccttctca tgtccattta ttcgttggga    240

tcattcctct caatggcata tgccatgtac accatcggtg ttatgtctga caactgcgag    300

aaggcttttg acaacaacgt cttcaggatc accacgcagt tgttctattt gagcaagttc    360

ctggagtata ttgactcctt ctatttgcca ctgatgggca agcctctgac ctggttgcaa    420

ttcttccatc atttgggggc accgatggat atgtggctgt tctataatta ccgaaatgaa    480

gctgtttgga tttttgtgct gttgaatggt ttcatccact ggatcatgta cggttattat    540

tggaccagat tgatcaagct gaagttcccc atgccaaaat ccctgattac atcaatgcag    600

atcattcaat tcaatgttgg tttctacatt gtctggaagt acaggaacat tccctgttat    660

cgccaagatg ggatgangat gtttggctgg ttcttcaatt acttttatgt tggcacagtc    720

ttgtgtttgt tcttgaattt ctatgtgcaa acgtata                             757


<210> SEQ ID NO 61
<211> LENGTH: 774
<212> TYPE: DNA
<213> ORGANISM: Euglena gracilis
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (218)..(220)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 61

tcaggatcac cacgcagttg ttctatttga gcangttcct ggagtatatt gactccttct     60

atttgccant gatgggcaag cntctgacct ggttgcaatt cttccatcat tngggggcac    120

cgatggatat gtggctgttc tataattacc gaaatgaagc tgtttggatt tttgtgctgt    180

tgaatggttt catccactgg atcatgtacg gttattannn gaccagattg atcaagctga    240

agttccccat gccaaaatcc ctgattacat caatgcagat cattcaattc aatgttggtt    300

tctacattgt ctggaagtac aggaacattc cctgttatcg ccaagatggg atgaggatgt    360
```

```
ttggctggtt cttcaattac ttttatgttg gcacagtctt gtgtttgttc ttgaatttct    420

atgtgcaaac gtatatcgtc aggaagcaca agggagccaa aaagattcag tgatatttcc    480

tcctctgcgg tggcctcttt tgacctcccc ttgacaccta taatgtggag gtgtcgggct    540

ctctccgtct caccagcact tgactctgca ggtgctcact tttatttttt acccatcttt    600

gcttgttgac cattcacctc tcccacttcc acatagtcca ttctaactgt tgcagactgc    660

ggtccatttt ttccagagct cccaatgacc atacgcgaca ccttgtnnnc ncccagccca    720

ttgtgcacaa ttcatagtgg catcgttttg ccttgatacg tgtgcatcca gcgg          774
```

```
<210> SEQ ID NO 62
<211> LENGTH: 1201
<212> TYPE: DNA
<213> ORGANISM: Euglena gracilis
<220> FEATURE:
<221> NAME/KEY: misc_feature
<222> LOCATION: (1134)..(1136)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t

<400> SEQUENCE: 62

gacatggcaa ctatgatttt attttgactg atagtgacct gttcgttgca acaaattgat     60

gagcaatgct tttttataat gccaactttg tacaaaaaag ttggattttt tttcgaacac    120

ttaatggagg tggtgaatga aatagtctca attgggcagg aagttttacc caaagttgat    180

tatgcccaac tctggagtga tgccagtcac tgtgaggtgc tttacttgtc catcgcattt    240

gtcatcttga agttcactct tggccccctt ggtccaaaag gtcagtctcg tatgaagttt    300

gttttcacca attacaacct tctcatgtcc atttattcgt tgggatcatt cctctcaatg    360

gcatatgcca tgtacaccat cggtgttatg tctgacaact gcgagaaggc ttttgacaac    420

aacgtcttca ggatcaccac gcagttgttc tatttgagca agttcctgga gtatattgac    480

tccttctatt tgccactgat gggcaagcct ctgacctggt tgcaattctt ccatcattg     540

ggggcaccga tggatatgtg gctgttctat aattaccgaa atgaagctgt ttggattttt    600

gtgctgttga atggtttcat ccactggatc atgtacggtt attattggac cagattgatc    660

aagctgaagt tccccatgcc aaaatccctg attacatcaa tgcagatcat tcaattcaat    720

gttggtttct acattgtctg gaagtacagg aacattccct gttatcgcca agatgggatg    780

aggatgtttg gctggttctt caattacttt tatgttggca cagtcttgtg tttgttcttg    840

aatttctatg tgcaaacgta tatcgtcagg aagcacaagg gagccaaaaa gattcagtga    900

tatttcctcc tctgcggtgg cctcttttga cctccccttg acacctataa tgtggaggtg    960

tcgggctctc tccgtctcac cagcacttga ctctgcaggt gctcactttt atttttttacc  1020

catctttgct tgttgaccat tcacctctcc cacttccaca tagtccattc taactgttgc   1080

agactgcggt ccatttttc cagagctccc aatgaccata cgcgacacct tgtnnncncc   1140

cagcccattg tgcacaattc atagtggcat cgttttgcct tgatacgtgt gcatccagcg   1200

g                                                                   1201
```

```
<210> SEQ ID NO 63
<211> LENGTH: 18
<212> TYPE: DNA
<213> ORGANISM: Artificial Sequence
<220> FEATURE:
<223> OTHER INFORMATION: M13F universal primer
```

<400> SEQUENCE: 63
tgtaaaacga cggccagt 18

<210> SEQ ID NO 64
<211> LENGTH: 258
<212> TYPE: PRT
<213> ORGANISM: Euglena gracilis

<400> SEQUENCE: 64

```
Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln
```

<210> SEQ ID NO 65
<211> LENGTH: 263
<212> TYPE: PRT
<213> ORGANISM: Isochrysis galbana

<400> SEQUENCE: 65

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
```

```
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260
```

<210> SEQ ID NO 66
<211> LENGTH: 777
<212> TYPE: DNA
<213> ORGANISM: Artificial Sequence
<220> FEATURE:
<223> OTHER INFORMATION: synthetic (codon-optimized) delta-9 elongase derived from Isochrysis galbana codon-optimized for expression in Yarrowia lipolytica

<400> SEQUENCE: 66

```
atggaggtcg tgaacgaaat cgtctccatt ggccaggagg ttcttcccaa ggtcgactat     60

gctcagctct ggtctgatgc ctcgcactgc gaggtgctgt acctctccat cgccttcgtc    120

atcctgaagt tcacccttgg tcctctcgga cccaagggtc agtctcgaat gaagtttgtg    180

ttcaccaact acaacctgct catgtccatc tactcgctgg gctccttcct ctctatggcc    240

tacgccatgt acaccattgg tgtcatgtcc gacaactgcg agaaggcttt cgacaacaat    300

gtcttccgaa tcaccactca gctgttctac ctcagcaagt tcctcgagta cattgactcc    360

ttctatctgc ccctcatggg caagcctctg acctggttgc agttctttca ccatctcgga    420

gctcctatgg acatgtggct gttctacaac taccgaaacg aagccgtttg gatctttgtg    480

ctgctcaacg gcttcattca ctggatcatg tacggctact attggacccg actgatcaag    540

ctcaagttcc ctatgcccaa gtccctgatt acttctatgc agatcattca gttcaacgtt    600

ggcttctaca tcgtctggaa gtaccggaac attccctgct accgacaaga tggaatgaga    660

atgtttggct ggtttttcaa ctacttctac gttggtactg tcctgtgtct gttcctcaac    720

ttctacgtgc agacctacat cgtccgaaag cacaagggag ccaaaaagat tcagtga       777
```

<210> SEQ ID NO 67
<211> LENGTH: 3497
<212> TYPE: DNA
<213> ORGANISM: Artificial Sequence
<220> FEATURE:
<223> OTHER INFORMATION: plasmid pEgD9ES

<400> SEQUENCE: 67

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acctcgcgaa    420
tgcatctaga tccatggagg tcgtgaacga aatcgtctcc attggccagg aggttcttcc    480
caaggtcgac tatgctcagc tctggtctga tgcctcgcac tgcgaggtgc tgtacctctc    540
catcgccttc gtcatcctga agttcaccct tggtcctctc ggacccaagg gtcagtctcg    600
aatgaagttt gtgttcacca actacaacct gctcatgtcc atctactcgc tgggctcctt    660
cctctctatg gcctacgcca tgtacaccat tggtgtcatg tccgacaact gcgagaaggc    720
tttcgacaac aatgtcttcc gaatcaccac tcagctgttc tacctcagca agttcctcga    780
gtacattgac tccttctatc tgcccctcat gggcaagcct ctgacctggt tgcagttctt    840
tcaccatctc ggagctccta tggacatgtg gctgttctac aactaccgaa acgaagccgt    900
ttggatcttt gtgctgctca acggcttcat tcactggatc atgtacggct actattggac    960
ccgactgatc aagctcaagt tccctatgcc caagtccctg attacttcta tgcagatcat   1020
tcagttcaac gttggcttct acatcgtctg gaagtaccgg aacattccct gctaccgaca   1080
agatggaatg agaatgtttg gctggttttt caactacttc tacgttggta ctgtcctgtg   1140
tctgttcctc aacttctacg tgcagaccta catcgtccga aagcacaagg gagccaaaaa   1200
gattcagtga gcggccgcat cggatcccgg gcccgtcgac tgcagaggcc tgcatgcaag   1260
cttggcgtaa tcatggtcat agctgtttcc tgtgtgaaat tgttatccgc tcacaattcc   1320
acacaacata cgagccggaa gcataaagtg taaagcctgg ggtgcctaat gagtgagcta   1380
actcacatta attgcgttgc gctcactgcc cgctttccag tcgggaaacc tgtcgtgcca   1440
gctgcattaa tgaatcggcc aacgcgcggg gagaggcggt ttgcgtattg ggcgctcttc   1500
cgcttcctcg ctcactgact cgctgcgctc ggtcgttcgg ctgcggcgag cggtatcagc   1560
tcactcaaag gcggtaatac ggttatccac agaatcaggg gataacgcag gaaagaacat   1620
gtgagcaaaa ggccagcaaa aggccaggaa ccgtaaaaag gccgcgttgc tggcgttttt   1680
ccataggctc cgcccccctg acgagcatca caaaaatcga cgctcaagtc agaggtggcg   1740
aaacccgaca ggactataaa gataccaggc gtttccccct ggaagctccc tcgtgcgctc   1800
tcctgttccg accctgccgc ttaccggata cctgtccgcc tttctccctt cgggaagcgt   1860
ggcgctttct catagctcac gctgtaggta tctcagttcg gtgtaggtcg ttcgctccaa   1920
gctgggctgt gtgcacgaac cccccgttca gcccgaccgc tgcgccttat ccggtaacta   1980
tcgtcttgag tccaacccgg taagacacga cttatcgcca ctggcagcag ccactggtaa   2040
caggattagc agagcgaggt atgtaggcgg tgctacagag ttcttgaagt ggtggcctaa   2100
ctacggctac actagaagaa cagtatttgg tatctgcgct ctgctgaagc cagttacctt   2160
```

```
cggaaaaaga gttggtagct cttgatccgg caaacaaacc accgctggta gcggtggttt   2220

ttttgtttgc aagcagcaga ttacgcgcag aaaaaaagga tctcaagaag atcctttgat   2280

cttttctacg gggtctgacg ctcagtggaa cgaaaactca cgttaaggga ttttggtcat   2340

gagattatca aaaaggatct tcacctagat ccttttaaat taaaaatgaa gttttaaatc   2400

aatctaaagt atatatgagt aaacttggtc tgacagttac caatgcttaa tcagtgaggc   2460

acctatctca gcgatctgtc tatttcgttc atccatagtt gcctgactcc ccgtcgtgta   2520

gataactacg atacgggagg gcttaccatc tggccccagt gctgcaatga taccgcgaga   2580

cccacgctca ccggctccag atttatcagc aataaaccag ccagccggaa gggccgagcg   2640

cagaagtggt cctgcaactt tatccgcctc catccagtct attaattgtt gccgggaagc   2700

tagagtaagt agttcgccag ttaatagttt gcgcaacgtt gttgccattg ctacaggcat   2760

cgtggtgtca cgctcgtcgt ttggtatggc ttcattcagc tccggttccc aacgatcaag   2820

gcgagttaca tgatccccca tgttgtgcaa aaaagcggtt agctccttcg gtcctccgat   2880

cgttgtcaga agtaagttgg ccgcagtgtt atcactcatg gttatggcag cactgcataa   2940

ttctcttact gtcatgccat ccgtaagatg cttttctgtg actggtgagt actcaaccaa   3000

gtcattctga gaatagtgta tgcggcgacc gagttgctct tgcccggcgt caatacggga   3060

taataccgcg ccacatagca gaactttaaa agtgctcatc attggaaaac gttcttcggg   3120

gcgaaaactc tcaaggatct taccgctgtt gagatccagt tcgatgtaac ccactcgtgc   3180

acccaactga tcttcagcat cttttacttt caccagcgtt tctgggtgag caaaaacagg   3240

aaggcaaaat gccgcaaaaa agggaataag ggcgacacgg aaatgttgaa tactcatact   3300

cttccttttt caatattatt gaagcattta tcagggttat tgtctcatga gcggatacat   3360

atttgaatgt atttagaaaa ataaacaaat aggggttccg cgcacatttc cccgaaaagt   3420

gccacctgac gtctaagaaa ccattattat catgacatta acctataaaa ataggcgtat   3480

cacgaggccc tttcgtc                                                  3497
```

<210> SEQ ID NO 68
<211> LENGTH: 9472
<212> TYPE: DNA
<213> ORGANISM: Artificial Sequence
<220> FEATURE:
<223> OTHER INFORMATION: plasmid pDMW263

<400> SEQUENCE: 68

```
catggcatgg atggtacgtc ctgtagaaac cccaacccgt gaaatcaaaa aactcgacgg     60

cctgtgggca ttcagtctgg atcgcgaaaa ctgtggaatt gatcagcgtt ggtgggaaag    120

cgcgttacaa gaaagccggg caattgctgt gccaggcagt tttaacgatc agttcgccga    180

tgcagatatt cgtaattatg cgggcaacgt ctggtatcag cgcgaagtct ttataccgaa    240

aggttgggca ggccagcgta tcgtgctgcg tttcgatgcg gtcactcatt acggcaaagt    300

gtgggtcaat aatcaggaag tgatggagca tcagggcggc tatacgccat ttgaagccga    360

tgtcacgccg tatgttattg ccgggaaaag tgtacgtatc accgtttgtg tgaacaacga    420

actgaactgg cagactatcc cgccgggaat ggtgattacc gacgaaaacg gcaagaaaaa    480

gcagtcttac ttccatgatt tctttaacta tgccgggatc catcgcagcg taatgctcta    540

caccacgccg aacacctggg tggacgatat caccgtggtg acgcatgtcg cgcaagactg    600

taaccacgcg tctgttgact ggcaggtggt ggccaatggt gatgtcagcg ttgaactgcg    660

tgatgcggat caacaggtgg ttgcaactgg acaaggcact agcgggactt tgcaagtggt    720
```

```
gaatccgcac ctctggcaac cgggtgaagg ttatctctat gaactgtgcg tcacagccaa    780

aagccagaca gagtgtgata tctacccgct tcgcgtcggc atccggtcag tggcagtgaa    840

gggcgaacag ttcctgatta accacaaacc gttctacttt actggctttg gtcgtcatga    900

agatgcggac ttacgtggca aaggattcga taacgtgctg atggtgcacg accacgcatt    960

aatggactgg attggggcca actcctaccg tacctcgcat taccettacg ctgaagagat   1020

gctcgactgg gcagatgaac atggcatcgt ggtgattgat gaaactgctg ctgtcggctt   1080

taacctctct ttaggcattg gtttcgaagc gggcaacaag ccgaaagaac tgtacagcga   1140

agaggcagtc aacggggaaa ctcagcaagc gcacttacag gcgattaaag agctgatagc   1200

gcgtgacaaa aaccacccaa gcgtggtgat gtggagtatt gccaacgaac cggatacccg   1260

tccgcaagtg cacgggaata tttcgccact ggcggaagca acgcgtaaac tcgacccgac   1320

gcgtccgatc acctgcgtca atgtaatgtt ctgcgacgct cacaccgata ccatcagcga   1380

tctctttgat gtgctgtgcc tgaaccgtta ttacggatgg tatgtccaaa gcggcgattt   1440

ggaaacggca gagaaggtac tggaaaaaga acttctggcc tggcaggaga aactgcatca   1500

gccgattatc atcaccgaat acggcgtgga tacgttagcc gggctgcact caatgtacac   1560

cgacatgtgg agtgaagagt atcagtgtgc atggctggat atgtatcacc gcgtctttga   1620

tcgcgtcagc gccgtcgtcg gtgaacaggt atggaatttc gccgattttg cgacctcgca   1680

aggcatattg cgcgttggcg gtaacaagaa agggatcttc actcgcgacc gcaaaccgaa   1740

gtcggcggct tttctgctgc aaaaacgctg gactggcatg aacttcggtg aaaaaccgca   1800

gcagggaggc aaacaatgat taattaacta gagcggccgc caccgcggcc cgagattccg   1860

gcctcttcgg ccgccaagcg acccgggtgg acgtctagag gtacctagca attaacagat   1920

agtttgccgg tgataattct cttaacctcc cacactcctt tgacataacg atttatgtaa   1980

cgaaactgaa atttgaccag atattgtgtc cgcggtggag ctccagcttt tgttcccttt   2040

agtgagggtt aatttcgagc ttggcgtaat catggtcata gctgtttcct gtgtgaaatt   2100

gttatccgct cacaattcca cacaacatac gagccggaag cataaagtgt aaagcctggg   2160

gtgcctaatg agtgagctaa ctcacattaa ttgcgttgcg ctcactgccc gctttccagt   2220

cgggaaacct gtcgtgccag ctgcattaat gaatcggcca acgcgcgggg agaggcggtt   2280

tgcgtattgg gcgctcttcc gcttcctcgc tcactgactc gctgcgctcg gtcgttcggc   2340

tgcggcgagc ggtatcagct cactcaaagg cggtaatacg gttatccaca gaatcagggg   2400

ataacgcagg aaagaacatg tgagcaaaag gccagcaaaa ggccaggaac cgtaaaaagg   2460

ccgcgttgct ggcgtttttc cataggctcc gcccccctga cgagcatcac aaaaatcgac   2520

gctcaagtca gaggtggcga aacccgacag gactataaag ataccaggcg tttccccctg   2580

gaagctccct cgtgcgctct cctgttccga ccctgccgct taccggatac ctgtccgcct   2640

ttctcccttc gggaagcgtg gcgctttctc atagctcacg ctgtaggtat ctcagttcgg   2700

tgtaggtcgt tcgctccaag ctgggctgtg tgcacgaacc ccccgttcag cccgaccgct   2760

gcgccttatc cggtaactat cgtcttgagt ccaacccggt aagacacgac ttatcgccac   2820

tggcagcagc cactggtaac aggattagca gagcgaggta tgtaggcggt gctacagagt   2880

tcttgaagtg gtggcctaac tacggctaca ctagaaggac agtatttggt atctgcgctc   2940

tgctgaagcc agttaccttc ggaaaaagag ttggtagctc ttgatccggc aaacaaacca   3000

ccgctggtag cggtggtttt tttgtttgca agcagcagat tacgcgcaga aaaaaaggat   3060

ctcaagaaga tcctttgatc ttttctacgg ggtctgacgc tcagtggaac gaaaactcac   3120
```

```
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatcccccat gttgtgcaaa aaagcggtta   3660
gctccttcgg tcctccgatc gttgtcagaa gtaagttggc cgcagtgtta tcactcatgg   3720
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata gacggttttt cgccctttga   4500
cgttggagtc cacgttcttt aatagtggac tcttgttcca aactggaaca acactcaacc   4560
ctatctcggt ctattctttt gatttataag ggattttgcc gatttcggcc tattggttaa   4620
aaaatgagct gatttaacaa aaatttaacg cgaattttaa caaaatatta acgcttacaa   4680
tttccattcg ccattcaggc tgcgcaactg ttgggaaggg cgatcggtgc gggcctcttc   4740
gctattacgc cagctggcga aagggggatg tgctgcaagg cgattaagtt gggtaacgcc   4800
agggttttcc cagtcacgac gttgtaaaac gacggccagt gaattgtaat acgactcact   4860
atagggcgaa ttgggtaccg ggccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga aatcttaaat atggatagca taaatgatat   5400
ctgcattgcc taattcgaaa tcaacagcaa cgaaaaaaat cccttgtaca acataaatag   5460
tcatcgagaa atatcaacta tcaaagaaca gctattcaca cgttactatt gagattatta   5520
```

-continued

```
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat ccttttgttt attacatggg   5820
ctggatacat aaaggtattt tgatttaatt ttttgcttaa attcaatccc ccctcgttca   5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacattttt gcttttacaa   6060
gtacaagtac atcgtacaac tatgtactac tgttgatgca tccacaacag tttgttttgt   6120
tttttttgt ttttttttt tctaatgatt cattaccgct atgtatacct acttgtactt   6180
gtagtaagcc gggttattgg cgttcaatta atcatagact tatgaatctg cacggtgtgc   6240
gctgcgagtt acttttagct tatgcatgct acttgggtgt aatattggga tctgttcgga   6300
aatcaacgga tgctcaaccg atttcgacag taataatttg aatcgaatcg gagcctaaaa   6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg   6480
aaatacagtg ccaaaagcca aggcactgag ctcgtctaac ggacttgata tacaaccaat   6540
taaaacaaat gaaaagaaat acagttcttt gtatcatttg taacaattac cctgtacaaa   6600
ctaaggtatt gaaatcccac aatattccca aagtccaccc ctttccaaat tgtcatgcct   6660
acaactcata taccaagcac taacctacca aacaccacta aaaccccaca aaatatatct   6720
taccgaatat acagtaacaa gctaccacca cactcgttgg gtgcagtcgc cagcttaaag   6780
atatctatcc acatcagcca caactccctt cctttaataa accgactaca cccttggcta   6840
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg cccttttat agagtcttat   7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac   7260
ttgagcatca tggcggcaga cagaatggtg gcaatggggt tgaccttctg cttgccgaga   7320
tcgggggcag atccgtgaca gggctcgtac agaccgaacg cctcgttggt gtcgggcaga   7380
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctgggggaat   7560
tcgtccttga ggactcgagt gacagtcttt cgccaaagtc gagaggaggc cagcacgttg   7620
gccttgtcaa gagaccacac gggaagaggg gggttgtgct gaagggccag gaaggcggcc   7680
attcgggcaa ttcgctcaac ctcaggaacg gagtaggtct cggtgtcgga agcgacgcca   7740
gatccgtcat cctcctttcg ctctccaaag tagatacctc cgacgagctc tcggacaatg   7800
atgaagtcgg tgccctcaac gtttcggatg ggggagagat cggcgagctt gggcgacagc   7860
agctggcagg gtcgcaggtt ggcgtacagg ttcaggtcct ttcgcagctt gaggagaccc   7920
```

```
tgctcgggtc gcacgtcggt tcgtccgtcg ggagtggtcc atacggtgtt ggcagcgcct   7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccgg aggcctcagc aacagacttg agcaccttga cggcctcggc aatcacctcg   8160
gggccacaga agtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtacccc agccggccgg gagtatgtcg gaggggacat   8460
acgagatcgt caagggtttg tggccaactg gtaaataaat gatgtcgacg tttaaacagt   8520
gtacgcagat ctactataga ggaacattta aattgccccg gagaagacgg ccaggccgcc   8580
tagatgacaa attcaacaac tcacagctga ctttctgcca ttgccactag gggggggcct   8640
ttttatatgg ccaagccaag ctctccacgt cggttgggct gcacccaaca ataaatgggt   8700
agggttgcac caacaaaggg atgggatggg gggtagaaga tacgaggata acggggctca   8760
atggcacaaa taagaacgaa tactgccatt aagactcgtg atccagcgac tgacaccatt   8820
gcatcatcta agggcctcaa aactacctcg gaactgctgc gctgatctgg acaccacaga   8880
ggttccgagc actttaggtt gcaccaaatg tcccaccagg tgcaggcaga aaacgctgga   8940
acagcgtgta cagtttgtct taacaaaaag tgagggcgct gaggtcgagc agggtggtgt   9000
gacttgttat agcctttaga gctgcgaaag cgcgtatgga tttggctcat caggccagat   9060
tgagggtctg tggacacatg tcatgttagt gtacttcaat cgccccctgg atatagcccc   9120
gacaataggc cgtggcctca tttttttgcc ttccgcacat ttccattgct cgatacccac   9180
accttgcttc tcctgcactt gccaacctta atactggttt acattgacca acatcttaca   9240
agcggggggc ttgtctaggg tatatataaa cagtggctct cccaatcggt tgccagtctc   9300
tttttccttt tctttcccca cagattcgaa atctaaacta cacatcacag aattccgagc   9360
cgtgagtatc cacgacaaga tcagtgtcga gacgacgcgt tttgtgtaat gacacaatcc   9420
gaaagtcgct agcaacacac actctctaca caaactaacc cagctctggt ac           9472
```

<210> SEQ ID NO 69
<211> LENGTH: 8165
<212> TYPE: DNA
<213> ORGANISM: Artificial Sequence
<220> FEATURE:
<223> OTHER INFORMATION: plasmid pZUF17

<400> SEQUENCE: 69

```
gtacgagccg gaagcataaa gtgtaaagcc tggggtgcct aatgagtgag ctaactcaca     60
ttaattgcgt tgcgctcact gcccgctttc cagtcgggaa acctgtcgtg ccagctgcat    120
taatgaatcg gccaacgcgc ggggagaggc ggtttgcgta ttgggcgctc ttccgcttcc    180
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
```

```
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
```

```
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg gggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
```

```
gagactgaaa taaatttagt ctgcagaact ttttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc cccctggata   6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc ggggggcttg tctagggtat atataaacag tggctctccc aatcggttgc   6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga gacgacgcgt tttgtgtaat gacacaatcc   6720
gaaagtcgct agcaacacac actctctaca caaactaacc cagctctcca tggctgagga   6780
taagaccaag gtcgagttcc ctaccctgac tgagctgaag cactctatcc ctaacgcttg   6840
ctttgagtcc aacctcggac tctcgctcta ctacactgcc cgagcgatct tcaacgcatc   6900
tgcctctgct gctctgctct acgctgcccg atctactccc ttcattgccg ataacgttct   6960
gctccacgct ctggtttgcg ccacctacat ctacgtgcag ggtgtcatct tctggggttt   7020
ctttaccgtc ggtcacgact gtggtcactc tgccttctcc cgataccact ccgtcaactt   7080
catcattggc tgcatcatgc actctgccat tctgactccc ttcgagtcct ggcgagtgac   7140
ccaccgacac catcacaaga acactggcaa cattgataag gacgagatct tctaccctca   7200
tcggtccgtc aaggacctcc aggacgtgcg acaatgggtc tacaccctcg gaggtgcttg   7260
gtttgtctac ctgaaggtcg gatatgctcc tcgaaccatg tcccactttg accccctgga   7320
ccctctcctg cttcgacgag cctccgctgt catcgtgtcc ctcggagtct gggctgcctt   7380
cttcgctgcc tacgcctacc tcacatactc gctcggcttt gccgtcatgg gcctctacta   7440
ctatgctcct ctctttgtct ttgcttcgtt cctcgtcatt actaccttct tgcatcacaa   7500
cgacgaagct actccctggt acggtgactc ggagtggacc tacgtcaagg gcaacctgag   7560
ctccgtcgac cgatcgtacg gagctttcgt ggacaacctg tctcaccaca ttggcaccca   7620
ccaggtccat cacttgttcc ctatcattcc ccactacaag ctcaacgaag ccaccaagca   7680
ctttgctgcc gcttaccctc acctcgtgag acgtaacgac gagcccatca ttactgcctt   7740
```

```
cttcaagacc gctcacctct ttgtcaacta cggagctgtg cccgagactg ctcagatttt   7800

caccctcaaa gagtctgccg ctgcagccaa ggccaagagc gactaagcgg ccgcaagtgt   7860

ggatggggaa gtgagtgccc ggttctgtgt gcacaattgg caatccaaga tggatggatt   7920

caacacaggg atatagcgag ctacgtggtg gtgcgaggat atagcaacgg atatttatgt   7980

ttgacacttg agaatgtacg atacaagcac tgtccaagta caatactaaa catactgtac   8040

atactcatac tcgtacccgg gcaacggttt cacttgagtg cagtggctag tgctcttact   8100

cgtacagtgt gcaatactgc gtatcatagt ctttgatgta tatcgtattc attcatgtta   8160

gttgc                                                               8165
```

<210> SEQ ID NO 70
<211> LENGTH: 7769
<212> TYPE: DNA
<213> ORGANISM: Artificial Sequence
<220> FEATURE:
<223> OTHER INFORMATION: plasmid pZUFmEgD9ES

<400> SEQUENCE: 70

```
ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc gggcaacggt ttcacttgag tgcagtggct    240

agtgctctta ctcgtacagt gtgcaatact gcgtatcata gtctttgatg tatatcgtat    300

tcattcatgt tagttgcgta cgagccggaa gcataaagtg taaagcctgg ggtgcctaat    360

gagtgagcta actcacatta attgcgttgc gctcactgcc cgctttccag tcgggaaacc    420

tgtcgtgcca gctgcattaa tgaatcggcc aacgcgcggg gagaggcggt ttgcgtattg    480

ggcgctcttc cgcttcctcg ctcactgact cgctgcgctc ggtcgttcgg ctgcggcgag    540

cggtatcagc tcactcaaag gcggtaatac ggttatccac agaatcaggg gataacgcag    600

gaaagaacat gtgagcaaaa ggccagcaaa aggccaggaa ccgtaaaaag gccgcgttgc    660

tggcgttttt ccataggctc cgcccccctg acgagcatca caaaaatcga cgctcaagtc    720

agaggtggcg aaacccgaca ggactataaa gataccaggc gtttccccct ggaagctccc    780

tcgtgcgctc tcctgttccg accctgccgc ttaccggata cctgtccgcc tttctccctt    840

cgggaagcgt ggcgctttct catagctcac gctgtaggta tctcagttcg gtgtaggtcg    900

ttcgctccaa gctgggctgt gtgcacgaac cccccgttca gcccgaccgc tgcgccttat    960

ccggtaacta tcgtcttgag tccaacccgg taagacacga cttatcgcca ctggcagcag   1020

ccactggtaa caggattagc agagcgaggt atgtaggcgg tgctacagag ttcttgaagt   1080

ggtggcctaa ctacggctac actagaagga cagtatttgg tatctgcgct ctgctgaagc   1140

cagttacctt cggaaaaaga gttggtagct cttgatccgg caaacaaacc accgctggta   1200

gcggtggttt ttttgtttgc aagcagcaga ttacgcgcag aaaaaaagga tctcaagaag   1260

atcctttgat cttttctacg gggtctgacg ctcagtggaa cgaaaactca cgttaaggga   1320

ttttggtcat gagattatca aaaaggatct tcacctagat ccttttaaat taaaaatgaa   1380

gttttaaatc aatctaaagt atatatgagt aaacttggtc tgacagttac caatgcttaa   1440

tcagtgaggc acctatctca gcgatctgtc tatttcgttc atccatagtt gcctgactcc   1500

ccgtcgtgta gataactacg atacgggagg gcttaccatc tggccccagt gctgcaatga   1560

taccgcgaga cccacgctca ccggctccag atttatcagc aataaaccag ccagccggaa   1620
```

```
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
```

```
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag gggagcacaa gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggcctttt tatatggcca agccaagctc   6180
tccacgtcgg ttgggctgca cccaacaata aatgggtagg gttgcaccaa caaagggatg   6240
ggatgggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
```

```
ccaaatgtcc caccaggtgc aggcagaaaa cgctggaaca gcgtgtacag tttgtcttaa   6480

caaaaagtga gggcgctgag gtcgagcagg gtggtgtgac ttgttatagc ctttagagct   6540

gcgaaagcgc gtatggattt ggctcatcag gccagattga gggtctgtgg acacatgtca   6600

tgttagtgta cttcaatcgc cccctggata tagccccgac aataggccgt ggcctcattt   6660

ttttgccttc cgcacatttc cattgctcga tacccacacc ttgcttctcc tgcacttgcc   6720

aaccttaata ctggtttaca ttgaccaaca tcttacaagc ggggggcttg tctagggtat   6780

atataaacag tggctctccc aatcggttgc cagtctcttt tttcctttct ttccccacag   6840

attcgaaatc taaactacac atcacagaat tccgagccgt gagtatccac gacaagatca   6900

gtgtcgagac gacgcgtttt gtgtaatgac acaatccgaa agtcgctagc aacacacact   6960

ctctacacaa actaacccag ctctggtacc atggaggtcg tgaacgaaat cgtctccatt   7020

ggccaggagg ttcttcccaa ggtcgactat gctcagctct ggtctgatgc ctcgcactgc   7080

gaggtgctgt acctctccat cgccttcgtc atcctgaagt tcacccttgg tcctctcgga   7140

cccaagggtc agtctcgaat gaagtttgtg ttcaccaact acaacctgct catgtccatc   7200

tactcgctgg gctccttcct ctctatggcc tacgccatgt acaccattgg tgtcatgtcc   7260

gacaactgcg agaaggcttt cgacaacaat gtcttccgaa tcaccactca gctgttctac   7320

ctcagcaagt tcctcgagta cattgactcc ttctatctgc ccctcatggg caagcctctg   7380

acctggttgc agttctttca ccatctcgga gctcctatgg acatgtggct gttctacaac   7440

taccgaaacg aagccgtttg gatctttgtg ctgctcaacg gcttcattca ctggatcatg   7500

tacggctact attggacccg actgatcaag ctcaagttcc ctatgcccaa gtccctgatt   7560

acttctatgc agatcattca gttcaacgtt ggcttctaca tcgtctggaa gtaccggaac   7620

attccctgct accgacaaga tggaatgaga atgtttggct ggtttttcaa ctacttctac   7680

gttggtactg tcctgtgtct gttcctcaac ttctacgtgc agacctacat cgtccgaaag   7740

cacaagggag ccaaaaagat tcagtgagc                                   7769
```

```
<210> SEQ ID NO 71
<211> LENGTH: 10206
<212> TYPE: DNA
<213> ORGANISM: Artificial Sequence
<220> FEATURE:
<223> OTHER INFORMATION: plasmid pZUFmE9SP8S

<400> SEQUENCE: 71
```

```
taagtcatac acaagtcagc tttcttcgag cctcatataa gtataagtag ttcaacgtat     60

tagcactgta cccagcatct ccgtatcgag aaacacaaca acatgcccca ttggacagat    120

catgcggata cacaggttgt gcagtatcat acatactcga tcagacaggt cgtctgacca    180

tcatacaagc tgaacaagcg ctccatactt gcacgctctc tatatacaca gttaaattac    240

atatccatag tctaacctct aacagttaat cttctggtaa gcctcccagc cagccttctg    300

gtatcgcttg gcctcctcaa taggatctcg gttctggccg tacagacctc ggccgacaat    360

tatgatatcc gttccggtag acatgacatc ctcaacagtt cggtactgct gtccgagagc    420

gtctcccttg tcgtcaagac ccaccccggg ggtcagaata agccagtcct cagagtcgcc    480

cttaggtcgg ttctgggcaa tgaagccaac cacaaactcg ggtcggatcg ggcaagctc    540

aatggtctgc ttggagtact cgccagtggc cagagagccc ttgcaagaca gctcggccag    600

catgagcaga cctctggcca gcttctcgtt gggagagggg actaggaact ccttgtactg    660

ggagttctcg tagtcagaga cgtcctcctt cttctgttca gagacagttt cctcggcacc    720
```

```
agctcgcagg ccagcaatga ttccggttcc gggtacaccg tgggcgttgg tgatatcgga    780
ccactcggcg attcggtgac accggtactg gtgcttgaca gtgttgccaa tatctgcgaa    840
ctttctgtcc tcgaacagga agaaaccgtg cttaagagca agttccttga gggggagcac    900
agtgccggcg taggtgaagt cgtcaatgat gtcgatatgg gttttgatca tgcacacata    960
aggtccgacc ttatcggcaa gctcaatgag ctccttggtg gtggtaacat ccagagaagc   1020
acacaggttg gttttcttgg ctgccacgag cttgagcact cgagcggcaa aggcggactt   1080
gtggacgtta gctcgagctt cgtaggaggg cattttggtg gtgaagagga gactgaaata   1140
aatttagtct gcagaacttt ttatcggaac cttatctggg gcagtgaagt atatgttatg   1200
gtaatagtta cgagttagtt gaacttatag atagactgga ctatacggct atcggtccaa   1260
attagaaaga acgtcaatgg ctctctgggc gtcgcctttg ccgacaaaaa tgtgatcatg   1320
atgaaagcca gcaatgacgt tgcagctgat attgttgtcg gccaaccgcg ccgaaaacgc   1380
agctgtcaga cccacagcct ccaacgaaga atgtatcgtc aaagtgatcc aagcacactc   1440
atagttggag tcgtactcca aaggcggcaa tgacgagtca gacagatact cgtcgacgtt   1500
taaacagtgt acgcagatct actatagagg aacatttaaa ttgccccgga gaagacggcc   1560
aggccgccta gatgacaaat tcaacaactc acagctgact ttctgccatt gccactaggg   1620
gggggccttt ttatatggcc aagccaagct ctccacgtcg gttgggctgc acccaacaat   1680
aaatgggtag ggttgcacca acaaagggat gggatggggg gtagaagata cgaggataac   1740
ggggctcaat ggcacaaata agaacgaata ctgccattaa gactcgtgat ccagcgactg   1800
acaccattgc atcatctaag ggcctcaaaa ctacctcgga actgctgcgc tgatctggac   1860
accacagagg ttccgagcac tttaggttgc accaaatgtc ccaccaggtg caggcagaaa   1920
acgctggaac agcgtgtaca gtttgtctta acaaaaagtg agggcgctga ggtcgagcag   1980
ggtggtgtga cttgttatag cctttagagc tgcgaaagcg cgtatggatt tggctcatca   2040
ggccagattg agggtctgtg gacacatgtc atgttagtgt acttcaatcg ccccctggat   2100
atagccccga caataggccg tggcctcatt tttttgcctt ccgcacattt ccattgctcg   2160
atacccacac cttgcttctc ctgcacttgc caaccttaat actggtttac attgaccaac   2220
atcttacaag cggggggctt gtctagggta tatataaaca gtggctctcc caatcggttg   2280
ccagtctctt ttttcctttc tttccccaca gattcgaaat ctaaactaca catcacagaa   2340
ttccgagccg tgagtatcca cgacaagatc agtgtcgaga cgacgcgttt tgtgtaatga   2400
cacaatccga aagtcgctag caacacacac tctctacaca aactaaccca gctctggtac   2460
catggaggtc gtgaacgaaa tcgtctccat tggccaggag gttcttccca aggtcgacta   2520
tgctcagctc tggtctgatg cctcgcactg cgaggtgctg tacctctcca tcgccttcgt   2580
catcctgaag ttcacccttg gtcctctcgg acccaagggt cagtctcgaa tgaagtttgt   2640
gttcaccaac tacaacctgc tcatgtccat ctactcgctg ggctccttcc tctctatggc   2700
ctacgccatg tacaccattg gtgtcatgtc cgacaactgc gagaaggctt tcgacaacaa   2760
tgtcttccga atcaccactc agctgttcta cctcagcaag ttcctcgagt acattgactc   2820
cttctatctg cccctcatgg gcaagcctct gacctggttg cagttctttc accatctcgg   2880
agctcctatg gacatgtggc tgttctacaa ctaccgaaac gaagccgttt ggatctttgt   2940
gctgctcaac ggcttcattc actggatcat gtacggctac tattggaccc gactgatcaa   3000
gctcaagttc cctatgccca agtccctgat tacttctatg cagatcattc agttcaacgt   3060
tggcttctac atcgtctgga agtaccggaa cattccctgc taccgacaag atggaatgag   3120
```

```
aatgtttggc tggtttttca actacttcta cgttggtact gtcctgtgtc tgttcctcaa   3180
cttctacgtg cagacctaca tcgtccgaaa gcacaaggga gccaaaaaga ttcagtgagc   3240
ggccgcaagt gtggatgggg aagtgagtgc ccggttctgt gtgcacaatt ggcaatccaa   3300
gatggatgga ttcaacacag ggatatagcg agctacgtgg tggtgcgagg atatagcaac   3360
ggatatttat gtttgacact tgagaatgta cgatacaagc actgtccaag tacaatacta   3420
aacatactgt acatactcat actcgtaccc gggcaacggt ttcacttgag tgcagtggct   3480
agtgctctta ctcgtacagt gtgcaatact gcgtatcata gtctttgatg tatatcgtat   3540
tcattcatgt tagttgcgta cgagccggaa gcataaagtg taaagcctgg ggtgcctaat   3600
gagtgagcta actcacatta attgcgttgc gctcactgcc cgctttccag tcgggaaacc   3660
tgtcgtgcca gctgcattaa tgaatcggcc aacgcgcggg gagaggcggt ttgcgtattg   3720
ggcgctcttc cgcttcctcg ctcactgact cgctgcgctc ggtcgttcgg ctgcggcgag   3780
cggtatcagc tcactcaaag gcggtaatac ggttatccac agaatcaggg gataacgcag   3840
gaaagaacat gtgagcaaaa ggccagcaaa aggccaggaa ccgtaaaaag gccgcgttgc   3900
tggcgttttt ccataggctc cgcccccctg acgagcatca caaaaatcga cgctcaagtc   3960
agaggtggcg aaacccgaca ggactataaa gataccaggc gtttccccct ggaagctccc   4020
tcgtgcgctc tcctgttccg accctgccgc ttaccggata cctgtccgcc tttctccctt   4080
cgggaagcgt ggcgctttct catagctcac gctgtaggta tctcagttcg gtgtaggtcg   4140
ttcgctccaa gctgggctgt gtgcacgaac cccccgttca gcccgaccgc tgcgccttat   4200
ccggtaacta tcgtcttgag tccaacccgg taagacacga cttatcgcca ctggcagcag   4260
ccactggtaa caggattagc agagcgaggt atgtaggcgg tgctacagag ttcttgaagt   4320
ggtggcctaa ctacggctac actagaagga cagtatttgg tatctgcgct ctgctgaagc   4380
cagttacctt cggaaaaaga gttggtagct cttgatccgg caaacaaacc accgctggta   4440
gcggtggttt ttttgtttgc aagcagcaga ttacgcgcag aaaaaaagga tctcaagaag   4500
atcctttgat cttttctacg gggtctgacg ctcagtggaa cgaaaactca cgttaaggga   4560
ttttggtcat gagattatca aaaaggatct tcacctagat ccttttaaat taaaaatgaa   4620
gttttaaatc aatctaaagt atatatgagt aaacttggtc tgacagttac caatgcttaa   4680
tcagtgaggc acctatctca gcgatctgtc tatttcgttc atccatagtt gcctgactcc   4740
ccgtcgtgta gataactacg atacgggagg gcttaccatc tggccccagt gctgcaatga   4800
taccgcgaga cccacgctca ccggctccag atttatcagc aataaaccag ccagccggaa   4860
gggccgagcg cagaagtggt cctgcaactt tatccgcctc catccagtct attaattgtt   4920
gccgggaagc tagagtaagt agttcgccag ttaatagttt gcgcaacgtt gttgccattg   4980
ctacaggcat cgtggtgtca cgctcgtcgt ttggtatggc ttcattcagc tccggttccc   5040
aacgatcaag gcgagttaca tgatccccca tgttgtgcaa aaaagcggtt agctccttcg   5100
gtcctccgat cgttgtcaga agtaagttgg ccgcagtgtt atcactcatg gttatggcag   5160
cactgcataa ttctcttact gtcatgccat ccgtaagatg cttttctgtg actggtgagt   5220
actcaaccaa gtcattctga gaatagtgta tgcggcgacc gagttgctct tgcccggcgt   5280
caatacggga taataccgcg ccacatagca gaactttaaa agtgctcatc attggaaaac   5340
gttcttcggg gcgaaaactc tcaaggatct taccgctgtt gagatccagt tcgatgtaac   5400
ccactcgtgc acccaactga tcttcagcat cttttacttt caccagcgtt tctgggtgag   5460
caaaaacagg aaggcaaaat gccgcaaaaa agggaataag ggcgacacgg aaatgttgaa   5520
```

```
tactcatact cttccttttt caatattatt gaagcattta tcagggttat tgtctcatga   5580
gcggatacat atttgaatgt atttagaaaa ataaacaaat aggggttccg cgcacatttc   5640
cccgaaaagt gccacctgac gcgccctgta gcggcgcatt aagcgcggcg ggtgtggtgg   5700
ttacgcgcag cgtgaccgct acacttgcca gcgccctagc gcccgctcct ttcgctttct   5760
tcccttcctt tctcgccacg ttcgccggct ttccccgtca agctctaaat cgggggctcc   5820
ctttagggtt ccgatttagt gctttacggc acctcgaccc caaaaaactt gattagggtg   5880
atggttcacg tagtgggcca tcgccctgat agacggtttt tcgccctttg acgttggagt   5940
ccacgttctt taatagtgga ctcttgttcc aaactggaac aacactcaac cctatctcgg   6000
tctattcttt tgatttataa gggattttgc cgatttcggc ctattggtta aaaaatgagc   6060
tgatttaaca aaaatttaac gcgaatttta acaaaatatt aacgcttaca atttccattc   6120
gccattcagg ctgcgcaact gttgggaagg gcgatcggtg cgggcctctt cgctattacg   6180
ccagctggcg aaagggggat gtgctgcaag gcgattaagt tgggtaacgc cagggttttc   6240
ccagtcacga cgttgtaaaa cgacggccag tgaattgtaa tacgactcac tatagggcga   6300
attgggtacc gggccccccc tcgaggtcga tggtgtcgat aagcttgata tcgaattcat   6360
gtcacacaaa ccgatcttcg cctcaaggaa acctaattct acatccgaga gactgccgag   6420
atccagtcta cactgattaa ttttcgggcc aataatttaa aaaaatcgtg ttatataata   6480
ttatatgtat tatatatata catcatgatg atactgacag tcatgtccca ttgctaaata   6540
gacagactcc atctgccgcc tccaactgat gttctcaata tttaaggggt catctcgcat   6600
tgtttaataa taaacagact ccatctaccg cctccaaatg atgttctcaa aatatattgt   6660
atgaacttat ttttattact tagtattatt agacaactta cttgctttat gaaaaacact   6720
tcctatttag gaaacaattt ataatggcag ttcgttcatt taacaattta tgtagaataa   6780
atgttataaa tgcgtatggg aaatcttaaa tatggatagc ataaatgata tctgcattgc   6840
ctaattcgaa atcaacagca acgaaaaaaa tcccttgtac aacataaata gtcatcgaga   6900
aatatcaact atcaaagaac agctattcac acgttactat tgagattatt attggacgag   6960
aatcacacac tcaactgtct ttctctcttc tagaaataca ggtacaagta tgtactattc   7020
tcattgttca tacttctagt catttcatcc cacatattcc ttggatttct ctccaatgaa   7080
tgacattcta tcttgcaaat tcaacaatta taataagata taccaaagta gcggtatagt   7140
ggcaatcaaa aagcttctct ggtgtgcttc tcgtatttat ttttattcta atgatccatt   7200
aaaggtatat atttatttct tgttatataa tccttttgtt tattacatgg gctggataca   7260
taaaggtatt ttgatttaat tttttgctta aattcaatcc cccctcgttc agtgtcaact   7320
gtaatggtag gaaattacca tacttttgaa gaagcaaaaa aaatgaaaga aaaaaaaaat   7380
cgtatttcca ggttagacgt tccgcagaat ctagaatgcg gtatgcggta cattgttctt   7440
cgaacgtaaa agttgcgctc cctgagatat tgtacatttt tgcttttaca agtacaagta   7500
catcgtacaa ctatgtacta ctgttgatgc atccacaaca gtttgttttg tttttttttg   7560
tttttttttt ttctaatgat tcattaccgc tatgtatacc tacttgtact tgtagtaagc   7620
cgggttattg gcgttcaatt aatcatagac ttatgaatct gcacggtgtg cgctgcgagt   7680
tacttttagc ttatgcatgc tacttgggtg taatattggg atctgttcgg aaatcaacgg   7740
atgctcaatc gatggttaat gctgctgtgt gctgtgtgtg tgtgttgttt ggcgctcatt   7800
gttgcgttat gcagcgtaca ccacaatatt ggaagcttat tagcctttct atttttttcgt   7860
ttgcaaggct taacaacatt gctgtggaga gggatgggga tatggaggcc gctggaggga   7920
```

```
gtcggagagg cgttttggag cggcttggcc tggcgcccag ctcgcgaaac gcacctagga   7980
ccctttggca cgccgaaatg tgccactttt cagtctagta acgccttacc tacgtcattc   8040
catgcgtgca tgtttgcgcc ttttttccct tgcccttgat cgccacacag tacagtgcac   8100
tgtacagtgg aggttttggg ggggtcttag atgggagcta aaagcggcct agcggtacac   8160
tagtgggatt gtatggagtg gcatggagcc taggtggagc ctgacaggac gcacgaccgg   8220
ctagcccgtg acagacgatg ggtggctcct gttgtccacc gcgtacaaat gtttgggcca   8280
aagtcttgtc agccttgctt gcgaacctaa ttcccaattt tgtcacttcg cacccccatt   8340
gatcgagccc taacccctgc ccatcaggca atccaattaa gctcgcattg tctgccttgt   8400
ttagtttggc tcctgcccgt ttcggcgtcc acttgcacaa acacaaacaa gcattatata   8460
taaggctcgt ctctccctcc caaccacact cactttttttg cccgtcttcc cttgctaaca   8520
caaaagtcaa gaacacaaac aaccacccca accccctttac acacaagaca tatctacagc   8580
aatggccatg ggcaagggtg gagacggtgg agcacaggct gtgtctggca ccgatgcctc   8640
cctcgctgag gtctcctctg tggacagcaa gtccgtccac gtggttctgt acggcaagcg   8700
agtggatgtc accaagttcc agaaggctca ccctggaggt tcgaaggtgt tccgaatctt   8760
tcaggagcga gacgccacag aacagttcga gtcctaccac tctcccaagg ccatcaagat   8820
gatggaaggt atgctcaaaa agtcggagga tgctcccgct tccgtgcctc ttccctctcg   8880
atccactatg ggcaccgagt tcaaggagat gatcgaacga cacaagagag ccggtctcta   8940
cgacccttgt cccttggacg agctgttcaa gctcaccatt gtccttgctc ctatctttgt   9000
gggagcctat ctcgttcgat ccggtgtctc tcctcttgct ggagccctgt cgatgggctt   9060
cggattctac ctcgacggct ggcttgctca cgactacctg catcacgcag tgttcaaggg   9120
ctccgtcaac acactcgtca aggccaacaa cgctatggga tacgccttgg gcttcctcca   9180
gggttacgac gttgcttggt ggcgagccag acacaacact catcacgtgt gcaccaacga   9240
ggacggctcc gatcccgaca tcaagacggc tcctctgctc atttacgtgc gagagaatcc   9300
ctccattgcc aagcggctca acttctttca gcgatggcaa cagtactact atgttcctac   9360
tatggccatt ctggatctct actggcgact ggagtctatc gcatacgtcg ctgtgcgact   9420
gcccaagatg tggatgcagg ctgccgctct tgccgctcac tacgcactcc tgtgttgggt   9480
cttcgctgcc catctcaacc tgattcctct catgatggtt gcacgaggtt tcgcgaccgg   9540
aatcgtggtc tttgccaccc actatggcga ggacattctc gaccgagagc acgtcgaagg   9600
catgactctg gtcgagcaga ccgccaagac ctcccgaaac atcactggtg gatggcttgt   9660
caacgtgctc accggcttca tttctctgca gaccgagcat catctgtttc ccatgatgcc   9720
tactggaaac ctcatgacca ttcaacccga ggttcgagac tttttcaaaa agcacggtct   9780
cgagtaccga gaaggaaacc tgtttcagtg cgtgcatcag aacatcaagg ctctcgcctt   9840
cgagcacctg cttcactaag cggccgcatt gatgattgga aacacacaca tgggttatat   9900
ctaggtgaga gttagttgga cagttatata ttaaatcagc tatgccaacg gtaacttcat   9960
tcatgtcaac gaggaaccag tgactgcaag taatatagaa tttgaccacc ttgccattct  10020
cttgcactcc tttactatat ctcatttatt tcttatatac aaatcacttc ttcttcccag  10080
catcgagctc ggaaacctca tgagcaataa catcgtggat ctcgtcaata gagggctttt  10140
tggactcctt gctgttggcc accttgtcct tgctgtctgg ctcattctgt ttcaacgcct  10200
tttaat                                                              10206
```

<210> SEQ ID NO 72
<211> LENGTH: 6871
<212> TYPE: DNA
<213> ORGANISM: Artificial Sequence
<220> FEATURE:
<223> OTHER INFORMATION: plasmid pEXPGUS1-C

<400> SEQUENCE: 72

```
aattcgtcct tgaggactcg agtgacagtc tttcgccaaa gtcgagagga ggccagcacg      60

ttggccttgt caagagacca cacgggaaga ggggggttgt gctgaagggc caggaaggcg     120

gccattcggg caattcgctc aacctcagga acggagtagg tctcggtgtc ggaagcgacg     180

ccagatccgt catcctcctt tcgctctcca aagtagatac ctccgacgag ctctcggaca     240

atgatgaagt cggtgccctc aacgtttcgg atgggggaga gatcggcgag cttgggcgac     300

agcagctggc agggtcgcag gttggcgtac aggttcaggt cctttcgcag cttgaggaga     360

ccctgctcgg gtcgcacgtc ggttcgtccg tcgggagtgg tccatacggt gttggcagcg     420

cctccgacag caccgagcat aatagagtca gcctttcggc agatgtcgag agtagcgtcg     480

gtgatgggct cgccctcctt ctcaatggca gctcctccaa tgagtcggtc ctcaaacaca     540

aactcggtgc cggaggcctc agcaacagac ttgagcacct tgacggcctc ggcaatcacc     600

tcggggccac agaagtcgcc gccgagaaga acaatcttct tggagtcagt cttggtcttc     660

ttagtttcgg gttccattgt ggatgtgtgt ggttgtatgt gtgatgtggt gtgtggagtg     720

aaaatctgtg gctggcaaac gctcttgtat atatacgcac ttttgcccgt gctatgtgga     780

agactaaacc tccgaagatt gtgactcagg tagtgcggta tcggctaggg acccaaacct     840

tgtcgatgcc gatagcgcta tcgaacgtac cccagccggc cgggagtatg tcggagggga     900

catacgagat cgtcaagggt ttgtggccaa ctggtaaata aatgatgtcg agggagtttg     960

gcgcccgttt tttcgagccc cacacgtttc ggtgagtatg agcggcggca gattcgagcg    1020

tttccggttt ccgcggctgg acgagagccc atgatggggg ctcccaccac cagcaatcag    1080

ggccctgatt acacacccac ctgtaatgtc atgctgttca tcgatggtta atgctgctgt    1140

gtgctgtgtg tgtgtgttgt ttggcgctca ttgttgcgtt atgcagcgta caccacaata    1200

ttggaagctt attagccttt ctatttttc gtttgcaagg cttaacaaca ttgctgtgga    1260

gagggatggg gatatggagg ccgctggagg gagtcggaga ggcgttttgg agcggcttgg    1320

cctggcgccc agctcgcgaa acgcacctag gaccctttgg cacgccgaaa tgtgccactt    1380

ttcagtctag taacgcctta cctacgtcat tccatgcgtg catgtttgcg cctttttcc    1440

cttgcccttg atcgccacac agtacagtgc actgtacagt ggaggttttg ggggggtctt    1500

agatgggagc taaaagcggc ctagcggtac actagtggga ttgtatggag tggcatggag    1560

cctaggtgga gcctgacagg acgcacgacc ggctagcccg tgacagacga tgggtggctc    1620

ctgttgtcca ccgcgtacaa atgtttgggc caaagtcttg tcagccttgc ttgcgaacct    1680

aattcccaat tttgtcactt cgcacccccca ttgatcgagc cctaacccct gcccatcagg    1740

caatccaatt aagctcgcat tgtctgcctt gtttagtttg gctcctgccc gtttcggcgt    1800

ccacttgcac aaacacaaac aagcattata tataaggctc gtctctccct cccaaccaca    1860

ctcacttttt tgcccgtctt cccttgctaa cacaaaagtc aagaacacaa acaaccaccc    1920

caaccccctt acacacaaga catatctaca gcaatggcca tggtacgtcc tgtagaaacc    1980

ccaacccgtg aaatcaaaaa actcgacggc ctgtgggcat tcagtctgga tcgcgaaaac    2040

tgtggaattg atcagcgttg gtgggaaagc gcgttacaag aaagccgggc aattgctgtg    2100

ccaggcagtt ttaacgatca gttcgccgat gcagatattc gtaattatgc gggcaacgtc    2160
```

```
tggtatcagc gcgaagtctt tataccgaaa ggttgggcag gccagcgtat cgtgctgcgt   2220
ttcgatgcgg tcactcatta cggcaaagtg tgggtcaata atcaggaagt gatggagcat   2280
cagggcggct atacgccatt tgaagccgat gtcacgccgt atgttattgc cgggaaaagt   2340
gtacgtatca ccgtttgtgt gaacaacgaa ctgaactggc agactatccc gccgggaatg   2400
gtgattaccg acgaaaacgg caagaaaaag cagtcttact tccatgattt ctttaactat   2460
gccgggatcc atcgcagcgt aatgctctac accacgccga acacctgggt ggacgatatc   2520
accgtggtga cgcatgtcgc gcaagactgt aaccacgcgt ctgttgactg gcaggtggtg   2580
gccaatggtg atgtcagcgt tgaactgcgt gatgcggatc aacaggtggt tgcaactgga   2640
caaggcacta gcgggacttt gcaagtggtg aatccgcacc tctggcaacc gggtgaaggt   2700
tatctctatg aactgtgcgt cacagccaaa agccagacag agtgtgatat ctacccgctt   2760
cgcgtcggca tccggtcagt ggcagtgaag ggcgaacagt tcctgattaa ccacaaaccg   2820
ttctacttta ctggctttgg tcgtcatgaa gatgcggact tacgtggcaa aggattcgat   2880
aacgtgctga tggtgcacga ccacgcatta atggactgga ttggggccaa ctcctaccgt   2940
acctcgcatt acccttacgc tgaagagatg ctcgactggg cagatgaaca tggcatcgtg   3000
gtgattgatg aaactgctgc tgtcggcttt aacctctctt taggcattgg tttcgaagcg   3060
ggcaacaagc cgaaagaact gtacagcgaa gaggcagtca acggggaaac tcagcaagcg   3120
cacttacagg cgattaaaga gctgatagcg cgtgacaaaa accacccaag cgtggtgatg   3180
tggagtattg ccaacgaacc ggatacccgt ccgcaagtgc acgggaatat ttcgccactg   3240
gcggaagcaa cgcgtaaact cgacccgacg cgtccgatca cctgcgtcaa tgtaatgttc   3300
tgcgacgctc acaccgatac catcagcgat ctctttgatg tgctgtgcct gaaccgttat   3360
tacggatggt atgtccaaag cggcgatttg gaaacggcag agaaggtact ggaaaaagaa   3420
cttctggcct ggcaggagaa actgcatcag ccgattatca tcaccgaata cggcgtggat   3480
acgttagccg ggctgcactc aatgtacacc gacatgtgga gtgaagagta tcagtgtgca   3540
tggctggata tgtatcaccg cgtctttgat cgcgtcagcg ccgtcgtcgg tgaacaggta   3600
tggaatttcg ccgattttgc gacctcgcaa ggcatattgc gcgttggcgg taacaagaaa   3660
gggatcttca ctcgcgaccg caaaccgaag tcggcggctt ttctgctgca aaaacgctgg   3720
actggcatga acttcggtga aaaaccgcag cagggaggca aacaatgatt aattaactag   3780
agcggccgcc accgcggccc gagattccgg cctcttcggc cgccaagcga cccgggtgga   3840
cgtctagagg tacctagcaa ttaacagata gtttgccggt gataattctc ttaacctccc   3900
acactccttt gacataacga tttatgtaac gaaactgaaa tttgaccaga tattgtgtcc   3960
gcggtggagc tccagctttt gttcccttta gtgagggtta atttcgagct tggcgtaatc   4020
atggtcatag ctgtttcctg tgtgaaattg ttatccgctc acaattccac acaacatacg   4080
agccggaagc ataaagtgta aagcctgggg tgcctaatga gtgagctaac tcacattaat   4140
tgcgttgcgc tcactgcccg ctttccagtc gggaaacctg tcgtgccagc tgcattaatg   4200
aatcggccaa cgcgcgggga gaggcggttt gcgtattggg cgctcttccg cttcctcgct   4260
cactgactcg ctgcgctcgg tcgttcggct gcggcgagcg gtatcagctc actcaaaggc   4320
ggtaatacgg ttatccacag aatcagggga taacgcagga aagaacatgt gagcaaaagg   4380
ccagcaaaag gccaggaacc gtaaaaaggc cgcgttgctg gcgtttttcc ataggctccg   4440
cccccctgac gagcatcaca aaaatcgacg ctcaagtcag aggtggcgaa acccgacagg   4500
actataaaga taccaggcgt ttccccctgg aagctccctc gtgcgctctc ctgttccgac   4560
```

```
cctgccgctt accggatacc tgtccgcctt tctcccttcg ggaagcgtgg cgctttctca   4620
tagctcacgc tgtaggtatc tcagttcggt gtaggtcgtt cgctccaagc tgggctgtgt   4680
gcacgaaccc cccgttcagc ccgaccgctg cgccttatcc ggtaactatc gtcttgagtc   4740
caacccggta agacacgact tatcgccact ggcagcagcc actggtaaca ggattagcag   4800
agcgaggtat gtaggcggtg ctacagagtt cttgaagtgg tggcctaact acggctacac   4860
tagaaggaca gtatttggta tctgcgctct gctgaagcca gttaccttcg gaaaaagagt   4920
tggtagctct tgatccggca aacaaaccac cgctggtagc ggtggttttt ttgtttgcaa   4980
gcagcagatt acgcgcagaa aaaaaggatc tcaagaagat cctttgatct tttctacggg   5040
gtctgacgct cagtggaacg aaaactcacg ttaagggatt ttggtcatga gattatcaaa   5100
aaggatcttc acctagatcc ttttaaatta aaaatgaagt tttaaatcaa tctaaagtat   5160
atatgagtaa acttggtctg acagttacca atgcttaatc agtgaggcac ctatctcagc   5220
gatctgtcta tttcgttcat ccatagttgc ctgactcccc gtcgtgtaga taactacgat   5280
acgggagggc ttaccatctg gccccagtgc tgcaatgata ccgcgagacc cacgctcacc   5340
ggctccagat ttatcagcaa taaaccagcc agccggaagg gccgagcgca gaagtggtcc   5400
tgcaacttta tccgcctcca tccagtctat taattgttgc cgggaagcta gagtaagtag   5460
ttcgccagtt aatagtttgc gcaacgttgt tgccattgct acaggcatcg tggtgtcacg   5520
ctcgtcgttt ggtatggctt cattcagctc cggttcccaa cgatcaaggc gagttacatg   5580
atcccccatg ttgtgcaaaa aagcggttag ctccttcggt cctccgatcg ttgtcagaag   5640
taagttggcc gcagtgttat cactcatggt tatggcagca ctgcataatt ctcttactgt   5700
catgccatcc gtaagatgct tttctgtgac tggtgagtac tcaaccaagt cattctgaga   5760
atagtgtatg cggcgaccga gttgctcttg cccggcgtca atacgggata ataccgcgcc   5820
acatagcaga actttaaaag tgctcatcat tggaaaacgt tcttcggggc gaaaactctc   5880
aaggatctta ccgctgttga gatccagttc gatgtaaccc actcgtgcac ccaactgatc   5940
ttcagcatct tttactttca ccagcgtttc tgggtgagca aaaacaggaa ggcaaaatgc   6000
cgcaaaaaag ggaataaggg cgacacggaa atgttgaata ctcatactct tcctttttca   6060
atattattga agcatttatc agggttattg tctcatgagc ggatacatat ttgaatgtat   6120
ttagaaaaat aaacaaatag gggttccgcg cacatttccc cgaaaagtgc cacctgacgc   6180
gccctgtagc ggcgcattaa gcgcggcggg tgtggtggtt acgcgcagcg tgaccgctac   6240
acttgccagc gccctagcgc ccgctccttt cgctttcttc ccttcctttc tcgccacgtt   6300
cgccggcttt ccccgtcaag ctctaaatcg ggggctccct ttagggttcc gatttagtgc   6360
tttacggcac ctcgacccca aaaaacttga ttagggtgat ggttcacgta gtgggccatc   6420
gccctgatag acggtttttc gccctttgac gttggagtcc acgttcttta atagtggact   6480
cttgttccaa actggaacaa cactcaaccc tatctcggtc tattcttttg atttataagg   6540
gattttgccg atttcggcct attggttaaa aaatgagctg atttaacaaa aatttaacgc   6600
gaattttaac aaaatattaa cgcttacaat ttccattcgc cattcaggct gcgcaactgt   6660
tgggaagggc gatcggtgcg ggcctcttcg ctattacgcc agctggcgaa agggggatgt   6720
gctgcaaggc gattaagttg ggtaacgcca gggttttccc agtcacgacg ttgtaaaacg   6780
acggccagtg aattgtaata cgactcacta tagggcgaat tgggtaccgg gccccccctc   6840
gaggtcgatg gtgtcgataa gcttgatatc g                                   6871
```

<210> SEQ ID NO 73
<211> LENGTH: 5460
<212> TYPE: DNA
<213> ORGANISM: Artificial Sequence
<220> FEATURE:
<223> OTHER INFORMATION: plasmid pZGD5T-CP

<400> SEQUENCE: 73

```
ggccgcattg atgattggaa acacacacat gggttatatc taggtgagag ttagttggac     60
agttatatat taaatcagct atgccaacgg taacttcatt catgtcaacg aggaaccagt    120
gactgcaagt aatatagaat ttgaccacct tgccattctc ttgcactcct ttactatatc    180
tcatttattt cttatataca aatcacttct tcttcccagc atcgagctcg gaaacctcat    240
gagcaataac atcgtggatc tcgtcaatag agggcttttt ggactccttg ctgttggcca    300
ccttgtcctt gctgtctggc tcattctgtt tcaacgcctt ttaattaatc gagcttggcg    360
taatcatggt catagctgtt tcctgtgtga aattgttatc cgctcacaat tccacacaac    420
atacgagccg gaagcataaa gtgtaaagcc tggggtgcct aatgagtgag ctaactcaca    480
ttaattgcgt tgcgctcact gcccgctttc cagtcgggaa acctgtcgtg ccagctgcat    540
taatgaatcg gccaacgcgc ggggagaggc ggtttgcgta ttgggcgctc ttccgcttcc    600
tcgctcactg actcgctgcg ctcggtcgtt cggctgcggc gagcggtatc agctcactca    660
aaggcggtaa tacggttatc cacagaatca ggggataacg caggaaagaa catgtgagca    720
aaaggccagc aaaaggccag gaaccgtaaa aaggccgcgt tgctggcgtt tttccatagg    780
ctccgccccc ctgacgagca tcacaaaaat cgacgctcaa gtcagaggtg gcgaaacccg    840
acaggactat aaagatacca ggcgtttccc cctggaagct ccctcgtgcg ctctcctgtt    900
ccgaccctgc cgcttaccgg atacctgtcc gcctttctcc cttcgggaag cgtggcgctt    960
tctcatagct cacgctgtag gtatctcagt tcggtgtagg tcgttcgctc caagctgggc   1020
tgtgtgcacg aaccccccgt tcagcccgac cgctgcgcct tatccggtaa ctatcgtctt   1080
gagtccaacc cggtaagaca cgacttatcg ccactggcag cagccactgg taacaggatt   1140
agcagagcga ggtatgtagg cggtgctaca gagttcttga agtggtggcc taactacggc   1200
tacactagaa ggacagtatt tggtatctgc gctctgctga agccagttac cttcggaaaa   1260
agagttggta gctcttgatc cggcaaacaa accaccgctg gtagcggtgg tttttttgtt   1320
tgcaagcagc agattacgcg cagaaaaaaa ggatctcaag aagatccttt gatcttttct   1380
acggggtctg acgctcagtg gaacgaaaac tcacgttaag ggattttggt catgagatta   1440
tcaaaaagga tcttcaccta gatcctttta aattaaaaat gaagttttaa atcaatctaa   1500
agtatatatg agtaaacttg gtctgacagt taccaatgct taatcagtga ggcacctatc   1560
tcagcgatct gtctatttcg ttcatccata gttgcctgac tccccgtcgt gtagataact   1620
acgatacggg agggcttacc atctggcccc agtgctgcaa tgataccgcg agacccacgc   1680
tcaccggctc cagatttatc agcaataaac cagccagccg gaagggccga gcgcagaagt   1740
ggtcctgcaa ctttatccgc ctccatccag tctattaatt gttgccggga agctagagta   1800
agtagttcgc cagttaatag tttgcgcaac gttgttgcca ttgctacagg catcgtggtg   1860
tcacgctcgt cgtttggtat ggcttcattc agctccggtt cccaacgatc aaggcgagtt   1920
acatgatccc ccatgttgtg caaaaaagcg gttagctcct tcggtcctcc gatcgttgtc   1980
agaagtaagt tggccgcagt gttatcactc atggttatgg cagcactgca taattctctt   2040
actgtcatgc catccgtaag atgcttttct gtgactggtg agtactcaac caagtcattc   2100
tgagaatagt gtatgcggcg accgagttgc tcttgcccgg cgtcaatacg ggataatacc   2160
```

```
gcgccacata gcagaacttt aaaagtgctc atcattggaa aacgttcttc ggggcgaaaa   2220

ctctcaagga tcttaccgct gttgagatcc agttcgatgt aacccactcg tgcacccaac   2280

tgatcttcag catcttttac tttcaccagc gtttctgggt gagcaaaaac aggaaggcaa   2340

aatgccgcaa aaaagggaat aagggcgaca cggaaatgtt gaatactcat actcttcctt   2400

tttcaatatt attgaagcat ttatcagggt tattgtctca tgagcggata catatttgaa   2460

tgtatttaga aaaataaaca aataggggtt ccgcgcacat ttccccgaaa agtgccacct   2520

gacgcgccct gtagcggcgc attaagcgcg gcgggtgtgg tggttacgcg cagcgtgacc   2580

gctacacttg ccagcgccct agcgcccgct cctttcgctt tcttcccttc ctttctcgcc   2640

acgttcgccg gctttccccg tcaagctcta aatcgggggc tccctttagg gttccgattt   2700

agtgctttac ggcacctcga ccccaaaaaa cttgattagg gtgatggttc acgtagtggg   2760

ccatcgccct gatagacggt ttttcgccct ttgacgttgg agtccacgtt ctttaatagt   2820

ggactcttgt tccaaactgg aacaacactc aaccctatct cggtctattc ttttgattta   2880

taagggattt tgccgatttc ggcctattgg ttaaaaaatg agctgattta acaaaaattt   2940

aacgcgaatt ttaacaaaat attaacgctt acaatttcca ttcgccattc aggctgcgca   3000

actgttggga agggcgatcg gtgcgggcct cttcgctatt acgccagctg gcgaaagggg   3060

gatgtgctgc aaggcgatta agttgggtaa cgccagggtt ttcccagtca cgacgttgta   3120

aaacgacggc cagtgaattg taatacgact cactataggg cgaattgggt accgggcccc   3180

ccctcgaggt cgacggtatc gatggaagcc ggtagaaccg ggctgcttgt gcttggagat   3240

ggaagccggt agaaccgggc tgcttggggg gatttggggc cgctgggctc caaagagggg   3300

taggcatttc gttggggtta cgtaattgcg gcatttgggt cctgcgcgca tgtcccattg   3360

gtcagaatta gtccggatag gagacttatc agccaatcac agcgccggat ccacctgtag   3420

gttgggttgg gtgggagcac ccctccacag agtagagtca aacagcagca gcaacatgat   3480

agttgggggt gtgcgtgtta aaggaaaaaa aagaagcttg ggttatattc ccgctctatt   3540

tagaggttgc gggatagacg ccgacggagg gcaatggcgc tatggaacct tgcggatatc   3600

catacgccgc ggcggactgc gtccgaacca gctccagcag cgtttttttcc gggccattga   3660

gccgactgcg accccgccaa cgtgtcttgg cccacgcact catgtcatgt tggtgttggg   3720

aggccacttt ttaagtagca caaggcacct agctcgcagc aaggtgtccg aaccaaagaa   3780

gcggctgcag tggtgcaaac ggggcggaaa cggcgggaaa aagccacggg ggcacgaatt   3840

gaggcacgcc ctcgaatttg agacgagtca cggccccatt cgcccgcgca atggctcgcc   3900

aacgcccggt cttttgcacc acatcaggtt accccaagcc aaacctttgt gttaaaaagc   3960

ttaacatatt ataccgaacg taggtttggg cgggcttgct ccgtctgtcc aaggcaacat   4020

ttatataagg gtctgcatcg ccggctcaat tgaatctttt ttcttcttct cttctctata   4080

ttcattcttg aattaaacac acatcaacca tgggaacgga ccaaggaaaa accttcacct   4140

gggaagagct ggcggcccat aacaccaagg acgacctact cttggccatc cgcggcaggg   4200

tgtacgatgt cacaaagttc ttgagccgcc atcctggtgg agtggacact ctcctgctcg   4260

gagctggccg agatgttact ccggtctttg agatgtatca cgcgtttggg gctgcagatg   4320

ccattatgaa gaagtactat gtcggtacac tggtctcgaa tgagctgccc atcttcccgg   4380

agccaacggt gttccacaaa accatcaaga cgagagtcga gggctacttt acggatcgga   4440

acattgatcc caagaataga ccagagatct ggggacgata cgctcttatc tttggatcct   4500

tgatcgcttc ctactacgcg cagctctttg tgcctttcgt tgtcgaacgc acatggcttc   4560
```

```
aggtggtgtt tgcaatcatc atgggatttg cgtgcgcaca agtcggactc aaccctcttc   4620

atgatgcgtc tcacttttca gtgacccaca accccactgt ctggaagatt ctgggagcca   4680

cgcacgactt tttcaacgga gcatcgtacc tggtgtggat gtaccaacat atgctcggcc   4740

atcaccccta caccaacatt gctggagcag atcccgacgt gtcgacgtct gagcccgatg   4800

ttcgtcgtat caagcccaac caaaagtggt ttgtcaacca catcaaccag cacatgtttg   4860

ttcctttcct gtacggactg ctggcgttca aggtgcgcat tcaggacatc aacattttgt   4920

actttgtcaa gaccaatgac gctattcgtg tcaatcccat ctcgacatgg cacactgtga   4980

tgttctgggg cggcaaggct ttctttgtct ggtatcgcct gattgttccc ctgcagtatc   5040

tgcccctggg caaggtgctg ctcttgttca cggtcgcgga catggtgtcg tcttactggc   5100

tggcgctgac cttccaggcg aaccacgttg ttgaggaagt tcagtggccg ttgcctgacg   5160

agaacgggat catccaaaag gactgggcag ctatgcaggt cgagactacg caggattacg   5220

cacacgattc gcacctctgg accagcatca ctggcagctt gaactaccag gctgtgcacc   5280

atctgttccc caacgtgtcg cagcaccatt atcccgatat tctggccatc atcaagaaca   5340

cctgcagcga gtacaaggtt ccataccttg tcaaggatac gttttggcaa gcatttgctt   5400

cacatttgga gcacttgcgt gttcttggac tccgtcccaa ggaagagtag gcagctaagc   5460
```

<210> SEQ ID NO 74
<211> LENGTH: 8630
<212> TYPE: DNA
<213> ORGANISM: Artificial Sequence
<220> FEATURE:
<223> OTHER INFORMATION: plasmid pYZDE2-S

<400> SEQUENCE: 74

```
ggtggagctc cagcttttgt tccctttagt gagggttaat ttcgagcttg gcgtaatcat     60

ggtcatagct gtttcctgtg tgaaattgtt atccgctcac aattccacac aacgtacgag    120

ccggaagcat aaagtgtaaa gcctggggtg cctaatgagt gagctaactc acattaattg    180

cgttgcgctc actgcccgct ttccagtcgg gaaacctgtc gtgccagctg cattaatgaa    240

tcggccaacg cgcggggaga ggcggtttgc gtattgggcg ctcttccgct tcctcgctca    300

ctgactcgct gcgctcggtc gttcggctgc ggcgagcggt atcagctcac tcaaaggcgg    360

taatacggtt atccacagaa tcaggggata acgcaggaaa gaacatgtga gcaaaaggcc    420

agcaaaaggc caggaaccgt aaaaaggccg cgttgctggc gtttttccat aggctccgcc    480

cccctgacga gcatcacaaa aatcgacgct caagtcagag gtggcgaaac ccgacaggac    540

tataaagata ccaggcgttt ccccctggaa gctccctcgt gcgctctcct gttccgaccc    600

tgccgcttac cggatacctg tccgcctttc tcccttcggg aagcgtggcg ctttctcata    660

gctcacgctg taggtatctc agttcggtgt aggtcgttcg ctccaagctg ggctgtgtgc    720

acgaaccccc cgttcagccc gaccgctgcg ccttatccgg taactatcgt cttgagtcca    780

acccggtaag acacgactta tcgccactgg cagcagccac tggtaacagg attagcagag    840

cgaggtatgt aggcggtgct acagagttct tgaagtggtg gcctaactac ggctacacta    900

gaaggacagt atttggtatc tgcgctctgc tgaagccagt taccttcgga aaaagagttg    960

gtagctcttg atccggcaaa caaaccaccg ctggtagcgg tggttttttt gtttgcaagc   1020

agcagattac gcgcagaaaa aaaggatctc aagaagatcc tttgatcttt tctacggggt   1080

ctgacgctca gtggaacgaa aactcacgtt aagggatttt ggtcatgaga ttatcaaaaa   1140

ggatcttcac ctagatcctt ttaaattaaa aatgaagttt taaatcaatc taaagtatat   1200
```

```
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc ccccccctcga  2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
```

-continued

```
tcatcccaca tattccttgg atttctctcc aatgaatgac attctatctt gcaaattcaa   3660
caattataat aagatatacc aaagtagcgg tatagtggca atcaaaaagc ttctctggtg   3720
tgcttctcgt atttattttt attctaatga tccattaaag gtatatattt atttcttgtt   3780
atataatcct tttgtttatt acatgggctg gatacataaa ggtattttga tttaattttt   3840
tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
cagaatctag aatgcggtat gcggtacatt gttcttcgaa cgtaaaagtt gcgctccctg   4020
agatattgta catttttgct tttacaagta caagtacatc gtacaactat gtactactgt   4080
tgatgcatcc acaacagttt gttttgtttt tttttgtttt tttttttttct aatgattcat   4140
taccgctatg tatacctact tgtacttgta gtaagccggg ttattggcgt tcaattaatc   4200
atagacttat gaatctgcac ggtgtgcgct gcgagttact tttagcttat gcatgctact   4260
tgggtgtaat attgggatct gttcggaaat caacggatgc tcaaccgatt tcgacagtaa   4320
taatttgaat cgaatcggag cctaaaatga acccgagtat atctcataaa attctcggtg   4380
agaggtctgt gactgtcagt acaaggtgcc ttcattatgc cctcaacctt accatacctc   4440
actgaatgta gtgtacctct aaaaatgaaa tacagtgcca aaagccaagg cactgagctc   4500
gtctaacgga cttgatatac aaccaattaa aacaaatgaa aagaaataca gttctttgta   4560
tcatttgtaa caattaccct gtacaaacta aggtattgaa atcccacaat attcccaaag   4620
tccacccctt tccaaattgt catgcctaca actcatatac caagcactaa cctaccaaac   4680
accactaaaa ccccacaaaa tatatcttac cgaatataca gtaacaagct accaccacac   4740
tcgttgggtg cagtcgccag cttaaagata tctatccaca tcagccacaa ctcccttcct   4800
ttaataaacc gactacaccc ttggctattg aggttatgag tgaatatact gtagacaaga   4860
cactttcaag aagactgttt ccaaaacgta ccactgtcct ccactacaaa cacacccaat   4920
ctgcttcttc tagtcaaggt tgctacaccg gtaaattata aatcatcatt tcattagcag   4980
ggcagggccc tttttataga gtcttataca ctagcggacc ctgccggtag accaacccgc   5040
aggcgcgtca gtttgctcct tccatcaatg cgtcgtagaa acgacttact ccttcttgag   5100
cagctccttg accttgttgg caacaagtct ccgacctcgg aggtggagga agagcctccg   5160
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg gggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg ggggaattcg tccttgagga ctcgagtgac agtctttcgc   5580
caaagtcgag aggaggccag cacgttggcc ttgtcaagag accacacggg aagagggggg   5640
ttgtgctgaa gggccaggaa ggcggccatt cgggcaattc gctcaacctc aggaacggag   5700
taggtctcgg tgtcggaagc gacgccagat ccgtcatcct cctttcgctc tccaaagtag   5760
atacctccga cgagctctcg gacaatgatg aagtcggtgc cctcaacgtt tcggatgggg   5820
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
```

```
cggcagatgt cgagagtagc gtcggtgatg ggctcgccct ccttctcaat ggcagctcct   6060
ccaatgagtc ggtcctcaaa cacaaactcg gtgccggagg cctcagcaac agacttgagc   6120
accttgacgg cctcggcaat cacctcgggg ccacagaagt cgccgccgag aagaacaatc   6180
ttcttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
gcacttttgc ccgtgctatg tggaagacta aacctccgaa gattgtgact caggtagtgc   6360
ggtatcggct agggacccaa accttgtcga tgccgatagc gctatcgaac gtaccccagc   6420
cggccgggag tatgtcggag gggacatacg agatcgtcaa gggtttgtgg ccaactggta   6480
aatttaaatg atgtcgacgc agtaggatgt cctgcacggg tctttttgtg ggtgtggag    6540
aaaggggtgc ttggagatgg aagccggtag aaccgggctg cttgtgcttg gagatggaag   6600
ccggtagaac cgggctgctt ggggggattt ggggccgctg ggctccaaag aggggtaggc   6660
atttcgttgg ggttacgtaa ttgcggcatt tgggtcctgc gcgcatgtcc cattggtcag   6720
aattagtccg gataggagac ttatcagcca atcacagcgc cggatccacc tgtaggttgg   6780
gttgggtggg agcacccctc cacagagtag agtcaaacag cagcagcaac atgatagttg   6840
ggggtgtgcg tgttaaagga aaaaaaagaa gcttgggtta tattcccgct ctatttagag   6900
gttgcgggat agacgccgac ggagggcaat ggcgccatgg aaccttgcgg atatcgatac   6960
gccgcggcgg actgcgtccg aaccagctcc agcagcgttt tttccgggcc attgagccga   7020
ctgcgacccc gccaacgtgt cttggcccac gcactcatgt catgttggtg ttgggaggcc   7080
actttttaag tagcacaagg cacctagctc gcagcaaggt gtccgaacca aagaagcggc   7140
tgcagtggtg caaacggggc ggaaacggcg ggaaaaagcc acgggggcac gaattgaggc   7200
acgccctcga atttgagacg agtcacggcc ccattcgccc gcgcaatggc tcgccaacgc   7260
ccggtctttt gcaccacatc aggttacccc aagccaaacc tttgtgttaa aaagcttaac   7320
atattatacc gaacgtaggt ttgggcgggc ttgctccgtc tgtccaaggc aacatttata   7380
taagggtctg catcgccggc tcaattgaat ctttttcttt cttctcttct ctatattcat   7440
tcttgaatta aacacacatc aatccatggc aaacagcagc gtgtgggatg atgtggtggg   7500
ccgcgtggag accggcgtgg accagtggat ggatggcgcc aagccgtacg cactcaccga   7560
tgggctcccg atgatggacg tgtccaccat gctggcattc gaggtgggat acatggccat   7620
gctgctcttc ggcatcccga tcatgaagca gatggagaag ccttttgagc tcaagaccat   7680
caagctcttg cacaacttgt ttctcttcgg actttccttg tacatgtgcg tggagaccat   7740
ccgccaggct atcctcggag gctacaaagt gtttggaaac gacatggaga agggcaacga   7800
gtctcatgct cagggcatgt ctcgcatcgt gtacgtgttc tacgtgtcca aggcatacga   7860
gttcttggat accgccatca tgatcctttg caagaagttc aaccaggttt ccttcttgca   7920
tgtgtaccac catgccactc atttttgcca tctggtgggc tatccgccaa gtacgctcca   7980
ggaggtgatg cgtacttttt cagtgatcct caactctttc gtgcacaccg tcatgtacgg   8040
catactactt cttctcctcc caagggttcg ggttcgtgaa gccaatcaag ccgtacatca   8100
ccacccttca gatgacccag ttcatggcaa tgcttgtgca gtccttgtac gactacctct   8160
tcccatgcga ctacccacag gctcttgtgc agctccttgg agtgtacatg atcaccttgc   8220
ttgccctctt cggcaacttt tttgtgcaga gctatcttaa aaagccaaaa aagagcaaga   8280
ccaactaaaa ctgcctgcat gatatgccgc tcgccggcgt tcgaattgac tcagaaagcg   8340
agttaaggcg acacgcaaac tctatatttt ttcaaacgtg ttgccgtcac tcattcgcca   8400
```

```
tctgtttact acgtgtctgt tcaatgagca tgttcttgaa tctaaagaat ctcgaatgtt   8460

ttttaaaaaa agaattcgat atcaagctta cgcgtcgacc cgggtggacg tctagaggta   8520

cctagcaatt aacagatagt ttgccggtga taattctctt aacctcccac actcctttga   8580

cataacgatt tatgtaacga aactgaaatt tgaccagata ttgtgtccgc              8630
```

<210> SEQ ID NO 75
<211> LENGTH: 6473
<212> TYPE: DNA
<213> ORGANISM: Artificial Sequence
<220> FEATURE:
<223> OTHER INFORMATION: plasmid pY5-22

<400> SEQUENCE: 75

```
ggtggagctc cagcttttgt tccctttagt gagggttaat ttcgagcttg gcgtaatcat     60

ggtcatagct gtttcctgtg tgaaattgtt atccgctcac aattccacac aacgtacgag    120

ccggaagcat aaagtgtaaa gcctggggtg cctaatgagt gagctaactc acattaattg    180

cgttgcgctc actgcccgct ttccagtcgg gaaacctgtc gtgccagctg cattaatgaa    240

tcggccaacg cgcggggaga ggcggtttgc gtattgggcg ctcttccgct tcctcgctca    300

ctgactcgct gcgctcggtc gttcggctgc ggcgagcggt atcagctcac tcaaaggcgg    360

taatacggtt atccacagaa tcaggggata acgcaggaaa gaacatgtga gcaaaaggcc    420

agcaaaaggc caggaaccgt aaaaaggccg cgttgctggc gtttttccat aggctccgcc    480

cccctgacga gcatcacaaa aatcgacgct caagtcagag gtggcgaaac ccgacaggac    540

tataaagata ccaggcgttt ccccctggaa gctccctcgt gcgctctcct gttccgaccc    600

tgccgcttac cggatacctg tccgcctttc tcccttcggg aagcgtggcg ctttctcata    660

gctcacgctg taggtatctc agttcggtgt aggtcgttcg ctccaagctg ggctgtgtgc    720

acgaaccccc cgttcagccc gaccgctgcg ccttatccgg taactatcgt cttgagtcca    780

acccggtaag acacgactta tcgccactgg cagcagccac tggtaacagg attagcagag    840

cgaggtatgt aggcggtgct acagagttct tgaagtggtg gcctaactac ggctacacta    900

gaaggacagt atttggtatc tgcgctctgc tgaagccagt taccttcgga aaaagagttg    960

gtagctcttg atccggcaaa caaaccaccg ctggtagcgg tggttttttt gtttgcaagc   1020

agcagattac gcgcagaaaa aaaggatctc aagaagatcc tttgatcttt tctacggggt   1080

ctgacgctca gtggaacgaa aactcacgtt aagggatttt ggtcatgaga ttatcaaaaa   1140

ggatcttcac ctagatcctt ttaaattaaa aatgaagttt taaatcaatc taaagtatat   1200

atgagtaaac ttggtctgac agttaccaat gcttaatcag tgaggcacct atctcagcga   1260

tctgtctatt tcgttcatcc atagttgcct gactccccgt cgtgtagata actacgatac   1320

gggagggctt accatctggc cccagtgctg caatgatacc gcgagaccca cgctcaccgg   1380

ctccagattt atcagcaata aaccagccag ccggaagggc cgagcgcaga agtggtcctg   1440

caactttatc cgcctccatc cagtctatta attgttgccg ggaagctaga gtaagtagtt   1500

cgccagttaa tagtttgcgc aacgttgttg ccattgctac aggcatcgtg gtgtcacgct   1560

cgtcgtttgg tatggcttca ttcagctccg gttcccaacg atcaaggcga gttacatgat   1620

cccccatgtt gtgcaaaaaa gcggttagct ccttcggtcc tccgatcgtt gtcagaagta   1680

agttggccgc agtgttatca ctcatggtta tggcagcact gcataattct cttactgtca   1740

tgccatccgt aagatgcttt tctgtgactg gtgagtactc aaccaagtca ttctgagaat   1800

agtgtatgcg gcgaccgagt tgctcttgcc cggcgtcaat acgggataat accgcgccac   1860
```

```
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc ccccccctcga  2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
tcatcccaca tattccttgg atttctctcc aatgaatgac attctatctt gcaaattcaa   3660
caattataat aagatatacc aaagtagcgg tatagtggca atcaaaaagc ttctctggtg   3720
tgcttctcgt atttattttt attctaatga tccattaaag gtatatattt atttcttgtt   3780
atataatcct tttgtttatt acatgggctg gatacataaa ggtattttga tttaattttt   3840
tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
cagaatctag aatgcggtat gcggtacatt gttcttcgaa cgtaaaagtt gcgctccctg   4020
agatattgta catttttgct tttacaagta caagtacatc gtacaactat gtactactgt   4080
tgatgcatcc acaacagttt gttttgtttt tttttgtttt tttttttttct aatgattcat  4140
taccgctatg tatacctact tgtacttgta gtaagccggg ttattggcgt tcaattaatc   4200
atagacttat gaatctgcac ggtgtgcgct gcgagttact tttagcttat gcatgctact   4260
```

```
tgggtgtaat attgggatct gttcggaaat caacggatgc tcaaccgatt tcgacagtaa   4320
ttaattaagt catacacaag tcagctttct tcgagcctca tataagtata agtagttcaa   4380
cgtattagca ctgtacccag catctccgta tcgagaaaca caacaacatg ccccattgga   4440
cagatcatgc ggatacacag gttgtgcagt atcatacata ctcgatcaga caggtcgtct   4500
gaccatcata caagctgaac aagcgctcca tacttgcacg ctctctatat acacagttaa   4560
attacatatc catagtctaa cctctaacag ttaatcttct ggtaagcctc ccagccagcc   4620
ttctggtatc gcttggcctc ctcaatagga tctcggttct ggccgtacag acctcggccg   4680
acaattatga tatccgttcc ggtagacatg acatcctcaa cagttcggta ctgctgtccg   4740
agagcgtctc ccttgtcgtc aagacccacc ccgggggtca gaataagcca gtcctcagag   4800
tcgcccttag gtcggttctg ggcaatgaag ccaaccacaa actcggggtc ggatcgggca   4860
agctcaatgg tctgcttgga gtactcgcca gtggccagag agcccttgca agacagctcg   4920
gccagcatga gcagacctct ggccagcttc tcgttgggag aggggactag gaactccttg   4980
tactgggagt tctcgtagtc agagacgtcc tccttcttct gttcagagac agtttcctcg   5040
gcaccagctc gcaggccagc aatgattccg gttccgggta caccgtgggc gttggtgata   5100
tcggaccact cggcgattcg gtgacaccgg tactggtgct tgacagtgtt gccaatatct   5160
gcgaactttc tgtcctcgaa caggaagaaa ccgtgcttaa gagcaagttc cttgaggggg   5220
agcacagtgc cggcgtaggt gaagtcgtca atgatgtcga tatgggtttt gatcatgcac   5280
acataaggtc cgaccttatc ggcaagctca atgagctcct tggtggtggt aacatccaga   5340
gaagcacaca ggttggtttt cttggctgcc acgagcttga gcactcgagc ggcaaaggcg   5400
gacttgtgga cgttagctcg agcttcgtag gagggcattt tggtggtgaa gaggagactg   5460
aaataaattt agtctgcaga actttttatc ggaaccttat ctggggcagt gaagtatatg   5520
ttatggtaat agttacgagt tagttgaact tatagataga ctggactata cggctatcgg   5580
tccaaattag aaagaacgtc aatggctctc tgggcgtcgc ctttgccgac aaaaatgtga   5640
tcatgatgaa agccagcaat gacgttgcag ctgatattgt tgtcggccaa ccgcgccgaa   5700
aacgcagctg tcagacccac agcctccaac gaagaatgta tcgtcaaagt gatccaagca   5760
cactcatagt tggagtcgta ctccaaaggc ggcaatgacg agtcagacag atactcgtcg   5820
actcaggcga cgacggaatt cctgcagccc atctgcagaa ttcaggagag accgggttgg   5880
cggcgtattt gtgtcccaaa aaacagcccc aattgcccca attgacccca aattgaccca   5940
gtagcgggcc caaccccggc gagagccccc ttcaccccac atatcaaacc tcccccggtt   6000
cccacacttg ccgttaaggg cgtagggtac tgcagtctgg aatctacgct tgttcagact   6060
ttgtactagt ttctttgtct ggccatccgg gtaacccatg ccggacgcaa aatagactac   6120
tgaaaatttt tttgctttgt ggttgggact ttagccaagg gtataaaaga ccaccgtccc   6180
cgaattacct ttcctcttct tttctctctc tccttgtcaa ctcacacccg aaatcgttaa   6240
gcatttcctt ctgagtataa gaatcattca ccatggatcc actagttcta gagcggccgc   6300
caccgcggcc cgagattccg gcctcttcgg ccgccaagcg acccgggtgg acgtctagag   6360
gtacctagca attaacagat agtttgccgg tgataattct cttaacctcc cacactcctt   6420
tgacataacg atttatgtaa cgaaactgaa atttgaccag atattgtgtc cgc          6473
```

<210> SEQ ID NO 76
<211> LENGTH: 427
<212> TYPE: PRT
<213> ORGANISM: Pavlova salina

<400> SEQUENCE: 76

```
Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
    50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
    130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175

His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
        195                 200                 205

Trp Trp Arg Ala Arg His Asn Thr His His Val Cys Thr Asn Glu Asp
    210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro
        275                 280                 285

Gln Ala Leu Ala Leu Val Ala His Tyr Ala Ile Val Ala Trp Val Phe
    290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                325                 330                 335

Asp Ala Asp Gln Val Arg His Met Thr Leu Val Glu Gln Thr Ala Leu
            340                 345                 350

Thr Ser Arg Asn Ile Ser Gly Gly Trp Leu Val Asn Val Leu Thr Gly
        355                 360                 365

Phe Ile Ser Leu Gln Thr Glu His His Leu Phe Pro Met Met Pro Thr
    370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
                405                 410                 415
```

```
Asn Ile Arg Ala Leu Ala Phe Glu His Leu Leu
            420                 425


<210> SEQ ID NO 77
<211> LENGTH: 421
<212> TYPE: PRT
<213> ORGANISM: Euglena gracilis

<400> SEQUENCE: 77

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285

Leu Thr Ser Leu Leu Val Phe Phe Val Ser Glu Leu Val Gly Gly Phe
    290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365
```

```
His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420


<210> SEQ ID NO 78
<211> LENGTH: 8953
<212> TYPE: DNA
<213> ORGANISM: Artificial Sequence
<220> FEATURE:
<223> OTHER INFORMATION: plasmid pY5-30

<400> SEQUENCE: 78

ggtggagctc cagcttttgt tccctttagt gagggttaat ttcgagcttg gcgtaatcat     60

ggtcatagct gtttcctgtg tgaaattgtt atccgctcac aattccacac aacatacgag    120

ccggaagcat aaagtgtaaa gcctggggtg cctaatgagt gagctaactc acattaattg    180

cgttgcgctc actgcccgct ttccagtcgg gaaacctgtc gtgccagctg cattaatgaa    240

tcggccaacg cgcggggaga ggcggtttgc gtattgggcg ctcttccgct tcctcgctca    300

ctgactcgct gcgctcggtc gttcggctgc ggcgagcggt atcagctcac tcaaaggcgg    360

taatacggtt atccacagaa tcaggggata acgcaggaaa gaacatgtga gcaaaaggcc    420

agcaaaaggc caggaaccgt aaaaaggccg cgttgctggc gtttttccat aggctccgcc    480

cccctgacga gcatcacaaa aatcgacgct caagtcagag gtggcgaaac ccgacaggac    540

tataaagata ccaggcgttt ccccctggaa gctccctcgt gcgctctcct gttccgaccc    600

tgccgcttac cggatacctg tccgcctttc tcccttcggg aagcgtggcg ctttctcata    660

gctcacgctg taggtatctc agttcggtgt aggtcgttcg ctccaagctg ggctgtgtgc    720

acgaaccccc cgttcagccc gaccgctgcg ccttatccgg taactatcgt cttgagtcca    780

acccggtaag acacgactta tcgccactgg cagcagccac tggtaacagg attagcagag    840

cgaggtatgt aggcggtgct acagagttct tgaagtggtg gcctaactac ggctacacta    900

gaaggacagt atttggtatc tgcgctctgc tgaagccagt taccttcgga aaaagagttg    960

gtagctcttg atccggcaaa caaaccaccg ctggtagcgg tggttttttt gtttgcaagc   1020

agcagattac gcgcagaaaa aaaggatctc aagaagatcc tttgatcttt tctacggggt   1080

ctgacgctca gtggaacgaa aactcacgtt aagggatttt ggtcatgaga ttatcaaaaa   1140

ggatcttcac ctagatcctt ttaaattaaa aatgaagttt taaatcaatc taaagtatat   1200

atgagtaaac ttggtctgac agttaccaat gcttaatcag tgaggcacct atctcagcga   1260

tctgtctatt tcgttcatcc atagttgcct gactccccgt cgtgtagata actacgatac   1320

gggagggctt accatctggc cccagtgctg caatgatacc gcgagaccca cgctcaccgg   1380

ctccagattt atcagcaata aaccagccag ccggaagggc cgagcgcaga agtggtcctg   1440

caactttatc cgcctccatc cagtctatta attgttgccg ggaagctaga gtaagtagtt   1500

cgccagttaa tagtttgcgc aacgttgttg ccattgctac aggcatcgtg gtgtcacgct   1560

cgtcgtttgg tatggcttca ttcagctccg gttcccaacg atcaaggcga gttacatgat   1620

cccccatgtt gtgcaaaaaa gcggttagct ccttcggtcc tccgatcgtt gtcagaagta   1680

agttggccgc agtgttatca ctcatggtta tggcagcact gcataattct cttactgtca   1740
```

```
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc ccccccctcga   2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
tcatcccaca tattccttgg atttctctcc aatgaatgac attctatctt gcaaattcaa   3660
caattataat aagatatacc aaagtagcgg tatagtggca atcaaaaagc ttctctggtg   3720
tgcttctcgt atttattttt attctaatga tccattaaag gtatatattt atttcttgtt   3780
atataatcct tttgtttatt acatgggctg gatacataaa ggtattttga tttaattttt   3840
tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
cagaatctag aatgcggtat gcggtacatt gttcttcgaa cgtaaaagtt gcgctccctg   4020
agatattgta catttttgct tttacaagta caagtacatc gtacaactat gtactactgt   4080
tgatgcatcc acaacagttt gttttgtttt tttttgtttt tttttttttct aatgattcat   4140
```

```
taccgctatg tatacctact tgtacttgta gtaagccggg ttattggcgt tcaattaatc   4200
atagacttat gaatctgcac ggtgtgcgct gcgagttact tttagcttat gcatgctact   4260
tgggtgtaat attgggatct gttcggaaat caacggatgc tcaaccgatt tcgacagtaa   4320
taatttgaat cgaatcggag cctaaaatga acccgagtat atctcataaa attctcggtg   4380
agaggtctgt gactgtcagt acaaggtgcc ttcattatgc cctcaacctt accatacctc   4440
actgaatgta gtgtacctct aaaaatgaaa tacagtgcca aaagccaagg cactgagctc   4500
gtctaacgga cttgatatac aaccaattaa aacaaatgaa aagaaataca gttctttgta   4560
tcatttgtaa caattaccct gtacaaacta aggtattgaa atcccacaat attcccaaag   4620
tccacccctt tccaaattgt catgcctaca actcatatac caagcactaa cctaccaaac   4680
accactaaaa ccccacaaaa tatatcttac cgaatataca gtaacaagct accaccacac   4740
tcgttgggtg cagtcgccag cttaaagata tctatccaca tcagccacaa ctcccttcct   4800
ttaataaacc gactacaccc ttggctattg aggttatgag tgaatatact gtagacaaga   4860
cactttcaag aagactgttt ccaaaacgta ccactgtcct ccactacaaa cacacccaat   4920
ctgcttcttc tagtcaaggt tgctacaccg gtaaattata aatcatcatt tcattagcag   4980
ggcagggccc tttttataga gtcttataca ctagcggacc ctgccggtag accaacccgc   5040
aggcgcgtca gtttgctcct tccatcaatg cgtcgtagaa acgacttact ccttcttgag   5100
cagctccttg accttgttgg caacaagtct ccgacctcgg aggtggagga agagcctccg   5160
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg gggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg ggggaattcg tccttgagga ctcgagtgac agtctttcgc   5580
caaagtcgag aggaggccag cacgttggcc ttgtcaagag accacacggg aagaggggg   5640
ttgtgctgaa gggccaggaa ggcggccatt cgggcaattc gctcaacctc aggaacggag   5700
taggtctcgg tgtcggaagc gacgccagat ccgtcatcct cctttcgctc tccaaagtag   5760
atacctccga cgagctctcg gacaatgatg aagtcggtgc cctcaacgtt tcggatgggg   5820
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
cggcagatgt cgagagtagc gtcggtgatg ggctcgccct ccttctcaat ggcagctcct   6060
ccaatgagtc ggtcctcaaa cacaaactcg gtgccggagg cctcagcaac agacttgagc   6120
accttgacgg cctcggcaat cacctcgggg ccacagaagt cgccgccgag aagaacaatc   6180
ttcttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
gcacttttgc ccgtgctatg tggaagacta aacctccgaa gattgtgact caggtagtgc   6360
ggtatcggct agggacccaa accttgtcga tgccgatagc gctatcgaac gtaccccagc   6420
cggccgggag tatgtcggag gggacatacg agatcgtcaa gggtttgtgg ccaactggta   6480
aataaatgat gtcgactcag gcgacgacgg aattcctgca gcccatctgc agaattcagg   6540
```

```
agagaccggg ttggcggcgt atttgtgtcc caaaaaacag ccccaattgc cccaattgac   6600
cccaaattga cccagtagcg ggcccaaccc cggcgagagc ccccttcacc ccacatatca   6660
aacctccccc ggttcccaca cttgccgtta agggcgtagg gtactgcagt ctggaatcta   6720
cgcttgttca gactttgtac tagtttcttt gtctggccat ccgggtaacc catgccggac   6780
gcaaaataga ctactgaaaa tttttttgct ttgtggttgg gactttagcc aagggtataa   6840
aagaccaccg tccccgaatt acctttcctc ttcttttctc tctctccttg tcaactcaca   6900
cccgaaatcg ttaagcattt ccttctgagt ataagaatca ttcaccatgg atggtacgtc   6960
ctgtagaaac cccaacccgt gaaatcaaaa aactcgacgg cctgtgggca ttcagtctgg   7020
atcgcgaaaa ctgtggaatt gatcagcgtt ggtgggaaag cgcgttacaa gaaagccggg   7080
caattgctgt gccaggcagt tttaacgatc agttcgccga tgcagatatt cgtaattatg   7140
cgggcaacgt ctggtatcag cgcgaagtct ttataccgaa aggttgggca ggccagcgta   7200
tcgtgctgcg tttcgatgcg gtcactcatt acggcaaagt gtgggtcaat aatcaggaag   7260
tgatggagca tcagggcggc tatacgccat ttgaagccga tgtcacgccg tatgttattg   7320
ccgggaaaag tgtacgtatc accgtttgtg tgaacaacga actgaactgg cagactatcc   7380
cgccgggaat ggtgattacc gacgaaaacg gcaagaaaaa gcagtcttac ttccatgatt   7440
tctttaacta tgccgggatc catcgcagcg taatgctcta caccacgccg aacacctggg   7500
tggacgatat caccgtggtg acgcatgtcg cgcaagactg taaccacgcg tctgttgact   7560
ggcaggtggt ggccaatggt gatgtcagcg ttgaactgcg tgatgcggat caacaggtgg   7620
ttgcaactgg acaaggcact agcgggactt tgcaagtggt gaatccgcac ctctggcaac   7680
cgggtgaagg ttatctctat gaactgtgcg tcacagccaa aagccagaca gagtgtgata   7740
tctacccgct tcgcgtcggc atccggtcag tggcagtgaa gggcgaacag ttcctgatta   7800
accacaaacc gttctacttt actggctttg gtcgtcatga agatgcggac ttacgtggca   7860
aaggattcga taacgtgctg atggtgcacg accacgcatt aatggactgg attggggcca   7920
actcctaccg tacctcgcat tacccttacg ctgaagagat gctcgactgg gcagatgaac   7980
atggcatcgt ggtgattgat gaaactgctg ctgtcggctt taacctctct ttaggcattg   8040
gtttcgaagc gggcaacaag ccgaaagaac tgtacagcga agaggcagtc aacggggaaa   8100
ctcagcaagc gcacttacag gcgattaaag agctgatagc gcgtgacaaa aaccacccaa   8160
gcgtggtgat gtggagtatt gccaacgaac cggatacccg tccgcaagtg cacgggaata   8220
tttcgccact ggcggaagca acgcgtaaac tcgacccgac gcgtccgatc acctgcgtca   8280
atgtaatgtt ctgcgacgct cacaccgata ccatcagcga tctctttgat gtgctgtgcc   8340
tgaaccgtta ttacggatgg tatgtccaaa gcggcgattt ggaaacggca gagaaggtac   8400
tggaaaaaga acttctggcc tggcaggaga aactgcatca gccgattatc atcaccgaat   8460
acggcgtgga tacgttagcc gggctgcact caatgtacac cgacatgtgg agtgaagagt   8520
atcagtgtgc atggctggat atgtatcacc gcgtctttga tcgcgtcagc gccgtcgtcg   8580
gtgaacaggt atggaatttc gccgattttg cgacctcgca aggcatattg cgcgttggcg   8640
gtaacaagaa agggatcttc actcgcgacc gcaaaccgaa gtcggcggct tttctgctgc   8700
aaaaacgctg gactggcatg aacttcggtg aaaaaccgca gcagggaggc aaacaatgat   8760
taattaacta gagcggccgc caccgcggcc cgagattccg gcctcttcgg ccgccaagcg   8820
acccgggtgg acgtctagag gtacctagca attaacagat agtttgccgg tgataattct   8880
```

-continued

```
cttaacctcc cacactcctt tgacataacg atttatgtaa cgaaactgaa atttgaccag   8940

atattgtgtc cgc                                                       8953
```

DELTA-8 DESATURASE AND ITS USE IN MAKING POLYUNSATURATED FATTY ACIDS

This application claims the benefit of U.S. Provisional Application No. 60/795,810, filed Apr. 28, 2006, and U.S. Provisional Application No. 60/837,789, filed Aug. 15, 2006, the entire contents of which are herein incorporated by reference.

FIELD OF THE INVENTION

This invention pertains to a polynucleotide sequence encoding a delta-8 desaturase and the use of this desaturase in making long-chain polyunsaturated fatty acids (PUFAs).

BACKGROUND OF THE INVENTION

Fatty acids (lipids) are water-insoluble organic biomolecules that can be extracted from cells and tissues by nonpolar solvents such as chloroform, ether or benzene. Lipids have several important biological functions, serving as (1) structural components of membranes; (2) storage and transport forms of metabolic fuels; (3) a protective coating on the surface of many organisms; and, (4) cell-surface components concerned in cell recognition, species specificity and tissue immunity. More specifically, polyunsaturated fatty acids (PUFAs) are important components of the plasma membrane of the cell, where they may be found in such forms as phospholipids and also can be found in triglycerides. PUFAs also serve as precursors to other molecules of importance in human beings and animals, including the prostacyclins, leukotrienes and prostaglandins. There are two main families of PUFAs (i.e., the omega-3 fatty acids and the omega-6 fatty acids).

The human body is capable of producing most of the PUFAs which it requires to function. However, eicosapentaenoic acid (EPA; 20:5, delta-5,8,11,14,17) and docosahexaenoic acid (DHA; 22:6, delta-4,7,10,13,16,19) cannot be synthesized efficiently by the human body and thus must be supplied through the diet. Since the human body cannot produce adequate quantities of these PUFAs, they are called essential fatty acids. Because of their important roles in human health and nutrition, EPA and DHA are the subject of much interest as discussed herein.

DHA is a fatty acid of the omega-3 series according to the location of the last double bond in the methyl end. It is synthesized via alternating steps of desaturation and elongation (see FIG. 12). Production of DHA is important because of its beneficial effect on human health. For example, increased intake of DHA has been shown to be beneficial or have a positive effect in inflammatory disorders (e.g., rheumatoid arthritis), Type II diabetes, hypertension, atherosclerosis, depression, myocardial infarction, thrombosis, some cancers and for prevention of the onset of degenerative disorders such as Alzheimer's disease. Currently the major sources of DHA are oils from fish and algae.

EPA and arachidonic acid (AA or ARA; 20:4, delta-5,8,11,14) are both delta-5 essential fatty acids. EPA belongs to the omega-3 series with five double bonds in the acyl chain, is found in marine food, and is abundant in oily fish from the North Atlantic. Beneficial or positive effects of increased intake of EPA have been shown in patients with coronary heart disease, high blood pressure, inflammatory disorders, lung and kidney diseases, Type II diabetes, obesity, ulcerative colitis, Crohn's disease, anorexia nervosa, burns, osteoarthritis, osteoporosis, attention deficit/hyperactivity disorder and early stages of colorectal cancer (see, for example, the review of McColl, J., *NutraCos.* 2(4):35-40 (2003)).

AA belongs to the omega-6 series with four double bonds. The lack of a double bond in the omega-3 position confers on AA different properties than those found in EPA. The eicosanoids produced from AA have strong inflammatory and platelet aggregating properties, whereas those derived from EPA have anti-inflammatory and anti-platelet aggregating properties. AA is recognized as the principal omega-6 fatty acid found in the human brain and an important component of breast milk and many infant formulas, based on its role in early neurological and visual development. AA can be obtained from some foods (such as meat, fish, and eggs), but the concentration is low.

Gamma-linolenic acid (GLA; 18:3, delta-6,9,12) is another essential fatty acid found in mammals. GLA is the metabolic intermediate for very long-chain omega-6 fatty acids and for various active molecules. In mammals, formation of long-chain PUFAs is rate-limited by delta-6 desaturation. Many physiological and pathological conditions such as aging, stress, diabetes, eczema, and some infections have been shown to depress the delta-6 desaturation step. In addition, GLA is readily catabolized from the oxidation and rapid cell division associated with certain disorders (e.g., cancer or inflammation).

As described above, research has shown that various omega fatty acids reduce the risk of heart disease, have a positive effect on children's development and on certain mental illnesses, autoimmune diseases and joint complaints. However, although there are many health benefits associated with a diet supplemented with these fatty acids, it is recognized that different PUFAs exert different physiological effects in the body (e.g., most notably, the opposing physiological effects of GLA and AA). Thus, production of oils using recombinant means is expected to have several advantages over production from natural sources. For example, recombinant organisms having preferred characteristics for oil production can be used, since the naturally occurring fatty acid profile of the host can be altered by the introduction of new biosynthetic pathways in the host and/or by the suppression of undesired pathways, thereby resulting in increased levels of production of desired PUFAs (or conjugated forms thereof) and decreased production of undesired PUFAs. Optionally, recombinant organisms can provide PUFAs in particular forms which may have specific uses; or, oil production can be manipulated such that the ratio of omega-3 to omega-6 fatty acids so produced is modified and/or a specific PUFA is produced without significant accumulation of other PUFA downstream or upstream products (e.g., production of oils comprising AA and lacking GLA).

The mechanism of PUFA synthesis frequently occurs via the delta-6 desaturation pathway. For example, long-chain PUFA synthesis in mammals proceeds predominantly by a delta-6 desaturation pathway, in which the first step is the delta-6 desaturation of linoleic acid (LA; 18:2, delta-9,12) and alpha-linolenic acid (ALA; 18:3, delta-9,12,15) to yield gamma-linolenic acid (GLA; 18:3, delta-6,9,12)) and stearidonic acid (STA; 18:4, delta-6,9,12,15), respectively. Further fatty acid elongation and desaturation steps give rise to arachidonic acid (AA or ARA) and eicosapentaenoic acid (EPA). Accordingly, genes encoding delta-6 desaturases, delta-6 elongase components (also identified as $C_{18/20}$ elongases) and delta-5 desaturases have been cloned from a variety of organisms including higher plants, algae, mosses, fungi, nematodes and humans. Humans can synthesize long-chain PUFAs from the essential fatty acids, LA and ALA; however biosynthesis of long-chain PUFAs is somewhat limited (they are regulated by dietary and hormonal changes), and LA and ALA must be obtained from the diet.

PCT Publication No. WO 02/26946 (published Apr. 4, 2002) describes isolated nucleic acid molecules encoding FAD4, FAD5, FAD5-2 and FAD6 fatty acid desaturase family members which are expressed in long-chain PUFA-producing organisms, e.g., *Thraustochytrium, Pythium irregulare, Schizichytrium* and *Crypthecodinium*. It is indicated that constructs containing the desaturase genes can be used in any expression system including plants, animals, and microorganisms for the production of cells capable of producing long-chain PUFAs.

PCT Publication No. WO 98/55625 (published Dec. 19, 1998) describes the production of PUFAs by expression of polyketide-like synthesis genes in plants.

PCT Publication No. WO 98/46764 (published Oct. 22, 1998) describes compositions and methods for preparing long-chain fatty acids in plants, plant parts and plant cells which utilize nucleic acid sequences and constructs encoding fatty acid desaturases, including delta-5 desaturases, delta-6 desaturases and delta-12 desaturases.

U.S. Pat. No. 6,075,183 (issued to Knutzon et al. on Jun. 13, 2000) describes methods and compositions for synthesis of long-chain PUFAs in plants.

U.S. Pat. No. 6,459,018 (issued to Knutzon et al. on Oct. 1, 2002) describes a method for producing STA in plant seed utilizing a construct comprising a DNA sequence encoding a delta-6 desaturase.

Spychalla et al. (*Proc. Natl. Acad. Sci. USA,* 94:1142-1147 (1997)) describes the isolation and characterization of a cDNA from *Caenorhabditis elegans* that, when expressed in *Arabidopsis*, encodes a fatty acid desaturase which can catalyze the introduction of an omega-3 double bond into a range of 18- and 20-carbon fatty acids.

An alternate pathway for the biosynthesis of AA and EPA operates in some organisms (i.e., the delta-9 elongase/delta-8 desaturase pathway). Here LA and ALA are first elongated to eicosadienoic acid (EDA; 20:2, delta-11,14) and eicosatrienoic acid (EtrA; 20:3, delta-11,14,17), respectively, by a delta-9 elongase. Subsequent delta-8 and delta-5 desaturation of these products yields AA and EPA. The delta-8 pathway is present inter alia, in euglenoid species where it is the dominant pathway for formation of 20-carbon PUFAs.

PCT Publication No. WO 2000/34439 (published Jun. 15, 2000) discloses amino acid and nucleic acid sequences for delta-5 and delta-8 desaturase enzymes. Based on the information presented in Applicants' Assignee's co-pending application having Provisional Application No. 60/583,041 filed Jun. 25, 2004 (U.S. application Ser. No. 11/166,003 filed Jun. 24, 2005 (PCT Publication No. WO 2006/012325 and WO 2006/012326; published Feb. 2, 2006)), it is apparent that the delta-8 desaturase nucleotide and amino acid sequences of PCT Publication No. WO 2000/34439 are not correct. However, the correct sequence is set forth in corresponding U.S. Pat. No. 6,825,017 (issued to Browse et al. on Nov. 30, 2004) that describes desaturases, in particular, delta-5 and delta-8 desaturases and their use in synthesizing PUFAs. Browse discloses the same delta-8 desaturase in U.S. Publication No. 2006090221 (published on Apr. 27, 2006).

Applicants' Assignee's co-pending application having U.S. application Ser. No. 11/166,003 filed Jun. 24, 2005 (PCT Publication No. WO 2006/012325 and WO 2006/012326; published Feb. 2, 2006) concerns a *Euglena gracilis* delta-8 desaturase.

Wallis et al. (*Arch. Biochem. and Biophys.* 365(2):307-316 (May 1999)) describes the cloning of a gene that appears to encode a delta-8 desaturase in *Euglena gracilis*. This sequence appears to be the same sequence disclosed in PCT Publication No. WO 2000/34439.

Qi et al. (*Nat. Biotech.* 22(6):739-45 (2004)) describes the production of long-chain PUFAs using, among other things, a delta-8 desaturase from *Euglena gracilis*; however, the complete sequence of the delta-8 desaturase is not provided.

PCT Publication No. WO 2004/057001 (published Jul. 8, 2004) discloses amino acid and nucleic acid sequences for a delta-8 desaturase enzyme from *Euglena gracilis.*

PCT Publication No. WO 2005/103253 (published Apr. 22, 2005) discloses amino acid and nucleic acid sequences for a delta-8 desaturase enzyme from *Pavlova salina* (see also U.S. Publication No. 2005/0273885).

Sayanova et al. (*FEBS Lett.* 580:1946-1952 (2006)) describes the isolation of and characterization of a cDNA from the free living soil amoeba *Acanthamoeba castellanii* that, when expressed in *Arabidopsis*, encodes a $C_{20}$ delta-8 desaturase.

An expansive study of PUFAs from natural sources and from chemical synthesis are not sufficient for commercial needs. Therefore, it is of interest to find alternative means to allow production of commercial quantities of PUFAs. Biotechnology offers an attractive route for producing long-chain PUFAs in a safe, cost efficient manner in microorganisms and plants.

With respect to microorganisms, many algae, bacteria, molds and yeast can synthesize oils in the ordinary course of cellular metabolism. Thus, oil production involves cultivating the microorganism in a suitable culture medium to allow for oil synthesis, followed by separation of the microorganism from the fermentation medium and treatment for recovery of the intracellular oil. Attempts have been made to optimize production of fatty acids by fermentive means involving varying such parameters as microorganisms used, media and conditions that permit oil production. However, these efforts have proved largely unsuccessful in improving yield of oil or the ability to control the characteristics of the oil composition produced. One class of microorganisms that has not been previously examined as a production platform for PUFAs (prior to work by the Applicants' Assignee), however, are the oleaginous yeasts. These organisms can accumulate oil up to 80% of their dry cell weight. The technology for growing oleaginous yeast with high oil content is well developed (for example, see EP 0 005 277 B1; Ratledge, C., *Prog. Ind. Microbiol.* 16:119-206 (1982)), and may offer a cost advantage compared to commercial micro-algae fermentation for production of omega-3 or omega-6 PUFAs. Whole yeast cells may also represent a convenient way of encapsulating omega-3 or omega-6 PUFA-enriched oils for use in functional foods and animal feed supplements.

Applicants' Assignee's co-pending application having U.S. Provisional Application No. 60/739,989 filed Nov. 23, 2005 (Attorney Docket No. BB-1562), discloses a delta-9 elongase from Eulgena gracilis.

WO 02/077213 (published Oct. 3, 2002) describes isolated nucleic acid molecules encoding a fatty acid elongase with specificity for linoleic acid or alpha-linolenic acid from *Isochrysis galbana* (i.e., delta-9 elongase).

U.S. Pat. No. 6,403,349 (issued Jun. 11, 2002) concerns the identification of nucleotide and amino acid sequences of an elongase gene derived from *Mortierella alpina.*

PCT Publication No. WO 2004/101757 and PCT Publication No. WO 2004/101753 (published Nov. 25, 2004) concern the production of PUFAs in oleaginous yeasts and are Applicants' Assignee's copending applications.

PCT Publication No. WO 2004/071467 (published Aug. 26, 2004) concerns the production of PUFAs in plants, while PCT Publication No. WO 2004/071178 (published Aug. 26, 2004) concerns annexin promoters and their use in expression of transgenes in plants; both are Applicants' Assignee's copending applications.

Applicants' Assignee's copending applications having U.S. application Ser. No. 10/985,109 and U.S. application Ser. No. 10/985,254 filed Nov. 10, 2004 (PCT Publication No. 2005/047479 and PCT Publication No. 2005/047480; published May 26, 2005) concerns delta-15 desaturase genes suitable for increasing levels of omega-3 fatty acids.

Applicants' Assignee's copending applications also include U.S. application Ser. No. 11/265,761 filed Nov. 2, 2005, U.S. application Ser. No. 11/264,784 filed Nov. 1, 2005, and U.S. application Ser. No. 11/264,737 filed Nov. 1, 2005 (methods of making EPA, ARA and DHA, respectively, in *Yarrowia lipolytica*), each claiming benefit of an earlier provisional filing date of Nov. 4, 2004.

SUMMARY OF THE INVENTION

The invention concerns an isolated polynucleotide comprising:

(a) a nucleotide sequence encoding a polypeptide having delta-8 desaturase activity, wherein the polypeptide has at least 80% amino acid identity, based on the Cluster V method of alignment, when compared to an amino acid sequence as set forth in SEQ ID NO:16;

(b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:15; or (c) a complement of the nucleotide sequence of (a) or (b), wherein the complement and the nucleotide sequence consist of the same number of nucleotides and are 100% complementary.

In a second embodiment, the invention concerns codon optimization, specifically, an isolated nucleic acid molecule which encodes a delta-8 desaturase enzyme as set forth in SEQ ID NO:57 wherein at least 162 codons are codon-optimized for expression in *Yarrowia* sp.

In a third embodiment, the invention concerns a recombinant DNA construct comprising any of the polynucleotides of the invention operably linked to at least one regulatory sequence.

In a fourth embodiment, the invention concerns a cell comprising the recombinant DNA construct of the invention. Of interest are cells selected from the group consisting of plants and yeast.

In a fifth embodiment, the invention concerns a transformed *Yarrowia* sp. comprising the recombinant construct of the invention.

In a sixth embodiment, the invention concerns a method for transforming a cell, comprising transforming a cell with the recombinant construct of the invention and selecting those cells transformed with the recombinant construct of the invention.

In a seventh embodiment, the invention concerns a method for producing a transformed plant comprising transforming a plant cell with a polynucleotide of the invention and regenerating a plant from the transformed plant cell. A preferred plant is soybean.

In an eighth embodiment, the invention concerns a method for producing yeast comprising transforming a yeast cell with a polynucleotide of the invention and growing yeast from the transformed yeast cell and, in particular, oleaginous yeast.

In a ninth embodiment, the invention concerns a seed comprising the recombinant construct of the invention.

In a tenth embodiment, the invention concerns method for making long-chain polyunsaturated fatty acids in a cell comprising:

(a) transforming a cell with the recombinant construct of the invention;

(b) selecting those transformed cells that make long-chain polyunsaturated fatty acids.

In an eleventh embodiment, the invention concerns oil obtained from seed comprising the recombinant construct of the invention or yeast comprising the recombinant construct of the invention.

In a twelfth embodiment, the invention concerns a method for making long-chain polyunsaturated fatty acids in a plant cell comprising:

(a) transforming a cell with the recombinant construct of the invention; and (b) selecting those transformed cells that make long-chain polyunsaturated fatty acids.

In a thirteenth embodiment, the invention concerns a method for producing at least one polyunsaturated fatty acid in a soybean cell comprising:

(a) transforming a soybean cell with a first recombinant DNA construct comprising an isolated polynucleotide encoding at least one delta-8 desaturase polypeptide, operably linked to at least one regulatory sequence and at least one additional recombinant DNA construct comprising an isolated polynucleotide, operably linked, to at least one regulatory sequence, encoding a polypeptide selected from the group consisting of a delta-4 desaturase, a delta-5 desaturase, a delta-6 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;

(b) regenerating a soybean plant from the transformed cell of step (a); and (c) selecting those seeds obtained from the plants of step (b) having an altered level of polyunsaturated fatty acids when compared to the level in seeds obtained from a nontransformed soybean plant.

In a fourteenth embodiment, the invention concerns an oilseed plant comprising:

(a) a first recombinant DNA construct comprising an isolated polynucleotide encoding at least one delta-8 desaturase polypeptide, operably linked to at least one regulatory sequence; and (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

Also of interest are seeds obtained from such oilseed plants and oil obtained from these seeds.

In a fifteenth embodiment, the invention concerns food or feed which incorporates oil of the invention.

In a sixteenth embodiment, the invention concerns food or feed comprising an ingredient derived from the processing of the seeds of the invention.

In an seventeenth embodiment, the invention concerns an isolated polynucleotide comprising a nucleotide sequence encoding a polypeptide having delta-8 desaturase activity, wherein the nucleotide sequence has at least 90% sequence identity, based on the BLASTN method of alignment, when compared to a nucleotide sequence as set forth in SEQ ID NO:15.

In an eighteenth embodiment, the invention concerns method for making long-chain polyunsaturated fatty acids in a cell having a reduced level of by-product fatty acids, said method comprising:

(a) transforming a host cell with at least one recombinant DNA construct comprising an isolated polynucleotide encoding at least two delta-8 desaturases operably linked to at least one regulatory sequence; and (b) selecting those transformed host cells obtained having a reduced level of by-product fatty acids, when compared to the level of such by-product fatty acids in a transformed host cell having at least one recombinant DNA construct comprising an isolated polynucleotide encoding one delta-8 desaturase operably linked to a regulatory sequence.

Biological Deposits

The following plasmids have been deposited with the American Type Culture Collection (ATCC), 10801 University Boulevard, Manassas, Va. 20110-2209, and bear the following designations, Accession Numbers and dates of deposit (Table 1).

TABLE 1

ATCC Deposits

| Plasmid | Accession Number | Date of Deposit |
|---|---|---|
| pKR72 | PTA-6019 | May 28, 2004 |
| pKR578 | PTA-6280 | Nov. 4, 2004 |
| pKR903 | PTA-7494 | Apr. 12, 2006 |

BRIEF DESCRIPTION OF THE DRAWINGS AND SEQUENCE LISTINGS

The invention can be more fully understood from the following detailed description and the accompanying drawings and Sequence Listing, which form a part of this application.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

FIGS. 8A and 8B show a table of the fatty acid profiles from somatic soybean embryos expressing the *Pavlova lutheri* delta-8 desaturase and *Isochrysis galbana* delta-9 elongase (see Example 12).

Figure 9:
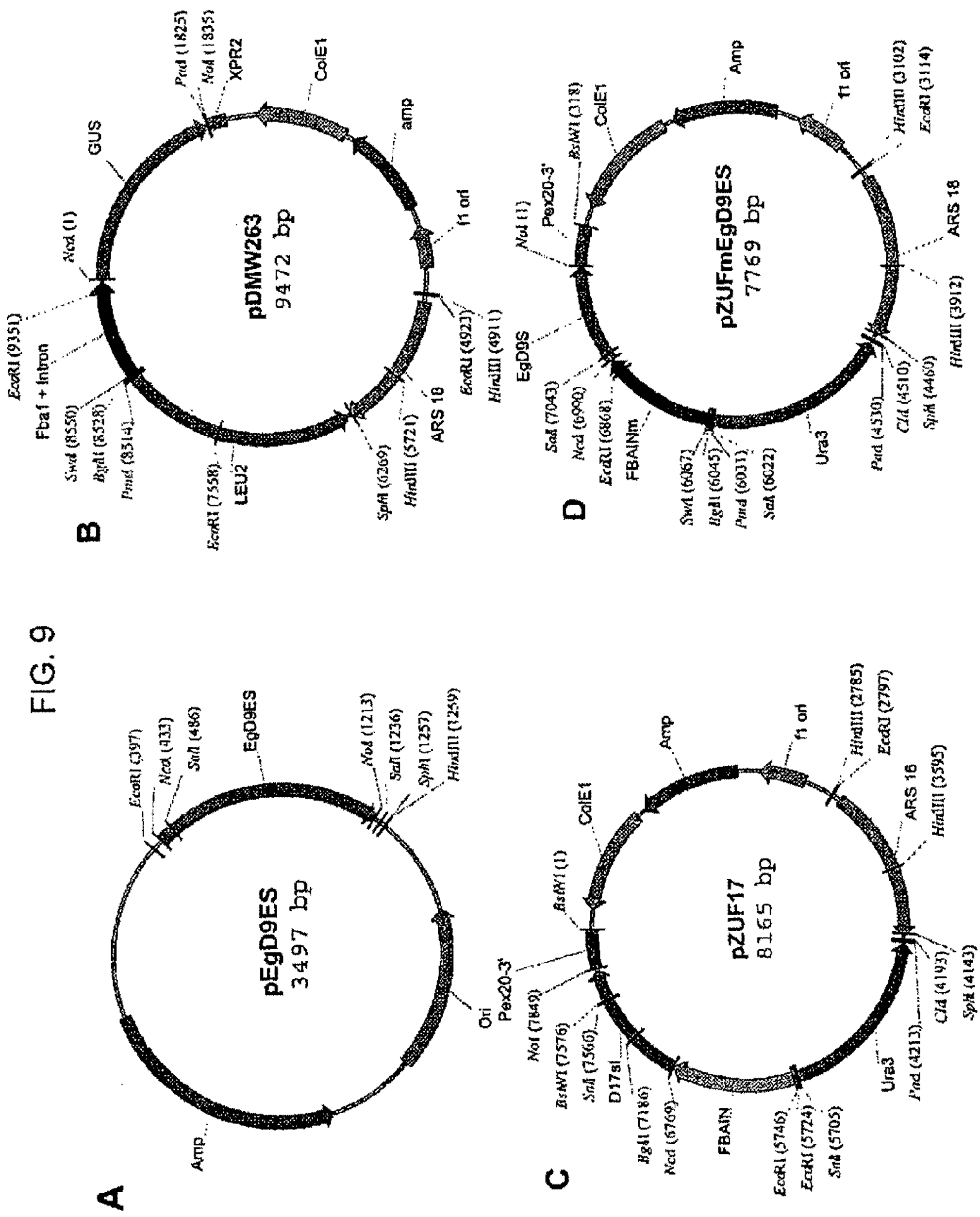

FIGS. 9-A, 9-B, 9-C and 9-D are maps of plasmids pEgD9ES, pDMW263, pZUF17 and pZUFmEgD9ES.

Figure 10:
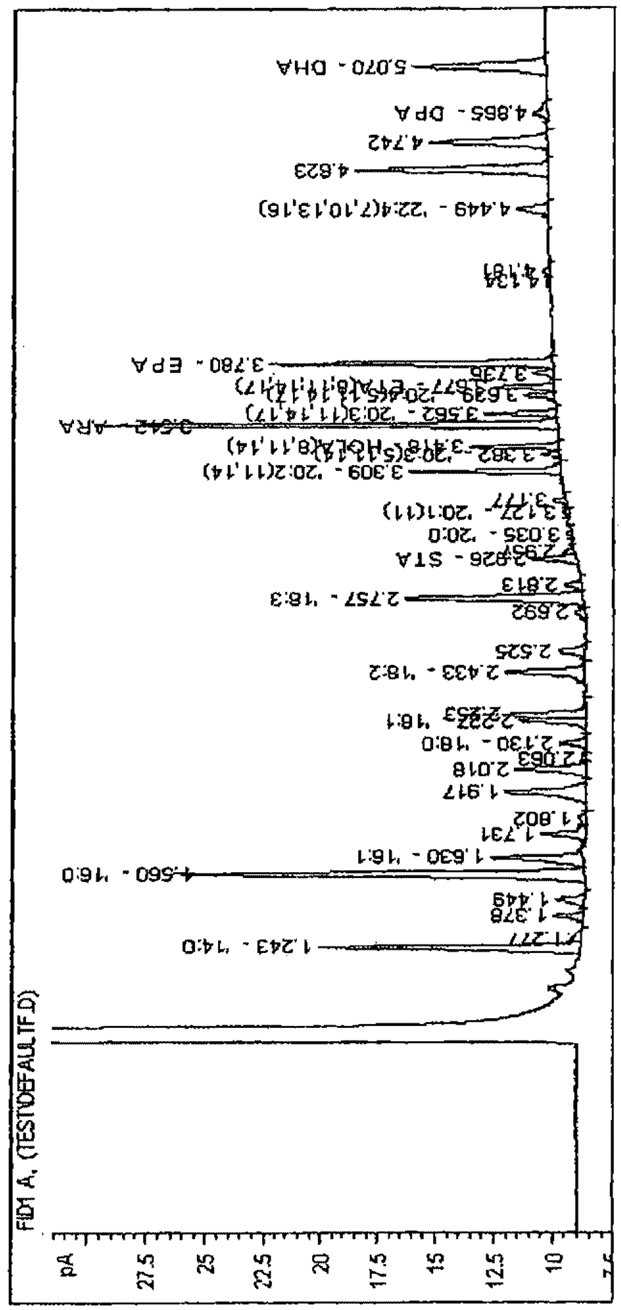

FIG. 10 shows a chromatogram of the lipid profile of an *Euglena gracilis* cell extract as described in the Examples.

FIGS. 11-A, 11-B, 11-C and 11-D is a map of plasmids pPiD8S, pEXPGUS1-C and pZGD5T-CP and pZUFmE9SP8S.

Figure 12:
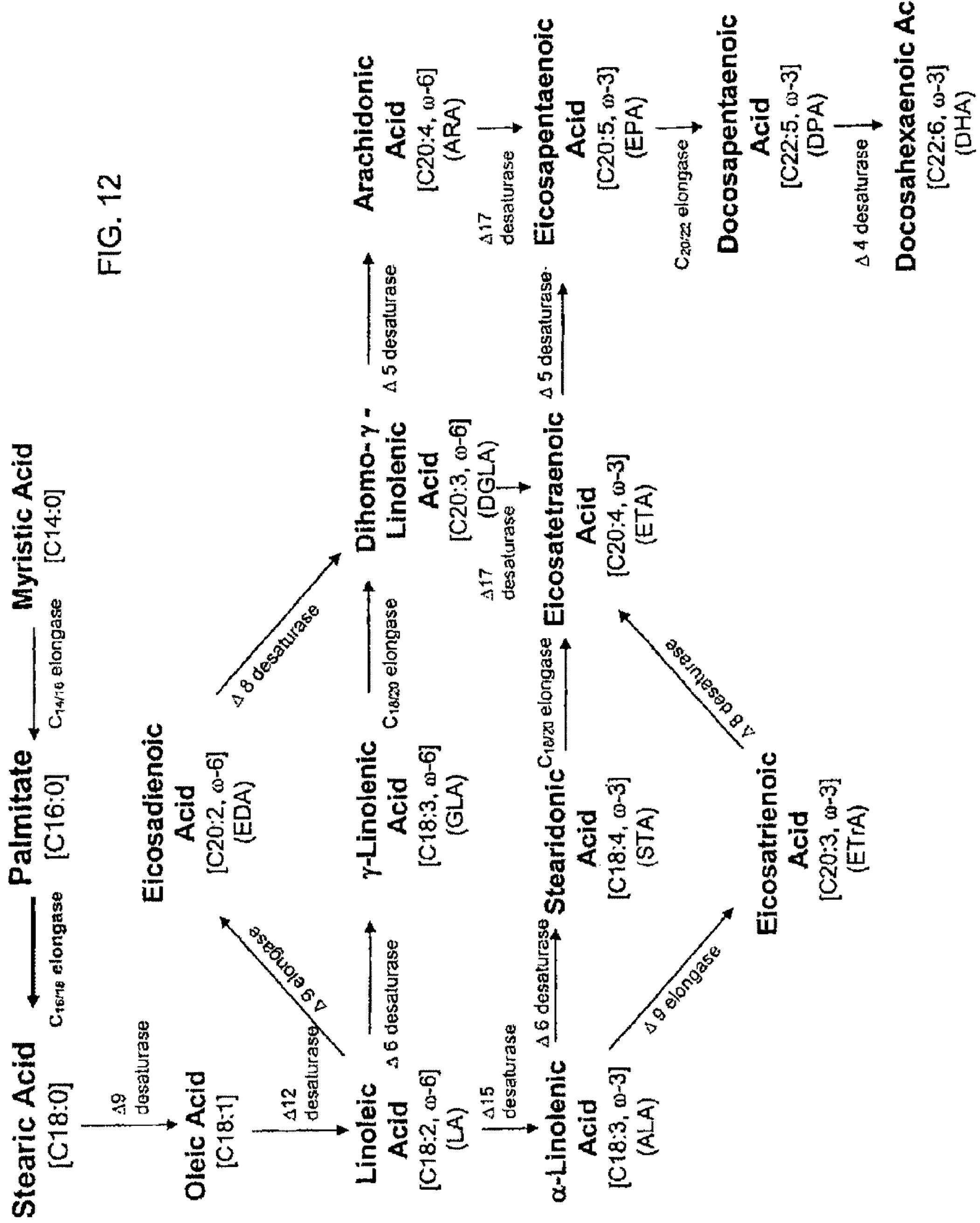

FIG. 12 is a representative omega-3 and omega-6 fatty acid pathway providing for the conversion of myristic acid through various intermediates to docosahexaenoic acid (DHA).

FIGS. 13A and 13B show a Clustal V alignment (with default parameters) of SEQ ID NO:16 (the amino acid sequence of the delta-8 desaturase of the instant invention), SEQ ID NO:76 (the amino acid sequence of *Pavlova salina* delta-8 desaturase sequence disclosed as SEQ ID NO:1 in PCT Publication No. WO 2005/103253; published Apr. 22, 2005), SEQ ID NO:77 (the amino acid sequence of *Euglena gracilis* delta-8 desaturase sequence disclosed as SEQ ID NO:2 in PCT Publication No. WO 2006/012325; published Feb. 2, 2006), SEQ ID NO:17 (the amino acid sequence for the *Rhizopus stolonifer* delta-6 fatty acid desaturase (NCBI Accession No. ABB96724 (GI 83027409), locus ABB96724, CDS DQ291156; Zhang et al., unpublished)) and SEQ ID NO:2 (the amino acid sequence for the *Rhizopus stolonifer* delta-6 fatty acid desaturase (NCBI Accession No. AAX22052 (GI 60499699), locus AAX22052, CDS AY795076; Lu et al., unpublished)).

Figure 7:
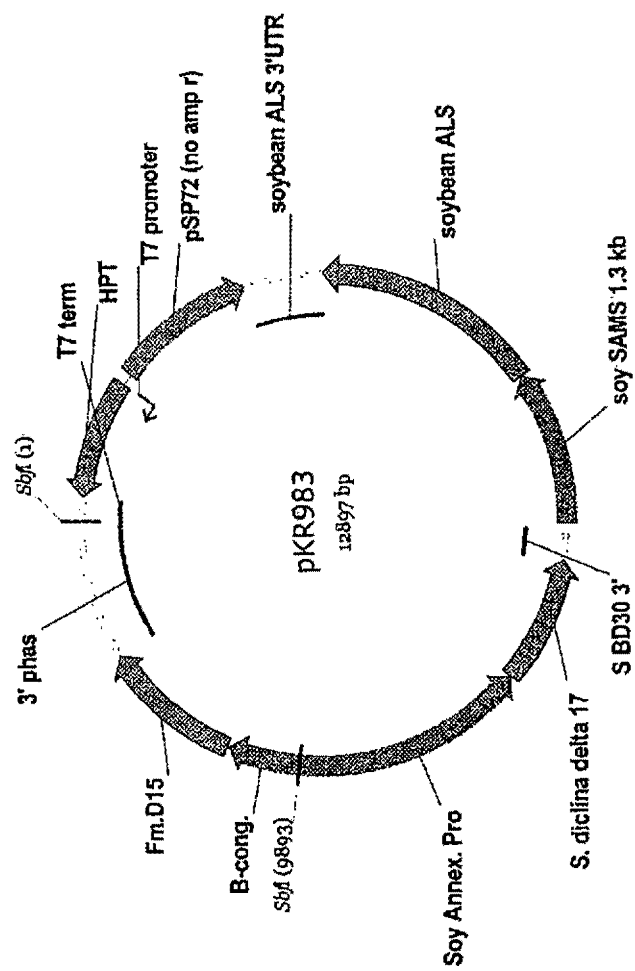
FIG. 7 is a map of plasmid pKR983 (soybean expression vector).

FIG. 14 shows the average fatty acid profile for the ten best EPA events of soybean embryogenic suspension culture (cv. Jack) transformed with the AscI fragments of pKR973 (SEQ ID NO:45, FIG. 5) and pKR983 (SEQ ID NO:56; FIG. 7) (see Example 22).

SEQ ID NO:1 is the sequence of the T7 primer.

SEQ ID NO:2 is the amino acid sequence for the *Rhizopus* stolonifer delta-6 fatty acid desaturase (NCBI Accession No. AAX22052 (GI 60499699), locus AAX22052, CDS AY795076; Lu et al., unpublished).

SEQ ID NO:3 is the sequence of a portion of the cDNA insert from clone eps1c.pk002.f22 (5' end of cDNA insert).

SEQ ID NO:4 is nucleotide sequence of the fully sequenced EST eps1c.pk002.f22:fis (full insert sequence—FIS).

SEQ ID NO:5 is the deduced amino acid sequence of SEQ ID NO:4 (clone eps1c.pk002.f22:fis).

SEQ ID NO:6 is the sequence of the SeqE primer.

SEQ ID NO:7 is the sequence of the SeqW primer.

SEQ ID NO:8 is the amino acid sequence of the *Mortierella alpina* delta-6 desaturase (NCBI Accession No. BAC82361 (GI 34221934), locus BAC82361, CDS AB070557; Sakuradani and Shimizu, *Biosci. Biotechnol. Biochem.* 67:704-711 (2003)).

SEQ ID NO:9 is the sequence of the AP1 universal primer.

SEQ ID NO:10 is the sequence of the GSP PvDES primer.

SEQ ID NO:11 is the sequence of the M13-28Rev primer.

SEQ ID NO:12 is the sequence of the PvDES seq primer.

SEQ ID NO:13 is the full 5' end sequence from genome walk of *Pavlova latheri* delta-8 desaturase.

SEQ ID NO:14 is the nucleotide sequence of the *Pavlova lutheri* delta-8 desaturase of the instant invention.

SEQ ID NO:15 is the nucleotide sequence of the CDS of SEQ ID NO:14 (Pavlova lutheri delta-8 desaturase of the instant invention).

SEQ ID NO:16 is the deduced amino acid sequence of SEQ ID NO:15 (delta-8 desaturase of the instant invention).

SEQ ID NO:17 is the amino acid sequence for the *Rhizopus* stolonifer delta-6 fatty acid desaturase (NCBI Accession No. ABB96724 (GI 83027409), locus ABB96724, CDS DQ291156; Zhang et al., unpublished).

SEQ ID NO:18 is the sequence of the PvDES5'Not-1 primer.

SEQ ID NO:19 is the sequence of the PvDES3'Not-1 primer.

SEQ ID NO:20 is the sequence of the GSP PvDES-2 primer.

SEQ ID NO:21 is the sequence of pY121.

SEQ ID NO:22 is the sequence of pKR123r.

SEQ ID NO:23 is the sequence of pKR900.

SEQ ID NO:24 is the sequence of pKR925.

SEQ ID NO:25 is the sequence of pKR902.

SEQ ID NO:26 is the sequence of pKR607.

SEQ ID NO:27 is the sequence of pKR903.

SEQ ID NO:28 is the sequence of the GPDsense primer.

SEQ ID NO:29 is the sequence of the GPDantisense primer.

SEQ ID NO:30 is the sequence of pY5-22GPD.

SEQ ID NO:31 is the sequence of pY118.

SEQ ID NO:32 is the nucleotide sequence of the CDS of *Euglena gracilis* delta-9 elongase.

SEQ ID NO:33 is the sequence of oEugEL1-1 primer.

SEQ ID NO:34 is the sequence of oEugEL1-2 primer.

SEQ ID NO:35 is the sequence of pKR906.

SEQ ID NO:36 is the sequence of pKR132.

SEQ ID NO:37 is the sequence of pKR953.

SEQ ID NO:38 is the sequence of pKR287.

SEQ ID NO:39 is the nucleotide sequence of the CDS of *Mortierella alpina* delta-5 desaturase, which is described in U.S. Pat. No. 6,075,183 and PCT Publication Nos. WO 2004/071467 and WO 200510479479.

SEQ ID NO:40 is the sequence of pKR277.

SEQ ID NO:41 is the sequence of pKR952.

SEQ ID NO:42 is the sequence of pKR457.

SEQ ID NO:43 is the sequence of the modified Kti/NotI/Kti3'Salb3' cassette.

SEQ ID NO:44 is the sequence of pKR970.

SEQ ID NO:45 is the sequence of pKR973.

SEQ ID NO:46 is the sequence of pKR72.

SEQ ID NO:47 is the sequence of pKR912.

SEQ ID NO:48 is the sequence of pKR886r.

SEQ ID NO:49 is the sequence of pKR271.

SEQ ID NO:50 is the sequence of pKR226.

SEQ ID NO:51 is the sequence of the oCon-1 primer.

SEQ ID NO:52 is the sequence of the oCon-2 primer.

SEQ ID NO:53 is the sequence of pKR179.

SEQ ID NO:54 is the sequence of pKR226.

SEQ ID NO:55 is the sequence of pKR582.

SEQ ID NO:56 is the sequence of pKR983.

SEQ ID NO:57 is the nucleotide sequence for the synthetic (codon-optimized) delta-8 desaturase derived from *Pavlova lutheri* codon-optimized for expression in *Yarrowia lipolytica.*

SEQ ID NO:58 is the sequence of pPiD8S.

SEQ ID NO:59 is the nucleotide sequence of the long-chain PUFA elongation enzyme from *Isochrysis galbana* (NCBI Accession No. AAL37626 (GI 17226123), locus AAL37626, CDS AF390174).

SEQ ID NO:60 is the 5' sequence of the cDNA insert from clone eeg1c.pk001.n5.f, while SEQ ID NO:61 is the 3' sequence of the cDNA insert from clone eeg1c.pk001.n5.f.

SEQ ID NO:61 is the 3' sequence of the cDNA insert from clone eeg1c.pk001.n5.f.

SEQ ID NO:62 is the sequence aligned from SEQ ID NO:60 and SEQ ID NO:61 (full cDNA sequence excluding polyA tail).

SEQ ID NO:63 is nucleotide sequence of the M13F universal primer.

SEQ ID NO:64 is the deduced amino acid sequence of SEQ ID NO:63 (delta-9 elongase—clone eeg1c.pk001.n5.f).

SEQ ID NO:65 amino acid sequence of the long-chain PUFA elongation enzyme from *Isochrysis galbana* (NCBI Accession No. AAL37626 (GI 17226123), locus AAL37626, CDS AF390174).

SEQ ID NO:66 is the nucleotide sequence of the synthetic (codon-optimized) delta-9 elongase derived from *Isochrysis galbana* codon-optimized for expression in *Yarrowia lipolytica.*

SEQ ID NO:67 is the sequence of pEgD9ES.

SEQ ID NO:68 is the sequence of pDMW263.

SEQ ID NO:69 is the sequence of pZUF17.

SEQ ID NO:70 is the sequence of pZUFmEgD9ES.

SEQ ID NO:71 is the sequence of pZUFmE9SP8S.

SEQ ID NO:72 is the sequence of pEXPGUS1-C.

SEQ ID NO:73 is the sequence of pZGD5T-CP.

SEQ ID NO:74 is the sequence of pYZDE2-S.

SEQ ID NO:75 is the sequence of pY5-22.

SEQ ID NO:76 is the amino acid sequence of *Pavlova salina* delta-8 desaturase sequence disclosed as SEQ ID NO:1 in PCT Publication No. WO 2005/103253 (published Apr. 22, 2005).

SEQ ID NO:77 is the amino acid sequence of *Euglena gracilis* delta-8 desaturase sequence disclosed as SEQ ID NO:2 in Applicants' Assignee's co-pending application having application Ser. No. 11/166,003 filed Jun. 24, 2005 (PCT Publication No. WO 2006/012325; published Feb. 2, 2006).

SEQ ID NO:78 is the sequence of pY5-30.

DETAILED DESCRIPTION OF THE INVENTION

All patents, patent applications, and publications cited herein are incorporated by reference in their entirety.

In the context of this disclosure, a number of terms shall be utilized.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Fatty acids are described herein by a simple notation system of "X:Y", wherein the number before the colon indicates the number of carbon atoms in the fatty acid and the number after the colon is the number of double bonds that are present. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)). Unless otherwise specified 18:1, 18:2 and 18:3 refer to oleic, LA and linolenic fatty acids. If not specifically written as otherwise, double bonds are assumed to be of the cis configuration. For instance, the double bonds in 18:2 (9,12) would be assumed to be in the cis configuration.

A representative pathway is illustrated in FIG. 12, providing for the conversion of myristic acid through various intermediates to DHA, which demonstrates how both omega-3 and omega-6 fatty acids may be produced from a common source.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase metabolic pathway (delta-15 desaturase, delta-9 elongase, delta-8 desaturase, delta-5 desaturase and delta-17 desaturase), EDA, ERA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase metabolic pathway (delta-15 desaturase, delta-9 elongase, delta-8 desaturase, delta-5 desaturase and delta-17 desaturase), sciadonic acid (SCl) and juniperonic acid (JUP) also can be produced by the action of a delta-5 desaturase on either EDA or ERA, respectively. They are considered to be "by-product fatty acids" since neither can be further converted to EPA by the action of other metabolic pathway enzymes.

A metabolic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of omega-3 and omega-6 fatty acids, the abbreviations that will be used throughout the remainder of the specification, and each compounds' chemical name.

TABLE 2

Nomenclature of Polyunsaturated Fatty Acids

| Common Name | Abbreviation | Chemical Name | Shorthand Notation |
|---|---|---|---|
| oleic | — | cis-9-octadecenoic | 18:1 |
| linoleic | LA | cis-9,12-octadecadienoic | 18:2 ω-6 |
| gamma-linolenic | GLA | cis-6,9,12-octadecatrienoic | 18:3 ω-6 |
| eicosadienoic | EDA | cis-11,14-eicosadienoic | 20:2 ω-6 |
| dihomo-gamma-linolenic | DGLA or HGLA | cis-8,11,14-eicosatrienoic | 20:3 ω-6 |
| sciadonic | SCI | cis-5,11,14-eicosatrienoic | 20:3b ω-6 |
| arachidonic | AA or ARA | cis-5,8,11,14-eicosatetraenoic | 20:4 ω-6 |
| alpha-linolenic | ALA | cis-9,12,15-octadecatrienoic | 18:3 ω-3 |
| stearidonic | STA | cis-6,9,12,15-octadecatetraenoic | 18:4 ω-3 |
| eicosatrienoic | ETrA or ERA | cis-11,14,17-eicosatrienoic | 20:3 ω-3 |
| eicosa-tetraenoic | ETA | cis-8,11,14,17-eicosatetraenoic | 20:4 ω-3 |
| juniperonic | JUP | cis-5,11,14,17-eicosatrienoic | 20:4b ω-3 |
| eicosa-pentaenoic | EPA | cis-5,8,11,14,17-eicosapentaenoic | 20:5 ω-3 |
| docosa-pentaenoic | DPA | cis-7,10,13,16,19-docosapentaenoic | 22:5 ω-3 |
| docosa-hexaenoic | DHA | cis-4,7,10,13,6,19-docosahexaenoic | 22:6 ω-3 |

The term "essential fatty acid" refers to a particular PUFA that an organism must ingest in order to survive, being unable to synthesize the particular essential fatty acid de nova. For example, mammals can not synthesize the essential fatty acid LA. Other essential fatty acids include, but are not limited to, GLA, DGLA, AA, EPA and DHA.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan. Such oils can contain long-chain PUFAs.

The term "PUFA biosynthetic pathway" refers to a metabolic process that converts oleic acid to LA, EDA, GLA, DGLA, AA, ALA, STA, ETrA, ETA, EPA, DPA and DHA. This process is well described in the literature (e.g., see PCT Publication No. WO 2005/003322). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

"Desaturase" is a polypeptide which can desaturate one or more fatty acids to produce a mono- or poly-unsaturated fatty acid or precursor which is of interest. Of particular interest herein are delta-8 desaturases that will desaturate a fatty acid between the eighth and ninth carbon atom numbered from the carboxyl-terminal end of the molecule and that can, for example, catalyze the conversion of EDA to DGLA and/or ETrA to ETA. Other useful fatty acid desaturases include, for example, (1) delta-5 desaturases that catalyze the conversion of DGLA to AA and/or ETA to EPA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of AA to EPA and/or DGLA to ETA; and (7) delta-9 desaturases that catalyze the conversion of palmitate to palmitoleic acid (16:1) and/or stearate to oleic acid (18:1).

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA, LA to EDA, ALA to ERA and EPA to DPA.

For the purposes herein, an enzyme catalyzing the first condensation reaction (i.e., conversion of malonyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). In like manner, and of particular interest herein, a "delta-9 elongase" is able to catalyze the conversion of LA and ALA to EDA and ETrA. It is important to note that some elongases have broad specificity and thus a single enzyme may be capable of catalyzing several elongase reactions (e.g., thereby acting as both a $C_{16/18}$ elongase and a $C_{18/20}$ elongase).

In preferred embodiments, it is desirable to empirically determine the specificity of a fatty acid elongase by transforming a suitable host with the gene for the fatty acid elongase and determining its effect on the fatty acid profile of the host. Fatty acid elongases from different species can display great variability in substrate specificity. For example, *Mortierella alpina* delta-6 elongase acts as a $C_{18/20}$ elongase (elongation of GLA to DGLA) in yeast, but can additionally act as a $C_{20/22}$ elongation of LA or ALA to EDA or ETrA, respectively, in soybean The term "delta-9 elongase/delta-8 desaturase pathway" refers to a elongase for the elongation of EPA to DPA or as a delta-9 elongase for the biosynthetic pathway for production of long-chain PUFAs. This pathway, at a minimum, comprises a delta-9 elongase and a delta-8 desaturase, thereby enabling biosynthesis of DGLA and/or ETA from LA and ALA, respectively.

The term "delta-9 elongase" refers to an enzyme that is capable of catalyzing at least one elongase reaction such as the elongation of linoleic (LA) or alpha-linolenic acid (ALA) to EDA or ETrA, respectively. It may act as a $C_{16/18}$ elongase, $C_{18/20}$ elongase and $C_{20/22}$ elongase and may have alternate, but not preferred, specificities for delta-5 and delta-6 fatty acids such as EPA and/or GLA, respectively.

The term "delta-8 desaturase" refers to an enzyme that is capable of catalyzing at least one desaturation reaction such as the desaturation of eicosadienoic acid (EDA) or eicosatrienoic acid (ETrA) to DGLA or ETA, respectively. It acts as a $C_{20}$ desaturase.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

"Sequence identity" or "identity" in the context of nucleic acid or polypeptide sequences refers to the nucleic acid bases or amino acid residues in the two sequences that are the same when aligned for maximum correspondence over a specified comparison window.

Thus, "percentage of sequence identity" refers to the valued determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASARGENE bioinformatics computing suite (DNASTAR Inc., Madison, Wis.). Multiple alignment of the sequences are performed using the Clustal V method of alignment (Higgins, D. G. and Sharp, P. M. (1989) *Comput. Appl. Biosci.* 5:151-153; Higgins, D. G. et al. (1992) *Comput. Appl. Biosci.* 8:189-191) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 55% to 100%. Indeed, any integer amino acid identity from 50% to 100% may be useful in describing the present invention. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described below.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "expression cassette" as used herein, refers to a discrete nucleic acid fragment into which a nucleic acid sequence or fragment can be moved.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present), Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.* 16:651-659 (1998); Gura, *Nature* 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (Elmayan et al., *Plant Cell* 10:1747-1757 (1998)).

The term "oleaginous" refers to those organisms that tend to store their energy source in the form of lipid (Weete, In: Fungal Lipid Biochemistry, 2nd Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The "Clustal V method of alignment" corresponds to the alignment method labeled Clustal V (described by Higgins and Sharp, CABIOS. 5:151-153 (1989)) and found in the MegAlign™ program of the LASERGENE bioinformatics computing suite (DNASTAR Inc., Madison, Wis.). The "default parameters" are the parameters preset by the manufacturer of the program. For multiple alignments, they correspond to GAP PENALTY=10 and GAP LENGTH PENALTY=10; and, for pairwise alignments, they are KTUPLE 1, GAP PENALTY=3, WINDOW=5 and DIAGONALS SAVED=5. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

"Progeny" comprises any subsequent generation of a plant.

The present invention concerns an isolated polynucleotide comprising:

(a) a nucleotide sequence encoding a polypeptide having delta-8 desaturase activity, wherein the polypeptide has at least 80% amino acid identity, based on the Clustal V method of alignment, when compared to an amino acid sequence as set forth in SEQ ID NO:16;
(b) a nucleotide sequence encoding a polypeptide having delta-8 desaturase activity, wherein the nucleotide sequence has at least 90% sequence identity, based on the BLASTN method of alignment, when compared to a nucleotide sequence as set forth in SEQ ID NO:15; or
(c) a complement of the nucleotide sequence of (a) or (b), wherein the complement and the nucleotide sequence consist of the same number of nucleotides and are 100% complementary.

In still another aspect, this invention concerns an isolated polynucleotide comprising a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:15.

It was found that a comparison of SEQ ID NO:15 and SEQ ID NO:57 using the BLASTN method of alignment with default parameters showed that these sequences had at least 86% sequence identity.

This delta-8 desaturase may be used alone or in combination with other desaturase and elongase components to produce various omega-6 and omega-3 PUFAs, including e.g., DGLA, ETA, AA, EPA, DPA and/or DHA (FIG. 12). One skilled in the art will recognize the appropriate combinations of the delta-8 desaturase of the invention herein in conjunction with a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase, based on the particular host cell (and its native PUFA profile and/or desaturase and/or elongase profile), the availability of substrate, and the desired end product(s).

At times, it may be desirable to minimize by-product fatty acids. The relative abundance of by-product fatty acids could be decreased by increasing total delta-8 desaturase activity. One approach to minimize by-product fatty acids would be to express more than one delta-8 desaturase (i.e., the same or different delta-8 desaturase). For instance, the presence of sciadonic acid (SCI) and/or juniperonic acid (JUP), commonly found in the seed lipids of gymnosperms (Wolff et al., *Lipids* 35(1):1-22 (2000)), such as those in the Pinaceae family (pine), might be considered by-product fatty acids of a delta-6 desaturase or delta-9-elongase pathway. Although these fatty acids are considered to have various health-enhancing properties themselves (Nakane et al., *Biol. Pharm. Bull.* 23: 758-761 (2000)), their presence as by-product fatty acids in an engineered PUFA pathway, such as in an oilseed crop, may not be desirable depending on the application.

In another embodiment, this invention concerns a recombinant construct comprising the polynucleotide of the invention operably linked to at least one regulatory sequence.

As was noted above, a promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, Kunitz trypsin inhibitor 3 promoter, annexin promoter, Gly1 promoter, beta subunit of beta conglycinin promoter, P34/Gly Bd m 30K promoter, albumin promoter, Leg A1 promoter and Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J Biol. Chem.* 265(21):12486-93 (1990)); (4) a tomato ubiquitin gene promoter (Rolifinke et al., *Gene.* 211(2):267-76 (1998)); (5) a soybean heat shock protein promoter (Schoffl et al., *Mol Gen Genet.* 217(2-3): 246-53 (1989)); and, (6) a maize H3 histone gene promoter (Atanassova et al., *Plant Mol Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual; 2nd* ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant. The term "genome" refers to the following: (1) the entire complement of genetic material (genes and non-coding sequences) is present in each cell of an organism, or virus or organelle; (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of claim 5.

Also of interest is a method for producing a transformed plant comprising transforming a plant cell with the polynucleotide of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci. U.S.A.* 84:3962-3966 (1987)), microinjection, or particle bombardment (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to, soybean, *Brassica* species, sunflower, maize, cotton, flax and safflower.

Examples of polyunsaturated fatty acids having at least twenty carbon atoms and five or more carbon-carbon double bonds include, but are not limited to, omega-3 fatty acids such as EPA, DPA and DHA. Seeds obtained from such plants are also within the scope of this invention as well as oil obtained from such seeds.

In one embodiment this invention concerns an oilseed plant comprising: a) a first recombinant DNA construct comprising an isolated polynucleotide encoding a delta-8 desaturase polypeptide, operably linked to at least one regulatory sequence; and b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase.

Such desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain polyunsaturated fatty acids in a plant cell comprising:

(a) transforming a cell with the recombinant construct of the invention; and (b) selecting those transformed cells that make long-chain polyunsaturated fatty acids.

In still another aspect, this invention concerns a method for producing at least one polyunsaturated fatty acid in a soybean cell comprising:

(a) transforming a soybean cell with a first recombinant DNA construct comprising an isolated polynucleotide encoding a delta-8 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase;

(b) regenerating a soybean plant from the transformed cell of step (a); and (c) selecting those seeds obtained from the plants of step (b) having an altered level of polyunsaturated fatty acids when compared to the level in seeds obtained from a nontransformed soybean plant.

Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

Generalized Steps for Soybean Oil and Byproduct Production

| Process Step | Process | Impurities Removed and/or By-Products Obtained |
|---|---|---|
| # 1 | soybean seed | |
| # 2 | oil extraction | meal |
| # 3 | degumming | lecithin |
| # 4 | alkali or physical refining | gums, free fatty acids, pigments |
| # 5 | water washing | soap |
| # 6 | bleaching | color, soap, metal |
| # 7 | (hydrogenation) | |
| # 8 | (winterization) | stearine |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995).

Soybean oil is liquid at room temperature because it is relatively low in saturated fatty acids when compared with oils such as coconut, palm, palm kernel and cocoa butter. Many processed fats (including spreads, confectionary fats, hard butters, margarines, baking shortenings, etc.) require varying degrees of solidity at room temperature and can only be produced from soybean oil through alteration of its physical properties. This is most commonly achieved through catalytic hydrogenation.

Hydrogenation is a chemical reaction in which hydrogen is added to the unsaturated fatty acid double bonds with the aid of a catalyst such as nickel. High oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have also become controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

Compared to other vegetable oils, the oils of the invention are believed to function similarly to other oils in food applications from a physical standpoint. Partially hydrogenated oils, such as soybean oil, are widely used as ingredients for soft spreads, margarine and shortenings for baking and frying.

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases. For example, palmitate is converted to its unsaturated derivative (palmitoleic acid (16:1)) by the action of a delta-9 desaturase. Similarly, palmitate is elongated by a $C_{16/18}$ fatty acid elongase to form stearic acid (18:0), which can be converted to its unsaturated derivative by a delta-9 desaturase to thereby yield oleic acid (18:1).

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid). The phosphate is then removed, by phosphatidic acid phosphatase, to yield 1,2-diacylglycerol. Triacylglycerol is formed upon the addition of a third fatty acid by the action of a diacylglycerol-acyl transferase.

Many microorganisms, including algae, bacteria, molds and yeasts, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means and the DNA sequences of some of these genes are publicly available. See, for example, AY131238, Y055118, AY055117, AF296076, AF007561, L11421, NM_031344, AF465283, AF465281, AF110510, AF465282, AF419296, AB052086, AJ250735, AF126799, AF126798 (delta-6 desaturases); AF199596, AF226273, AF320509, AB072976, AF489588, AJ510244, AF419297, AF07879, AF067654, AB022097 (delta-5 desaturases); AAG36933, AF110509, AB020033, AAL13300, AF417244, AF161219, AY332747, AAG36933, AF110509, X86736, AF240777, AB007640, AB075526, AP002063 (delta-12 desaturases); NP_441622, BAA18302, BAA02924, AAL36934 (delta-15 desaturases); AF338466, AF438199, E11366, E11367, D83185, U90417, AF085500, AY504633, NM_069854, AF230693 (delta-9 desaturases); AF390174 (delta-9 elongase); AF139720 and CQ831420 (delta-8 desaturase); and AX464731, NM_119617, NM_134255, NM_134383, NM_134382, NM_068396, NM_068392, NM_070713, NM_068746, NM_064685 (elongases).

Additionally, the patent literature provides many additional DNA sequences of genes (and/or details concerning several of the genes above and their methods of isolation) involved in PUFA production (e.g., PCT Publication No. WO 02/077213 (delta-9 elongases); PCT Publication No. WO 00/34439, WO 04/057001 and U.S. Pat. No. 6,825,017 (delta-8 desaturases); U.S. Pat. No. 5,968,809 (delta-6 desaturases); U.S. Pat. No. 5,972,664 and U.S. Pat. No. 6,075,183 (delta-5 desaturases); POT Publication No. WO 94/11516, U.S. Pat. No. 5,443,974, PCT Publication No. WO 03/099216 and PCT Publication No. WO 05/047485 (delta-12 desaturases); PCT Publication No. WO 93/11245 (delta-15 desaturases); PCT Publication No. WO 91/13972 and U.S. Pat. No. 5,057,419 (delta-9 desaturases); U.S. Publication No. 2003/0196217 A1 (delta-17 desaturase); and PCT Publication No. WO 00/12720 and PCT Publication No. WO 2002/077213, U.S. Pat. No. 6,403,349, U.S. Pat. No. 6,677,145, and U.S. Publication No. 2004/0111763 ($C_{14/16}$, $C_{16/18}$ and $C_{18/20}$ elongases)). Each of these patents and applications are herein incorporated by reference in their entirety.

As will be obvious to one skilled in the art, the particular functionalities required to be introduced into a microbial host organism for production of a particular PUFA final product will depend on the host cell (and its native PUFA profile and/or desaturase/elongase profile), the availability of substrate and the desired end product(s). LA, GLA, EDA, DGLA, AA, ALA, STA, ETrA, ETA, EPA, DPA and DHA may all be produced in oleaginous yeasts, by introducing various combinations of the following PUFA enzyme functionalities: a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and/or a $C_{20/22}$ elongase. One skilled in the art will be able to identify various candidate genes encoding each of the above enzymes, according to publicly available literature (e.g., GenBank), the patent literature, and experimental analysis of microorganisms having the ability to produce PUFAs. The sequences may be derived from any source, e.g., isolated from a natural source (from bacteria, algae, fungi, plants, animals, etc.), produced via a semi-synthetic route or synthesized de novo. In some embodiments, manipulation of genes endogenous to the host is preferred; for other purposes, it is necessary to introduce heterologous genes.

Although the particular source of the desaturase and elongase genes introduced into the host is not critical to the invention, considerations for choosing a specific polypeptide having desaturase or elongase activity include (1) the substrate specificity of the polypeptide, (2) whether the polypeptide or a component thereof is a rate-limiting enzyme, (3) whether the desaturase or elongase is essential for synthesis of a desired PUFA, and/or (4) co-factors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired PUFA.

In some cases, the host organism in which it is desirable to produce PUFAs will possess endogenous genes encoding some PUFA biosynthetic pathway enzymes. For example, oleaginous yeast can typically produce 18:2 fatty acids (and some have the additional capability of synthesizing 18:3 fatty acids); thus, oleaginous yeast typically possess native delta-12 desaturase activity and may also have delta-15 desaturases. In some embodiments, therefore, expression of the native desaturase enzyme is preferred over a heterologous (or "foreign") enzyme since (1) the native enzyme is optimized for interaction with other enzymes and proteins within the cell, and (2) heterologous genes are unlikely to share the same codon preference in the host organism. Additionally, advantages are incurred when the sequence of the native gene is known, as it permits facile disruption of the endogenous gene by targeted disruption.

In many instances, however, the appropriate desaturases and elongases are not present in the host organism of choice to enable production of the desired PUFA products. Thus, it is necessary to introduce heterologous genes. In one embodiment of the present invention, work was conducted toward the goal of the development of an oleaginous yeast that accumulates oils enriched in long-chain omega-3 and/or omega-6 fatty acids via expression of a delta-9 elongase/delta-8 desaturase pathway, to enable production of EDA, DGLA, ARA, ALA, ETrA, ETA, EPA, DPA and/or DNA.

In order to express genes encoding the delta-9 elongase/delta-8 desaturase pathway for the biosynthesis of long-chain PUFAs (e.g., AA and EPA) in these organisms, it was therefore necessary to (1) identify a suitable delta-9 elongase and delta-8 desaturase that functioned relatively efficiently in oleaginous yeast based on substrate-feeding trials, and, (2) subject the delta-9 elongase and delta-8 desaturase gene to codon-optimization techniques (infra) to further enhance the expression of the heterologous enzymes in the alternate oleaginous yeast host, to thereby enable maximal production of omega-3 and/or omega-6 fatty acids.

It will be obvious to one of skill in the art that heterologous genes will be expressed with variable efficiencies in an alternate host. Thus, omega-3 and/or omega-6 PUFA production may be optimized by selection of a particular desaturase or elongase whose level of expression in a heterologous host is preferred relative to the expression of an alternate desaturase or elongase in the host organism of interest. Furthermore, it may be desirable to modify the expression of particular PUFA biosynthetic pathway enzymes to achieve optimal conversion efficiency of each, according to the specific PUFA product composition of interest. A variety of genetic engineering techniques are available to optimize expression of a particular enzyme. Two such techniques include codon optimization and gene mutation, as described below. Genes produced by, for example, either of these two methods, having desaturase and/or elongase activity(s) would be useful in the invention herein for synthesis of omega-3 and/or omega-6 PUFAs.

As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Then, the coding sequence for a polypeptide of interest having desaturase or elongase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In the present invention, it is desirable to modify a portion of the codons encoding the polypeptide having delta-8 desaturase activity, to enhance the expression of the gene in a host organism including, but not limited to, a plant, plant parts and/or oleaginous yeast *Yarrowia lipolytica*. The nucleic acid sequence of the native gene (i.e., the *Pavlova lutheri* delta-8 desaturase defined herein as SEQ ID NOs:14, 15 and 16) is modified to employ host-preferred codons. This wildtype desaturase has 423 amino acids (SEQ ID NO:16); in the codon-optimized gene (SEQ ID NO:57), 166 bp of the 1272 bp coding region (13.1%) and 161 codons are codon-optimized (38.1%) and the translation initiation site is modified.

The skilled artisan will appreciate that modulation of the *Pavlova lutheri* delta-8 desaturase as well as numerous other heterologous delta-8 desaturases from variable sources can be codon-optimized to improve their expression in an oleaginous yeast host (e.g, see Example 18 herein, wherein a synthetic codon-optimized delta-8 desaturase derived from *Pavlova lutheri* was created for expression in *Yarrowia lipolytica*). The present invention comprises the complete sequence of the synthetic codon-optimized gene as reported in the accompanying Sequence Listing (SEQ ID NO:57), the complement of those complete sequences, and substantial portions of those sequences. Furthermore, the codon-optimization method described in PCT Publication No. WO 2004/101753 and described herein for optimization of the *Pavlova lutheri* delta-8 desaturase is equally applicable to other genes in the omega-3/omega-6 fatty acid biosynthetic pathway.

Methods for synthesizing sequences and bringing sequences together are well established in the literature. For example, in vitro mutagenesis and selection, site-directed mutagenesis, error prone PCR (Melnikov et al., *Nucleic Acids Research,* 27(4):1056-1062 (February 1999)), "gene shuffling" or other means can be employed to obtain mutations of naturally occurring desaturase or elongase genes (wherein such mutations may include deletions, insertions and point mutations, or combinations thereof). This would permit production of a polypeptide having desaturase or elongase activity, respectively, in vivo with more desirable physical and kinetic parameters for function in the host cell such as a longer half-life or a higher rate of production of a desired PUFA. Or, if desired, the regions of a polypeptide of interest (i.e., a desaturase or an elongase) important for enzymatic activity can be determined through routine mutagenesis, expression of the resulting mutant polypeptides and determination of their activities. An overview of these techniques are described in PCT Publication No. WO 2004/101757. All such mutant proteins and nucleotide sequences encoding them that are derived from the codon-optimized gene described herein are within the scope of the present invention.

Microbial production of omega-3 and/or omega-6 fatty acids has several advantages. For example, (1) many microbes are known with greatly simplified oil compositions compared with those of higher organisms, making purification of desired components easier, (2) microbial production is not subject to fluctuations caused by external variables, such as weather and food supply, (3) microbially produced oil is substantially free of contamination by environmental pollutants, (4) microbes can provide PUFAs in particular forms which may have specific uses, and (5) microbial oil production can be manipulated by controlling culture conditions, notably by providing particular substrates for microbially expressed enzymes, or by addition of compounds/genetic engineering to suppress undesired biochemical pathways.

In addition to these advantages, production of omega-3 and/or omega-6 fatty acids from recombinant microbes provides the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs. For example, it is possible to modify the ratio of omega-3 to omega-6 fatty acids so produced, produce either omega-3 or omega-6 fatty acids exclusively while eliminating production of the alternate omega fatty acid, or engineer production of a specific PUFA without significant accumulation of other PUFA downstream or upstream products (e.g., enable biosynthesis of AA, EPA and/or DHA via the delta-9 elongase/delta-8 desaturase pathway, thereby avoiding synthesis of GLA and/or STA).

The genes and gene products described herein may be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the preferred desaturase and/or elongase sequences. These chimeric genes could then be introduced into appropriate microorganisms via transformation to provide high-level expression of the encoded enzymes.

Accordingly, it is expected that introduction of chimeric genes encoding a PUFA biosynthetic pathway, under the control of the appropriate promoters will result in increased production of omega-3 and/or omega-6 fatty acids. It is contemplated that it will be useful to express various combinations of these PUFA desaturase and elongase genes together in a host microorganism. It will be obvious to one skilled in the art that the particular genes included within a particular expression cassette(s) will depend on the host cell, its ability to synthesize PUFAs using native desaturases and elongases, the availability of substrate and the desired end product(s). For example, it may be desirable for an expression cassette to be constructed comprising genes encoding one or more of the following enzymatic activities: a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/16}$ elongase, a $C_{18/20}$ elongase and/or a $C_{20/22}$ elongase. As such, the present invention encompasses a method of producing PUFAs comprising exposing a fatty acid substrate to the PUFA enzyme(s) described herein, such that the substrate is converted to the desired fatty acid product. Thus, each PUFA gene and corresponding enzyme product described herein (e.g., a wildtype, codon-optimized, synthetic and/or mutant enzyme having appropriate desaturase or elongase activity) can be used directly or indirectly for the production of PUFAs. Direct production of PUFAs occurs wherein the fatty acid substrate is converted directly into the desired fatty acid product without any intermediate steps or pathway intermediates. For example, production of AA would occur in a host cell which produces or which is provided DGLA, by adding or introducing into said cell an expression cassette that provides delta-5 desaturase activity. Similarly, expression of the delta-8 desaturase of the invention permits the direct synthesis of EDA and ETrA (when provided LA and ALA, respectively, as substrate). Thus, for example, the present invention may encompass a method of producing either EDA or ETrA, respectively, comprising:

a) providing a host organism including, but not limited to, an oleaginous yeast comprising: (i) a gene encoding a delta-8 desaturase polypeptide as set forth in SEQ ID NO:16 or SEQ ID NO:57; and (ii) a source of desaturase substrate consisting of either EDA or ETrA, respectively; and,
b) growing the yeast of step (a) in the presence of a suitable fermentable carbon source wherein the gene encoding a delta-8 desaturase polypeptide is expressed and EDA is converted to DGLA or ETrA is converted to ETA, respectively; and,
c) optionally recovering the DGLA or ETA, respectively, of step (b).

In some preferred embodiments, the nucleotide sequence of a gene encoding a delta-8 desaturase polypeptide is set forth in SEQ ID NO:57 wherein at least 162 codons have been optimized for expression in *Yarrowia*.

In contrast, multiple genes encoding the PUFA biosynthetic pathway may be used in combination, such that a series of reactions occur to produce a desired PUFA. For example, expression cassette(s) encoding delta-9 elongase, delta-8 desaturase, delta-5 desaturase and delta-17 desaturase activity would enable a host cell that naturally produces LA, to instead produce ARA (such that LA is converted to EDA by delta-9 elongase; EDA may then be converted to DGLA by a delta-8 desaturase; DGLA is then converted to ARA by a delta-5 desaturase). In a related manner, expression of the delta-8 desaturase of the invention enables the direct/indirect production of ETA, EPA, DPA and/or DHA as down-stream PUFAs, if subsequent desaturase and elongation reactions are catalyzed. In a preferred embodiment, wherein the host cell is an oleaginous yeast, expression cassettes encoding each of the enzymes necessary for PUFA biosynthesis will need to be introduced into the organism, since naturally produced PUFAs in these organisms are limited to 18:2 fatty acids (i.e., LA), and less commonly, 18:3 fatty acids (i.e., ALA). Alternatively, substrate feeding may be required.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of desaturase and/or elongase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest, alternatively, stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from (1) genes in the glycolytic pathway, such as alcohol dehydrogenase, glyceraldehyde-3-phosphate-dehydrogenase (PCT Publication No. WO 2005/003310), phosphoglycerate mutase (PCT Publication No. WO 20051003310), fructose-bisphosphate aldolase (PCT Publication No. WO 2005/049805), phosphoglucose-isomerase, phosphoglycerate kinase, glycerol-3-phosphate O-acyltransferase (PCT Publication No. WO 2006/031937), etc.; or (2) regulatable genes such as acid phosphatase, lactase, metallothionein, glucoamylase, the translation elongation factor EF1-$\alpha$ (TEF) protein (U.S. Pat. No. 6,265,185), ribosomal protein S7 (U.S. Pat. No. 6,265,185), ammonium transporter proteins (U.S. application Ser. No. 11/185,301), export proteins, etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, as demonstrated in the invention herein in *Yarrowia lipolytica*, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding $\gamma$-interferon and $\alpha$-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation in the host organism and correct folding of the protein in the host organism; (5) the intrinsic stability of the mRNA and protein of the cloned gene within the host cell; and, (6) the codon usage within the cloned gene, such that its frequency approaches the frequency of preferred codon usage of the host cell. Each of these types of modifications are encompassed in the present invention, as means to further optimize expression of the PUFA biosynthetic pathway enzymes.

Once the DNA encoding a desaturase or elongase polypeptide suitable for expression in an oleaginous yeast has been obtained, it is placed in a plasmid vector capable of autonomous replication in a host cell; or, it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

A method of expressing genes in *Yarrowia lipolytica* is by integration of linear DNA into the genome of the host; and, integration into multiple locations within the genome can be particularly useful when high level expression of genes are desired. Toward this end, it is desirable to identify a sequence within the genome that is present in multiple copies.

Schmid-Berger et al. (*J. Bact.* 176(9):2477-2482 (1994)) discovered the first retrotransposon-like element Ylt1 in *Yarrowia lipolytica*. This retrotransposon is characterized by the presence of long terminal repeats (LTRs; each approximately 700 bp in length) called zeta regions. Ylt1 and solo zeta elements were present in a dispersed manner within the genome in at least 35 copies/genome and 50-60 copies/genome, respectively; both elements were determined to function as sites of homologous recombination. Further, work by Juretzek et al. (*Yeast* 18:97-113 (2001)) demonstrated that gene expression could be dramatically increased by targeting plasmids into the repetitive regions of the yeast genome (using linear DNA with LTR zeta regions at both ends), as compared to the expression obtained using low-copy plasmid transformants. Thus, zeta-directed integration can be ideal as a means to ensure multiple integration of plasmid DNA into *Yarrowia lipolytica*, thereby permitting high-level gene expression. Unfortunately, however, not all strains of *Yarrowia lipolytica* possess zeta regions (e.g., the strain identified as ATCC Accession No. 20362). When the strain lacks such regions, it is also possible to integrate plasmid DNA comprising expression cassettes into alternate loci to reach the desired copy number for the expression cassette. For example, preferred alternate loci include: the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus, the Lip1 gene locus (Gen Bank Accession No. Z50020) and/or the Lip2 gene locus (GenBank Accession No. AJ012632).

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology,* 194:186-187 (1991)]), protoplast fusion, holistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication No. WO 04/101757. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura-mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura− phenotype, wherein selection occurs based on 5-FOA resistance. Then, a cluster of multiple chimeric genes and a new Ura3 gene could be integrated into a different locus of the *Yarrowia* genome to thereby produce a new strain having a Ura+ phenotype. Subsequent integration would produce a new Ura3-strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the recombinantly expressed desaturases and/or elongases (and optionally other PUFA enzymes that are expressed within the host cell) may be produced by the host either naturally or transgenically, or they may be provided exogenously.

Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This may require metabolic engineering directly within the PUFA biosynthetic pathway or additional manipulation of pathways that contribute carbon to the PUFA biosynthetic pathway.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this.

To maximize production of omega-6 unsaturated fatty acids, it is well known to one skilled in the art that production is favored in a host microorganism that is substantially free of ALA. Thus, preferably, the host is selected or obtained by removing or inhibiting delta-15 or omega-3 type desaturase activity that permits conversion of LA to ALA. The endogenous desaturase activity can be reduced or eliminated by, for example, (1) providing a cassette for transcription of antisense sequences to the delta-15 desaturase transcription product, (2) disrupting the delta-15 desaturase gene through insertion, substitution and/or deletion of all or part of the target gene; or (3) using a host cell which naturally has [or has been mutated to have] low or no delta-15 desaturase activity. Inhibition of undesired desaturase pathways can also be accomplished through the use of specific desaturase inhibitors such as those described in U.S. Pat. No. 4,778,630.

Alternatively, it may be desirable to maximize production of omega-3 fatty acids (and minimize synthesis of omega-6 fatty acids). Thus, one could utilize a host microorganism wherein the delta-12 desaturase activity that permits conversion of oleic acid to LA is removed or inhibited, using any of the means described above (see also e.g., PCT Publication No. WO 2004/104167, herein incorporated entirely by reference). Subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

Beyond the immediate PUFA biosynthetic pathway, it is expected that manipulation of several other enzymatic pathways leading to the biosynthesis of precursor fatty acids may contribute to the overall net biosynthesis of specific PUFAs. Identification and manipulation of these related pathways will be useful in the future.

Additional copies of desaturase and elongase genes may be introduced into the host to increase the output of omega-3 and/or omega-6 fatty acid biosynthetic pathways. Expression of the desaturase or elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of the desaturase or elongase genes, as demonstrated in the instant invention, is to increase the translational efficiency of the encoded mRNAs by replacement of codons in the native gene with those for optimal gene expression in the selected host microorganism.

Conversely, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al. *J. Bacterial.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based (e.g., mutagenesis via UV radiation/chemical agents or use of transposable elements/transposons; see PCT Publication No. WO 2004/101757).

Within the context of the present invention, it may be useful to modulate the expression of the fatty acid biosynthetic pathway by any one of the methods described above. For example, the present invention provides methods whereby genes encoding key enzymes in the biosynthetic pathways are introduced into oleaginous yeasts for the production of omega-3 and/or omega-6 fatty acids. It will be particularly useful to express these genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial host cells for production of omega fatty acids may include microbial hosts that grow on a variety of feedstocks, including simple or complex carbohydrates, fatty acids, organic acids, oils and alcohols, and/or hydrocarbons over a wide range of temperature and pH values.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Yarrowia lipolytica* strains designated as ATCC Accession Nos. 20362, 8862, 18944, 76982 and/or LGAM S(7)1 (Papanikolaou, S., and Aggelis, G., *Bioresour. Technol.* 82(1):43-9 (2002)).

The transformed microbial host cell is grown under conditions that optimize desaturase and elongase activities and produce the greatest and the most economical yield of the preferred PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., yeast nitrogen base (Difco Laboratories, Detroit, Mich.)).

Fermentation media in the present invention must contain a suitable carbon source. Suitable carbon sources are taught in WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for PUFA production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. at al., *Ind. Appl. Single Cell Oils*, D. J. Kyle and R. Colin, eds. pp 61-97 (1992)).

Preferred growth media in the present invention are common commercially prepared media, such as yeast nitrogen base (Difco Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. This approach is described in PCT Publication No. WO 2004/101757, as are various suitable fermentation process designs (i.e., batch, fed-batch and continuous) and considerations during growth.

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details.

The market place currently supports a large variety of food and feed products, incorporating omega-3 and/or omega-6 fatty acids (particularly ARA, EPA and DHA). It is contemplated that the plant oils of the invention and the yeast oils of the invention comprising long-chain PUFAs will function in food and feed products to impart the health benefits of current formulations. More specifically, oils of the invention containing omega-3 and/or omega-6 fatty acids will be suitable for use in a variety of food and feed products including, but not limited to food analogs, meat products, cereal products, baked foods, snack foods and dairy products.

Additionally the present oils may be used in formulations to impart health benefit in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

A "food analog" is a food-like product manufactured to resemble its food counterpart, whether meat, cheese, milk or the like, and is intended to have the appearance, taste, and texture of its counterpart. Thus, the term "food" as used herein also encompasses food analogs. Food analogs can be made use processes well known to those skilled in the art. U.S. Pat. Nos. 6,355,296 B1 and 6,187,367 B1 describe emulsified meat analogs and emulsified meat extenders. U.S. Pat. No. 5,206,050 B1 describes soy protein curd useful for cooked food analogs (also can be used as a process to form a curd useful to make food analogs). U.S. Pat. No. 4,284,656 to Hwa describes a soy protein curd useful for food analogs. U.S. Pat. No. 3,988,485 to Hibbert at al. describes a meat-like protein food formed from spun vegetable protein fibers. U.S. Pat. No. 3,950,564 to Puski et al. describes a process of making a soy based meat substitute and U.S. Pat. No. 3,925,566 to Reinhart et al. describes a simulated meat product. For example, soy protein that has been processed to impart a structure, chunk or fiber for use as a food ingredient is called "textured soy protein" (TSP). TSPs are frequently made to resemble meat, seafood, or poultry in structure and appearance when hydrated.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

The beverage can be in a liquid or in a dry powdered form. For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the long-chain PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

A health food product is any food product that imparts a health benefit and include functional foods, medical foods, medical nutritionals and dietary supplements. Additionally, the oils of the invention may be used in standard pharmaceutical compositions (e.g., the long-chain PUFA containing oils could readily be incorporated into the any of the above mentioned food products, to thereby produce a functional or medical food). For example, more concentrated formulations comprising ARA, EPA or DHA include capsules, powders, tablets, softgels, gelcaps, liquid concentrates and emulsions which can be used as a dietary supplement in humans or animals other than humans.

Animal feeds are generically defined herein as products intended for use as feed or for mixing in feed for animals other than humans. The long-chain PUFA containing oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming which concerns the propagation, cultivation or farming of aquatic organisms and/or animals in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica:*

*Yarrowia lipolytica* strains with ATCC Accession Nos. 20362, 76982 and 90812 were purchased from the American Type Culture Collection (Rockville, Md.). *Yarrowia lipolytica* strains were typically grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol. Biotechnol.* 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica:*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G. and Nishida, I., *Arch Biochem Biophys.* 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

*Pavlova lutheri* (CCMP459) cDNA Synthesis, Library Construction and Sequencing A cDNA library of *Pavlova lutheri* (CCMP459) was synthesized as described in PCT Publication No. WO 2004/071467 ((published Aug. 26, 2004). Briefly, frozen pellets of Pav459 were obtained from Provasoli-Guillard National Center for Culture of Marine Phytoplankton (CCMP, West Boothbay Harbor, Me.). These pellets were crushed in liquid nitrogen and total RNA was extracted from Pav459 by using the Qiagen RNeasy® Maxi Kit (Qiagen, Valencia, Calif.), per manufacturers instructions. From this total RNA, mRNA was isolated using oligo dT cellulose resin, which was then used for the construction of a cDNA library using the pSport1 vector (Invitrogen, Carlsbad, Calif.). The cDNA thus produced was directionally cloned (5' SalI/3'NotI) into pSport1 vector. The Pav459 library contained approximately $6.1\times10^5$ clones per mL, each with an average insert size of approximately 1200 bp. The *Pavlova lutheri* library was named eps1c.

For sequencing, clones first were recovered from archived glycerol cultures grown/frozen in 384-well freezing media plates, and inoculated with an automatic QPix® colony picker (Genetix) in 96-well deep-well plates containing LB+100 mg/mL ampicillin. After growing 20 hours at 37° C., cells were pelleted by centrifugation and stored at −20° C. Plasmids then were isolated on an Eppendorf 5Prime robot, using a modified 96-well format alkaline lysis miniprep method (Eppendorf PerfectPrep®). Briefly, a filter and vacuum manifold was used to facilitate removal of cellular debris after acetate precipitation. Plasmid DNA was then bound on a second filter plate directly from the filtrate, washed, dried and eluted.

Plasmids were end-sequenced in 384-well plates, using vector-primed T7 primer (SEQ ID NO:1) and the ABI BigDye version 3 Prism sequencing kit. For the sequencing reaction, 100-200 ng of template and 6.4 pmoL of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

Example 2

Identification of Delta-8 Desaturase Enzyme Homologs from *Pavlova lutheri* cDNA Library eps1c cDNA clones encoding *Pavlova lutheri* delta-8 desaturase homologs (hereby called delta-8 desaturases) were identified by conducting BLAST (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States, *Nat. Genet.* 3:266-272 (1993)) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone eps1c.pk002.f22 revealed similarity of the protein encoded by the cDNA to the delta-6 desaturase from *Rhizopus stolonifer* (SEQ ID NO:2) (NCBI Accession No. AAX22052 (GI 60499699), locus AAX22052, CDS AY795076; Lu et al., unpublished). The sequence of a portion of the cDNA insert from clone eps1c.pk002.f22 is shown in SEQ ID NO:3 (5' end of cDNA insert). Subsequently, the full insert sequence (eps1c.pk002.f22:fis) was obtained and is shown in SEQ ID NO:4. Sequence for the deduced amino acid sequence (from nucleotide 1 of SEQ ID NO:4 to the first stop codon at nucleotide 864 of SEQ ID NO:4) is shown in SEQ ID NO:5. Full insert sequencing was carried out using a modified transposition protocol. Clones identified for FIS were recovered from archived glycerol stocks as single colonies, and plasmid DNA was isolated via alkaline lysis. Plasmid templates were transposed via the Template Generation System (TGS II) transposition kit (Finnzymes Oy, Espoo, Finland), following the manufacturer's protocol. The transposed DNA was transformed into EH10B electro-competent cells (Edge BioSystems, Gaithersburg, Md.) via electroporation. Multiple transformants were randomly selected from each transposition reaction, plasmid DNA was prepared, and templates were sequenced as above (ABI BigDye v3.1) outward from the transposition event site, utilizing unique primers SeqE (SEQ ID NO:6) and SeqW (SEQ ID NO:7).

Sequence data was collected (ABI Prism Collections software) and assembled using the Phrap sequence assembly program (P. Green, University of Washington, Seattle). Assemblies are viewed by the Consed sequence editor (D. Gordon, University of Washington, Seattle) for final editing.

The amino acid sequence set forth in SEQ ID NO:5 was evaluated by BLASTP, yielding a pLog value of 19.52 (E value of 3e-20) versus the delta-6 desaturase from *Mortierella alpina* (SEQ ID NO:8) (NCBI Accession No. BAC82361 (GI 34221934), locus BAC82361, CDS AB070557; Sakuradani and Shimizu, *Biosci. Biotechnol. Biochem.* 67:704-711 (2003)). Based on the results from the BLASTP comparison to the *Mortierella alpina* and other fatty acid desaturases, the *Pavlova lutheri* delta-8 desaturase was not full length and was lacking sequence at the 5' end.

Example 3

Cloning a Full-Length Delta-8 Desaturase from *Pavlova lutheri* Genomic DNA

Genomic DNA was isolated from *Pavlova lutheri* (CCMP459) using the Qiagen DNeasy® Plant Maxi Prep Kit according to the manufacturer's protocol. Using 1 maxi column per 1 gm of frozen cell pellet, a total of 122 pg of genomic DNA was isolated from 4 gm of *Pavlova lutheri* culture. The final concentration of genomic DNA was 22.8 ng/μL. GenomeWalker libraries were synthesized using the Universal GenomeWalker™ kit (BD Biosciences Clonetech, Palo Alto, Calif.) following the manufacturer's protocol (Prot #PT3042-1, version PRO3300). Briefly, four restriction digests were set up as per the protocol using 300 ng of genomic DNA per reaction. After phenol clean up, pellets were dissolved in 4 μL of water and adapters were ligated as per the protocol.

For the primary PCR, the Advantage®-GC Genomic PCR kit (BD Biosciences Clonetech) was used following the manufacturer's protocol (Prot #PT3090-1, version #PR1X433). For each restriction digest, 1 μL of library was combined with 22.8 μL of PCR grade water, 10 μL of 5×GC Genomic PCR Reaction Buffer, 2.2 μL of 25 mM $Mg(CH_3CO_2)_2$, 10 μL of GC-Melt (5 M), 1 μL of 50×dNTP mix (10 mM each), 1 μL of Advantage-GC Genomic Pol. Mix (50×), 1 μL of Universal GenomeWalker™ primer AP1 (10 μM, SEQ ID NO:9) and 1 μL of GSP PvDES (10 μM, SEQ ID NO:10). After denaturation at 95° C., the following reaction conditions were repeated 35 times: 94° C. for 30 sec, 68° C. for 6 min. After these reaction conditions, an additional extension at 68° C. was carried out for 6 min followed by cooling to 15° C. until removed.

The primary PCR reaction for each library was analyzed by agarose gel electrophoresis and DNA bands with molecular weights around 6 kb, 3.5 kb, 2.5 kb and 1.2 kb were observed. DNA bands for each library were purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol and inserts were sequenced using the T7 (SEQ ID NO:1) and M13-28Rev (SEQ ID NO:11) primers as described above. Additional sequence was then obtained using a gene-specific sequencing primer PvDES seq (SEQ ID NO:12) that was derived from the newly acquired sequence data. The full 5' end sequence obtained by genome walking is shown in SEQ ID NO:13. The sequence of the overlapping regions of the genomic sequence (SEQ ID NO:13) and the fully sequenced EST eps1c.pk002.f22:fis (SEQ ID NO:4) were aligned using Sequencher™ (Version 4.2, Gene Codes Corporation, Ann Arbor, Mich.) using the Large Gap assembly algorithm. Interestingly, the comparison showed that the EST that was originally sequenced (SEQ ID NO:4) was lacking 459 bp when compared to the genomic sequence (SEQ ID NO:13). This missing sequence in the EST appeared to be a deletion rather than an intron as no clear intron splice sites were identified in the genomic DNA at the 5' end of the gene. The genomic sequence for the 5' end (SEQ ID NO:13) was combined with the 3' end of the EST sequence (SEQ ID NO:4) to give SEQ ID NO:14. Using EditSeq™ 6.1 sequence analysis software (DNASTAR Inc., Madison, Wis.), an ORF was identified (SEQ ID NO:15). The amino acid sequence coded for by SEQ ID NO:15 is shown in SEQ ID NO:16.

The amino acid sequence set forth in SEQ ID NO:16 was evaluated by BLASTP, yielding a pLog value of 35.10 (E value of 8e-36) versus the delta-6 desaturase from *Rhizopus stolonifer* (SEQ ID NO:17) (NCBI Accession No. ABB96724 (GI 83027409), locus ABB96724, CDS DQ291156; Zhang et al., unpublished). Furthermore, the *Pavlova lutheri* delta-8 desaturase is 78.0% identical to the *Pavlova salina* delta-8 desaturase sequence (SEQ ID NO:76) disclosed in PCT Publication No. WO 2005/103253 (published Apr. 22, 2005) using the Jotun Hein method. Sequence percent identity calculations performed by the Jotun Hein method (Hein, J. J., *Meth. Enz.* 183:626-645 (1990)) were done using the MegAlign™ v6.1 program of the LASARGENE bioinformatics computing suite (DNASTAR Inc., Madison, Wis.) with the default parameters for pairwise alignment (KTUPLE=2). The *Pavlova lutheri* delta-8 desaturase is 76.4% identical to the *Pavlova salina* delta-8 desaturase sequence using the Clustal V method. Sequence percent identity calculations performed by the Clustal V method (Higgins, D. G. and Sharp, P. M., *Comput. Appl. Biosci.* 5:151-153 (1989); Higgins et al., *Comput. Appl. Biosci.* 8:189-191 (1992)) were done using the MegAlign™ v6.1 program of the LASARGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10). BLAST scores and probabilities indicate that the instant nucleic acid fragment (SEQ ID NO:15) encodes an entire *Pavlova lutheri* delta-8 desaturase.

FIGS. 13A and 13B show a Clustal V alignment (with default parameters) of SEQ ID NO:16 (the amino acid sequence of the delta-8 desaturase of the instant invention), SEQ ID NO:76 (the amino acid sequence of *Pavlova salina* delta-8 desaturase sequence disclosed as SEQ ID NO:1 in PCT Publication No. WO 2005/103253; published Apr. 22, 2005), SEQ ID NO:77 (the amino acid sequence of *Euglena gracilis* delta-8 desaturase sequence disclosed as SEQ ID NO:2 in PCT Publication No. WO 2006/012325; published Feb. 2, 2006), SEQ ID NO:17 (the amino acid sequence for the *Rhizopus stolonifer* delta-6 fatty acid desaturase (NCBI Accession No. ABB96724 (GI 83027409), locus ABB96724, CDS DQ291156; Zhang et al., unpublished)) and SEQ ID NO:2 (the amino acid sequence for the *Rhizopus stolonifer* delta-6 fatty acid desaturase (NCBI Accession No. AAX22052 (GI 60499699), locus AAX22052, CDS AY795076; Lu et al., unpublished)). The results of the Clustal V alignment show that SEQ ID NO:16 is 76.4%, 22.6%, 22.2%, and 22.2% identical to SEQ ID NO:76, SEQ ID NO:77, SEQ ID NO:17 and SEQ ID NO:2, respectively.

Example 4

Cloning the *Pavlova lutheri* Delta-8 Desaturase from *Pavlova lutheri* cDNA

*Pavlova lutheri* (CCMP459) was obtained from CCMP and grown in 250 mL flasks containing 50 mL of F/2-Si medium (made using F/2 Family Medium Kit-KIT20F2 and Filtered Seqwater-SEA2 from CCMP) at 26° C. with shaking at 150 rpm. Cultures were transferred to new medium on a weekly basis using 1:4 (old culture:new medium) dilution.

Cultures from 28 flasks (1400 mL) were combined, cells were pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided. In this way, 2.6 mg of total RNA (2.6 mg/mL) was obtained from the pellet. The mRNA was isolated from 1.25 mg of total RNA using the mRNA Purification Kit (Amersham Biosciences, Piscataway, N.J.) following the manufacturer's protocol provided. In this way, 112 μg of mRNA was obtained.

cDNA was synthesized from 224 ng of mRNA using the SuperScript™ First-Strand Synthesis System for RT-PCR Kit (Invitrogen™ Life Technologies, Carlsbad, Calif.) with the provided oligo(dT) primer according to the manufacturer's protocol. After RNase H treatment as per the protocol, the *Pavlova lutheri* delta-8 desaturase was amplified from the resulting cDNA with oligonucleotide primers PvDES5'Not-1 (SEQ ID NO:18) and PvDES3'Not-1 (SEQ ID NO:19) using the conditions described below.

cDNA (2 μL) from the reaction described above was combined with 50 pmol of PvDES5'Not-1 (SEQ ID NO:18), 50 pmol of PvDES3'Not-1 (SEQ ID NO:19), 1 μL of PCR nucleotide mix (10 mM, Promega, Madison, Wis.), 5 μL of 10×PCR buffer (Invitrogen Corporation), 1.5 μL of $MgCl_2$ (50 mM, Invitrogen Corporation), 0.5 μL of Taq polymerase (Invitrogen Corporation) and water to 50 μL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 μL and a DNA band with molecular weight around 1.3 kb was observed. The remaining 45 μL of product was separated by agarose gel electrophoresis and the DNA purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol. Multiple clones were sequenced using the T7 (SEQ ID NO:1), M13-28Rev (SEQ ID NO:11) and PvDes-2 (SEQ ID NO:20) oligonucleotides. The sequence of the clones tested were identical to that of SEQ ID NO:15 and one of the correct clones (pLF113) was chosen for further expression studies.

Example 5

Figure 1:
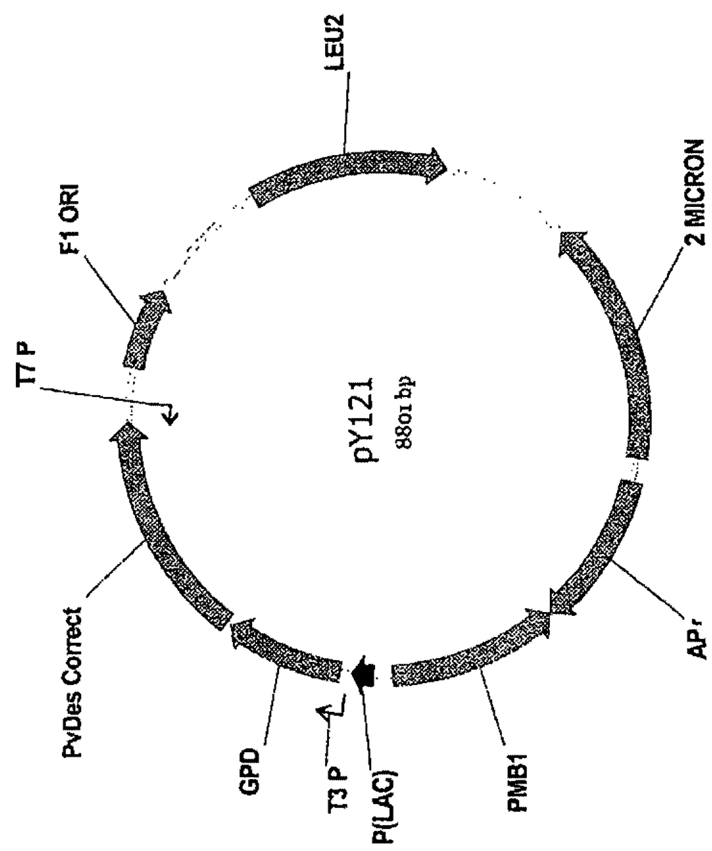
FIG. 1 is a map of plasmid pY121 (yeast expression vector).

Cloning the *Pavlova lutheri* Delta-8 Desaturase into a Yeast Expression Vector The yeast episomal plasmid (YEp)-type vector pRS425 (Christianson et al., *Gene* 110:119-122 (1992)) contains sequences from the *Saccharomyces cerevisiae* 2μ endogenous plasmid, a LEU2 selectable marker and sequences based on the backbone of a multifunctional phagemid, pBluescript II SK(+). The *Saccharomyces cerevisiae* strong, constitutive glyceraldehyde-3-phosphate dehydrogenase (GPD) promoter was cloned between the SacII and SpeI sites of pRS425 in the same way as described by Jia et al. (*Physiol. Genom.* 3:83-92 (2000)) to produce pGPD-425. A NotI site was introduced into the BamHI site of pGPD-425, thus giving a NotI site flanked by BamHI sites, and this plasmid was called pY-75. The *Pavlova lutheri* delta-8 desaturase was released from pLF113 (from Example 4) by digestion with NotI and cloned into the NotI site of pY75 to produce pY121 (SEQ ID NO:21; FIG. 1).

Example 6

Cloning the *Pavlova lutheri* Delta-8 Desaturase into a *Yarrowia* Expression Vector The *Yarrowia* GPD promoter was amplified from plasmid pYZDE2-S (SEQ ID NO:74) using oligonucleotides GPD-sense (SEQ ID NO:28) and GPDantisense (SEQ ID NO:29). The "*Yarrowia* GPD" promoter within this chimeric gene refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (WO 2005/003310). The resulting DNA fragment was digested with SalI/NotI and cloned into the SalI/NotI fragment of pY5-22 (SEQ ID NO:75) thus replacing the TEF promoter and giving pY5-22GPD (SEQ ID NO: 30).

Figure 4:
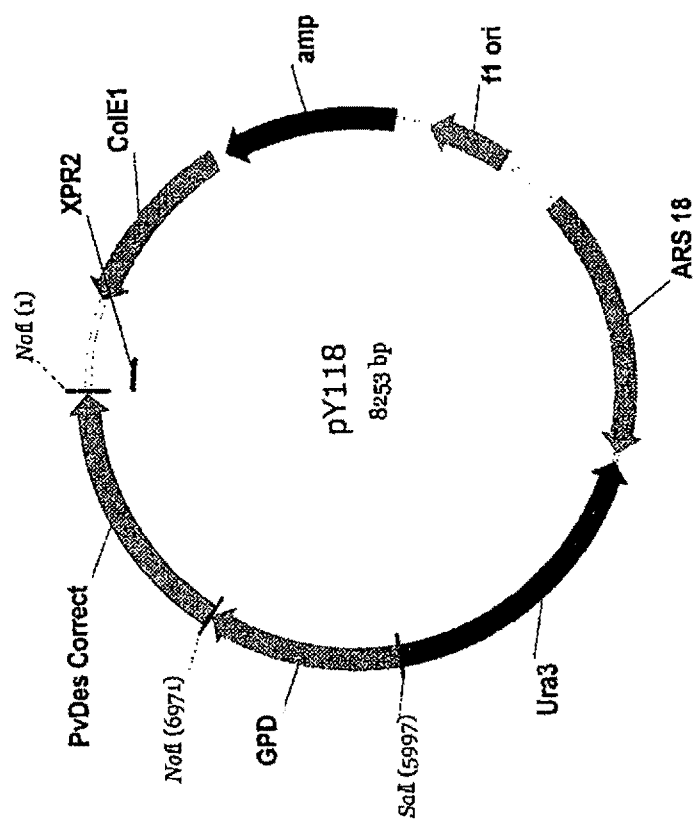
FIG. 4 is a map of plasmid pY118 (Yarrowia expression vector)

The *Pavlova lutheri* delta-8 desaturase was released from pLF113 (from Example 4) by digestion with NotI and cloned into the NotI site of pY5-22GPD to produce pY118 (SEQ ID NO:31; FIG. 4).

Example 7

Cloning the *Pavlova lutheri* Delta-8 Desaturase into a Soybean Expression Vector Vector pKR123r (SEQ ID NO:22), which was previously described in PCT Publication No. WO 2004/071467 (published Aug. 26, 2004; the contents of which are hereby incorporated by reference), contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965 (KTi/NotI/KTi3' cassette). The *Pavlova lutheri* delta-8 desaturase (SEQ ID NO:15) was released from pLF113 (from Example 4) by digestion with NotI and cloned into the NotI site of pKR123r to produce pKR900 (SEQ ID NO:23).

Plasmid pKR72 (ATCC Accession No. PTA-6019; SEQ ID NO:46, 7085 bp sequence), a derivative of pKS123 which was previously described in PCT Publication No. WO 2002/008269 (the contents of which are hereby incorporated by reference), contains the hygromycin B phosphotransferase gene (HPT) (Gritz, L. and Davies, J., *Gene* 25:179-188 (1983)), flanked by the T7 promoter and transcription terminator (T7prom/hpt/T7term cassette), and a bacterial origin of replication (ori) for selection and replication in bacteria (e.g., *E. coli*). In addition, pKR72 also contains the hygromycin B phosphotransferase gene, flanked by the 35S promoter (Odell et al., *Nature* 313:810-812 (1985)) and NOS 3' transcription terminator (Depicker et al., *J. Mol. Appl. Genet.* 1:561-570

(1982)) (35S/hpt/NOS3' cassette) for selection in plants such as soybean. pKR72 also contains a NotI restriction site, flanked by the promoter for the α' subunit of β-conglycinin (Beachy et al., *EMBO J.* 4:3047-3053 (1985)) and the 3' transcription termination region of the phaseolin gene (Doyle et al., *J. Biol. Chem.* 261:9228-9238 (1986)), thus allowing for strong tissue-specific expression in the seeds of soybean of genes cloned into the NotI site. The βcon/NotI/Phas3' cassette in plasmid pKR72 was removed by digestion with HindIII and the fragment containing the HPT gene was re-ligated to give pKR325 (SEQ ID NO:24), previously described in PCT Publication No. WO 2006/012325 (the contents of which are hereby incorporated by reference).

Figure 2:
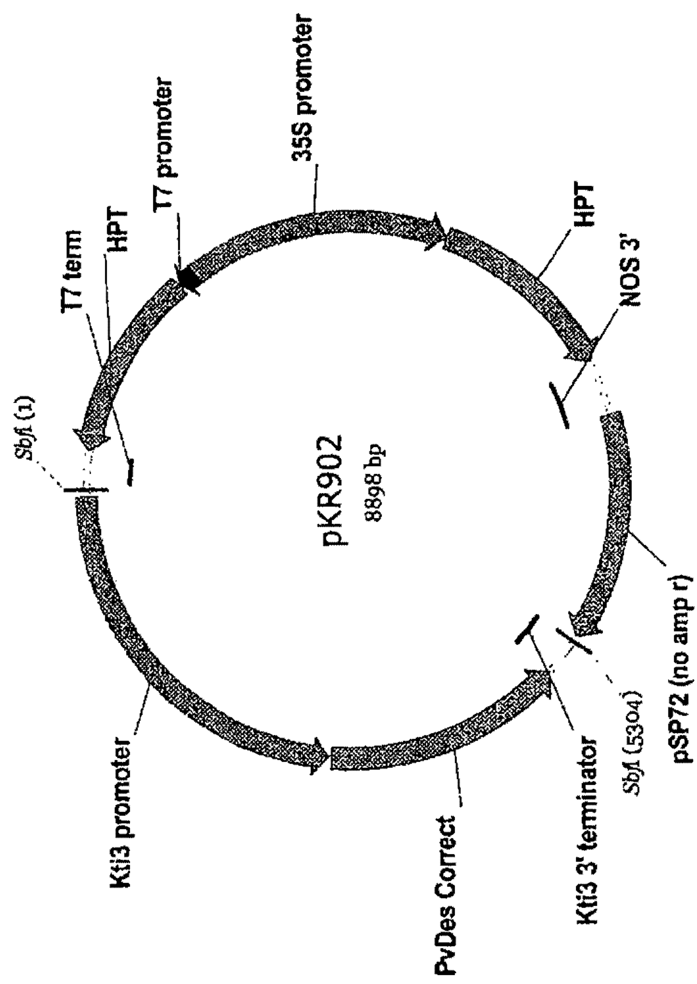
FIG. 2 is a map of plasmid pKR902 (soybean expression vector).

Plasmid pKR900 (SEQ ID NO:23) was then digested with SbfI and the fragment containing the *Pavlova lutheri* delta-8 desaturase was cloned into the SbfI site of pKR325 to produce pKR902 (SEQ ID NO:25). A schematic depiction of pK902 is shown in FIG. 2.

Example 8

Figure 3:
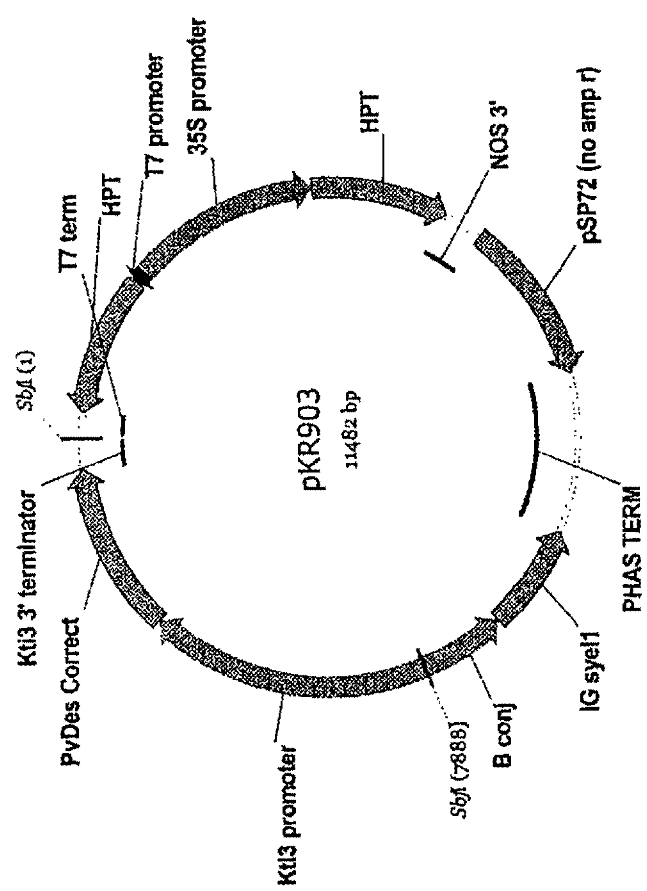
FIG. 3 is a map of plasmid pKR903 (soybean expression vector).

Cloning the *Pavlova lutheri* Delta-8 Desaturase into a Soybean Expression Vector and Co-expression with the *Isochrysis galbana* Delta-9 Elongase Plasmid pKR900 (from Example 7; SEQ ID NO:23) was digested with SbfI and the fragment containing the *Pavlova lutheri* delta-8 desaturase was cloned into the SbfI site of pKR607 (SEQ ID NO:26), previously described in PCT Publication No. WO 2006/012325 (the contents of which are hereby incorporated by reference) to give pKR903 (SEQ ID NO:27). In this way, the *Pavlova lutheri* delta-8 desaturase is co-expressed with the *Isochrysis galbana* delta-9 elongase behind strong, seed-specific promoters. A schematic depiction of pK903 (ATCC Accession No. PTA-7494) is shown in FIG. 3.

Example 9

Functional Analysis of the *Pavlova lutheri* Delta-8 Desaturase in *Saccharomyces cerevisiae*

*Saccharomyces cerevisiae* expression plasmids pY121 and pY75 (from Example 5) were transformed into *Saccharomyces cerevisiae* INVSC1 (Invitrogen Corporation) using standard lithium acetate transformation procedures. Transformants were selected on DOBA media supplemented with CSM-leu (Qbiogene, Carlsbad, Calif.). Transformants were evaluated for delta-6, delta-8 and delta-5 desaturase activities in the following way. Transformants from each plate were inoculated into 2 mL of DOB medium supplemented with CSM-leu (Qbiogene) and 0.2% tergitol. Cells were grown for 1 day at 30° C. after which, 0.1 mL was transferred to 3 mL of the same medium supplemented with either linoleic acid [LA-18:2(9,12)], α-linolenic acid [ALA-18:3(9,12,15)], dihomo-gamma-linolenic acid [DGLA-20:3(8,11,14)], eicosadienoic acid [EDA-20:2(11,14)] or eicosatrienoic acid [ERA-20:3(11,14,17)] to 0.175 mM. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.* 276 (1):38-46 (1990)) with 500 μL of 1% sodium methoxide for 30 min. at 50° C. after which 500 μL of 1M sodium chloride and 100 μL of heptane were added. After thorough mixing and centrifugation, fatty acid methyl esters (FAMEs) were analyzed by GC as described supra. In so doing, no desaturation activity for any of the substrates tested could be detected.

Example 10

Functional Analysis of the *Pavlova lutheri* Delta-8 Desaturase in *Yarrowia lipolytica*

A uracil ura3 auxotrophic strain of *Yarrowia lipolytica* (strain Y2224) was used for functional assays. To produce Y2224, *Yarrowia lipolytica* (ATCC Accession No. 20362) cells from a YPD plate were streaked onto a minimal medium plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto minimal medium plates containing 200 mg/mL 5-FOA and minimal medium plates lacking uracil and uridine to confirm uracil ura3 auxotrophy. One confirmed auxotroph was designated Y2224.

*Yarrowia lipolytica* strain Y2224 was grown at 28° C. on YPD agar (1% yeast extract, 2% bactopeptone, 2% glucose, 2% agar). For selection of transformants, minimal medium (0.17% yeast nitrogen base (DIFCO Laboratories, Detroit, Mich.) without ammonium sulfate or amino acids, 2% glucose, 0.1% proline, pH 6.1) was used. Supplements of adenine, leucine, lysine and/or uracil are added to a final concentration of 0.01%.

Transformation of *Yarrowia lipolytica*

Plasmid pY118, containing the *Pavlova lutheri* delta-8 desaturase, or pY5-22GPD, the vector control, were transformed into *Yarrowia lipolytica* strain Y2224 as described in the General Methods.

Briefly, *Yarrowia lipolytica* Strain #2224 was streaked onto a YPD plate and grown at 30° C. for approximately 18 h. Several large loopfuls of cells were scraped from the plate and resuspended in 1 mL of transformation buffer containing: 0.25 mL of 50% PEG, average MW 3350; 0.125 mL of 2 M Li acetate, pH 6.0; 0.125 mL of 2M DTT; and 50 μg sheared salmon sperm DNA. About 500 ng of pY118 or pY5-22GPD plasmid DNA were incubated in 100 μL of resuspended cells, and maintained at 39° C. for 1 h with vortex mixing at 15 min intervals. The cells were plated onto minimal media plates lacking uracil and maintained at 30° C. for 2 to 3 days Single colonies of transformant *Yarrowia lipolytica* containing pY118 or pY5-22GPD were grown in 3 mL minimal media lacking uracil supplemented with 0.2% tergitol at 30° C. for 1 day. After this, 0.1 mL was transferred to 3 mL of the same medium supplemented with either no fatty acid, α-linolenic acid [ALA-18:3(9,12,15)], dihomo-gamma-linolenic acid [DGLA-20:3(8,11,14)], eicosadienoic acid [EDA-20:2 (11,14)] or eicosatrienoic acid [ERA-20:3(11,14,17)] to 0.175 mM. These were incubated for 16 h at 30° C., 250 rpm and then pellets were obtained by centrifugation. Cells were washed once with water, pelleted by centrifugation and air dried. Pellets were transesterified as described supra. FAMEs from cells containing pY118 were analyzed by GC as for cells containing pY121 in Example 9. In so doing, no desaturation activity for any of the substrates tested could be detected.

Example 11

Transformation of Somatic Soybean Embryo Cultures

Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 hr day/night photoperiod at light intensity of 60-85 μE/m2/s. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., *Nature,* 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB1 medium (25-30 cotyledons per plate). Plates were wrapped with fiber tape and stored for 8 weeks. After this time secondary embryos were cut and placed into SB196 liquid media for 7 days.

Preparation of DNA for Bombardment:

Either an intact plasmid or a DNA plasmid fragment containing the genes of interest and the selectable marker gene were used for bombardment. Fragments from soybean expression plasmids pKR902 and pKR903 were obtained by gel isolation of digested plasmids. In each case, 100 μg of plasmid DNA was used in 0.5 mL of the specific enzyme mix described below. Plasmids were digested with Ascl (100 units) in NEBuffer 4 (20 mM Tris-acetate, 10 mM magnesium acetate, 50 mM potassium acetate, 1 mM dithiothreitol, pH 7.9), 100 μg/mL BSA, and 5 mM beta-mercaptoethanol at 37° C. for 1.5 hr. The resulting DNA fragments were separated by gel electrophoresis on 1% SeaPlaque GTG agarose (BioWhitaker Molecular Applications) and the DNA fragments containing gene cassettes were cut from the agarose gel. DNA was purified from the agarose using the GELase digesting enzyme following the manufacturer's protocol.

A 50 μL aliquot of sterile distilled water containing 3 mg of gold particles was added to 5 μL of a 1 μg/μL DNA solution (either intact plasmid or DNA fragment prepared as described above), 50 μL 2.5M $CaCl_2$ and 20 μL of 0.1 M spermidine. The mixture was shaken 3 min on level 3 of a vortex shaker and spun for 10 sec in a bench microfuge. After a wash with 400 μL of 100% ethanol, the pellet was suspended by sonication in 40 μL of 100% ethanol. Five μL of DNA suspension was dispensed to each flying disk of the Biolistic PDS1000/HE instrument disk. Each 5 μL aliquot contained approximately 0.375 mg gold particles per bombardment (i.e., per disk).

Tissue Preparation and Bombardment with DNA:

Approximately 150-200 mg of 7 day old embryonic suspension cultures were placed in an empty, sterile 60×15 mm petri dish and the dish was covered with plastic mesh. Tissue was bombarded 1 or 2 shots per plate with membrane rupture pressure set at 1100 PSI and the chamber was evacuated to a vacuum of 27-28 inches of mercury. Tissue was placed approximately 3.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six days post-bombardment, the SB196 is exchanged with fresh SB196 containing 30 mg/L hygromycin. The selection media was refreshed weekly. Four to six weeks post-selection, green, transformed tissue may was observed growing from untransformed, necrotic embryogenic clusters. Isolated, green tissue was removed and inoculated into multiwell plates to generate new, clonally propagated, transformed embryogenic suspension cultures.

Embryo Maturation:

Embryos were cultured for four-six weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 μE/m$^2$s. After this time embryo clusters were removed to a solid agar media, SB166, for 1-2 weeks. Clusters were then subcultured to medium SB103 for 3 weeks. During this period, individual embryos were removed from the clusters and screened for alterations in their fatty acid compositions as described supra.

Media Recipes:

| SB 196 - FN Lite Liquid Proliferation Medium (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g sucrose
2 mL 2,4-D (20 mg/L final concentration)
pH 5.7
8 g TC agar SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g activated charcoal
pH 5.7
2 g gelrite SB 103 Solid Medium (Per Liter)

1 package MS salts (Gibco/BRL—Cat. No. 11117-066)
1 mL B5 vitamins 1000× stock
60 g maltose
750 mg MgCl2 hexahydrate
pH 5.7
2 g gelrite SB 71-4 Solid Medium (Per Liter)

1 bottle Gamborg's B5 salts w/sucrose (Gibco/BRL—Cat. No. 21153-036)
pH 5.7
5 g TC agar 2,4-D Stock Obtain premade from Phytotech Cat. No. D 295—concentration 1 mg/mL B5 Vitamins Stock (Per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

Example 12

Functional Analysis of the *Pavlova lutheri* Delta-8 Desaturase in Somatic Soybean Embryos Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

Transgenic somatic soybean embryos containing pKR902 (Example 7) or pKR903 (Example 8) were analyzed in the following way. Fatty acid methyl esters were prepared from single, matured, somatic soy embryos by transesterification. Individual embryos were placed in a vial containing 50 μL of trimethylsulfonium hydroxide (TMSH) and 0.5 mL of hexane and incubated for 30 min at room temperature while shaking. Fatty acid methyl esters (5 μL injected from hexane layer) were separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.). Routinely, 5-10 embryos per event were analyzed by GC, using the methodology described above.

Embryo fatty acid profiles for 20 events (5 embryos each) containing pKR902 (Example 7—*Pavlova lutheri* delta-8 desaturase only) were obtained. No delta-6 desaturase activity (i.e., conversion of LA to GLA or ALA to STA) could be detected in any of the events analyzed.

Embryo fatty acid profiles for 6 lines containing pKR903 (Example 8—*Pavlova lutheri* delta-8 desaturase and *Isochrysis galbana* delta-9 elongase) are shown in FIGS. 8A and 8B. Calculated overall % desaturation, % desaturation for n-3 and n-6 substrates and desaturation ratios are also shown in FIGS. 8A and 8B.

In summary of FIGS. 8A and 8B, the *Pavlova lutheri* delta-8 desaturase works well in soybean to convert both EDA and ERA to DGLA and ETA, respectively. The line with the highest average DGLA content (1890-3-5) had embryos with an average DGLA content of 20.7% and an average ETA content of 3.9%. The highest DGLA and ETA content for an individual embryo from this line was 26.3% and 5.4%, respectively. The highest average overall % desaturation (calculation described below) was 72.7% with the highest overall % desaturation for an individual embryo being 83.1%. When broken down into % desaturation for the n-6 and n-3 substrates, the highest average % desaturation was 80.5% and 47.9% for EDA and ERA, respectively. The highest % desaturation for an individual embryo was 89.9% and 55.9% for EDA and ERA, respectively. The *Pavlova lutheri* delta-8 desaturase has a preference for EDA over ERA with the average desaturation ratio ranging from 1.7 to 3.3. Interestingly, some GLA accumulates in embryos were the delta-8 desaturase is expressed well.

Furthermore, in summary of FIGS. 8A and 8B, the overall % desaturation (C20% delta-8 desaturation) was calculated by dividing the sum of the wt. % for DGLA and ETA by the sum of the wt. % for EDA, DGLA, ERA and ETA and multiplying by 100 to express as a %. The individual n-6 delta-8 desaturation (EDA % delta-8 desaturation) was calculated by dividing the sum of the wt. % for DGLA by the sum of the wt. % for EDA and DGLA and multiplying by 100 to express as a %. Similarly, the individual n-3 delta-8 desaturation (ERA % delta-8 desaturation) shown was calculated by dividing the sum of the wt. % for ETA by the sum of the wt. for ERA and ETA and multiplying by 100 to express as a %. The ratio of delta-8 desaturation for n-6 versus n-3 substrates (ratio EDA/ERA % desaturation) was obtained by dividing the EDA % delta-8 desaturation by the ERA % delta-8 desaturation.

Example 13

Cloning the *Pavlova lutheri* Delta-8 Desaturase into a Soybean Expression Vector Containing the *Euglena gracilis* Delta-9 Elongase and *Mortierella alpina* Delta-5 Desaturase The *Euglena gracilis* delta-9 elongase (SEQ ID NO:32) was amplified with oligonucleotide primers oEugEL1-1 (SEQ ID NO:33) and oEugEL1-2 (SEQ ID NO:34) using the VentR® DNA Polymerase (Cat. No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:35).

Plasmid pKR906 was digested with NotI and the fragment containing the *Euglena gracilis* delta-9 elongase was cloned into plasmid pKR132 (SEQ ID NO:36, which is described in PCT Publication No. WO 2004/071467) to give pKR953 (SEQ ID NO:37).

Vector pKR287 (SEQ ID NO:38; which is described in PCT Publication No. WO 2004/071467, published Aug. 26, 2004; the contents of which are hereby incorporated by reference), contains the *Mortierella alpina* delta-5 desaturase (SEQ ID NO:39), which is described in U.S. Pat. No. 6,075,183 and PCT Publication Nos. WO 2004/071467 and WO 2005/047479 (the contents of which are hereby incorporated by reference), flanked by the soybean glycinin Gy1 promoter and the pea leguminA2 3' termination region (Gy1/MaD5/legA2 cassette). Vector pKR287 was digested with SbfI/BsiWI and the fragment containing the Gy1/MaD5/legA2 cassette was cloned into the SbfI/BsiWI fragment of pKR277 (SEQ ID NO:40; which is described in PCT Publication No. WO 2004/071467, the contents of which are hereby incorporated by reference) to produce pK952 (SEQ ID NO:41).

Vector pKR457 (SEQ ID NO:42), which was previously described in PCT Publication No. WO 2005/047479 (the contents of which are hereby incorporated by reference), contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (Kti/NotI/Kti3'Salb3' cassette). Through a number of subcloning steps, sequences containing Asp718 restriction sites were added to the 5' and 3' ends of the Kti/NotI/Kti3'Salb3' cassette to give SEQ ID NO:43. After cloning the NotI fragment of pLF113 (Example 4), containing the *Pavlova lutheri* delta-8 desaturase, into the modified Kti/NotI/Kti3'SaIb3' cassette (SEQ ID NO:43), the DNA fragment was digested with Asp718 and cloned into the SbfI site of pKR952 (SEQ ID NO:41) to give pKR970 (SEQ ID NO:44).

Figure 5:
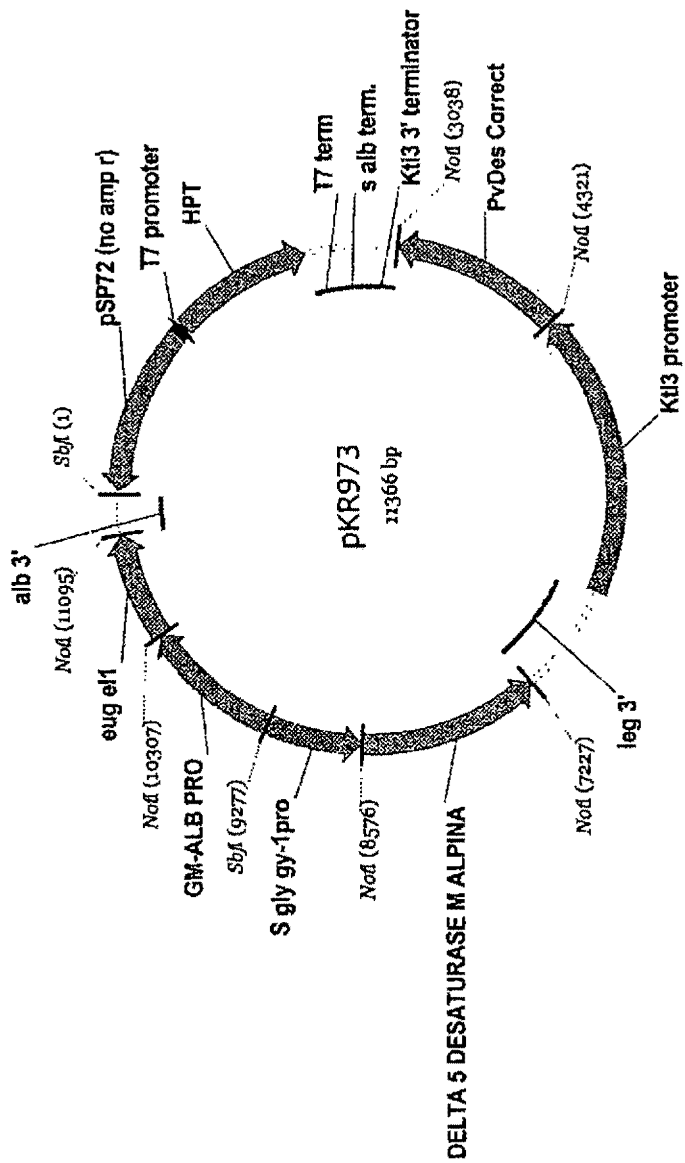
FIG. 5 is a map of plasmid pKR973 (soybean expression vector).

Plasmid pKR953 (SEQ ID NO:37) was digested with PstI and the fragment containing the *Euglena gracilis* delta-9 elongase was cloned into the SbfI site of pKR970 (SEQ ID NO:44) to give pKR973 (SEQ ID NO:45, FIG. 5).

In this way, the *Pavlova lutheri* delta-8 desaturase could be co-expressed with the *Mortierella alpina* delta-5 desaturase and the *Euglena gracilis* delta-9 elongase behind strong, seed-specific promoters.

Example 14

Figure 6:
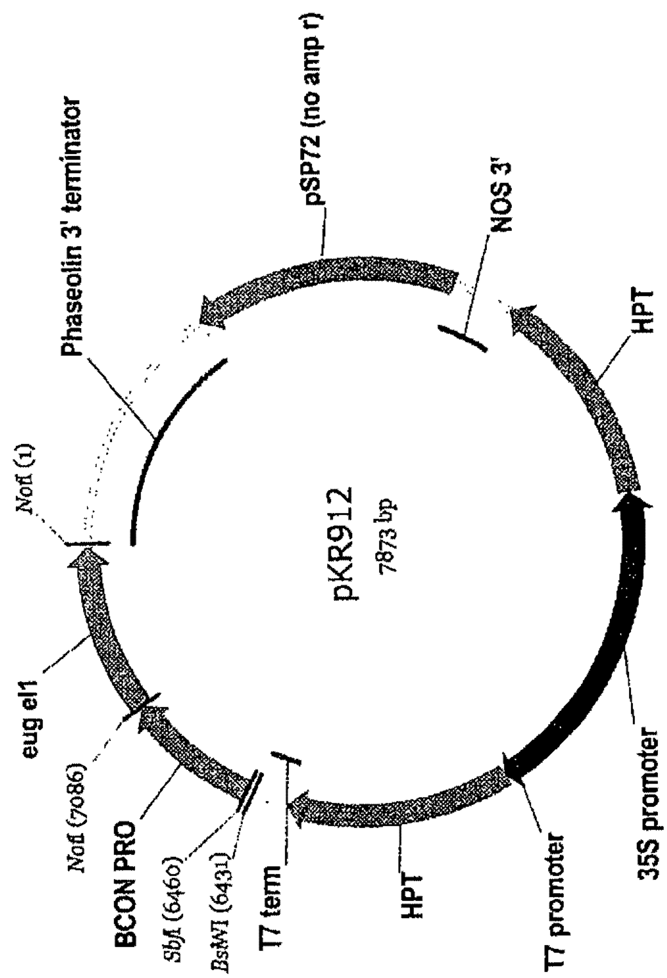
FIG. 6 is a map of plasmid pKR912 (soybean expression vector).

Cloning the *Euglena gracilis* Delta-9 Elongase into a Soybean Expression Vector The gene for the *Euglena gracilis* delta-9 elongase (SEQ ID NO:32) is released from pKR906 (SEQ ID NO:35) by digestion with NotI and cloned into the NotI site of pKR72 (SEQ ID NO:46 and has ATCC Accession No. PTA-6019) to produce pKR912 (SEQ ID NO:47). A schematic depiction of pKR912 is shown in FIG. 6.

Example 15

Construction of a Vector Containing the *Saprolegnia diclina* Delta-17 Desaturase and *Fusarium moniliforme* Delta-15 Desaturase Vector pKR886r (SEQ ID NO:48) was made by cloning the PstI fragment, containing the Ann/Sdd17/BD30 cassette from pKR271 (SEQ ID NO:49, which is described in PCT Publication No. WO 2004/071467) into the SbfI site of pKR226 (SEQ ID NO:50, which is described in PCT Publication No. WO 2004/071467).

The βcon/NotI/Phas3' cassette in plasmid pKR72 (SEQ ID NO:46 and has ATCC Accession No. PTA-6019) was amplified using oligonucleotide primers oCon-1 (SEQ ID NO:51) and oCon-2 (SEQ ID NO:52) using the VentR® DNA Polymerase (Cat. No. M0254S, New England Biolabs Inc., Beverly, Mass.) following the manufacturer's protocol. The resulting DNA fragment was digested with XbaI and cloned into the XbaI site of pUC19, to produce pKR179 (SEQ ID NO:53).

The *Fusarium monoliforme* delta-15 desaturase was released from plasmid pKR578 (SEQ ID NO:54, which is described in PCT Publication No. WO 2005/047479 and has ATCC Accession No. PTA-6280) by digestion with NotI and was cloned into the NotI site of plasmid pKR179 to give pKR582 (SEQ ID NO:55).

Vector pKR582 was digested with PstI and the fragment containing the *Fusarium monoliforme* delta-15 desaturase was cloned into the SbfI site of pKR886r (SEQ ID NO:48) to give pKR983 (SEQ ID NO:56). A schematic depiction of pKR983 is shown in FIG. 7.

Example 16

Co-Expressing Other Promoter/Gene/Terminator Cassette Combinations

In addition to the genes, promoters, terminators and gene cassettes described herein, one skilled in the art can appreciate that other promoter/gene/terminator cassette combinations can be synthesized in a way similar to, but not limited to, that described herein. For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 4) and a transcription terminator (such as those listed in, but not limited to, Table 5) is used to clone the desired gene. NotI sites can be added to a gene of interest such as those listed in, but not limited to, Table 6 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 4

| Seed-specific Promoters | | |
|---|---|---|
| Promoter | Organism | Promoter Reference |
| β-conglycinin α'-subunit | soybean | Beachy et al., *EMBO J.* 4: 3047-3053 (1985) |
| kunitz trypsin inhibitor | soybean | Jofuku et al., *Plant Cell* 1: 1079-1093 (1989) |
| Annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., *Mol. Gen. Genet.* 225: 148-157 (1991) |
| β-conglycinin β-subunit | soybean | WO 2004/071467 |
| BD30 (also called P34) | soybean | WO 2004/071467 |
| legumin A2 | pea | Rerie et al., *Mol. Gen. Genet.* 225: 148-157 (1991) |

TABLE 5

| Transcription Terminators | | |
|---|---|---|
| Transcription Terminator | Organism | Reference |
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 6

| EPA Biosynthetic Pathway Genes | | |
|---|---|---|
| Gene | Organism | Reference |
| delta-6 desaturase | *Saprolegnia diclina* | WO 2002/081668 |
| delta-6 desaturase | *Mortierella alpina* | U.S. Pat. No. 5,968,809 |
| elongase | *Mortierella alpina* | WO 2000/12720 U.S. Pat. No. 6,403,349 |
| delta-5 desaturase | *Mortierella alpina* | U.S. Pat. No. 6,075,183 |
| delta-5 desaturase | *Saprolegnia diclina* | WO 2002/081668 |
| delta-15 desaturase | *Fusarium moniliforme* | WO 2005/047479 |
| delta-17 desaturase | *Saprolegnia diclina* | WO 2002/081668 |
| elongase | *Thraustochytrium aureum* | WO 2002/08401 U.S. Pat. No. 6,677,145 |
| elongase | *Pavlova* sp. | Pereira et al., *Biochem. J.* 384: 357-366 (2004) |
| delta-4 desaturase | *Schizochytrium aggregatum* | WO 2002/090493 |
| delta-9 elongase | *Isochrysis galbana* | WO 2002/077213 |
| delta-9 elongase | *Euglena gracilis* | U.S. Provisional Application No. 60/739,989 |
| delta-8 desaturase | *Euglena gracilis* | WO 2000/34439 U.S. Pat. No. 6,825,017 WO 2004/057001 WO 2006/012325 |
| delta-8 desaturase | *Acanthamoeba castellanii* | Sayanova et al., *FEBS Lett.* 580: 1946-1952 (2006) |
| delta-8 desaturase | *Pavlova salina* | WO 2005/103253 |
| delta-8 desaturase | *Pavlova lutheri* | instant application |

Example 17

Synthesis of a Codon-Optimized Delta-8 Desaturase Gene Derived from *Pavlova lutheri* in *Yarrowia lipolytica*

The codon usage of the delta-8 desaturase gene of *Pavlova lutheri* (SEQ ID NO:14; Example 4, supra) was optimized for expression in *Yarrowia lipolytica*, in a manner similar to that described in PCT Publication No. WO 2004/101753. Specifically, a codon-optimized delta-8 desaturase gene (designated “PiD8S”; SEQ ID NO:57) was designed based on the coding sequence of the delta-8 desaturase gene of the instant invention (SEQ ID NO:14), according to the *Yarrowia* codon usage pattern (PCT Publication No. WO 2004/101753), the consensus sequence around the ‘ATG’ translation initiation codon, and the general rules of RNA stability (Guhaniyogi, G. and Brewer, J., *Gene* 265(1-2):11-23 (2001)). In addition to modification of the translation initiation site, 161 bp of the 1272 bp coding region were modified (13.1%) and 161 codons were optimized (38.1%). None of the modifications in the codon-optimized gene changed the amino acid sequence of the encoded protein (SEQ ID NO:16). The designed PiD8S gene was synthesized by GenScript Corporation (Piscataway, N.J.) and cloned into pUC57 (GenBank Accession No. Y14837) to generate pPiD8S (SEQ ID NO:58; FIG. 11-A).

Example 18

Construction of Plasmid pZUFmEgD9ES, Comprising a Codon-Optimized Delta-9 Elongase Gene Derived from *Euglena gracilis*

The present Example describes the construction of plasmid pZUFmEgD9ES (SEQ ID NO:70), comprising a synthetic delta-9 elongase gene (derived from *Euglena gracilis*) that was codon-optimized for *Yarrowia lipolytica* (designated herein as “EgD9S” or “EgD9ES”). Plasmid pZUFmEgD9ES (SEQ ID NO: 70; FIG. 9-D) was constructed by three-way ligation using fragments from plasmids pEgD9ES, pDMW263 and pZUF17 (SEQ ID NO:67, SEQ ID NO:68 and SEQ ID NO:69, respectively; FIGS. 9-A, 9-B and 9-C, respectively). This plasmid was utilized to construct plasmid pZUFmE9SP8S (SEQ ID NO:71) comprising the synthetic codon-optimized PiD8S from Example 17 and EgD9S as described herein in Example 19, infra.

*Euglena gracilis* Growth Conditions, Lipid Profile and mRNA Isolation:

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining 1 g of sodium acetate, 1 g of beef extract (U126-01, Difco Laboratories, Detroit, Mich.), 2 g of Bacto® tryptone (0123-17-3, Difco Laboratories) and 2 g of Bacto® yeast extract (0127-17-9, Difco Laboratories) in 970 mL of water. After filter sterilizing, 30 mL of soil-water supernatant (15-3790, Carolina Biological Supply Company, Burlington, N.C.) was aseptically added to give the final Eg medium. *Euglena gracilis* cultures were grown at 23° C. with a 16 h light, 8 h dark cycle for 2 weeks with no agitation.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Nu-Chek Prep, Inc. Cat. No. U-99-A) and the resulting chromatogram is shown in FIG. 10.

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 μg of mRNA was obtained.

*Euglena gracilis* cDNA Synthesis, Library Construction and Sequencing:

A cDNA library was generated using the Cloneminer™ cDNA Library Construction Kit (Cat. No. 18249-029, Invitrogen Corporation, Carlsbad, Calif.) and following the manufacturer's protocol provided (Version B, 25-0608). Using the non-radiolabeling method, cDNA was synthesized from 3.2 μg of mRNA (described above) using the Biotin-attB2-Oligo (dT) primer. After synthesis of the first and second strand, the attB1 adapter was added, ligated and the cDNA was size fractionated using column chromatography. DNA from fractions 7 and 8 (size ranging from ~800-1500 bp) were concentrated, recombined into pDONR™ 222 and transformed into *E. coli* ElectroMAX™ DH10B™ T1 Phage-Resistant cells (Invitrogen Corporation). The *Euglena gracilis* library was named eeg1c.

For sequencing, clones first were recovered from archived glycerol cultures grown/frozen in 384-well freezing media plates, and replicated with a sterile 384 pin replicator (Genetix, Boston, Mass.) in 384-well microtiter plates containing LB+75 μg/mL Kanamycin (replicated plates). Plasmids then were isolated, using the Templiphi DNA sequencing template amplification kit method (Amersham Biosciences) following the manufacturer's protocol. Briefly, the Templiphi method uses bacteriophage ϕ29 DNA polymerase to amplify circular single-stranded or double-stranded DNA by isothermal rolling circle amplification (Dean et al., *Genome Res.* 11:1095-1099 (2001); Nelson et al., *Biotechniques* 32:S44-S47 (2002)). After growing 20 h at 37° C., cells from the replicated plate were added to 5 μL of dilution buffer and denatured at 95° C. for 3 min to partially lyse cells and release the denatured template. 5 μL of Templiphi premix then were added to each sample and the resulting reaction mixture was incubated at 30° C. for 16 h, then at 65° C. for 10 min to inactivate the ϕ29 DNA polymerase activity. DNA quantification with the PicoGreen® dsDNA Quantitation Reagent (Molecular Probes) was performed after diluting the amplified samples 1:3 in distilled water.

The amplified products then were denatured at 95° C. for 10 min and end-sequenced in 384-well plates, using the M13F universal primer (SEQ ID NO:63), and the ABI BigDye version 3.1 Prism Sequencing Kit. For the sequencing reaction, 100-200 ng of templates and 6.4 μmol of primers were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3730xl automated sequencers.

Identification of Long-Chain Polyunsaturated Fatty Acid Elongation Enzyme Homologs from *Euglena gracilis* cDNA Library eeg1c:

cDNA clones encoding long-chain polyunsaturated fatty acid elongation enzyme homologs (i.e., LC-PUFA ELO homologs or delta-9 elongases) were identified and analyzed by conducting BLAST searches for similarity to sequences contained in the BLAST "nr" database, as described supra (see Example 2).

The BLASTX search using the nucleotide sequences from clone eeg1c.pk001.n5.f revealed similarity of the protein encoded by the cDNA to the long-chain PUFA elongation enzyme from *Isochrysis galbana* (SEQ ID NO:59) (NCBI Accession No. AAL37626 (GI 17226123), locus AAL37626, CDS AF390174; Qi et al., *FEBS Lett.* 510(3):159-165 (2002)). The sequence of a portion of the cDNA insert from clone eeg1c.pk001.n5.f is shown in SEQ ID NO:60 (5' end of cDNA insert). Additional sequence was obtained from the 3' end of the cDNA insert of eeg1c.pk001.n5.1 as described above, but using the poly(A) tail-primed WobbleT oligonucleotides. Briefly, the WobbleT primer is an equimolar mix of 21 mer poly(T)A, poly(T)C and poly(T)G, used to sequence the 3' end of cDNA clones.

The 3' end sequence is shown in SEQ ID NO:61. Both the 5' and 3' sequences were aligned using Sequencher™ (Version 4.2, Gene Codes Corporation, Ann Arbor, Mich.) and the resulting sequence for the cDNA is shown in SEQ ID NO:62. Sequence for the coding sequence from the cDNA in eeg1c.pk001.n5.f and the corresponding deduced amino acid sequence is shown in SEQ ID NO:32 and SEQ ID NO:64, respectively.

The amino acid sequence set forth in SEQ ID NO:64 was evaluated by BLASTP, yielding a pLog value of 38.70 (E value of 2e-39) versus the *Isochrysis galbana* sequence (SEQ ID NO:65). The *Euglena gracilis* delta-9 elongase is 39.4% identical to the *Isochrysis galbana* delta-9 elongase sequence using the Jotun Hein method. Sequence percent identity calculations performed by the Jotun Hein method (Hein, J. J., *Meth. Enz.* 183:626-645 (1990)) were done using the MegAlign™ v6.1 program of the LASARGENE bioinformatics computing suite (DNASTAR Inc., Madison, Wis.) with the default parameters for pairwise alignment (KTUPLE=2). The *Euglena gracilis* delta-9 elongase is 31.8% identical to the *Isochrysis galbana* delta-9 elongase sequence using the Clustal V method. Sequence percent identity calculations performed by the Clustal V method (Higgins, D. G. and Sharp, P. M., *Comput. Appl. Biosci.* 5:151-153 (1989); Higgins et al., *Comput. Appl. Biosci.* 8:189-191 (1992)) were done using the MegAlign™ v6.1 program of the LASARGENE bioinformatics computing suite (DNASTAR Inc., Madison, Wis. ) with the default parameters for pairwise alignment (KTUPLE=1, GAP PENALTY=3, WINDOW=5 and DIAGONALS SAVED=5 and GAP LENGTH PENALTY=10). BLAST scores and probabilities indicate that the instant nucleic acid fragment (SEQ ID NO:32) encode an entire *Euglena gracilis* delta-9 elongase.

Synthesis of the Codon-Optimized Delta-9 Elongase Gene:

The codon usage of the delta-9 elongase gene of *Euglena gracilis* (SEQ ID NOs:32 and 64) was optimized for expression in *Yarrowia lipolytica*, in a manner similar to that described supra (see Example 17) and WO 2004/101753. Specifically, a codon-optimized delta-9 elongase gene (designated "EgD9S"), SEQ ID NO:66) was designed, based on the coding sequence of the delta-9 elongase (clone eeg1c.pk001.n5.f), according to the *Yarrowia* codon usage pattern, the consensus sequence around the 'ATG' translation initiation codon, and the general rules of RNA stability (Guhaniyogi, G. and Brewer, J., supra)). In addition to the modification of the translation initiation site, 117 bp of the 777 bp coding region were modified (15.1%) and 106 codons were optimized (40.9%). None of the modifications in the codon-optimized gene changed the amino acid sequence of the encoded protein (SEQ ID NO:64). The designed EgD9S (also "EgD9ES") gene was synthesized by GenScript Corporation (Piscataway, N.J.) and was cloned into pUC57 (GenBank Accession No. Y14837) to generate pEgD9ES (SEQ ID NO:67; FIG. 9-A).

Construction of Plasmid pDMW263:

Plasmid pY5-30 (SEQ ID NO:78) (previously described in PCT Publication No. WO 2005/003310 (the contents of which are hereby incorporated by reference) is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene (AmpR) for selection in *E. coli*; a *Yarrowia* LEU2 gene for selection in *Yarrowia*; and a chimeric TEF::GUS::XPR gene. Plasmid pDMW263 (SEQ ID NO:68; FIG. 9-B) was created from pY5-30, by replacing the TEF promoter with the *Yarrowia lipolytica* FBAINm promoter (PCT Publication No. WO 2005/049805) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 7 summarizes the components of pDMW263.

TABLE 7

Components of Plasmid pDMW263

| RE Sites and Nucleotides Within SEQ ID NO: 68 | Description of Fragment and Chimeric Gene Components |
|---|---|
| 4992-4296 | ARS18 sequence (GenBank Accession No. A17608) |
| SalI/SacII (8505-2014) | FBAINm::GUS::XPR, comprising: FBAINm: *Yarrowia lipolytica* FBAINm promoter (WO 2005/049805) GUS: *E. coli* gene encoding β-glucuronidase (Jefferson, R. A., Nature. 14: 342: 837-838 (1989)) XPR: ~100 bp of the 3' region of the *Yarrowia* Xpr gene (GenBank Accession No. M17741) |
| 6303-8505 | *Yarrowia* Leu2 gene (GenBank Accession No. AF260230) |

Construction of Plasmid pZUF17:

Plasmid pZUF17 (SEQ ID NO:69; FIG. 9-C) possesses a similar backbone to that of pDMW236. However, the plasmid comprises a *Yarrowia* Ura3 gene for selection in *Yarrowia* and a chimeric FBAIN::D17S::Pex20 gene, instead of the LEU2 gene and chimeric FBAINm::GUS::XPR gene of pDMW263. Table 8 summarizes the components of pZUF17.

TABLE 8

Components of Plasmid pZUF17

| RE Sites and Nucleotides Within SEQ ID NO: 69 | Description of Fragment and Chimeric Gene Components |
|---|---|
| 2866-4170 | ARS18 sequence (GenBank Accession No. A17608) |
| ClaI/PacI (5750-8165) | FBAIN::D17S::Pex20, comprising: FBAIN: *Yarrowia lipolytica* FBAIN promoter (WO 2005/049805) Δ17S: synthetic Δ17 desaturase gene derived from *Saprolegnia diclina* (US 2003/0196217 A1), codon-optimized for *Yarrowia lipolytica* (WO 2004/101757) Pex20: Pex20 terminator sequence of *Yarrowia* Pex20 gene (GenBank Accession No. AF054613) |
| 5703-4216 | *Yarrowia* Ura3 gene (GenBank Accession No. AJ306421) |

Final Construction of Plasmid pZUFmEgD9ES:

The NcoI/NotI fragment from plasmid pEgD9ES (SEQ ID NO:67; FIG. 9-A; comprising EgD9ES) and the SalI/NcoI fragment from pDMW263 (SEQ ID NO:68; FIG. 9-B; comprising the *Yarrowia lipolytica* FBAINm promoter) were used directionally to replace the SalI/NotI fragment of pZUF17 (SEQ ID NO:69; FIG. 9-C). This resulted in generation of pZUFmEgD9ES (SEQ ID NO:70; FIG. 9-D), comprising a chimeric FBAINm::EgD9ES::Pex20 gene.

Example 19

Construction of Plasmid pZUFmE9SP8S, Comprising the Codon-Optimized Delta-8 Desaturase Gene Derived from *Pavlova lutheri* and the Codon-Optimized Delta-9 Elongase Gene Derived from *Euglena gracilis*

The present Example describes the construction of plasmid pZUFmE9SP8S (SEQ ID NO:71), comprising the synthetic codon-optimized PiD8S from Example 17 and the synthetic codon-optimized EgD9ES from Example 18. Plasmid pZUFmE9SP8S (SEQ ID NO:71; FIG. 11-D) was constructed by four-way ligation using fragments from plasmids pPID8S, pZUFmEgD9ES, pEXPGUS1-C and pZGD5T-CP (SEQ ID NO:58, SEQ ID NO:70, SEQ ID NO:72 and SEQ ID NO:73, respectively; FIGS. 11-A, 9-D, 11-B and 11-C, respectively). This plasmid was utilized to test functional co-expression of PiD8S and EgD9ES, as described in Example 20, infra.

Plasmid pEXPGUS1-C:

Plasmid pEXPGUS1-C (SEQ ID NO:72; FIG. 11-B) comprises a chimeric EXP1::GUS::XPR gene (nucleotides 953-3963 of SEQ ID NO:72). The "EXP1" promoter within this chimeric gene refers to the 5' upstream untranslated −1000 to −1 bp region in front of the 'ATG' translation initiation codon of a protein encoded by the *Yarrowia lipolytica* "YALI0C12034g" gene (GenBank Accession No. XM_501745) and that is necessary for expression. Based on significant homology of "YALI0C12034g" to the sp|Q12207 *Saccharomyces cerevisiae* non-classical export protein 2 (whose function is involved in a novel pathway of export of proteins that lack a cleavable signal sequence), this gene was designated as the exp1 gene, encoding a protein designated as EXP1 (U.S. application Ser. No. 11/265,761). "GUS" and "XPR" are defined as described above in Table 7.

Plasmid pZGD5T-CP:

Plasmid pZGD5T-CP (SEQ ID NO:73; FIG. 11-C) comprises a chimeric GPD::MAD5::Pex16 gene (nucleotides 3200-346 of SEQ ID NO:73). The "GPD" promoter within this chimeric gene refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (PCT Publication No. WO 2005/003310). The "MAD5" coding region of the chimeric gene corresponds to the *Mortierella alpina* A5 desaturase gene (GenBank Accession No. AF067654), while "Pex16" refers to the Pex16 terminator of the *Yarrowia* Pex16 gene (GenBank Accession No. U75433).

Final Construction of Plasmid pZUFmE9SP8S:

The NcoI/NotI fragment of plasmid pPiD8S (SEQ ID NO:58; FIG. 11-A; comprising the synthetic delta-8 desaturase gene of the present invention (i.e., PiD8S), the ClaI/NcoI fragment from pEXPGUS1-C (SEQ ID NO:72; FIG. 11-B; comprising the EXP1 promoter), and the NotI/PacI fragment from plasmid pZGD5T-CP (SEQ ID NO:73; FIG. 11-C; comprising the Pex16 terminator) were used directionally to replace the ClaI/PacI fragment of pZUFmEgD9ES (SEQ ID NO:70; FIG. 9-D) to generate pZUFmE9SP8S (SEQ ID NO:71; FIG. 11-D).

Example 20

Functional Expression of Plasmid pZUFmE9SP8S in *Yarrowia lipolytica*

The present Example describes expression of plasmid pZUFmE9SP8S, comprising the chimeric FBAINm::EgD9ES::Pex20 gene and the chimeric EXP::PiD8S::Pex16 gene. Expression of pZUFmE9SP8S in *Yarrowia lipolytica* led to the production of up to 2.8% EDA and 0.5% of DGLA.

Specifically, pZUFmE9SP8S (SEQ ID NO:71; FIG. 11-D) was transformed into *Yarrowia lipolytica* Y20362U (an autonomous Ura-mutant of ATCC Accession No. 20362, that was generated by selecting for FOA resistance) as described supra. The transformant cells were plated onto MM selection media plates and maintained at 30° C. for 2 to 3 days. Fifteen (15) transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 2.8% EDA (C20:2) and 0.3% of DGLA (C20:3) of total lipids produced in 13 of these 15 transformants, wherein the conversion efficiency of EDA to DGLA in these 13 strains was at an average rate of about 9.7%. Strain #7 produced 2.8% EDA and 0.5% of DGLA, with a conversion efficiency of about 15%. The term "conversion efficiency" refers to the efficiency by which a particular enzyme (e.g., the codon-optimized delta-8 desaturase identified herein as PiD8S) can convert substrate (i.e., FDA) to product (i.e., DGLA). The conversion efficiency was measured according to the following formula: ([product]/[substrate+product])*100, where 'product' includes the immediate product and all products in the pathway derived from it.

Example 21

Chlorsulfuron Selection (ALS) and Plant Regeneration

Chlorsulfuron (ALS) Selection:

Following bombardment, the tissue is divided between 2 flasks with fresh SB196 media and cultured as described in Example 11. Six to seven days post-bombardment, the SB196 is exchanged with fresh SB196 containing selection agent of 100 ng/mL chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants:

In order to obtain whole plants from embryogenic suspension cultures, the tissue must be regenerated. Embryos are matured as described in Example 11. After subculturing on medium SB103 for 3 weeks, individual embryos can be removed from the clusters and screened for alterations in their fatty acid compositions as described in Example 12. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for fatty acids as described in Example 12.

Media recipes can be found in Example 11 and chlorsulfuron stock is 1 mg/mL in 0.01 N ammonium hydroxide.

Example 22

Co-Expression of the *Euglena gracilis* Delta-9 Elongase with the *Pavlova lutheri* (CCMP459) Delta-8 Desaturase, the *Mortierella alpina* Delta-5 Desaturase, the *Saprolegnia diclina* Delta-17 Desaturase and the *Fusarium moniliforme* Delta-15 Desaturase in Soybean Embryos Transformed with Soybean Expression Vectors pKR973 and pKR983

Soybean embryogenic suspension culture (cv. Jack) was transformed with the Asci fragments of pKR973 (SEQ ID NO:45, FIG. 5) and pKR983 (SEQ ID NO:56; FIG. 7) (fragments containing the expression cassettes), as described for production in Example 11. Transformants were selected using chlorsulfuron as described in Example 21 and embryos were matured as described in Example 11. A subset of soybean embryos generated from each event (ten embryos per event) were harvested and analyzed for fatty acid composition as described in Example 12. Fatty acids were identified by comparison of retention times to those for authentic standards.

In this way, 243 events transformed with pKR973 and pKR983 were analyzed. From the 243 events analyzed, 117 were identified that produced EPA in at least one embryo out of ten analyzed at a relative abundance greater than 1.0% of the total fatty acids. Of these, 15 were identified that produced EPA in at least one embryo out of ten analyzed at a relative abundance greater than 10.0% of the total fatty acids. The average fatty acid profile for the ten best EPA events (average of seven to ten individual embryos) is shown in FIG. 14. Fatty acids are identified as 16:0 (palmitate), 18:0 (stearic acid), 18:1 (oleic acid), LA, GLA, ALA, EDA, DGLA, ARA, ERA, JUN, ETA, EPA and DPA; and, fatty acid compositions listed in FIG. 14 are expressed as a weight percent (wt. %) of total fatty acids. For FIG. 14, fatty acids listed as "others" include: 18:2 (5,9), STA, 20:0, 20:1(11), 20:2 (7,11) or 20:2 (8,11) and 20:3 (5,11,14). Each of these fatty acids is present at a relative abundance of less than 1% of the total fatty acids. The activity of the *Pavlova lutheri* (CCMP459) delta-8 desaturase is expressed as percent delta-8 desaturation (% Desat), calculated according to the following formula: ([product]/[substrate+product])*100.

More specifically, the combined percent delta-8 desaturation for EDA and ERA is shown as "Total delta-8% Desat", determined as: ([DGLA+ARA+ERA+ETA+EPA+DPA]/[EDA+DGLA+ARA+ERA+JUN+ETA+EPA+DPA])*100.

In summary of FIG. 14, the *Pavlova lutheri* (CCMP459) delta-8 desaturase functioned in soybean to convert both EDA and ERA to DGLA and ETA, respectively, and these were further converted to other LC-PUFAs. Line AFS 4802-3-14, the high EPA line with the highest average overall % delta-8 desaturation, had overall % delta-8 desaturation of 82.5%.

What is claimed is:

1. An isolated polypeptide comprising an amino acid sequence having at least 80% sequence identity, based on the Clustal V method of alignment, when compared to SEQ ID NO:16.

2. The polypeptide of claim 1, wherein the amino acid sequence of the polypeptide has at least 85% sequence identity, based on the Clustal V method of alignment, when compared to SEQ ID NO:16.

3. The polypeptide of claim 1, wherein the amino acid sequence of the polypeptide has at least 90% sequence identity, based on the Clustal V method of alignment, when compared to SEQ ID NO:16.

4. The polypeptide of claim 1, wherein the amino acid sequence of the polypeptide comprises (a) SEQ ID NO:16; or (b) an amino acid sequence that differs from the amino acid sequences in (a) by at least one conservative amino acid substitution.

5. The polypeptide of claim 1, wherein the amino acid sequence of the polypeptide has at least 95% sequence identity, based on the Clustal V method of alignment, when compared to SEQ ID NO:16.

* * * * *